US007109228B2

(12) United States Patent
Jones et al.

(10) Patent No.: US 7,109,228 B2
(45) Date of Patent: Sep. 19, 2006

(54) PYRAZOLE DERIVATIVES

(75) Inventors: Lyn Howard Jones, Sandwich (GB); Charles Eric Mowbray, Sandwich (GB); David Anthony Price, Sandwich (GB); Matthew Duncan Selby, Sandwich (GB); Paul Anthony Stupple, Sandwich (GB)

(73) Assignee: Agouron Pharmaceuticals, Inc., La Jolla, CA (US)

( * ) Notice: Subject to any disclaimer, the term of this patent is extended or adjusted under 35 U.S.C. 154(b) by 380 days.

(21) Appl. No.: 10/118,512

(22) Filed: Apr. 5, 2002

(65) Prior Publication Data

US 2003/0100554 A1 May 29, 2003

Related U.S. Application Data

(60) Provisional application No. 60/346,727, filed on Jan. 7, 2002, provisional application No. 60/289,570, filed on May 8, 2001.

(30) Foreign Application Priority Data

| Apr. 10, 2001 | (GB) | ................... | 0108999.4 |
| Nov. 15, 2001 | (GB) | ................... | 0127426.5 |

(51) Int. Cl.
*A61K 31/415* (2006.01)
*C07D 231/18* (2006.01)

(52) U.S. Cl. .................. 514/407; 514/341; 546/375.7; 546/376.1; 548/364.1; 548/366.1; 548/366.4; 548/366.7; 548/369.7; 548/370.1; 548/370.4; 548/370.7

(58) Field of Classification Search ............. 548/364.1, 548/366.1, 366.4, 366.7, 369.7, 370.1, 370.4, 548/370.7; 514/407
See application file for complete search history.

(56) References Cited

U.S. PATENT DOCUMENTS

| 3,303,200 A | 2/1967 | Wolf et al. ................. 260/310 |
| 3,963,742 A | 6/1976 | Cross et al. ................. 260/311 |
| 4,000,301 A | 12/1976 | Walworth .................... 424/273 |
| 4,041,046 A | 8/1977 | Cross et al. ................. 548/375 |

FOREIGN PATENT DOCUMENTS

| EP | 538156 A1 | 4/1993 | .................. 231/16 |
| EP | 0786455 A1 | 7/1997 | |
| EP | 658547 B1 | 11/1998 | .................. 231/18 |
| WO | 9111172 | 8/1991 | |
| WO | 9402518 | 2/1994 | |
| WO | 9422830 | 10/1994 | .................... 213/2 |
| WO | 9429300 | 12/1994 | .................... 409/4 |
| WO | 9602138 | 2/1996 | .................... 43/56 |
| WO | 9855148 | 12/1998 | |

OTHER PUBLICATIONS

Dzvinchuk et al., Chemical Abstracts, vol. 112:77066, 1990.*
Kato et al., Chemical Abstracts, vol. 108:93811, 1998.*
Kirsten et al., Chemical Abstracts, vol. 105:60431, 1986.*
Genin et al., J. Med. Chem., vol. 43 p. 1034-1040 (2000).
Berge et al., J. Pharm. Sci., vol. 66, pp. 1-19 (1977).
Ferres, Drugs of Today, vol. 19, No. 9, pp. 499-538 (1983).
Bundgaard, Elsevier, Design of Prodrugs, Chapter 1 (1985).
Attanasi et al., "Reaction of Some 1,2-Diaza-1,3-butadienes with Activated Methine Compounds. A Straightforward Entry to 1,4-Dihydropyridazine, Pyridazine, and 4,5(4H,5H)-Cyclopropylpyrazole Derivatives", J. Org. Chem., 1998, 63, 9880-9887.
Beilstein Registry No. 331922 (Update Date May 13, 1992).
Lipinski et al., "Bronchodilator and Antiulcer Phenoxypyrimidinones", L. Med. Chem., 1980, 23, 1026-1031.
Munch-Peterson and Hauser, "Acylations of Certain α-Alkoxy and α-Aryloxy Ketones and Esters", J. Am. Chem. Soc., 71, 1949, 770-773.
Olsen, et al., "Synthesis of Functionalized Aryloxy 1,3-Butadienes and Their Transformation to Diaryl Ethers via Diels-Alder Cycloaddition Reactions", J. Org. Chem., 1995, 60, 6025-6031.
Regitz and Schafer, "Stabile Enole von α-[Aryl(Alkl)oxy]dibenzoylmethanen", Liebigs Ann Chem, 1981, 1172-1185.
Smodis and Stanovnik, "The Synthesis and Transformations of Substituted 2-Hydroxy-3-dimethylaminopropenoates. The Preparation of Condensed 3-Hydroxypyran-2-ones", Tetrahedron 54, 1998, 9799-9810.

* cited by examiner

*Primary Examiner*—Richard L. Raymond
(74) *Attorney, Agent, or Firm*—Keith D. Hutchinson; Bryan C. Zielinski; Peter C. Richardson

(57) ABSTRACT

This invention relates to pyrazole derivatives of formula (I)

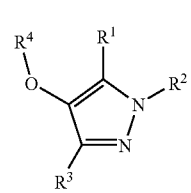

or pharmaceutically acceptable salts, solvates or derivatives thereof, and to processes for the preparation thereof, intermediates used in their preparation of, compositions containing them and the uses of such derivatives. The compounds of the present invention bind to the enzyme reverse transcriptase and are modulators, especially inhibitors thereof. As such, the compounds of the present invention are useful in the treatment of a variety of disorders including those in which the inhibition of reverse transcriptase is implicated. Disorders of interest include those caused by Human Immunodificiency Virus (HIV) and genetically related retroviruses, such as Acquired Immune Deficiency Syndrome (AIDS).

35 Claims, No Drawings

PYRAZOLE DERIVATIVES

CROSS-REFERENCE TO RELATED APPLICATIONS

This non-provisional patent application claims priority to United Kingdom Application No. 0108999.4, filed Apr. 10, 2001, United Kingdom Application No. 0127426.5, filed Nov. 15, 2001, U.S. Patent Application No. 60/289,570, filed May 8, 2001, and U.S. Patent Application No. 60/346,727, filed Jan. 7, 2002, each of which is hereby incorporated in its entirety.

FIELD OF THE INVENTION

This invention relates to pyrazole derivatives and to processes for the preparation thereof, intermediates used in their preparation, compositions containing them and the uses of such derivatives.

The compounds of the present invention bind to the enzyme reverse transcriptase and are modulators, especially inhibitors thereof. Reverse transcriptase is implicated in the infectious lifecycle of HIV, and compounds which interfere with the function of this enzyme have shown utility in the treatment of conditions including AIDS. There is a constant need to provide new and better modulators, especially inhibitors, of HIV reverse transcriptase since the virus is able to mutate, becoming resistant to the effects of known modulators.

The compounds of the present invention are useful in the treatment of a variety of disorders including those in which the inhibition of reverse transcriptase is implicated. Disorders of interest include those caused by Human Immunodeficiency Virus (HIV) and genetically related retroviruses, such as Acquired Immune Deficiency Syndrome (AIDS).

European patent application EP 0 786 455 A1 discloses a class of imidazole compounds which inhibit the growth of HIV. A class of N-phenylpyrazoles which act as reverse transcriptase inhibitors are disclosed in *J. Med. Chem.*, 2000, 43, 1034. Antiviral activity is ascribed to a class of N-(hydroxyethyl)pyrazole derivatives in U.S. Pat. No. 3,303,200.

According to the present invention there is provided a compound of the formula

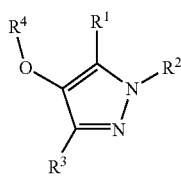

(I)

or a pharmaceutically acceptable salt, solvate or derivative thereof, wherein:

either $R^1$ is H, $C_1$–$C_6$ alkyl, $C_3$–$C_7$ cycloalkyl, phenyl, benzyl, halo, —CN, —$OR^7$, —$CO_2R^{10}$, —$CONR^5R^{10}$, $R^8$ or $R^9$, said $C_1$–$C_6$ alkyl, $C_3$–$C_7$ cycloalkyl, phenyl and benzyl being unsubstituted or substituted by halo, —CN, —$OR^{10}$, —$S(O)_xR^{10}$, —$CO_2R^{10}$, —$CONR^5R^{10}$, —$OCONR^5R^{10}$, —$NR^5CO_2R^{11}$, —$NR^{10}R^{10}R^{11}$, —$NR^5COR^{10}$, —$SO_2NR^5R^{10}$, —$NR^5CONR^5R^{10}$, —$NR^5SO_2R^{10}$ or $R^{10}$; and $R^2$ is H, $C_1$–$C_6$ alkyl, $C_3$–$C_6$ alkenyl, $C_3$–$C_6$ alkynyl, $C_3$–$C_7$ cycloalkyl, $C_3$–$C_7$ cycloalkenyl, phenyl, benzyl, $R^8$ or $R^9$, said $C_1$–$C_6$ alkyl, $C_3$–$C_7$ cycloalkyl, phenyl and benzyl being unsubstituted or substituted by halo, —$OR^5$, —$OR^{12}$, —CN, —$CO_2R^7$, —$OCONR^5R^5$, —$CONR^5R^5$, —$C(=NR^5)NR^5OR^5$, —$CONR^5NR^5R^5$, —$NR^6R^6$, —$NR^5R^{12}$, —$NR^5COR^5$, —$NR^5COR^8$, —$NR^5COR^{12}$, —$NR^5CO_2R^5$, —$NR^5CONR^5R^5$, —$SO_2NR^5R^5$, —$NR^5SO_2R^5$, —$NR^5SO_2NR^5R^5$, $R^8$ or $R^9$;

or, $R^1$ and $R^2$, when taken together, represent unbranched $C_3$–$C_4$ alkylene, unsubstituted or substituted by oxo, wherein one methylene group of said $C_3$–$C_4$ alkylene may be replaced by an oxygen atom or a nitrogen atom, said nitrogen atom being unsubstituted or substituted by $R^{10}$;

$R^3$ is H, $C_1$–$C_6$ alkyl, $C_3$–$C_7$ cycloalkyl, phenyl, benzyl, halo, —CN, —$OR^7$, —$CO_2R^5$, —$CONR^5R^5$, $R^8$ or $R^9$, said $C_1$–$C_6$ alkyl, $C_3$–$C_7$ cycloalkyl, phenyl and benzyl being unsubstituted or substituted by halo, —CN, —$OR^5$, —$CO_2R^5$, —$CONR^5R^5$, —$OCONR^5R^5$, —$NR^5CO_2R^5$, —$NR^6R^6$, —$NR^5COR^5$, —$SO_2NR^5R^5$, —$NR^5CONR^5R^5$, —$NR^5SO_2R^5$, $R^8$ or $R^9$;

$R^4$ is phenyl, naphthyl or pyridyl, each being unsubstituted or substituted by $R^8$, halo, —CN, $C_1$–$C_6$ alkyl, $C_1$–$C_6$ haloalkyl, $C_3$–$C_7$ cycloalkyl, $C_1$–$C_6$ alkoxy, —$CONR^5R^5$, $OR^{13}$, $So_xR^6$, O—($C_1$–$C_6$ alkylene)—$CONR^5R^5$, O—($C_1$–$C_6$ alkylene)—$NR^5R^5$, or O—($C_1$–$C_6$ alkylene)—$OR^6$;

each $R^5$ is independently either H, $C_1$–$C_6$ alkyl or $C_3$–$C_7$ cycloalkyl or, when two $R^5$ groups are attached to the same nitrogen atom, those two groups taken together with the nitrogen atom to which they are attached represent azetidinyl, pyrrolidinyl, piperidinyl, homopiperidinyl, piperazinyl, homopiperazinyl or morpholinyl, said azetidinyl, pyrrolidinyl, piperidinyl, homopiperidinyl, piperazinyl, homopiperazinyl and morpholinyl being unsubstituted or substituted by $C_1$–$C_6$ alkyl or $C_3$–$C_7$ cycloalkyl;

each $R^6$ is independently either H, $C_1$–$C_6$ alkyl or $C_3$–$C_7$ cycloalkyl;

$R^7$ is $C_1$–$C_6$ alkyl or $C_3$–$C_7$ cycloalkyl;

$R^8$ is a five or six-membered, aromatic heterocyclic group containing (i) from 1 to 4 nitrogen heteroatom(s) or (ii) 1 or 2 nitrogen heteroatom(s) and 1 oxygen or 1 sulphur heteroatom or (iii) 1 or 2 oxygen or sulphur heteroatom(s), said heterocyclic group being unsubstituted or substituted by halo, oxo, —CN, —$COR^5$, —$CONR^5R^5$, —$SO_2NR^5R^5$, —$NR^5SO_2R^5$, —$OR^5$, —$NR^5R^5$, —($C_1$–$C_6$ alkylene)—$NR^5R^5$, $C_1$–$C_6$ alkyl, fluoro($C_1$–$C_6$)alkyl or $C_3$–$C_7$ cycloalkyl;

$R^9$ is a four to seven-membered, saturated or partially unsaturated heterocyclic group containing (i) 1 or 2 nitrogen heteroatom(s) or (ii) 1 nitrogen heteroatom and 1 oxygen or 1 sulphur heteroatom or (iii) 1 oxygen or sulphur heteroatom, said heterocyclic group being unsubstituted or substituted by oxo, $C_1$–$C_6$ alkyl, $C_3$–$C_7$ cycloalkyl, —$SO_2R^5$, —$CONR^5R^5$, —$COOR^5$, —CO—($C_1$–$C_6$ alkylene)—$OR^5$ or —$COR^5$ and unsubstituted or substituted on a carbon atom which is not adjacent to a heteroatom by halo, —$OR^5$, —$NR^5R^5$, —$NR^5COR^5$, —$NR^5COOR^5$, —$NR^5CONR^5R^5$, —$NR^5SO_2R^5$ or —CN;

$R^{10}$ is H, $R^8$, $R^9$, $R^{13}$, $C_1$–$C_6$ alkyl, $C_3$–$C_7$ cycloalkyl or —($C_1$–$C_6$ alkyl)—($C_3$–$C_7$ cycloalkyl), said $C_1$–$C_6$ alkyl and $C_3$–$C_7$ cycloalkyl being unsubstituted or substituted by —$OR^5$, —$OR^{13}$, $R^8$, $R^9$, $R^{13}$ or —$COR^{13}$;

$R^{11}$ is H, $C_1$–$C_6$ alkyl or $C_3$–$C_7$ cycloalkyl, said $C_1$–$C_6$ alkyl and $C_3$–$C_7$ cycloalkyl being unsubstituted or substituted by —$OR^5$, —$NR^5R^5$, —$NR^5COR^5$, —$CONR^5R^5$, $R^8$ or $R^9$;

$R^{12}$ is $C_1$–$C_6$ alkyl substituted by $R^8$, $R^9$, —$OR^5$, —$CONR^5R^5$, —$NR^5COR^5$ or —$NR^5R^5$;

$R^{13}$ is phenyl unsubstituted or substituted by halo, —CN, —$COR^5$, —$CONR^5R^5$, —$SO_2NR^5R^5$, —$NR^5SO_2R^5$, —$OR^5$, —$NR^5R^5$, —($C_1$–$C_6$ alkylene)—$NR^5R^5$, $C_1$–$C_6$ alkyl, halo($C_1$–$C_6$)alkyl or $C_3$–$C_7$ cycloalkyl; and x is 0, 1 or 2;

with the proviso that (a) when $R^1$ and $R^3$ are both phenyl, $R^2$ is not methyl; and (b) when $R^1$ is ethoxy and $R^3$ is ethoxycarbonyl, $R^2$ is not phenyl.

In the above definitions, halo means fluoro, chloro, bromo or iodo. Unless otherwise stated, alkyl, alkenyl, alkynyl, alkylene and alkoxy groups containing the requisite number of carbon atoms can be unbranched or branched chain. Examples of alkyl include methyl, ethyl, n-propyl, i-propyl, n-butyl, i-butyl, sec-butyl and t-butyl. Examples of alkenyl include ethenyl, propen-1-yl, propen-2-yl, propen-3-yl, 1-buten-1-yl, 1-buten-2-yl, 1-buten-3-yl, 1-buten-4-yl, 2-buten-1-yl, 2-buten-2-yl, 2-methylpropen-1-yl or 2-methylpropen-3-yl. Examples of alkynyl include ethynyl, propyn-1-yl, propyn-3-yl, 1-butyn-1-yl, 1-butyn-3-yl, 1-butyn-4-yl, 2-butyn-1-yl. Examples of alkylene include methylene, 1,1-ethylene, 1,2-ethylene, 1,1-propylene, 1,2-propylene, 2,2-propylene and 1,3-propylene. Examples of alkoxy include methoxy, ethoxy, n-propoxy, i-propoxy, n-butoxy, i-butoxy, sec-butoxy and t-butoxy. Examples of cycloalkyl include cyclopropyl, cyclobutyl, cyclopentyl, cyclohexyl and cycloheptyl. Where $R^1$ and $R^2$ are taken together, they form, along with the nitrogen atom and the carbon atom of the pyrazole ring to which they are attached, a 5- or 6-membered ring. Where a heterocyclic group $R^8$ or $R^9$ is attached to an oxygen, sulphur or nitrogen heteroatom the heterocyclic group $R^8$ or $R^9$ must be linked through a ring carbon atom. Further, where a heterocyclic group $R^9$ is attached to an oxygen, sulphur or nitrogen heteroatom the heterocyclic group $R^9$ must be linked through a ring carbon atom that is not adjacent to a ring heteroatom.

The pharmaceutically acceptable salts of the compounds of the formula (I) include the acid addition and the base salts thereof.

Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, para-toluenesulphonate and pamoate salts.

Suitable base salts are formed from bases which form non-toxic salts and examples are the sodium, potassium, aluminium, calcium, magnesium, zinc and diethanolamine salts.

For a review on suitable salts see Berge et al, *J. Pharm. Sci.*, 66, 1–19, 1977.

The pharmaceutically acceptable solvates of the compounds of the formula (I) include the hydrates thereof.

Also included within the present scope of the compounds of the formula (I) are polymorphs thereof.

The compounds of formula (I) may be modified to provide pharmaceutically acceptable derivatives thereof at any of the functional groups in the compounds. Examples of such derivatives are described in: Drugs of Today, Volume 19, Number 9, 1983, pp 499–538; Topics in Chemistry, Chapter 31, pp 306–316; and in "Design of Prodrugs" by H. Bundgaard, Elsevier, 1985, Chapter 1 (the disclosures in which documents are incorporated herein by reference) and include: esters, carbonate esters, hemi-esters, phosphate esters, nitro esters, sulfate esters, sulfoxides, amides, sulphonamides, carbamates, azo-compounds, phosphamides, glycosides, ethers, acetals and ketals.

A compound of the formula (I) may contain one or more asymmetric carbon atoms and therefore exist in two or more stereoisomeric forms. The present invention includes the individual stereoisomers of the compounds of the formula (I) together with, where appropriate, the individual tautomers thereof, and mixtures thereof.

Separation of diastereoisomers may be achieved by conventional techniques, e.g., by fractional crystallisation, chromatography or high performance liquid chromatography (HPLC) of a stereoisomeric mixture of a compound of the formula (I) or a suitable salt or derivative thereof. An individual enantiomer of a compound of the formula (I) may also be prepared from a corresponding optically pure intermediate or by resolution, such as by HPLC of the corresponding racemate using a suitable chiral support or by fractional crystallisation of the diastereoisomeric salts formed by reaction of the corresponding racemate with a suitable optically active acid or base, as appropriate.

Preferably, $R^1$, when taken separately, is H, $C_1$–$C_6$ alkyl, $C_3$–$C_7$ cycloalkyl or —$OR^7$, said $C_1$–$C_6$ alkyl and $C_3$–$C_7$ cycloalkyl being unsubstituted or substituted by halo, —CN, —$OR^{10}$, $S(O)_xR^{10}$, —$CO_2R^{10}$, —$CONR^5R^{10}$, —$OCONR^5R^{10}$, —$NR^5CO_2R^{10}$, —$NR^{10}R^{11}$, —$NR^5COR^{10}$, —$SO_2NR^5R^{10}$, —$NR^5CONR^5R^{10}$, —$NR^5SO_2R^{10}$ or $R^{10}$.

Preferably, $R^1$, when taken separately, is H, $C_1$–$C_6$ alkyl, $C_3$–$C_7$ cycloalkyl or —$OR^7$, said $C_1$–$C_6$ alkyl being unsubstituted or substituted by halo, —$OR^{10}$, —$NR^{10}R^{11}$, —$NR^5COR^{10}$ or $R^{10}$.

Preferably, $R^1$, when taken separately, is H, $C_1$–$C_4$ alkyl, cyclopropyl, or —$OCH_3$, said $C_1$–$C_4$ alkyl being unsubstituted or substituted by bromo, —OH, —O($C_1$–$C_2$ alkyl), —$NR^{10}R^{11}$, —$NHCOR^{13}$ or $R^{10}$.

Preferably, $R^1$, when taken separately, is H, —$CH_3$, —$CH_2CH_3$, —$CH(CH_3)_2$, $C(CH_3)_3$, cyclopropyl, —$OCH_3$, —$CH_2OH$, —$CH_2OCH_3$, —$CH_2OCH_2CH_3$, —$CH_2Br$, —$CH_2NH_2$, —$CH_2NHCH_3$, —$CH_2N(CH_3)_2$, —$CH_2NHCH_2$(cyclopropyl), —$CH_2NHCH_2CH_2OCH_3$, —$CH_2NHCH_2CH_2NHCOCH_3$, —$CH_2NHCO$(4-cyanophenyl), —$CH_2NHCO$(3-cyanophenyl), —$CH_2NHCH_2$(4-cyanophenyl), —$CH_2NHCH_2$(4-fluorophenyl), —$CH_2NHCH_2$(4-methoxyphenyl), —$CH_2NHCH_2$(4-aminosulphonylphenyl), —$CH_2NHCH_2$(4-aminocarbonylphenyl), —$CH_2NHCH_2$(pyrid-3-yl), —$CH_2N(CH_3)$(4-cyanophenylmethyl), —$CH_2N(CH_2CH_2OH)$(4-cyanophenylmethyl), 4-methoxypiperidin-1-ylmethyl, 4-aminocarbonylpiperidin-1-ylmethyl, 4-methylcarbonylaminopiperidin-1-ylmethyl, piperazin-1-ylmethyl, 4-methylpiperazin-1-ylmethyl, 4-methylcarbonylpiperazin-1-ylmethyl, 4-methoxymethylcarbonylpiperazin-1-ylmethyl, 4-methoxycarbonylpiperazin-1-ylmethyl, 4-methylsulphonylpiperazin-1-ylmethyl, morpholin-4-ylmethyl, 2-methylimidazol-1-ylmethyl, pyrazol-1-ylmethyl or 1,2,4-triazol-1-ylmethyl.

Preferably, $R^1$, when taken separately, is, —$CH_3$, —$CH_2CH_3$, cyclopropyl, —$CH_2NHCH_2$(4-cyanophenyl), —$CH_2NHCH_2$(4-fluorophenyl), —$CH_2NHCH_2$(4-methoxyphenyl), —$CH_2NHCH_2$(4-aminosulphonylphenyl) or —$CH_2NHCH_2$(4-aminocarbonylphenyl).

Preferably, $R^2$, when taken separately, is H, $C_1$–$C_6$ alkyl, $C_3$–$C_6$ alkenyl or $R^9$, said $C_1$–$C_6$ alkyl being unsubstituted or substituted by halo, —$OR^5$, —$OR^{12}$, —CN, —$CO_2R^7$, —$OCONR^5R^5$, —$CONR^5R^5$, —$C(=NR^5)NR^5OR^5$, —$CONR^5NR^5R^5$, —$NR^6R^6$, —$NR^5R^{12}$, —$NR^5COR^5$, —NR$^5$COR$^8$, —NR$^5$COR$^{12}$, —NR$^5$CO$_2$R$^5$, —NR$^5$CONR$^5$R$^5$, —SO$_2$NR$^5$R$^5$, —NR$^5$SO$_2$R$^5$, R$^8$ or R$^9$.

Preferably, R$^2$, when taken separately, is H, C$_1$–C$_6$ alkyl, C$_3$–C$_6$ alkenyl or R$^9$, said C$_1$–C$_6$ alkyl being unsubstituted or substituted by —OR$^5$, —OR$^{12}$, —CN, —CO$_2$R$^7$, —CONR$^5$R$^5$, —C(=NR$^5$)NR$^5$OR$^5$, —CONR$^5$NR$^5$R$^5$, —NR$^6$R$^6$, —NR$^5$R$^{12}$, —NR$^5$COR$^8$, —NR$^5$COR$^{12}$, —NR$^5$CO$_2$R$^5$, R$^8$ or R$^9$.

Preferably, R$^2$, when taken separately, is H, C$_1$–C$_3$ alkyl, propenyl or R$^9$, said C$_1$–C$_3$ alkyl being unsubstituted or substituted by —OH, —OCH$_3$, —OCH$_2$CH$_2$NH$_2$, —CN, —CO$_2$CH$_3$, —CO$_2$CH$_2$CH$_3$, —CONH$_2$, —C(=NH)NHOH, —CONHNH$_2$, —NH$_2$, —NHCH$_3$, —N(CH$_3$)$_2$, —NHCH$_2$CH$_2$NHCOCH$_3$, —NHCH$_2$CH$_2$OCH$_3$, —NHCH$_2$R$^9$, —NHCOR$^8$, —NHCOCH$_2$OCH$_3$, —NHCO$_2$C(CH$_3$)$_3$, R$^3$ or R$^9$.

Preferably, R$^2$, when taken separately, is H, methyl, —CH$_2$CH=CH$_2$, —CH$_2$CN, —CH$_2$OCH$_3$, —CH$_2$CONH$_2$, —CH$_2$CONHNH$_2$, —CH$_2$CO$_2$CH$_3$, —CH$_2$CO$_2$CH$_2$CH$_3$, —CH$_2$C(=NH)NHOH, —CH$_2$CH$_2$OH, —CH$_2$CH$_2$OCH$_3$, —CH$_2$CH$_2$NH$_2$, —CH$_2$CH$_2$NHCOCH$_2$OCH$_3$, —CH$_2$CH$_2$NHCO$_2$C(CH$_3$)$_3$, 2-(pyrid-2-ylcarbonylamino)eth-1-yl, 2-(pyrazin-2-ylcarbonylamino)eth-1-yl, —CH$_2$CH$_2$OCH$_2$CH$_2$NH$_2$, —CH$_2$CH$_2$NHCH$_3$, —CH$_2$CH$_2$N(CH$_3$)$_2$, —CH$_2$CH$_2$NHCH$_2$CH$_2$NHCOCH$_3$, —CH$_2$CH$_2$NHCH$_2$CH$_2$OCH$_3$, —CH$_2$CH(OH)CH$_3$, (3-hydroxypyrazol-5-yl)methyl, 2-hydroxy-1,3,4-oxadiazol-5-ylmethyl, 2-amino-1,3,4-oxadiazol-5-yl, 5-hydroxy-1,2,4-oxadiazol-3-ylmethyl, 6-hydroxy-2-methylpyrimidin-4-ylmethyl, 6-hydroxy-2-aminopyrimidin-4-ylmethyl, 2-(morpholin-4-yl)eth-1-yl, 2-(4-methylcarbonylpiperazin-1-yl)eth-1-yl, morpholin-3-ylmethyl, (2-(tetrahydrofuran-2-ylmethylamino)eth-1-yl, 1-methylazetidin-3-yl or azetidin-3-yl.

Preferably, R$^2$, when taken separately, is H, —CH$_2$CH$_2$OH or —CH$_2$CH$_2$NH$_2$.

Preferably, R$^1$ and R$^2$, when taken together, represent unbranched C$_3$–C$_4$ alkylene, unsubstituted or substituted by oxo, wherein one methylene group of said C$_3$–C$_4$ alkylene is replaced by an oxygen atom or a nitrogen atom, said nitrogen atom being unsubstituted or substituted by R$^{10}$.

Preferably, R$^1$ and R$^2$, when taken together, represent unbranched propylene wherein one methylene group is replaced by an oxygen atom or unbranched butylene wherein one methylene group is replaced by a nitrogen atom, said propylene and butylene being unsubstituted or substituted by oxo and said nitrogen atom being unsubstituted or substituted by R$^{10}$.

Preferably, R$^1$ and R$^2$, when taken together, represent $^x$—OCH$_2$CH$_2$—$^y$, $^x$—CONHCH$_2$CH$_2$—$^y$, $^x$—CH$_2$NHCH$_2$CH$_2$—$^y$, $^x$—CH$_2$N(CH$_3$)CH$_2$CH$_2$—$^y$, $^x$—CH$_2$N(4-cyanophenylmethyl)CH$_2$CH$_2$—$^y$ or $^x$—CH$_2$N(4-methoxyphenylmethyl)CH$_2$CH$_2$—$^y$ wherein 'x' represents the point of attachment to the carbon atom of the pyrazole ring and 'y' represents the point of attachment to the nitrogen atom of the pyrazole ring.

Preferably, R$^3$ is H or C$_1$–C$_6$ alkyl, said C$_1$–C$_6$ alkyl being unsubstituted or substituted by halo, —CN, —OR$^5$, —CO$_2$R$^5$, —CONR$^5$R$^5$, —OCONR$^5$R$^5$, —NR$^5$CO$_2$R$^5$, —NR$^6$R$^6$, —NR$^5$COR$^5$, —SO$_2$NR$^5$R$^5$, —NR$^5$CONR$^5$R$^5$, —NR$^5$SO$_2$R$^5$, R$^8$ or R$^9$.

Preferably, R$^3$ is H or C$_1$–C$_6$ alkyl.

Preferably, R$^3$ is H or C$_1$–C$_4$ alkyl.

Preferably, R$^3$ is H, —CH$_3$, —CH$_2$CH$_3$, —CH(CH$_3$)$_2$ or —C(CH$_3$)$_3$.

Preferably, R$^3$ is —CH$_3$, —CH$_2$CH$_3$, —CH(CH$_3$)$_2$ or cyclopropyl.

Preferably, R$^4$ is phenyl unsubstituted or substituted by R$^8$, halo, —CN, C$_1$–C$_6$ alkyl, C$_1$–C$_6$ haloalkyl, C$_3$–C$_7$ cycloalkyl or C$_1$–C$_6$ alkoxy.

Preferably, R$^4$ is phenyl substituted by R$^8$, halo, —CN, C$_1$–C$_6$ alkyl, C$_1$–C$_6$ haloalkyl, C$_3$–C$_7$ cycloalkyl or C$_1$–C$_6$ alkoxy.

Preferably, R$^4$ is phenyl substituted by halo, —CN or C$_1$–C$_6$ alkyl.

Preferably, R$^4$ is phenyl substituted by fluoro, chloro, —CN or methyl.

Preferably, R$^4$ is 3-cyanophenyl, 4-chlorophenyl, 3-chlorophenyl, 2-chlorophenyl, 3-fluorophenyl, 2-fluorophenyl, 3,5-dichlorophenyl, 2,6-dichlorophenyl, 2,3-dichlorophenyl, 2,4-dichlorophenyl, 3,4-dichlorophenyl, 2,5-dichlorophenyl, 2,6-difluorophenyl, 2,3-difluorophenyl, 3,5-difluorophenyl, 2,5-difluorophenyl, 3,5-dicyanophenyl, 3,5-dimethylphenyl, 4-fluoro-3-methylphenyl, 3-cyano-4-fluorophenyl, 3-cyano-5-fluorophenyl, 2-chloro-4-cyanophenyl, 3-chloro-5-cyanophenyl, 3-cyano-5-methylphenyl or 4-cyano-2,6-dimethylphenyl.

Preferably, R$^4$ is 3,5-dicyanophenyl, 3-cyano-5-fluorophenyl, 3-chloro-5-cyanophenyl or 3-cyano-5-methylphenyl.

In an alternative set of preferences:

Preferably, R$^4$ is phenyl unsubstituted or substituted by R$^8$, halo, —CN, C$_1$–C$_6$ alkyl, C$_1$–C$_6$ haloalkyl, C$_3$–C$_7$ cycloalkyl, C$_1$–C$_6$ alkoxy, —CONR$^5$R$^5$, OR$^{13}$, So$_x$R$^6$, O—(C$_1$–C$_6$ alkylene)—CONR$^5$R$^5$, O—(C$_1$–C$_6$ alkylene)—NR$^5$R$^5$, or O—(C$_1$–C$_6$ alkylene)—OR$^6$; or naphthyl.

Preferably, R$^4$ is phenyl substituted by R$^8$, halo, —CN, C$_1$–C$_6$ alkyl, C$_1$–C$_6$ haloalkyl, C$_3$–C$_7$ cycloalkyl, C$_1$–C$_6$ alkoxy, —CONR$^5$R$^5$, OR$^{13}$, So$_x$R$^5$, O—(C$_1$–C$_6$ alkylene)—CONR$^5$R$^5$, O—(C$_1$–C$_6$ alkylene)—NR$^5$R$^5$, or O—(C$_1$–C$_6$ alkylene)—OR$^6$.

Preferably, R$^8$ is pyrrolyl, imidazolyl, pyrazolyl, 1,2,3-triazolyl, 1,2,4-triazolyl, tetrazolyl, oxazolyl, isoxazolyl, thiazolyl, isothiazolyl, 1,2,4-oxadiazolyl, 1,3,4-oxadiazolyl, furanyl, thienyl, pyridinyl, pyridazinyl, pyrimidinyl or pyrazinyl, each being unsubstituted or substituted by halo, —CN, —COR$^5$, —CONR$^5$R$^5$, —SO$_2$NR$^5$R$^5$, —NR$^5$SO$_2$R$^5$, —OR$^5$, —NR$^5$R$^5$, —(C$_1$–C$_6$ alkylene)—NR$^5$R$^5$, C$_1$–C$_6$ alkyl, fluoro(C$_1$–C$_6$)alkyl or C$_3$–C$_7$ cycloalkyl.

Preferably, R$^8$ is imidazolyl, pyrazolyl, 1,2,4-triazolyl, 1,2,4-oxadiazolyl, 1,3,4-oxadiazolyl, pyridinyl, pyrazinyl or pyrimidinyl, each being unsubstituted or substituted by halo, —CN, —COR$^5$, —CONR$^5$R$^5$, —SO$_2$NR$^5$R$^5$, —NR$^5$SO$_2$R$^5$, —OR$^5$, —NR$^5$R$^5$, —(C$_1$–C$_6$ alkylene)—NR$^5$R$^5$, C$_1$–C$_6$ alkyl, fluoro(C$_1$–C$_6$)alkyl or C$_3$–C$_7$ cycloalkyl.

Preferably, R$^8$ is imidazolyl, pyrazolyl, 1,2,4-triazolyl, 1,2,4-oxadiazolyl, 1,3,4-oxadiazolyl, pyridinyl, pyrazinyl or pyrimidinyl, each being unsubstituted or substituted by —OR$^5$, —NR$^5$R$^5$ or C$_1$–C$_6$ alkyl.

Preferably, R$^8$ is imidazolyl, pyrazolyl, 1,2,4-triazolyl, 1,2,4-oxadiazolyl, 1,3,4-oxadiazolyl, pyridinyl, pyrazinyl or pyrimidinyl, each being unsubstituted or substituted by —OH, —NH$_2$ or methyl.

Preferably, R$^8$ is pyrazol-1-yl, 2-methylimidazol-1-yl, 1,2,4-triazol-1-yl, 3-hydroxypyrazol-5-yl, 2-hydroxy-1,3,4-oxadiazol-5-yl, 2-amino-1,3,4-oxadiazol-5-yl, 5-hydroxy-1,2,4-oxadiazol-3-yl, 2-methyl-4-hydroxypyrimidin-6-yl, 2-amino-4-hydroxypyrimidin-6-yl, pyridin-3-yl, pyridin-2-yl or pyrazin-2-yl.

Preferably, R$^9$ is azetidinyl, tetrahydropyrrolyl, piperidinyl, azepinyl, oxetanyl, tetrahydrofuranyl, tetrahydropyranyl, oxepinyl, morpholinyl, piperazinyl or diazepinyl, each being unsubstituted or substituted by oxo, $C_1$–$C_6$ alkyl, $C_3$–$C_7$ cycloalkyl, —$SO_2R^5$, —$CONR^5R^5$, —$COOR^5$, —CO—($C_1$–$C_6$ alkylene)—$OR^5$ or —$COR^5$ and unsubstituted or substituted on a carbon atom which is not adjacent to a heteroatom by halo, —$OR^5$, —$NR^5R^5$, —$NR^5COR^5$, —$NR^5COOR^5$, —$NR^5CONR^5R^5$, —$NR^5SO_2R^5$ or —CN.

Preferably, $R^9$ is azetidinyl, piperidinyl, tetrahydrofuranyl, piperazinyl or morpholinyl, each being optionally substituted by oxo, $C_1$–$C_6$ alkyl, $C_3$–$C_7$ cycloalkyl, —$SO_2R^5$, —$CONR^5R^5$, —$COOR^5$, —CO—($C_1$–$C_6$ alkylene)—$OR^5$ or —$COR^5$ and unsubstituted or substituted on a carbon atom which is not adjacent to a heteroatom by halo, —$OR^5$, —$NR^5R^5$, —$NR^5COR^5$, —$NR^5COOR^5$, —$NR^5CONR^5R^5$, —$NR^5SO_2R^5$ or —CN.

Preferably, $R^9$ is azetidinyl, piperidinyl, tetrahydrofuranyl, piperazinyl or morpholinyl, each being unsubstituted or substituted by $C_1$–$C_6$ alkyl, —$SO_2R^5$, —$CONR^5R^5$, —$COOR^5$, —CO—($C_1$–$C_6$ alkylene)—$OR^5$ or —$COR^5$ and unsubstituted or substituted on a carbon atom which is not adjacent to a heteroatom by —$OR^5$ or —$NR^5COR^5$.

Preferably, $R^9$ is azetidinyl, piperidinyl, tetrahydrofuranyl, piperazinyl or morphoninyl, each being unsubstituted or substituted by —$CH_3$, —$SO_2CH_3$, —$CONH_2$, —$COOCH_3$, —$COCH_2OCH_3$ or —$COCH_3$ and unsubstituted or substituted on a carbon atom which is not adjacent to a heteroatom by —$OCH_3$ or —$NHCOCH_3$.

Preferably, $R^9$ is 4-methoxypiperidin-1-yl, 4-aminocarbonylpiperidin-1-yl, 4-methylcarbonylaminopiperidin-1-yl, piperazin-1-yl, 4-methylpiperazin-1-yl, 4-methylcarbonylpiperazin-1-yl, 4-methoxymethylcarbonylpiperazin-1-yl, 4-methoxycarbonylpiperazin-1-yl, 4-methylsulphonylpiperazin-1-yl, morpholin-4-yl, tetrahydrofuran-2-yl, morpholin-3-yl, azetidin-3-yl or 1-methylazetidin-3-yl.

Preferably, $R^{10}$ is H, $R^8$, $R^9$, $R^{13}$, $C_1$–$C_6$ alkyl or —($C_1$–$C_6$ alkyl)—($C_3$–$C_7$ cycloalkyl), said $C_1$–$C_6$ alkyl being unsubstituted or substituted by —$OR^5$, —$OR^{13}$, $R^8$, $R^9$, $R^{13}$ or —$COR^{13}$.

Preferably, $R^{10}$ is H, $R^8$, $R^9$, $R^{13}$, $C_1$–$C_6$ alkyl or —($C_1$–$C_6$ alkyl)—($C_3$–$C_7$ cycloalkyl), said $C_1$–$C_6$ alkyl being unsubstituted or substituted by —$OR^5$ or $R^{13}$.

Preferably, $R^{10}$ is H, $R^8$, $R^9$, $R^{13}$, —$CH_3$, —$CH_2CH_3$ or —$CH_2$(cyclopropyl), said —$CH_3$ and —$CH_2CH_3$ being unsubstituted or substituted by —$OCH_3$ or $R^{13}$.

Preferably, $R^{10}$ is H, $R^8$, $R^9$, $R^{13}$, —$CH_3$, —$CH_2CH_3$, —$CH_2CH_2OCH_3$, —$CH_2$(cyclopropyl), 4-cyanophenylmethyl, 4-fluorophenylmethyl, 4-methoxyphenylmethyl, 4-aminosulphonylphenylmethyl or 4-aminocarbonylphenylmethyl.

Preferably, $R^{11}$ is H or $C_1$–$C_6$ alkyl, said $C_1$–$C_6$ alkyl being unsubstituted or substituted by —$OR^5$, —$NR^5R^5$, —$NR^5COR^5$, —$CONR^5R^5$, $R^8$ or $R^9$.

Preferably, $R^{11}$ is H or $C_1$–$C_6$ alkyl, said $C_1$–$C_6$ alkyl being unsubstituted or substituted by —$OR^5$ or —$NR^5COR^5$.

Preferably, $R^{11}$ is H, —$CH_3$ or —$CH_2CH_3$, said —$CH_3$ and —$CH_2CH_3$ being unsubstituted or substituted by —OH or —$NHCOCH_3$.

Preferably, $R^{11}$ is H, —$CH_3$, —$CH_2CH_2NHCOCH_3$ or —$CH_2CH_2OH$.

Preferably, $R^{12}$ is $C_1$–$C_4$ alkyl substituted by $R^8$, $R^9$, —$OR^5$, —$CONR^5R^5$, —$NR^5COR^5$ or —$NR^5R^5$.

Preferably, $R^{12}$ is $C_1$–$C_4$ alkyl substituted by $R^9$, —$OR^5$, —$NR^5COR^5$ or —$NR^5R^5$.

Preferably, $R^{12}$ is $C_1$–$C_2$ alkyl substituted by tetrahydrofuranyl, —$OCH_3$, —$NHCOCH_3$ or —$NH_2$.

Preferably, $R^{12}$ is —$CH_2CH_2NH_2$, —$CH_2CH_2OCH_3$, tetrahydrofuran-2-ylmethyl, —$CH_2CH_2NHCOCH_3$ or —$CH_2OCH_3$.

Preferably, $R^{13}$ is phenyl substituted by halo, —CN, —$COR^5$, —$CONR^5R^5$, —$SO_2NR^5R^5$, —$NR^5SO_2R^5$, —$OR^5$, —$NR^5R^5$, —($C_1$–$C_6$ alkylene)—$NR^5R^5$, $C_1$–$C_6$ alkyl, halo($C_1$–$C_6$)alkyl or $C_3$–$C_7$ cycloalkyl.

Preferably, $R^{13}$ is phenyl substituted by halo, —CN, —$CONR^5R^5$, —$SO_2NR^5R^5$ or —$OR^5$.

Preferably, $R^{13}$ is phenyl substituted by fluoro, —CN, —$CONH_2$, —$SO_2NH_2$ or —$OCH_3$.

Preferably, $R^{13}$ is 4-cyanophenyl, 3-cyanophenyl, 4-fluorophenyl, 4-methoxyphenyl, 4-aminocarbonylphenyl or 4-aminosulphonylphenyl.

Preferred groups of compounds according to the invention include all combinations of the preferred definitions for individual substituents given above.

Also preferred according to the invention are the compounds of formula (I)

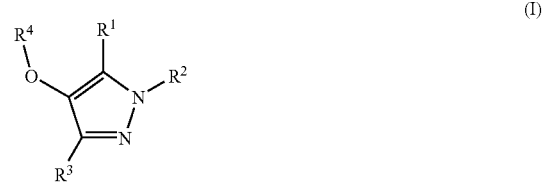

or a pharmaceutically acceptable salt, solvate or derivative thereof, wherein:

$R^1$ is H, $C_1$–$C_6$ alkyl, —$OC_1$–$C_6$ alkyl, —$OC_3$–$C_7$ cycloalkyl, said $C_1$–$C_6$ alkyl being unsubstituted or substituted by $R^{15}$;

$R^2$ is H, $C_1$–$C_3$ alkyl, propenyl or C-linked $R^{15}$, said $C_1$–$C_3$ alkyl being unsubstituted or substituted by —OH, —$OCH_3$, —$OCH_2CH_2NH_2$, —CN, —$CO_2CH_3$, —$CONH_2$, —C(=NH)$NH_2$, —$CONHNH_2$, —$NH_2$, —$NHCH_3$, —$N(CH_3)_2$, —$NHCH_2CH_2NHCOCH_3$, —$NHCH_2CH_2OCH_3$, —$NHCH_2R^{15}$, —$NHCOR^{15}$, —$NHCOCH_2OCH_3$, or $R^{15}$ $R^3$ is $C_1$–$C_6$ alkyl;

$R^4$ is phenyl unsubstituted or substituted by halo, —CN, $C_1$–$C_6$ alkyl, $C_1$–$C_6$ haloalkyl, $C_3$–$C_7$ cycloalkyl or $C_1$–$C_6$ alkoxy; and $R^{15}$ is azetidinyl, tetrahydrofuranyl, morpholinyl, piperazinyl, pyrazolyl, oxadiazolyl, pyridinyl or pyrimidinyl each being unsubstituted or substituted by —OH, —$NH_2$, oxo or $C_1$–$C_6$ alkyl or —CO($C_1$–$C_6$ alkyl).

Preferred individual compounds according to the invention include the Examples below, particularly Examples 117, 118, 119, 120, 122, 123, 124, 125, 126, 127 and 128, and the pharmaceutically acceptable salts and solvates thereof.

All of the compounds of the formula (I) can be prepared by conventional routes such as the procedures described in the general methods presented below or by the specific methods described in the Examples section, or by similar methods thereto. The present invention also encompasses any one or more of these processes for preparing the compounds of formula (I), in addition to any novel intermediates used therein.

In the following general methods, $R^1$, $R^2$, $R^3$ and $R^4$ are as previously defined for a compound of the formula (I) unless otherwise stated.

Except where either $R^1$ or $R^3$ is halo, —$OR^8$ or —CN, compounds of the formula (I) may be prepared using the route shown in Scheme 1 that follows.

In Scheme 1, compounds of the formula (I) may be prepared by the condensation of a compound of the formula (II) with a compound of the formula $$H_2NNHR^2 \quad (V),$$

or a salt or hydrate thereof, optionally in the presence of an acid or a base, the base preferably being a tertiary amine base such as triethylamine and the acid preferably being acetic acid. In a typical procedure, a solution of the compound of the formula (II) in a suitable solvent, such as ethanol, is treated with the compound of the formula (V), or the salt or hydrate thereof, and, if used, the appropriate acid or base, at a temperature of from room temperature to the reflux temperature of the solvent. In a preferred procedure, the reaction mixture is heated under reflux.

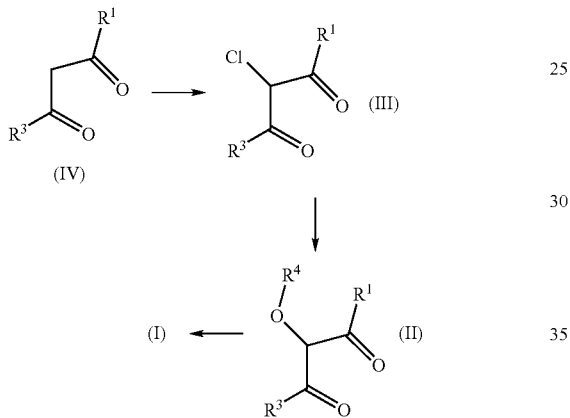

Functional equivalents of compounds of the formula (II) may also be used in this reaction. These include compounds of the formula (VI) or (VII), in which $L^1$ and $L^2$, respectively, are each suitable leaving groups, preferably —$N(C_1$–$C_6$ alkyl$)_2$, Most preferably —$N(CH_3)_2$.

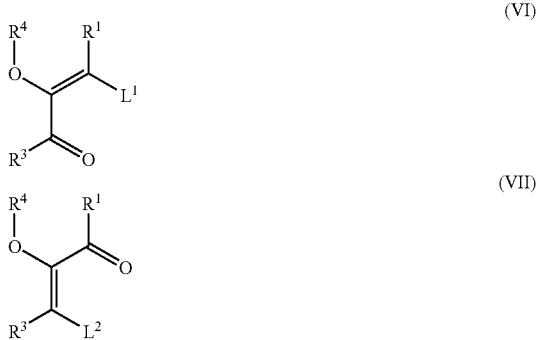

Thus, a compound of the formula (I) may be prepared by the condensation of a compound of the formula (VI) or (VII) with a compound of the formula (V), or a salt or hydrate thereof, optionally in the presence of an acid or a base, the base preferably being a tertiary amine base such as triethylamine and the acid preferably being acetic acid. In a typical procedure, a solution of the compound of the formula (VI) or (VII) in a suitable solvent, such as ethanol, is treated with the compound of the formula (V), or the salt or hydrate thereof, and, if used, the appropriate acid or base, at a temperature of from room temperature to the reflux temperature of the solvent. In a preferred procedure, the reaction mixture is heated under reflux. Compounds of the formula (VI) or (VII) are particularly suitable for the synthesis of compounds of the formula (I) in which $R^1$ or $R^3$, respectively, is H.

Compounds of the formula (VI) in which $R^1$ is H and $L^1$ is dimethylamino may be prepared by the reaction of a compound of the formula (VIII) with dimethylformamide dimethylacetal at an elevated temperature, preferably at about 100° C. Compounds of the formula (VII) in which $R^1$ is H and $L^1$ is dimethylamino may be prepared by the reaction of a compound of the formula (IX) under the same conditions. Other compounds of the formula (VI) or (VII) in which $L^1$ or $L^2$ is dimethylamino may be prepared analogously.

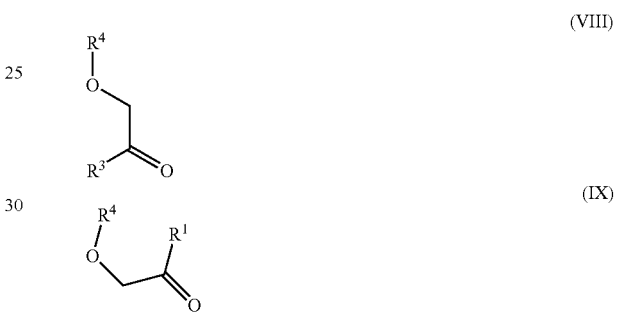

Compounds of the formula (VIII) are either commercially available or may be prepared by the reaction of a compound of the formula $$R^3COCH_2Br \quad (X)$$

with a compound of the formula $$R^4OH \quad (XI).$$

In a typical procedure, a solution of the compound of the formula (XI) in a suitable solvent, such as acetone, is treated with a suitable base, such as caesium carbonate, and the compound of the formula (X). In a preferred procedure, the reaction mixture is heated, for example under reflux. Optionally, a nucleophilic catalyst such as sodium iodide or tetrabutylammonium iodide may be added.

Compounds of the formula (IX) are either commercially available or may be prepared from a compound of the formula $$R^1COCH_2Br \quad (XII)$$

and a compound of the formula (XI) in the same way that a compound of the formula (VIII) may be prepared from a compound of the formula (X).

Compounds of the formula (II) may be prepared by the reaction of a compound of the formula (III) with a compound of the formula (XI).

In a typical procedure, a solution of the compound of the formula (III) in a suitable solvent such as acetone is treated with a compound of the formula (XI) and a suitable base, such as potassium or caesium carbonate, and heated, preferably under reflux. Optionally, a nucleophilic catalyst such as sodium iodide or tetrabutylammonium iodide may be added.

Compounds of the formula (III) are either commercially available or may be prepared by the reaction of a compound of the formula (IV) with a chlorinating reagent. In a typical procedure, a cooled solution of the compound of the formula (IV) in a suitable solvent such as acetonitrile is treated first with tetrabutylammonium bromide and chlorotrimethylsilane and then dry dimethylsulphoxide. In another typical procedure, the compound of the formula (IV) is treated with sulphuryl chloride, optionally in the presence of a suitable solvent such as dichloromethane.

Compounds of the formula (I) in which $R^1$ or $R^3$ is $-OR^8$ may be prepared using the route shown in Scheme 2 that follows, in which $R^a$ is $C_1$–$C_6$ alkyl and $L^3$ is a suitable leaving group, preferably trifluoromethanesulphonate.

In Scheme 2, compounds of the formula (I) in which $R^1$ is $-OR^8$ may be prepared by the reaction of a compound of the formula (XIII) with an alcohol of the formula $R^8OH$ (XXI)

in the presence of a suitable palladium catalyst and carbon monoxide. In a typical procedure a mixture of the compound of the formula (XIII), a suitable palladium catalyst such as 1,1'-bis(diphenylphosphino)ferrocenepalladium(II)chloride, the alcohol of the formula (XXI) and, optionally, a suitable solvent such as N,N-dimethylformamide is heated, preferably to about 50° C., under an atmosphere of carbon monoxide, preferably at a pressure of 345 kPa.

Scheme 2

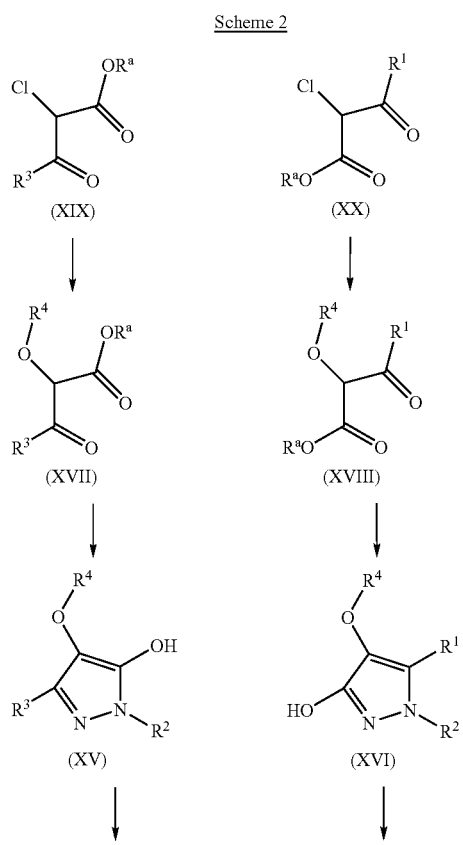

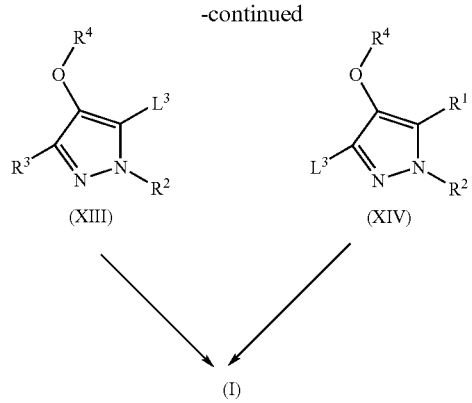

Compounds of the formula (XIII) may be prepared by the derivatisation of a compound of the formula (XV). In the case where $L^3$ is trifluoromethanesulphonate, a suitable derivatising agent is phenyltriflamide. In a typical procedure, where $L^3$ is trifluoromethanesulphonate, a solution of the compound of the formula (XV) and a suitable base, preferably a trialkylamine base such as triethylamine, in a suitable solvent such as dichloromethane is treated with phenyltriflamide.

Compound of the formula (XV) may be prepared by the reaction of a compound of the formula (XVII) with a compound of the formula (V), or a salt or hydrate thereof, optionally in the presence of an acid or a base, the base preferably being a tertiary amine base such as triethylamine and the acid preferably being acetic acid. In a typical procedure, a solution of the compound of the formula (XVII) in a suitable solvent, such as ethanol, is treated with the compound of the formula (V), or the salt or hydrate thereof, and, if used, the appropriate acid or base, at a temperature of from room temperature to the reflux temperature of the solvent. In a preferred procedure, the reaction mixture is heated under reflux.

Compounds of the formula (XVII) may be prepared by the reaction of a compound of the formula (XIX) with a compound of the formula (XI). In a typical procedure, a solution of the compound of the formula (XVII) in a suitable solvent such as acetone is treated with a compound of the formula (XI) and a suitable base, such as potassium or caesium carbonate, and heated, preferably under reflux. Optionally, a nucleophilic catalyst such as sodium iodide or tetrabutylammonium iodide may be added.

In Scheme 2, compounds of the formula (I) in which $R^3$ is $-OR^8$ may be prepared from a compound of the formula (XX) in the same way that a compound of the formula (I) in which $R^1$ is $-OR^8$ is prepared from a compound of the formula (XIX), as set out above, mutatis mutandis.

Chloroketoesters of the formula (XIX) and (XX) are either commercially available or may be prepared by the chlorination of the corresponding ketoesters, for instance using sulphonyl chloride.

Alternatively, compounds of the formula (I) in which $R^1$ or $R^3$ is $-OR^8$ may be prepared from compounds of the formula (XV) or (XVI), respectively, by reaction with a compound of the formula (XXI) under dehydrating conditions, e.g., using the Mitsunobu reaction. In a typical procedure, a solution of the compound of the formula (XV) or (XVI) in a suitable solvent, such as tetrahydrofuran is treated with diethylazodicarboxylate, triphenylphosphine and a compound of the formula (XXI).

Compounds of the formula (I) in which $R^1$ or $R^3$ is halo can be prepared by the reaction, respectively, of a compound of the formula (XV) or a compound of the formula (XVI) with a suitable halogenating agent. In a typical procedure, the compound of the formula (XV) or (XVI) is treated with $POCl_3$, optionally in the presence of a suitable solvent such as dimethylformamide, to give a compound of the formula (I) in which $R^1$ or $R^3$, respectively, is chloro.

It will be appreciated by those skilled in the art that, in many cases, compounds of the formula (I) may be converted into other compounds of the formula (I) by functional group transformations. For instance:

(a) compounds of the formula (I) in which $R^2$ is H may be converted into compounds of the formula (I) in which $R^2$ is optionally substituted $C_1$–$C_6$ alkyl by reaction with an appropriate alkylating agent. In a typical procedure, a solution of a compound of the formula (I) in which $R^2$ is H in a suitable solvent such as ethanol or N,N-dimethylformamide is treated with an alkyl bromide and a base such as sodium ethoxide or sodium hydride and heated at a temperature of from room temperature to the reflux temperature of the solvent. A preferred combination is N,N-dimethylformamide as the solvent, sodium hydride as the base and room temperature as the temperature. Examples of specific alkylating agents include bromoacetonitrile, ethyl 4-chloroacetoacetate, methyl bromoacetate and chloroethylamine hydrochloride. The use of further specific alkylating agents is illustrated by the Examples below;

(b) compounds of the formula (I) in which $R^1$, $R^2$ or $R^3$ contains an ester functionality may be reduced with a suitable reducing agent, such as lithium aluminium hydride, to give corresponding compounds of the formula (I) in which $R^1$, $R^2$ or $R^3$ contains a hydroxy group. In a typical procedure, a solution of the compound of the formula (I), in which $R^1$, $R^2$ or $R^3$ contains an ester group, in a suitable solvent, such as diethyl ether, is treated with lithium aluminium hydride, preferably with cooling to a temperature of from −78° C. to 0° C.;

(c) compounds of the formula (I) in which $R^1$, $R^2$ or $R^3$ are substituted by a heterocycle of the formula $R^6$ may be prepared by standard heterocycle-forming reactions well known to the skilled man (see, for example, Advanced Organic Chemistry, 3rd Edition, by Gerry March or Comprehensive Heterocyclic Chemistry, A. R. Katritzky, C. W. Rees, E. F. V. Scriven, Volumes 1–11). For instance, compounds of the formula (I) in which $R^2$ is (2-amino-6-hydroxypyrimidin-4-yl)methyl may be prepared by the sequential reaction of a compound of the formula (I) in which $R^2$ is H with chloroacetoacetate and then guanidine hydrochloride. This and other similar heterocycle-forming reactions are illustrated by the Examples below;

(d) compounds of the formula (I) in which $R^1$ or $R^3$ is —$CO_2R^5$, wherein $R^5$ is other than H, may be converted into compounds of the formula (I) in which $R^1$ or $R^3$, respectively, is —$CO_2H$ by hydrolysis. Typically the reaction will be carried out in a suitable solvent, such as aqueous ethanol, or aqueous 1,4-dioxan and in the presence of a base such as sodium hydroxide. Such an acid may be converted to a primary amide by reaction with ammonia and a suitable coupling agent, such as a carbodiimide, e.g. dicyclohexylcarbodiimide. Such a primary amide may then be converted into a nitrile by dehydration with a suitable dehydrating agent, such as phosphoryl chloride; and (e) compounds of the formula (I) in which $R^1$ or $R^3$ is $C_1$–$C_6$ alkyl may be converted into the compounds of the formula (I) in which $R^1$ or $R^3$, respectively, is $C_1$–$C_6$ alkyl substituted by halo (such as bromo), by halogenation, using a suitable halogenating agent. Conveniently the reaction is effected in the presence of a solvent, such as a haloalkane (e.g. dichloromethane) and at ambient temperature. Suitable halogenating agents include halogens (e.g. bromine) or N-halosuccinimides (e.g. N-bromsuccinimide).

Compounds of the formula (I) containing an —OH, —NH— or —$NH_2$ group may be prepared by the deprotection of the corresponding compound bearing an —$OP^1$, —$NP^1$— or —$NHP^1$ group, respectively, wherein the group $P^1$ is a suitable protecting group. Examples of suitable protecting groups will be apparent to the skilled person [see, for instance, 'Protecting groups in Organic Synthesis (Second Edition)' by Theodora W. Green and Peter G. M. Wuts, 1991, John Wiley and Sons]. Such compounds bearing an —$OP^1$, —$NP^1$— or —$NHP^1$ group may be prepared using the routes described above, mutatis mutandis.

Compounds of the formula (IV), (V) and (XXI) are either commercially available or easily prepared by methods well known to those skilled in the art.

The compounds of the formula (I) can be administered alone but will generally be administered in admixture with a suitable pharmaceutical excipient, diluent or carrier selected with regard to the intended route of administration and standard pharmaceutical practice.

For example, the compounds of the formula (I) can be administered orally, buccally or sublingually in the form of tablets, capsules, multi-particulates, gels, films, ovules, elixirs, solutions or suspensions, which may contain flavouring or colouring agents, for immediate-, delayed-, modified-, sustained-, pulsed- or controlled-release applications. The compounds of the formula (I) may also be administered as fast-dispersing or fast-dissolving dosage forms or in the form of a high energy dispersion or as coated particles. Suitable formulations of the compounds of the formula (I) may be in coated or uncoated form, as desired.

Such solid pharmaceutical compositions, for example, tablets, may contain excipients such as microcrystalline cellulose, lactose, sodium citrate, calcium carbonate, dibasic calcium phosphate, glycine and starch (preferably corn, potato or tapioca starch), disintegrants such as sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

GENERAL EXAMPLE

A formulation of the tablet could typically contain from 0.01 mg to 500 mg of active compound whilst tablet fill weights may range from 50 mg to 1000 mg. An example of a formulation for a 10 mg tablet is illustrated below:

| Ingredient | % w/w |
| --- | --- |
| Compound of the formula (I) or salt | 10.000* |
| Lactose | 64.125 |
| Starch | 21.375 |
| Croscarmellose sodium | 3.000 |
| Magnesium Stearate | 1.500 |

*Quantity adjusted in accordance with drug activity.

The tablets are manufactured by a standard process, for example, direct compression or a wet or dry granulation process. The tablet cores may be coated with appropriate overcoats.

Solid compositions of a similar type may also be employed as fillers in gelatin or HPMC capsules. Preferred excipients in this regard include lactose, starch, a cellulose, milk sugar or high molecular weight polyethylene glycols. For aqueous suspensions and/or elixirs, the compounds of the formula (I) may be combined with various sweetening or flavouring agents, colouring matter or dyes, with emulsifying and/or suspending agents and with diluents such as water, ethanol, propylene glycol and glycerin, and combinations thereof.

The compounds of the formula (I) can also be administered parenterally, for example, intravenously, intra-arterially, intraperitoneally, intrathecally, intraventricularly, intraurethrally, intrasternally, intracranially, intramuscularly or subcutaneously, or they may be administered by infusion or needleless injection techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds of the formula (I) will usually be from 0.01 to 30 mg/kg, preferably from 0.01 to 5 mg/kg (in single or divided doses).

Thus tablets or capsules of the compound of the formula (I) may contain from 1 to 500 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. The skilled person will appreciate that, in the treatment of certain conditions the compounds of the formula (I) may be taken as a single dose as needed or desired.

The compounds of formula (I) can also be administered intranasally or by inhalation and are conveniently delivered in the form of a dry powder inhaler or an aerosol spray presentation from a pressurised container, pump, spray, atomiser or nebuliser, with or without the use of a suitable propellant, e.g., dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the formula (I) and a suitable powder base such as lactose or starch.

Alternatively, the compounds of the formula (I) can be administered in the form of a suppository or pessary, or they may be applied topically in the form of a gel, hydrogel, lotion, solution, cream, ointment or dusting powder. The compounds of the formula (I) may also be dermally or transdermally administered, for example, by the use of a skin patch. They may also be administered by the pulmonary or rectal routes.

They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the formula (I) can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the formula (I) may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

It is to be appreciated that all references herein to treatment include curative, palliative and prophylactic treatment.

Oral administration is preferred.

Included within the scope of the present invention are embodiments comprising the co-administration of a compound of the present invention with one or more additional therapeutic agents, and compositions containing a compound of the present invention along with one or more additional therapeutic agents. Such a combination therapy is especially useful for the prevention and/or treatment of infection by HIV and related retroviruses which may evolve rapidly into strains resistant to any monotherapy. Alternatively, additional therapeutic agents may be desirable to treat diseases and conditions which result from or accompany the disease being treated with the compound of the present invention. For example, in the treatment of an HIV or related retroviral infection, it may be desirable to additionally treat opportunistic infections, neoplasms and other conditions which occur as a result of the immuno-compromised state of the patient being treated.

Preferred combinations of the present invention include simultaneous or sequential treatment with a compound of the formula (I), as defined above, or a pharmaceutically acceptable salt thereof, and:

(a) one or more reverse transcriptase inhibitors such as zidovudine, didanosine, zalcitabine, stavudine, lamivudine, abacavir and adefovir;
(b) one or more non-nucleoside reverse transcriptase inhibitors such as nevirapine, delavirdine and efavirenz;
(c) one or more HIV protease inhibitors such as indanivir, ritonavir, saquinavir and nelfinavir;
(d) one or more CCR5 antagonists such as TAK-779;
(e) one or more CXCR4 antagonists such as AMD-3100;
(f) one or more integrase inhibitors;
(g) one or more inhibitors of viral fusion such as T-20;
(h) one or more investigational drugs such as trizivir, KNI-272, amprenavir, GW-33908, FTC, PMPA, S-1153, MKC-442, MSC-204, MSH-372, DMP450, PNU-140690, ABT-378, KNI-764, DPC-083, TMC-120 or TMC-125; or
(i) one or more antifungal or antibacterial agents such as fluconazole.

The activity of the compounds of the invention as reverse transcriptase inhibitors and as agents for treating HIV infections may be measured using the following assays.

A. Inhibition of HIV-1 Reverse Transcriptase Enzyme

The reverse transcriptase activity of the compounds of the invention may be assayed as following. Using the purified recombinant HIV-1 reverse transcriptase (RT, EC, 2.7.7.49) obtained by expression in *Escherichia Coli*, a 96-well plate assay system was established for assaying a large number of samples using either the Poly(rA)-oligo(dT) Reverse Transcriptase [3H]-SPA enzyme assay system (Amersham NK9020) or the [3H]-flashplate enzyme assay system (NEN—SMP 103) and following the manufacturer's recommendations. The compounds were dissolved in 100% DMSO and diluted with the appropriate buffer to a 5% final DMSO concentration. The inhibitory activity was expressed in percent inhibition relative to the DMSO control. The concentration at which the compound inhibited the reverse transcriptase by 50% was expressed as the $IC_{50}$ of the compound. The compounds of examples 7, 20 and 51, when tested according to the above procedure, had $IC_{50}$ values of, respectively, 39000, 3200 and 248 nanomolar.

B. Anti-Human Immunodeficiency Virus (HIV-1) Cell Culture Assay

The anti-HIV activity of selected Examples of the invention was assayed by the following procedures.

1) SupT1 cells were cultured in an RPMI-1640 medium supplemented with 10% foetal calf serum and were split so that they were in growth phase on the day of use.
2) The compounds were dissolved in 100% DMSO and diluted with the above culture medium to predetermined concentrations and distributed in 20 µl aliquots into a 96-well microtiter plate (0.1% DMSO final concentration).
3) To prepare infected cells, 100 µl of $R^F$ viruses (TCID50 of $10^7$/ml) were added to $10^6$ cells and incubated for 1 hour at 37° C. The cells were then washed twice in PBS and resuspended in the culture medium at a density of $2.2 \times 10^5$ cells/ml. 180 µl of these infected cells was transferred to wells of the 96 well plate containing the compounds.
4) The plate was incubated in a $CO_2$ incubator at 37° C. for 4 days. The cell survival rates were measured following the manufacturer's recommendations (CellTiter 96® $AQ_{ueous}$ Non-Radioactive Assay—Promega (cat no: G5430)). The concentration at which the compound inhibited the cytotoxic effect of the virus by 50% was expressed as the $EC_{50}$.

Thus the invention provides:

(i) a compound of the formula (I) or a pharmaceutically acceptable salt, solvate or derivative thereof;
(ii) a process for the preparation of a compound of the formula (I) or a pharmaceutically acceptable salt, solvate or derivative thereof;
(iii) a pharmaceutical composition including a compound of the formula (I) or a pharmaceutically acceptable salt, solvate or derivative thereof, together with a pharmaceutically acceptable excipient, diluent or carrier;
(iv) a compound of the formula (I) or a pharmaceutically acceptable salt, solvate or composition thereof, for use as a medicament;
(v) a compound of the formula (I) or a pharmaceutically acceptable salt, solvate or composition thereof, for use as a reverse transcriptase inhibitor or modulator;
(vi) a compound of the formula (I) or a pharmaceutically acceptable salt, solvate or composition thereof, for use in the treatment of an HIV, or genetically-related retroviral, infection or a resulting acquired immune deficiency syndrome (AIDS);
(vii) the use of a compound of the formula (I) or of a pharmaceutically acceptable salt, solvate or composition thereof, for the manufacture of a medicament having reverse transcriptase inhibitory or modulating activity;
(viii) the use of a compound of the formula (I) or of a pharmaceutically acceptable salt, solvate or composition thereof, for the manufacture of a medicament for the treatment of an HIV, or genetically-related retroviral, infection or a resulting acquired immune deficiency syndrome (AIDS);
(ix) a method of treatment of a mammal, including a human being, with a reverse transcriptase inhibitor or modulator including treating said mammal with an effective amount of a compound of the formula (I) or with a pharmaceutically acceptable salt, solvate or composition thereof;
(x) a method of treatment of a mammal, including a human being, to treat an HIV, or genetically-related retroviral, infection or a resulting acquired immune deficiency syndrome (AIDS) including treating said mammal with an effective amount of a compound of the formula (I) or with a pharmaceutically acceptable salt, solvate or composition thereof; and
(xi) certain novel intermediates disclosed herein.

The following Examples illustrate the preparation of the compounds of the formula (I). The synthesis of certain intermediates used therein are described in the Preparations section that follows the Examples.

[1]H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The following abbreviations have been used: HRMS, high resolution mass spectrometry; hplc, high performance liquid chromatography; nOe, nuclear Overhauser effect; m.p., melting point; $CDCl_3$, deuterochloroform; $D_6$-DMSO, deuterodimethylsulphoxide; $CD_3OD$, deuteromethanol. Where thin layer chromatography (TLC) has been used it refers to silica gel TLC using silica gel 60 $F_{254}$ plates, $R_f$ is the distance travelled by a compound divided by the distance travelled by the solvent front on a TLC plate.

Example 1

2-[4-(3,5-Dichlorophenoxy)-3,5-dimethyl-1H-pyrazol-1-yl]ethanol

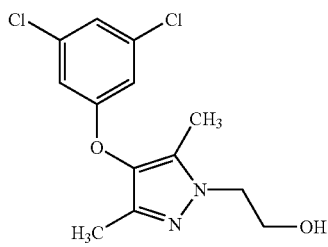

2-Hydroxyethyl hydrazine (21.5 μL, 0.316 mmol) was added to a stirred solution of the β-diketone of Preparation 1 (75 mg, 0.287 mmol) in ethanol (2.9 ml) at room temperature under nitrogen and the resulting orange solution was heated under reflux for 18 hours. After cooling, the mixture was concentrated under reduced pressure. The residue was dissolved in dichloromethane (20 ml) and washed with 2M hydrochloric acid (10 ml) and brine (10 ml) and then dried over magnesium sulphate, filtered and concentrated under reduced pressure to leave a viscous orange oil. The crude product was purified by flash chromatography on silica gel eluting with pentane:ethyl acetate (10:1, by volume) then dichloromethane to provide the title compound (32 mg) as a white powder, m.p. 114–115° C.

$^1$H-NMR (400 MHz, CDCl$_3$): δ=2.08 (s, 3H), 2.10 (s, 3H), 3.30 (t, 1H), 4.06 (m, 4H), 6.79 (s, 2H), 7.01 (s, 1H). LRMS (thermospray): m/z [MH$^+$] 301. Microanalysis: Found: C, 51.76; H, 4.64; N, 9.20. C$_{13}$H$_{14}$Cl$_2$N$_2$O$_2$ requires C, 51.85; H, 4.69; N, 9.30%.

Example 2

2-[4-(3,5-Dichlorophenoxy)-3,5-diethyl-1H-pyrazol-1-yl]ethanol

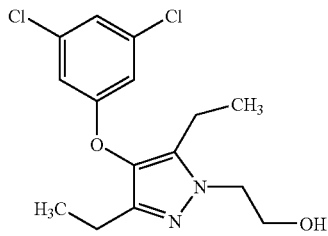

3,5-Dichlorophenol (501 mg, 3.07 mmol), potassium carbonate (467 mg, 3.38 mmol) and finally sodium iodide (461 mg, 3.07 mmol) were added sequentially to a stirred solution of the chloroketone of Preparation 2 (500 mg, 3.07 mmol) in acetone (15 ml), at room temperature and under nitrogen, producing an orange/red suspension. The mixture was heated under reflux for 22½ hours producing a yellow suspension. After cooling the mixture was diluted with water (10 ml) and the acetone was removed under reduced pressure in a fumehood (caution: possible residual lachrymator). The residue was diluted with 2M hydrochloric acid and extracted with dichloromethane (1×20 ml, 2×10 ml). The combined organic layers were washed with brine (20 ml), dried over magnesium sulphate, filtered and concentrated under reduced pressure to leave crude 4-(3,5-dichlorophenoxy)-3,5-heptanedione as an orange oil (777 mg). A portion of the crude 4-(3,5-dichlorophenoxy)-3,5-heptanedione (250 mg, ca. 0.865 mmol) was dissolved in ethanol (8.6 ml) and treated with 2-hydroxethyl hydrazine (65 μL, 0.951 mmol). The resulting solution was heated under reflux for 16 hours producing a red solution. After cooling, the mixture was concentrated under reduced pressure and the residue was dissolved in dichloromethane (20 ml). The resulting solution was washed with 2M hydrochloric acid (10 ml), 1 N sodium hydroxide solution (10 ml) and brine (10 ml), dried over magnesium sulphate, filtered and concentrated under reduced pressure to leave an orange oil (102 mg). The crude product was purified by flash chromatography on silica gel eluting with methanol:dichloromethane (5:95, by volume) to provide the title compound (23 mg) as an orange oil which solidified to a waxy solid on standing.

$^1$H-NMR (400 MHz, CDCl$_3$): δ=1.08 (t, 3H), 1.12 (t, 3H), 2.38 (q, 2H), 2.48 (q, 2H), 3.69 (br.s, 1H), 4.02 (m, 4H), 6.76 (s, 2H), 6.97 (s, 1H). LRMS (thermospray): m/z [MH$^+$] 329.

Example 3

4-(3,5-Dichlorophenoxy)-3,5-diethyl-1H-pyrazole

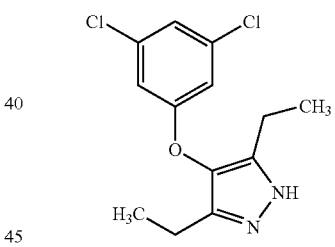

A mixture of the chloroketone of Preparation 2 (5 g, 30.8 mmol), 3,5-dichlorophenol (5 g, 30.8 mmol), caesium carbonate (10 g, 30.8 mmol) and acetone (40 ml) was heated under reflux for 18 hours. After cooling, a solid was removed by filtration and washed with dichloromethane (100 ml). The combined filtrates were concentrated under reduced pressure. The crude product was dissolved in ethanol (20 ml), hydrazine hydrate (1.5 ml, 30.8 mmol) was added and the mixture was heated at 60° C. for 30 minutes under nitrogen. After cooling, the mixture was concentrated under reduced pressure and the residue was purified by flash chromatography on silica gel eluting with ether:pentane (1:1, by volume) to provide the title compound (5.5 g) as a yellow oil which solidified on standing to leave a yellow solid, m.p. 114–115° C.

$^1$H-NMR (300 MHz, CDCl$_3$): δ=1.15 (6H, t), 2.48 (4H, q), 6.78 (2H, s), 6.95 (1H, s). LRMS (thermospray): m/z [MH$^+$] 285. Microanalysis: Found: C, 54.93; H, 5.05; N, 9.94. C$_{13}$H$_{14}$Cl$_2$N$_2$O requires C, 54.75; H, 4.95; N, 9.82%.

Example 4

[4-(3,5-Dichlorophenoxy)-3,5-diethyl-1H-pyrazol-1-yl]acetonitrile

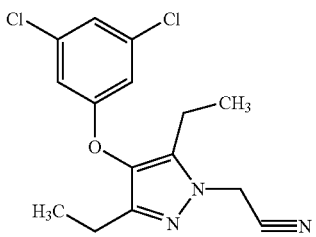

Sodium hydride (60% dispersion in oil, 470 mg, 11.8 mmol) was added to a stirred solution of 4-(3,5-dichlorophenoxy)-3,5-diethyl-1H-pyrazole (3 g, 10.5 mmol, Example 3) in dry N,N-dimethylformamide (20 ml) at 0° C. under nitrogen. The mixture was stirred for 5 minutes during which time hydrogen was evolved and then bromoacetonitrile (0.81 ml, 11.6 mmol) was added. The yellow solution turned dark brown and a precipitate formed. Further dry N,N-dimethylformamide (5 ml) was added to aid dissolution and after 45 minutes the reaction mixture was quenched by the addition of water (1 ml). The mixture was partitioned between water (150 ml) and diethyl ether (2×150 ml). The combined organic layers were washed with water (50 ml) and brine (100 ml), dried over magnesium sulphate and concentrated under reduced pressure. The crude product was purified by flash chromatography on silica gel eluting with dichloromethane to provide the title compound (3.2 g) as a yellow powder, m.p. 70–72° C.

$^1$H-NMR (400 MHz, CDCl$_3$): δ=1.14 (6H, m), 2.38 (2H, q), 2.56 (2H, q), 4.92 (2H, s), 6.75 (2H, s), 7.00 (1H, s). Microanalysis: Found: C, 55.43; H, 4.69; N, 12.71. C$_{15}$H$_{15}$Cl$_2$N$_3$O requires C, 55.57; H, 4.60; N, 12.96%.

Example 5

5-{[4-(3,5-Dichlorophenoxy)-3,5-diethyl-1H-pyrazol-1-yl]methyl}-1H-pyrazol-3-ol

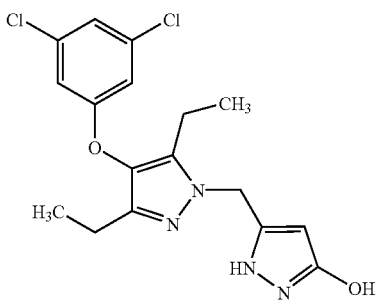

A mixture of the ester (120 mg, 0.29 mmol) of Preparation 3, hydrazine hydrate (16 mg, 0.29 mmol) and ethanol (5 ml) was stirred and heated at 60° C. for 2 hours under nitrogen. After cooling, the mixture was concentrated under reduced pressure and the resulting white solid was stirred in ethyl acetate and then collected by filtration to give the title compound (60 mg) as a white solid, m.p. 142–144° C.

$^1$H-NMR (400 MHz, DMSO-d$_6$): δ=0.89 (3H, t). 0.99 (3H, t), 2.26 (2H, q), 2.45 (2H, q), 5.01 (2H, s), 5.19 (1H, s), 6.88 (2H, s), 7.21 (1H, s). LRMS (electrospray): m/z [M–H$^+$] 379. Microanalysis: Found: C, 55.39; H, 4.72; N, 14.69. C$_{17}$H$_{18}$Cl$_2$N$_4$O$_2$ requires C, 53.56; H, 4.76; N, 14.69%.

Example 6

6-{[4-(3,5-Dichlorophenoxy)-3,5-diethyl-1H-pyrazol-1-yl]methyl}-2-methyl-4(3H)-pyrimidinone

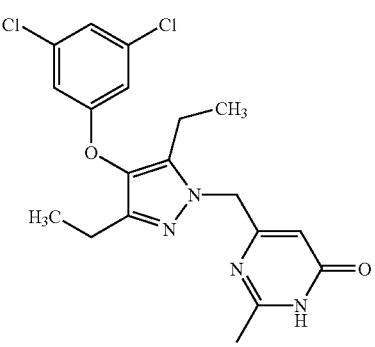

A mixture of the ester (140 mg, 0.34 mmol) of Preparation 3, acetamidine hydrochloride (95 mg, 1.0 mmol), sodium ethoxide (68 mg, 1.0 mmol) and ethanol (5 ml) was stirred and heated at 70° C. for 1 hour under nitrogen. After cooling, the mixture was concentrated under reduced pressure. The resulting oil was dissolved in dichloromethane (50 ml), washed with water (20 ml), dried over magnesium sulphate and concentrated under reduced pressure to leave the title compound as a white foam (100 mg).

$^1$H-NMR (300 MHz, CDCl$_3$): δ=1.10 (3H, t), 1.19 (3H, t), 2.48 (7H, m), 5.08 (2H, s), 5.72 (1H, s), 6.82 (2H, s), 7.03 (1H, s). LRMS (thermospray): m/z [MH$^+$] 407.

Example 7

2-Amino-6-{[4-(3,5-dichlorophenoxy)-3,5-diethyl-1H-pyrazol-1-yl]methyl}-4(3H)-pyrimidinone

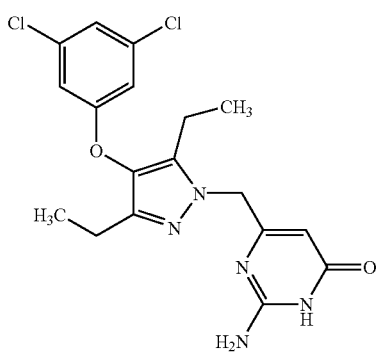

A mixture of the ester (150 mg, 0.365 mmol) from Preparation 3 and guanidine hydrochloride (104 mg, 1.08 mmol) and sodium ethoxide (73 mg, 1.08 mmol) in ethanol (5 ml) was stirred and heated at 70° C. for 3 hours under nitrogen. After cooling the mixture was concentrated under reduced pressure and the resulting oil was dissolved in dichloromethane (50 ml), washed with water (20 ml), dried over magnesium sulphate and concentrated under reduced pressure. The crude product was purified by chromatography on silica gel eluting with dichloromethane:methanol: ammonia (90:10:1, by volume) to give the title compound as a white solid (30 mg), m.p. 238–240° C.

$^1$H-NMR (400 MHz, DMSO-$d_6$): δ=0.91 (3H, t), 0.99 (3H, t), 2.29 (2H, q), 2.44 (2H, q), 4.75 (1H, s), 4.81 (2H, s), 6.58 (2H, br.s), 6.87 (2H, s), 7.22 (1H, s). LRMS (thermospray): m/z [MH$^+$] 408.

Example 8

2-[4-(3,5-Dichlorophenoxy)-3,5-diethyl-1H-pyrazol-1-yl]-N-hydroxyethanimidamide

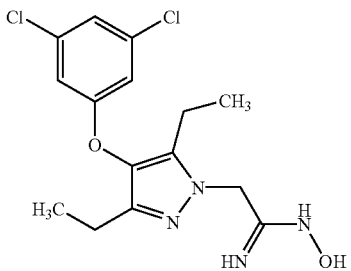

Hydroxylamine hydrochloride (1.1 g, 15.8 mmol) and potassium carbonate (2.1 g, 15.2 mmol) were added to a suspension of the nitrile (1 g, 3.1 mmol) of Example 4 in a mixture of methanol (25 ml) and water (10 ml) which was then heated under reflux for 3 days. After cooling, the mixture was extracted with dichloromethane (2×250 ml) and the combined organic layers were washed with brine (100 ml), dried over magnesium sulphate, filtered and concentrated under reduced pressure to afford the product as a white solid (1.1 g), m.p. 128–130° C.

$^1$H-NMR (300 MHz, CD$_3$OD): δ=1.10 (6H, m), 2.40 (2H, q), 2.60 (2H, q), 4.65 (2H, s), 6.90 (2H, s), 7.10 (1H, s). LRMS (electrospray): m/z [MH$^+$] 357.

Example 9

Methyl [4-(3,5-dichlorophenoxy)-3,5-diethyl-1H-pyrazol-1-yl]acetate

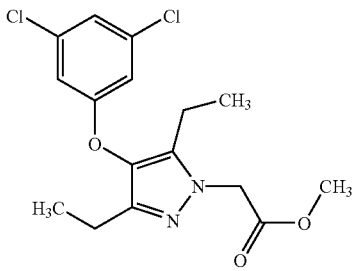

Methyl bromoacetate (984 μL, 10 mmol) and then sodium hydride (60% dispersion in oil, 801 mg, 20.1 mmol) were added to a stirred solution of the pyrazole (2.6 g, 9.12 mmol) of Example 3 in dry N,N'-dimethylformamide (25 ml) at 0° C. under nitrogen. After stirring for 1 hour at 0° C. ice-water (100 ml) was added and the mixture was extracted with ether (3×50 ml). The combined ether layers were dried over magnesium sulphate, filtered and concentrated under reduced pressure. The residue was purified by flash chromatography on silica gel eluting with ethyl acetate:pentane (20:80, by volume) to provide the title compound (780 mg) as a yellow oil which partly crystallised on standing.

$^1$H-NMR (400 MHz, CDCl$_3$): δ=1.10 (6H, m), 2.44 (4H, m), 3.78 (3H, s), 4.80 (2H, s), 6.69 (2H, s), 6.99 (1H, s). LRMS (thermospray): m/z [MH$^+$] 357.

Example 10

2-[4-(3,5-Dichlorophenoxy)-3,5-diethyl-1H-pyrazol-1-yl]acetamide

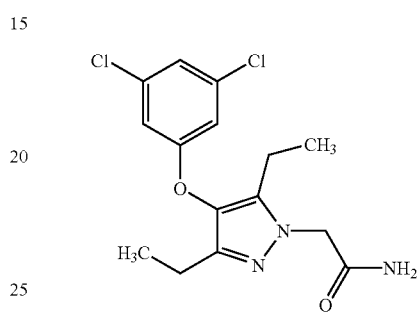

1,1'-Carbonyl diimidazole (71 mg, 0.44 mmol) was added to stirred solution of the acid (125 mg, 0.36 mmol) of Preparation 4 in dry N,N-dimethylformamide at room temperature and the reaction mixture was stirred for 30 minutes. Concentrated aqueous ammonia (d=0.880 g/cm$^3$, ca. 0.1 ml, ca. 1.8 mmol) was added and stirring was continued for 10 minutes. The solvent was removed under reduced pressure and the residue was partitioned between water (10 ml) and ethyl acetate (10 ml). The organic layer was concentrated under reduced pressure and the residue was purified by chromatography on silica gel, eluting with ethyl acetate, to give the title compound as a white solid (60 mg), m.p. 164–166° C.

$^1$H-NMR (300 MHz, CDCL$_3$): δ=1.15 (6H, m), 2.50 (4H, m), 4.70 (2H, s), 5.50 (1H, br. s), 6.21 (1H, br. s), 6.78 (2H, s), 7.04 (1H, s). LRMS (thermospray): m/z [MH$^+$] 342.

Example 11

2-[4-(3,5-Dichlorophenoxy)-3,5-diethyl-1H-pyrazol-1-yl]acetohydrazide

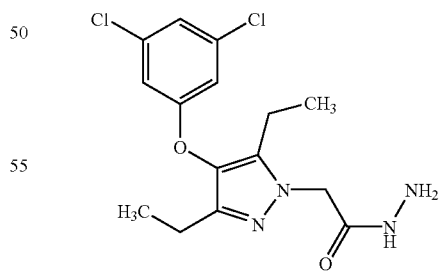

Hydrazine hydrate (520 μL, 10.9 mmol) was added to a solution of the ester (780 mg, 2.18 mmol) of Example 9 in ethanol (25 ml) and the resulting mixture was heated under reflux for 18 hours. After cooling, the precipitate was collected by filtration and washed with ether (50 ml) to afford the title compound (550 g) as a white solid, m.p. >250° C.

$^1$H-NMR (300 MHz, CD$_3$OD): δ=1.10 (6H, m), 2.39 (2H, q), 2.55 (2H, q), 4.72 (2H, s), 6.93 (2H, s), 7.09 (1H, s). LRMS (electrospray): m/z [MH$^+$] 357.

Example 12

5-{[4-(3,5-Dichlorophenoxy)-3,5-diethyl-1H-pyrazol-1-yl]methyl}-1,3,4-oxadiazol-2(3H)-one

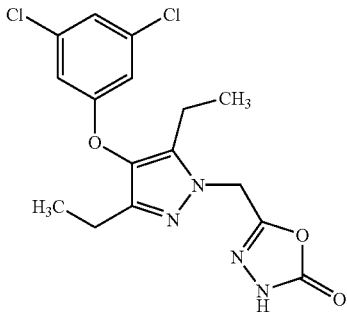

A stirred solution of the hydrazide (275 mg, 0.77 mmol) of Example 11 and 1,1'-carbonyl diimidazole 187 mg, 1.16 mmol) in dioxane (50 ml) was heated under reflux for 18 hours. After cooling, the mixture was concentrated under reduced pressure and the residue was dissolved in dichloromethane (50 ml) and washed with water (25 ml). The organic layer was dried over magnesium sulphate, filtered and concentrated under reduced pressure. The residue was purified by flash chromatography on silica gel eluting with dichloromethane:methanol (95:5, by volume) to afford the title compound (112 mg) as a white solid m.p. 138–142° C.

$^1$H-NMR (400 MHz, CDCl$_3$): δ=1.10 (6H, m), 2.40 (2H, q), 2.55 (2H, q), 5.07 (2H, s), 6.76 (2H, s), 6.98 (1H, s), 10.45 (1H, br. s). LRMS (electrospray): m/z [MH$^+$] 383.

Example 13

2-[4-(3,5-Dichlorophenoxy)-3,5-diethyl-1H-pyrazol-1-yl]ethylamine

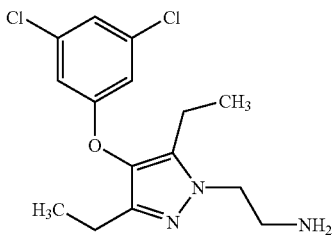

A mixture of the pyrazole (390 mg, 1.37 mmol) of Example 3 and chloroethylamine hydrochloride (238 mg, 2.05 mmol) was stirred and heated at 150° C. for 24 hours. After cooling, the mixture was partitioned between saturated aqueous sodium bicarbonate solution (100 ml) and dichloromethane (2×50 ml). The combined organic layers were washed with brine (30 ml), dried over magnesium sulphate, filtered and concentrated under reduced pressure. The resulting brown oil was purified by flash chromatography on silica gel eluting with dichloromethane:methanol (90:10, by volume) to afford the title compound (244 mg) as a brown oil.

$^1$H-NMR (400 MHz, CDCl$_3$): δ=1.09 (6H, m), 2.41 (2H, q), 2.52 (2H, q), 3.18 (2H, t), 4.02 (2H, t), 6.78 (2H, s), 6.99 (1H, s). LRMS (electrospray): m/z [MH$^+$] 330. Microanalysis: Found: C, 52.28; H, 5.70; N, 11.75. C$_{15}$H$_{19}$Cl$_2$N$_3$O.H$_2$O requires C, 52.03; H, 6.11; N, 12.14%.

Example 14

3-{[4-(3,5-Dichlorophenoxy)-3,5-diethyl-1H-pyrazol-1-yl]methyl}-1,2,4-oxadiazol-5-ol

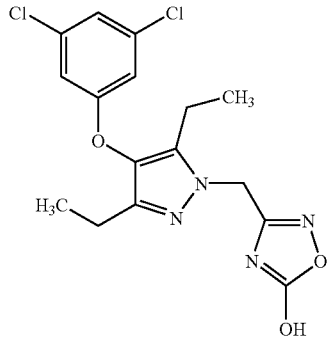

Ethylchloroformate (0.30 ml, 3.08 mmol) was added to a stirred solution of the amidoxime of Example 8 (500 mg, 1.39 mmol) in pyridine (8 ml) at 0° C. under nitrogen and the resulting solution was stirred for 10 minutes. The mixture was concentrated under reduced pressure and the residue was dissolved in a mixture of water (4 ml), tetrahydrofuran (4 ml) and 1M aqueous sodium hydroxide solution (2 ml). The mixture was heated under reflux for 1 hour, cooled to room temperature and stirred for a further 2 days. The resulting solution was diluted with 2M aqueous hydrochloric acid (20 ml) and extracted with ethyl acetate (2×50 ml). The combined organic layers were washed with brine (50 ml), dried over magnesium sulphate, filtered and evaporated under reduced pressure to leave a yellow oil. The oil was purified by flash column chromatography on silica gel eluting with pentane:ethyl acetate (50:50, by volume) to yield a white solid. The solid was dissolved in a mixture of tetrahydrofuran (1 ml) and 1M aqueous sodium hydroxide solution (10 ml) and then heated under reflux for 24 hours. The resulting solution was diluted with 2M hydrochloric acid (20 ml) and extracted with dichloromethane (2×50 ml). The combined organic layers were washed with brine (50 ml), dried over magnesium sulphate, filtered and evaporated under reduced pressure to give the title compound (113 mg) as a white solid m.p. 94–96° C.

$^1$H-NMR (400 MHz, CDCl$_3$): δ=1.14 (m, 6H), 2.56 (m, 4H), 5.06 (s, 2H), 6.75 (s, 2H), 7.03 (s, 1H). LRMS (electrospray): m/z [M−(H$^+$)] 381.

Example 15

5-{[4-(3,5-Dichlorophenoxy)-3,5-diethyl-1H-pyrazol-1-yl]methyl}-1,3,4-oxadiazol-2-amine

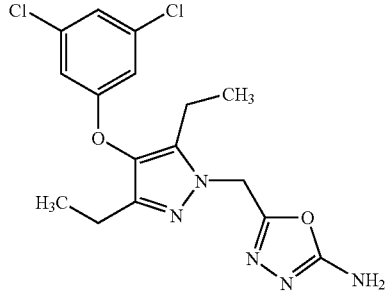

Cyanogen bromide (49 mg, 0.462 mmol) was added to a stirred solution of the hydrazide of Example 11 (150 mg, 0.420 mmol) in ethanol (30 ml), at room temperature, under nitrogen and the resulting solution was heated to reflux for 2.5 hours. After cooling, the mixture was concentrated under reduced pressure to leave a brown oil. The crude product was purified by flash column chromatography on silica gel eluting with dichloromethane:methanol:ammonia (98:1.75:0.25, by volume) to provide the title compound (71 mg) as a white powder, m.p. 226–228° C.

$^1$H-NMR (400 MHz, CDCl$_3$): δ=1.00 (m, 6H), 2.29 (m, 2H), 2.55 (m, 2H), 5.34 (s, 2H), 6.90 (s, 2H), 7.07 (s, 2H), 7.24 (s, 1H). LRMS (electrospray): m/z [MH$^+$] 382. Microanalysis: Found: C, 49.82; H, 4.52; N, 17.81. C$_{16}$H$_{17}$Cl$_2$N$_5$O$_2$.0.25H$_2$O requires C, 49.69; H, 4.56; N, 18.11%.

Example 16

N-{2-[4-(3,5-Dichlorophenoxy)-3,5-diethyl-1H-pyrazol-1-yl]ethyl}-2-methoxyacetamide

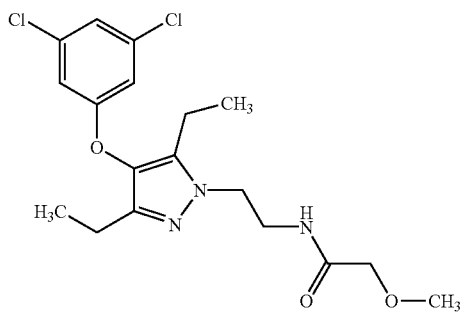

A solution of the pyrazole of Example 13 (53 mg, 0.161 mmol), 1-(3-(dimethylamino)propyl)-3-ethylcarbodiimide hydrochloride (34 mg, 0.178 mmol) and 4-(dimethylamino)pyridine (22 mg, 0.178 mmol) in dichloromethane (1 ml) was added to a stirred solution of methoxyacetic acid (14.2 μL, 0.178 mmol) in dichloromethane (1 ml) at room temperature. The reaction was stirred for 12 hours and then concentrated under a stream of nitrogen to leave a yellow solid. The crude product was purified by flash column chromatography on silica gel eluting with dichloromethane:methanol (98:2, by volume) to provide the title compound (54 mg) as a brown solid, m.p. 75–76° C.

$^1$H-NMR (400 MHz, CDCl$_3$): δ=1.08 (t, 3H), 1.18 (t, 3H), 2.42 (q, 2H), 2.52 (q, 2H), 3.39 (s, 3H), 3.75 (m, 2H), 3.90 (s, 2H), 4.13 (t, 2H), 6.79 (s, 2H), 6.99 (s, 1H), 7.21 (br s, 1H). LRMS (electrospray): m/z [MH$^+$] 400; [M–(H$^+$)] 398. Microanalysis: Found: C, 54.09; H, 5.79; N, 10.39. C$_{18}$H$_{23}$Cl$_2$N$_3$O$_3$ requires C, 54.01; H, 5.79; N, 10.50%.

Examples 17 and 18

The compounds of the following tabulated Examples of the general formula:

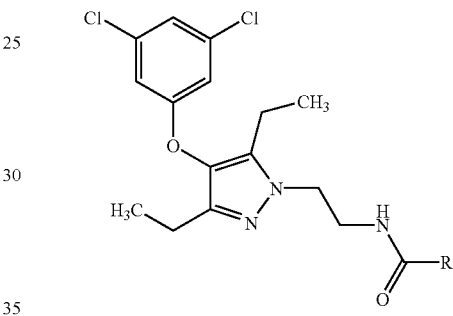

were prepared by a similar method to that of Example 16 using the appropriate acid starting material and the pyrazole of Example 13.

| Example No. | R | LRMS (thermospray) | Analytical Data |
|---|---|---|---|
| 17 | ![pyridin-2-yl] | m/z [MH$^+$] 433 | $^1$H-NMR (400MHz, CDCl$_3$): δ = 1.06 (t, 3H), 1.18 (t, 3H), 2.44 (q, 2H), 2.52 (q, 2H), 3.92 (m, 2H), 4.24 (t, 2H), 6.79 (s, 2H), 6.99 (s, 1H), 7.40 (m, 1H), 7.82 (m, 1H), 8.19 (m, 1H), 8.52 (br s, 2H), 8.55 (m, 1H). Microanalysis: Found: C, 57.01; H, 5.08; N, 11.94. C$_{21}$H$_{22}$Cl$_2$N$_4$O$_2$ requires C, 58.21; H, 5.12; N, 12.03%. |
| 18 | ![pyrazin-2-yl] | m/z [MH$^+$] 434 | $^1$H-NMR (400MHz, CDCl$_3$): δ = 1.08 (t, 3H), 1.18 (t, 3H), 2.42 (q, 2H), 2.52 (q, 2H), 3.96 (m, 2H), 4.24 (t, 2H), 6.79 (s, 2H), 7.01 (s, 1H), 8.22 (br s, 1H), 8.54 (d, 1H), 8.78 (d, 1H), 9.40 (s, 1H). |

Example 19

3-{[3,5-Diethyl-1-(2-hydroxyethyl)-1H-pyrazol-4-yl]oxy}benzonitrile

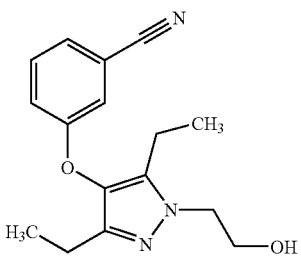

A mixture of the chloroketone of Preparation 2 (243 mg, 1.50 mmol), 3-cyanophenol (155 mg, 1.50 mmol), cesium carbonate (488 mg, 1.50 mmol) and acetone (10 ml) was heated under reflux for 2 hours. After cooling, the solid was removed by filtration and the filtrate was concentrated under reduced pressure to leave a brown oil. The oil was dissolved in ethanol (10 ml), hydroxyethylhydrazine (114 mg, 1.50 mmol) was added and the mixture was heated at 60° C. for 18 hours. After cooling, the mixture was concentrated under reduced pressure. A solution of the residue in dichloromethane (10 ml) was washed with 2M aqueous hydrochloric acid (5 ml) and water (5 ml), dried over magnesium sulphate, filtered and concentrated under reduced pressure to leave a yellow oil. The crude product was purified by flash column chromatography on silica gel eluting with ethyl acetate to provide the title compound (80 mg) as a colourless oil.

$^1$H-NMR (400 MHz, CDCl$_3$): δ=1.10 (m, 6H), 2.40 (q, 2H), 2.50 (q, 2H), 3.68 (br s, 1H), 4.07 (m, 4H), 7.12 (s, 1H), 7.14 (d, 1H), 7.28 (d, 2H). LRMS (electrospray): m/z [MH$^+$] 286; [MNa$^+$] 308.

Examples 20 to 38

The compounds of the following tabulated Examples of the general formula:

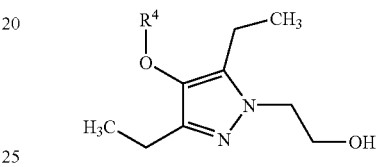

were prepared by a similar method to that of Example 19 using the appropriate phenols and the chloroketone of Preparation 2.

| Example No. | R$^4$ | LRMS (electrospray) | Analytical Data |
|---|---|---|---|
| 20 | ![3,5-dimethyl-4-cyanophenyl] | m/z [MH$^+$] 314. | $^1$H-NMR (400MHz, CDCl$_3$): δ = 0.99 (t, 3H), 1.09 (t, 3H), 2.18 (s, 6H), 2.25 (q, 2H), 2.40 (q, 2H), 3.78 (br s, 1H), 4.00 (m, 4H), 7.34 (s, 2H). |
| 21 | ![3-chloro-4-cyanophenyl] | m/z [MH$^+$] 320. | $^1$H-NMR (400MHz, CDCl$_3$): δ = 1.10 (m, 6H), 2.40 (q, 2H), 2.53 (q, 2H), 3.56 (br s, 1H), 4.04 (m, 2H), 4.08 (m, 2H), 6.80 (d, 1H), 7.44 (d, 1H), 7.72 (s, 1H). Accurate Mass: Found: 320.1165 [MH$^+$]; C$_{16}$H$_{18}$ClN$_3$O$_2$ requires 320.1161 [MH$^+$]. |
| 22 | ![2-fluoro-6-cyanophenyl] | m/z [MH$^+$] 304. | $^1$H-NMR (400MHz, CDCl$_3$): δ = 1.10 (m, 6H), 2.39 (q, 2H), 2.50 (q, 2H), 4.60 (m, 4H), 7.05 (m, 1H), 7.14 (m, 2H). |

-continued

| Example No. | R⁴ | LRMS (electrospray) | Analytical Data |
|---|---|---|---|
| 23 |  | m/z [MH⁺] 295. | ¹H-NMR (400MHz, CDCl₃): δ = 1.09 (m, 6H), 2.41 (m, 2H), 2.51 (m, 2H), 3.78 (br s, 1H), 4.06 (m, 4H), 6.81 (m, 2H), 7.21 (m, 2H).<br>Microanalysis: Found: C, 60.88; H, 6.49; N, 9.40. C₁₅H₁₉ClN₂O₂ requires C, 61.12; H, 6.50; N, 9.50%. |
| 24 | 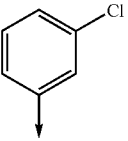 | m/z [MH⁺] 295. | ¹H-NMR (400MHz, CDCl₃): δ = 1.09 (t, 3H), 1.14 (t, 3H), 2.41, (q, 2H), 2.52 (q, 2H), 3.79 (br s, 1H), 4.05 (m, 4H), 6.78 (d, 1H), 6.88 (s, 1H), 6.98 (d, 1H), 7.19 (t, 1H). |
| 25 | 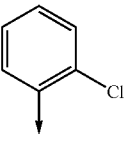 | M/z [MH⁺] 1 295. | ¹H-NMR (400MHz, CDCl₃): δ = 1.08 (t, 3H), 1.15 (t, 3H), 2.44 (q, 2H), 2.54 (q, 2H), 4.02 (m, 2H), 4.09 (m, 2H), 6.69 (d, 1H), 6.94 (t, 1H), 7.10 (t, 1H), 7.40 (d, 1H). |
| 26 | 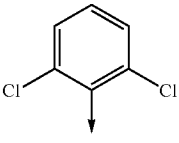 | M/z [MH⁺] 329. | ¹H-NMR (400MHz, CDCl₃): δ = 1.01 (t, 3H), 1.10 (t, 3H), 2.38 (q, 2H), 2.49 (q, 2H), 3.84 (br s, 1H), 3.99 (m, 4H), 7.01 (t, 1H), 7.30 (d, 2H).<br>Accurate Mass: Found: 329.0822 [MH⁺]; C₁₅H₁₈Cl₂N₂O₂ requires 329.0818 [MH⁺]. |
| 27 | 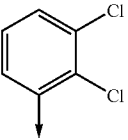 | m/z [M-(H⁺)] 328. | ¹H-NMR (400MHz, CDCl₃): δ = 1.09 (t, 3H), 1.14 (t, 3H), 2.41 (q, 2H), 2.51 (q, 2H), 4.03 (m, 2H), 4.07 (m, 2H), 6.60 (d, 1H), 7.04 (t, 1H), 7.10 (t, 1H). |
| 28 | 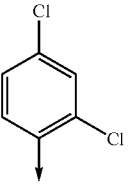 | m/z [MH⁺] 329. | ¹H-NMR (400MHz, CDCl₃): δ = 1.08 (t, 3H), 1.14 (t, 3H), 2.41 (q, 2H), 2.51 (q, 2H), 4.03 (m, 2H), 4.08 (m, 2H), 6.62 (d, 1H), 7.09 (d, 1H).<br>Microanalysis: Found: C, 54.66; H, |
| 29 | 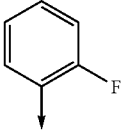 | m/z [MH⁺] 279. | ¹H-NMR (400MHz, CDCl₃): δ = 1.10 (t, 3H), 1.14 (t, 3H), 2.44 (q, 2H), 2.55 (q, 2H), 3.79 (br s, 1H), 4.06 (m, 4H), 6.71 (m, 1H), 6.98 (m, 2H), 7.12 (m, 1H). |
| 30 | 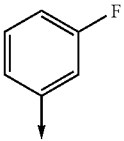 | m/z [MH⁺] 279. | ¹H-NMR (400MHz, CDCl₃): δ = 1.09 (t, 3H), 1.12 (t, 3H), 2.43 (q, 2H), 2.52 (q, 2H), 3.78 (br s, 1H), 4.04 (m, 4H), 6.59 (m, 1H), 6.75 (m, 2H), 7.20 (m, 2H). |
| 31 | 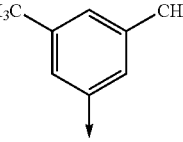 | m/z [MH⁺] 289. | ¹H-NMR (400MHz, CDCl₃): δ = 1.10 (t, 3H), 1.17 (t, 3H), 2.25 (s, 6H), 2.42 (q, 2H), 2.52 (q, 2H), 3.90 (br s, 1H), 4.05 (m, 4H), 6.49 (s, 2H), 6.62 (s, 1H). |

| Example No. | R⁴ | LRMS (electrospray) | Analytical Data |
|---|---|---|---|
| 32 | 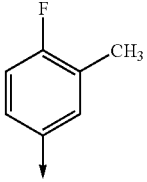 | m/z [MH⁺] 293. | ¹H-NMR (400MHz, CDCl₃): δ = 1.09 (t, 3H), 1.14 (t, 3H), 2.22 (s, 3H), 2.42 (q, 2H), 2.31 (q, 2H), 3.83 (br s, 1H), 4.03 (m, 4H), 6.60 (m, 1H), 6.70 (m, 1H), 6.88 (m, 1H). |
| 33 | 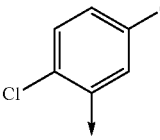 | m/z [MH⁺] 329. | ¹H-NMR (400MHz, CDCl₃): δ = 1.11 (t, 3H), 1.17 (t, 3H), 2.42 (q, 2H), 2.54 (q, 2H), 4.06 (m, 4H), 6.69 (s, 1H), 6.94 (d, 1H), 7.34 (d, 1H). Microanalysis: Found: C, 54.84; H, 5.67; N, 8.48. C₁₅H₁₈Cl₂N₂O₂ requires C, 54.72; H, 5.51; N, 8.51%. |
| 34 | 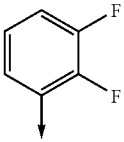 | m/z [MH⁺] 297. | ¹H-NMR (400MHz, CDCl₃): δ = 1.09 (3, 3H), 1.12 (t, 3H), 2.42 (q, 2H), 2.50 (q, 2H), 3.68 (br s, 1H), 4.01 (m, 4H), 6.47 (m, 1H), 6.77 (m, 1H), 6.86 (m, 1H). Microanalysis: Found: C, 60.57; H, 6.23; N, 9.52. C₁₅H₁₈F₂N₂O₂ requires C, 60.80; H, 6.12; N, 9.45%. |
| 35 | 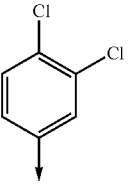 | m/z [MH⁺] 329. | ¹H-NMR (400MHz, CDCl₃): δ = 1.08 (t, 3H), 1.12 (t, 3H), 2.41 (q, 2H), 2.51 (q, 2H), 3.73 (br s, 1H), 4.08 (m, 4H), 6.75 (d, 1H), 6.98 (s, 1H), 7.31 (d, 1H). Microanalysis: Found: C, 54.70; H, 5.54; N, 8.50. C₁₅H₁₈Cl₂N₂O₂ requires C, 54.72; H, 5.51; N, 8.51%. |
| 36 | 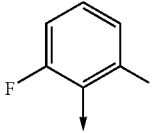 | m/z [MH⁺] 297. | ¹H-NMR (400MHz, CDCl₃): δ = 1.08 (t, 3H), 1.12 (t, 3H), 2.49 (q, 2H), 2.60 (q, 2H), 3.81 (br s, 1H), 3.99 (m, 4H), 6.91 (m, 2H), 6.99 (m, 1H). |
| 37 | 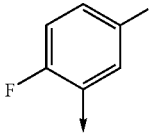 | m/z [MH⁺] 297. | ¹H-NMR (400MHz, CDCl₃): δ = 1.09 (t, 3H), 1.15 (t, 3H), 2.45 (q, 2H), 2.55 (q, 2H), 3.70 (br s, 1H), 4.06 (m, 4H), 6.46 (m, 1H), 6.62 (m, 1H), 7.08 (m, 1H). |
| 38 | 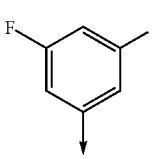 | m/z [MH⁺] 297. | ¹H-NMR (400MHz, CDCl₃): δ = 1.08 (t, 3H), 1.14 (t, 3H), 2.41 (q, 2H), 2.53 (q, 2H), 3.72 (br s, 1H), 4.05 (m, 4H), 6.43 (m, 3H). |

Example 39

4-(3,5-Dichlorophenoxy)-3,5-diethyl-1-(2-methoxyethyl)-1H-pyrazole

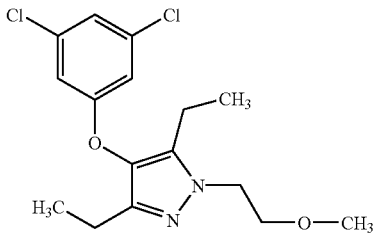

Sodium hydride (60% dispersion in oil, 34 mg, 0.850 mmol) was added to a stirred solution of 4-(3,5-dichlorophenoxy)-3,5-diethyl-1H-pyrazole of Example 3 (200 mg, 0.701 mmol) and methoxyethyl bromide (117 mg, 0.850 mmol) in dry N,N-dimethylformamide (2 ml) at 0° C. under nitrogen. The mixture was stirred at 0° C. for 45 minutes during which time hydrogen was evolved and the yellow solution turned dark brown. The reaction mixture was quenched by the addition of water (5 ml) and the mixture concentrated under reduced pressure. The residue was dissolved in ethyl acetate (20 ml) and washed with water (10 ml) and brine (10 ml) and then dried over magnesium sulphate, filtered and concentrated under reduced pressure to leave a brown oil. The crude product was purified by flash column chromatography on silica gel eluting with pentane:diethyl ether (80:20, by volume) to provide the title compound (140 mg) as a colourless oil.

$^1$H-NMR (300 MHz, CDCl$_3$): δ=1.09–1.15 (m, 6H), 2.41–2.49 (q, 2H), 2.51–2.57 (q, 2H), 3.34 (s, 3H), 3.74–3.78 (t, 2H), 4.15–4.17 (t, 2H), 6.81 (s, 2H), 7.01 (s, 1H). LRMS (thermospray): m/z [MH$^+$] 343. Microanalysis: Found: C, 56.25; H, 5.94; N, 7.95. C$_{16}$H$_{20}$Cl$_2$N$_2$O$_2$ requires C, 55.99; H, 5.87; N, 8.16%.

Examples 40 and 41

The compounds of the following tabulated Examples of the general formula:

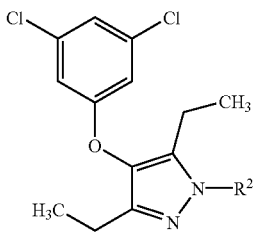

were prepared by a similar method to that of Example 39 using the appropriate halides and the pyrazole of Example 3.

| Example No. | R$^2$ | LRMS (thermospray) | Analytical Data |
|---|---|---|---|
| 40 | —O—CH$_3$ (CH$_2$O-CH$_3$) | m/z [MH$^+$] 329. | $^1$H-NMR (300MHz, CDCl$_3$): δ = 1.13–1.18 (m, 6H), 2.45 (q, 2H), 2.60 (q, 2H), 3.37 (s, 3H), 5.34 (s, 2H), 6.80 (s, 2H), 7.02 (s, 1H). Microanalysis: Found: C, 54.72; H, 5.46; N, 8.40. C$_{15}$H$_{18}$Cl$_2$N$_2$O$_2$ requires C, 54.72; H, 5.51; N, 8.51%. |
| 41 | CH$_3$ | m/z [MH$^+$] 299. | $^1$H-NMR (300MHz, CDCl$_3$): δ = 1.15 (m, 6H), 2.48 (m, 4H), 3.79 (s, 3H), 6.82 (s, 2H), 7.01 (s, 1H). Microanalysis: Found: C, 56.08; H, 5.37; N, 9.29. C$_{14}$H$_{16}$Cl$_2$N$_2$O requires C, 56.20; H, 5.39; N, 9.36%. |

Example 42

4-(3,5-Dichlorophenoxy)-3-ethyl-1H-pyrazole

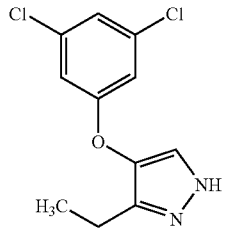

A solution of the enamine of Preparation 6 (2.88 g, 10.0 mmol) and hydrazine hydrate (0.49 ml, 10.0 mmol) in ethanol (10 ml) was heated under reflux for 12 hours. After cooling further hydrazine hydrate (0.49 ml, 10.0 mmol) was added and the reaction was heated under reflux for 3 hours. After cooling the mixture was concentrated under reduced pressure and the residue was purified by flash column chromatography on silica gel eluting with cyclohexane:ethyl acetate (80:20, by volume) and then cyclohexane:ethyl acetate (60:40, by volume) to provide the title compound (620 mg) as a yellow oil.

$^1$H-NMR (400 MHz, CDCl$_3$): δ=1.23 (t, 3H), 2.66 (q, 2H), 6.87 (s, 2H), 7.02 (s, 1H), 7.40 (s, 1H). LRMS (electrospray): m/z [MH$^+$] 257; [M–(H$^+$)] 255.

Example 43

4-{2-[4-(3,5-Dichlorophenoxy)-3,5-diethyl-1H-pyrazol-1-yl]ethyl}morpholine

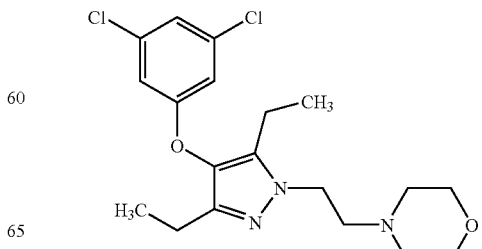

Osmium tetroxide (1.00 ml of a 2.5% w/v solution in tert-butanol) was added dropwise to a stirred solution of the pyrazole of Example 64 (3.00 g, 9.23 mmol) and sodium periodate (4.93 g, 23.1 mmol) in acetone (90 ml) and water (30 ml) at room temperature. A white precipitate formed after 5 minutes and the suspension was stirred for a further 3 hours. The solid was removed by filtration and the filtrate was concentrated under reduced pressure. The residue was partitioned between ethyl acetate (300 ml) and water (100 ml) and the organic phase was separated, dried over magnesium sulphate, filtered and concentrated under reduced pressure to yield an intermediate aldehyde. An aliquot of the aldehyde (100 mg, 0.305 mmol) was dissolved in dichloromethane (5 ml) and morpholine (30 mg, 0.344 mmol) and glacial acetic acid (17.1 μL, 0.305 mmol) were added. After stirring at room temperature for 5 minutes sodium triacetoxyborohydride (95 mg, 0.451 mmol) was added in one portion and the reaction was stirred for 1 hour. After this time the resultant mixture was diluted with dichloromethane (20 ml) and partitioned between water (30 ml) and dichloromethane (20 ml). The organic phase was washed with 2M aqueous sodium hydroxide solution (10 ml), dried over magnesium sulphate, filtered and concentrated under reduced pressure. The crude product was purified by flash chromatography on silica gel eluting with dichloromethane:methanol:ammonia (95:4:1, by volume) to provide the title compound (125 mg) as a colourless oil.

$^1$H-NMR (400 MHz, CDCl$_3$): δ=1.06 (m, 6H), 2.12 (m, 8H), 2.75 (t, 2H), 3.64 (m, 4H), 4.04 (t, 2H), 6.73 (s, 2H), 6.95 (s, 1H). LRMS (thermospray): m/z [MH$^+$] 398. Microanalysis: Found: C, 57.18; H, 6.31; N, 10.36. C$_{19}$H$_{25}$Cl$_2$N$_3$O$_2$ requires C, 57.29; H, 6.33; N, 10.55%.

Examples 44 to 49

The compounds of the following tabulated Examples of the general formula:

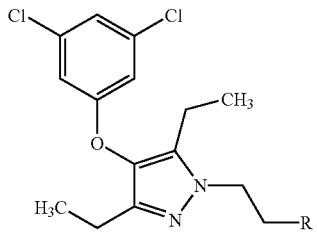

were prepared by a similar method to that of Example 43 using the appropriate amine starting material and the pyrazole of Example 64.

| Example No. | R | LRMS (thermospray) | Analytical Data |
|---|---|---|---|
| 44 | 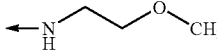 | m/z [MH$^+$] 386. | $^1$H-NMR (300MHz, CDCl$_3$): δ = 1.09–1.17 (m, 6H), 2.40–2.47 (q, 2H), 2.50–2.56 (q, 2H), 2.80–2.82 (t, 2H), 3.07–3.11 (t, 2H), 3.36 (s, 3H), 3.47–3.51 (t, 2H), 4.09–4.11 (t, 2H), 6.81 (s, 2H), 7.01 (s, 1H). |
| 45 | 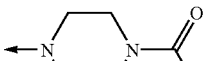 | m/z [MH$^+$] 439. | $^1$H-NMR (400MHz, CDCl$_3$): δ = 1.04 (m, 6H), 2.00 (s, 3H), 2.38 (m, 6H), 2.44 (q, 2H), 2.77 (q, 2H), 3.38 (m, 2H), 3.55 (m, 2H), 4.05 (m, 2H), 6.71 (s, 2H), 6.92 (s, 1H). |
| 46 |  | m/z [MH$^+$] 356. | $^1$H-NMR (400MHz, CDCl$_3$): δ = 1.05 (m, 6H), 2.23 (s, 6H), 2.38 (q, 2H), 2.45 (q, 2H), 2,69 (m, 2H), 4.03 (m, 2H), 6.75 (s, 2H), 6.95 (s, 1H). |
| 47 | 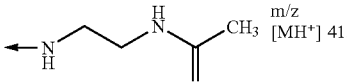 | m/z [MH$^+$] 413. | $^1$H-NMR (400MHz, CDCl$_3$): δ = 1.08 (m, 6H), 1.59 (br s, 1H), 1.91 (s, 3H), 2.38 (q, 2H), 2.48 (q, 2H), 2.71 (m, 2H), 2.99 (m, 2H), 3.28 (m, 2H), 4.02 (m, 2H), 6.09 (br s, 1H), 6.71 (s, 2H), 6.95 (s, 1H). Microanalysis: Found: C, 54.86; H, 6.32; N, 13.33. C$_{19}$H$_{26}$Cl$_2$N$_4$O$_2$ requires C, 55.21; H, 6.34; N, 13.55%. m.p. 69–70° C. |
| 48 | 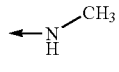 | m/z [MH$^+$] 342. | $^1$H-NMR (400MHz, CDCl$_3$): δ = 1.08 (m, 7H), 2.39 (m, 2H), 2.42 (s, 3H), 2.49 (q, 2H), 3.00 (m, 2H), 4.05 (m, 2H), 6.78 (s, 2H), 6.96 (s, 1H). |
| 49 | 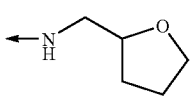 | m/z [MH$^+$] 412. | $^1$H-NMR (400MHz, CDCl$_3$): δ = 1.05 (m, 6H), 1.49 (m, 1H), 1.81 (m, 4H), 2.42 (q, 2H), 2.52 (q, 2H), 2.64 (m, 2H), 3.08 (t, 2H), 3.76 (m, 1H), 3.79 (m, 1H), 4.00 (m, 1H), 6.78 (s, 2H), 6.98 (s, 1H). Microanalysis: Found: C, 57.78; H, 6.68; N, 9.90. C$_{20}$H$_{27}$Cl$_2$N$_3$O$_2$ requires C, 58.13; H, 6.61; N, 10.17%. |

Example 50

3-{[4-(3,5-Dichlorophenoxy)-3,5-diethyl-1H-pyrazol-1-yl]methyl}morpholine

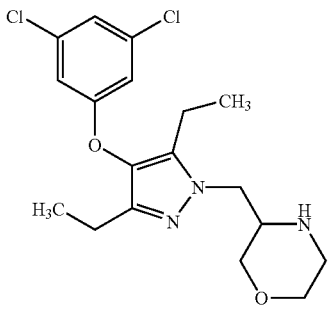

Sodium hydride (60% dispersion in oil, 37 mg, 0.925 mmol) was added to a stirred solution of the mesylate of Preparation 11 (273 mg, 0.925 mmol) and the pyrazole of Example 3 (220 mg, 0.772 mmol) in dry N,N-dimethylformamide (4 ml) at 0° C. under nitrogen. The mixture was heated at 50° C. for 3 hours during which time the yellow solution turned dark brown. The reaction mixture was quenched by the addition of water (5 ml) and the mixture was concentrated under reduced pressure. A solution of the residue in ethyl acetate (20 ml) was washed with water (10 ml) and brine (10 ml), dried over magnesium sulphate, filtered and concentrated under reduced pressure to leave a brown oil. The oil was dissolved in dichloromethane (3 ml), trifluoroacetic acid (1 ml) was added and the reaction was stirred at room temperature for 12 hours. The mixture was concentrated under reduced pressure and the residue was dissolved in ethyl acetate (10 ml) and washed with 1M aqueous hydrochloric acid (2×5 ml). The combined aqueous phases were neutralised with solid sodium carbonate and extracted with ethyl acetate (3×20 ml). The combined ethyl acetate layers were dried over magnesium sulphate, filtered and concentrated under reduced pressure. The crude product was purified by flash column chromatography on silica gel eluting with dichloromethane:methanol:ammonia (95:4:1, by volume) to provide the title compound (3 mg) as a colourless oil.

$^1$H-NMR (400 MHz, CDCl$_3$): δ=1.15 (m, 6H), 2.41 (q, 2H), 2.51 (q, 2H), 2.89 (m, 2H), 3.30 (m, 2H), 3.58 (m, 1H), 3.78 (m, 2H), 3.87 (d, 2H), 6.88 (s, 2H), 7.00 (1H, s). LRMS (thermospray): m/z [MH$^+$] 384.

Example 51

1-(3-Azetidinyl)-4-(3,5-dichlorophenoxy)-3,5-diethyl-1H-pyrazole

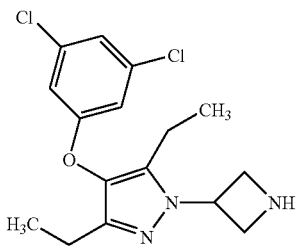

Sodium hydride (60% dispersion in oil, 30 mg, 0.750 mmol) was added to a stirred solution of the pyrazole of Example 3 (200 mg, 0.702 mmol) and 1-benzhydryl-3-azetidinyl methanesulfonate (222 mg, 0.702 mmol) (see J. Org. Chem., 1972, 37, 3953) in N,N-dimethylformamide (5 ml) at 0° C. under nitrogen. The mixture was heated at 50° C. for 4 hours and then cooled to room temperature. The reaction mixture was quenched by the addition of water (30 ml) and the aqueous mixture was extracted with ether (2×50 ml). The combined organic phases were washed with water (10 ml) and brine (10 ml), dried over magnesium sulphate, filtered and concentrated under reduced pressure to leave a brown oil. The oil was purified by flash column chromatography on silica gel eluting with dichloromethane to provide the intermediate (60 mg) as a yellow oil. The oil was dissolved in dichloromethane (5 ml) and 1-chloroethylchloroformate (20 μL, 0.182 mmol) was added at room temperature under nitrogen. The mixture was heated under reflux for 4 hours, cooled to room temperature and concentrated under reduced pressure to leave a yellow oil. The oil was dissolved in methanol (5 ml) and the resulting solution was heated under reflux for 1 hour, cooled to room temperature and concentrated under reduced pressure. The crude product was purified by flash column chromatography on silica gel eluting with dichloromethane:methanol:ammonia (95:4:1, by volume) to provide the title compound (17 mg) as a colourless oil.

$^1$H-NMR (400 MHz, CDCl$_3$): δ=1.08 (t, 3H), 1.16 (t, 3H), 2.48 (m, 4H), 3.87 (t, 2H), 4.40 (t, 2H), 5.07 (q, 1H), 6.79 (s, 2H), 7.01 (m, 1H). LRMS (thermospray): m/z [MH$^+$] 340.

Example 52

7-(3,5-Dichlorophenoxy)-6-ethyl-2,3-dihydropyrazolo[5.1-b][1,3]oxazole

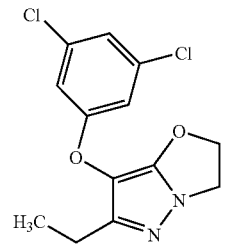

The triflate of Preparation 15 (282 mg, 0.500 mmol), tributylvinyltin (175 μL, 0.600 mmol), palladium dibenzylidene acetone (23 mg, 0.025 mmol), triphenyl arsine (12 mg, 0.040 mmol) and lithium chloride (64 mg, 1.50 mmol) were heated in N,N-dimethylformamide (3 ml) at 80° C. under nitrogen for 12 hours. The reaction was cooled to room temperature and partitioned between water (20 ml) and ethyl acetate (20 ml). The organic layer was washed with brine (10 ml), dried over magnesium sulphate, filtered and concentrated under reduced pressure. The crude product was purified by flash column chromatography on silica gel eluting with pentane:ethyl acetate (90:10, by volume) to provide the title compound (34 mg) as a colourless oil.

$^1$H-NMR (400 MHz, CDCl$_3$): δ=1.16 (t, 3H), 2.45 (q, 2H), 4.29 (t, 2H), 5.03 (t, 2H), 6.89 (s, 2H), 7.02 (s, 1H). LRMS (thermospray): m/z [MH$^+$] 299.

Example 53

4-(3,5-Dichlorophenoxy)-3,5-dimethyl-1H-pyrazole

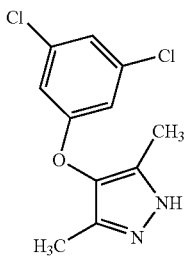

A mixture of 3-chloro-2,4-pentanedione (5.00 g, 37.0 mmol), 3,5-dichlorophenol (6.03 g, 37.0 mmol), cesium carbonate (12.0 g, 37.0 mmol) and acetone (40 ml) was heated under reflux for 18 hours. After cooling the solid was removed by filtration and the filtrate concentrated under reduced pressure. The intermediate was dissolved in ethanol (30 ml) and hydrazine hydrate (1.85 g, 37.0 mmol) was added and the mixture heated at 60° C. for 30 minutes. After cooling the mixture was concentrated under reduced pressure and the residue purified by flash column chromatography on silica gel eluting with ethyl acetate:pentane (30:70, by volume) to provide the title compound (3.00 g) as a yellow oil which solidified on standing to leave a yellow solid, m.p. 85–87° C.

$^1$H-NMR (300 MHz, CDCl$_3$): δ=2.14 (s, 6H), 5.24 (br s, 1H), 6.81 (s, 2H), 7.02 (s, 1H). LRMS (thermospray): m/z [MH$^+$] 257. Microanalysis: Found: C, 49.58; H, 4.06; N, 11.05. C$_{11}$H$_{10}$Cl$_2$N$_2$O.0.4H$_2$O requires C, 49.98; H, 4.12; N, 10.60%.

Example 54

1-[4-(3,5-Dichlorophenoxy)-3,5-diethyl-1H-pyrazol-1-yl]-2-propanol

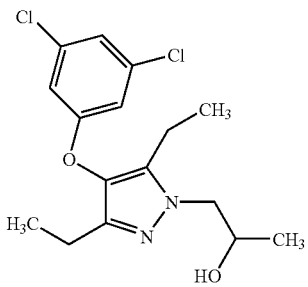

Osmium tetroxide (1.00 ml of a 2.5% w/v solution in tert-butanol) was added dropwise to a stirred solution of the pyrazole of Example 64 (3.00 g, 9.23 mmol) and sodium periodate (4.93 g, 23.1 mmol) in acetone (90 ml) and water (30 ml) at room temperature. A white precipitate formed after 5 minutes and the suspension was stirred for a further 3 hours. The solid was removed by filtration and the filtrate was concentrated under reduced pressure. The residue was partitioned between ethyl acetate (300 ml) and water (100 ml) and the organic phase was separated, dried over magnesium sulphate, filtered and concentrated under reduced pressure to yield the intermediate aldehyde. An aliquot of the aldehyde (250 mg, 0.765 mmol) was dissolved in tetrahydrofuran (5 ml) and stored under nitrogen. In a separate flask, anhydrous cerium trichloride (377 mg, 1.53 mmol) was added to a stirred solution of methyl magnesium bromide (0.51 ml of a 3M solution in ether, 1.53 mmol) in tetrahydrofuran (5 ml) at room temperature under nitrogen. The mixture was stirred at room temperature for 1.5 hours and the aldehyde in tetrahydrofuran was added dropwise. The mixture was stirred for 12 hours and the reaction was then quenched with 1M aqueous acetic acid at room temperature. The mixture was diluted with dichloromethane (20 ml), washed with water (5 ml) and brine (5 ml), dried over magnesium sulphate, filtered and concentrated under reduced pressure. The crude product was purified by flash column chromatography on silica gel eluting with pentane:ethyl acetate (70:30, by volume) to provide the title compound (30 mg) as a colourless oil.

$^1$H-NMR (400 MHz, CDCl$_3$): δ=1.05 (t, 3H), 1.10 (t, 3H), 1.21 (d, 2H), 2.40 (q, 2H), 2.47 (q, 2H), 3.79 (dd, 1H), 3.97 (dd, 1H), 4.24 (s, 1H), 6.76 (s, 2H), 6.98 (s, 1H). LRMS (thermospray): m/z [MH$^+$] 343.

Example 55

2-{2-[4-(3,5-Dichlorophenoxy)-3,5-diethyl-1H-pyrazol-1-yl)ethoxy}ethanamine

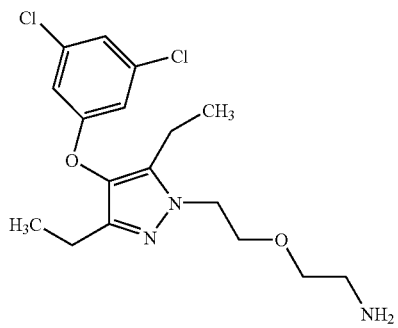

Sodium hydride (60% dispersion in oil, 24 mg, 0.600 mmol) was added to a stirred solution of the pyrazole of Example 2 (100 mg, 0.303 mmol) in dry N,N-dimethylformamide (4 ml) at 0° C. under nitrogen. The mixture was stirred at 0° C. for 30 minutes and 2-chloroethylamine hydrochloride (53 mg, 0.455 mmol) was added. The reaction mixture was stirred at 0° C. for 30 minutes and then stirred at room temperature for 30 minutes. The reaction was cooled to 0° C., further sodium hydride (60% dispersion in oil, 24 mg, 0.600 mmol) and 2-chloroethylamine hydrochloride (53 mg, 0.455 mmol) were added and the reaction was stirred for 1 hour. The reaction was quenched by the addition of water (5 ml) and extracted with ether (10 ml). The organic layer was washed with 2M aqueous hydrochloric acid (30 ml). The acid was neutralised with solid sodium carbonate and extracted with ether (3×20 ml). The combined ether layers were dried over magnesium sulphate, filtered and concentrated under reduced pressure. The crude product was purified by flash column chromatography on silica gel eluting with dichloromethane:methanol:ammonia (95:4:1, by volume) to provide the title compound (21 mg) as a colourless oil.

$^1$H-NMR (400 MHz, CDCl$_3$): δ=1.19 (m, 6H), 2.42 (q, 2H), 2.58 (q, 2H), 2.80 (t, 2H), 3.38 (t, 2H), 3.81 (t, 2H), 4.18 (t, 2H), 6.78 (s, 2H), 7.02 (s, 1H). LRMS (thermospray): m/z [MH$^+$] 372.

Example 56

4-{[4-(3,5-Dichlorophenoxy)-3-methyl-1H-pyrazol-5-yl]methyl}morpholine

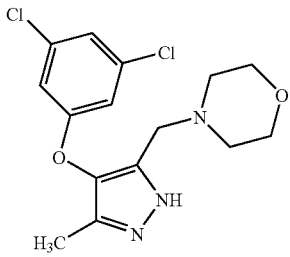

Morpholine (140 µL, 1.59 mmol) was added in one portion to a stirred solution of the bromide of Preparation 8 (200 mg, 0.531 mmol) in isopropanol (4 ml) at room temperature. The mixture was heated at 50° C. for 1 hour, cooled to room temperature and concentrated under reduced pressure to leave a yellow oil. The crude product was purified by flash column chromatography on silica gel eluting with ethyl acetate to provide the title compound (60 mg) as a colourless oil.
$^1$H-NMR (400 MHz, CDCl$_3$): δ=2.13 (s, 3H), 2.42 (m, 4H), 3.38 (s, 2H), 3.64 (m, 4H), 6.79 (s, 2H), 7.02 (s, 1H). LRMS (thermospray): m/z [MH$^+$] 342.

Example 57

4-(3,5-Dichlorophenoxy)-3-methyl-5-[(2-methyl-1H-imidazol-1-yl)methyl]-1H-pyrazole

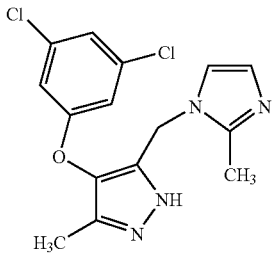

Sodium hydride (60% dispersion in oil, 32 mg, 0.800 mmol) was added to a stirred solution of 2-methylimidazole (65 mg, 0.800 mmol) in N,N-dimethylformamide (5 ml) at 0° C. under nitrogen. The mixture was stirred for 10 minutes and then the bromide of Preparation 8 (100 mg, 0.261 mmol) was added and the reaction was stirred at room temperature for 1 hour. The reaction mixture was quenched by the addition of 1M aqueous sodium hydroxide solution (5 ml) and the mixture was concentrated under reduced pressure. A solution of the residue in ethyl acetate (20 ml) was washed with water (10 ml) and brine (10 ml), dried over magnesium sulphate, filtered and concentrated under reduced pressure to leave a brown oil. The crude product was purified by flash column chromatography on silica gel eluting with dichloromethane:methanol:ammonia (95:4.5:0.5, by volume) to provide the title compound (10 mg) as a colourless oil.
$^1$H-NMR (300 MHz, CDCl$_3$): δ=2.14 (s, 3H), 2.35 (s, 3H), 4.89 (s, 2H), 6.68 (s, 2H), 6.78 (s, 1H), 6.82 (s, 1H), 7.03 (s, 1H). LRMS (thermospray): m/z [MH$^+$] 337.

Example 58

2-[4-(3,5-Dichlorophenoxy)-3-ethyl-5-methoxy-1H-pyrazol-1-yl]ethanol

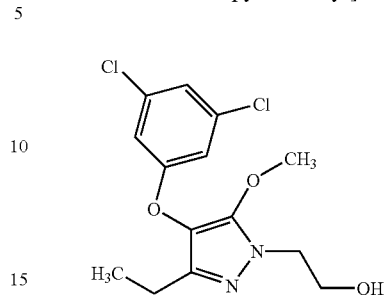

The triflate of Preparation 15 (282 mg, 0.500 mmol) was dissolved in methanol (3 ml) and 1,1'-bis(diphenylphosphino)ferrocenepalladium(II)chloride (18 mg, 0.025 mmol) was added in one portion at room temperature. The mixture was heated at 50° C. under an atmosphere of carbon monoxide (345 kPa, 50 psi) for 10 hours. The reaction was cooled to room temperature and concentrated under reduced pressure to leave a brown oil. The oil was dissolved in a mixture of tetrahydrofuran (0.5 ml), glacial acetic acid (1.0 ml) and water (0.5 ml) and stirred at room temperature for 12 hours. The solvent was removed under a stream of nitrogen to leave a yellow solid and the crude product was purified by flash column chromatography on silica gel eluting with dichloromethane:acetonitrile (95:5, by volume) and then dichloromethane:acetonitrile (90:10, by volume) to provide the title compound (6 mg) as a colourless oil.
$^1$H-NMR (300 MHz, CDCl$_3$): δ=1.13 (t, 3H), 2.41 (q, 2H), 3.44 (br s, 1H), 3.94 (s, 3H), 4.23 (m, 4H), 6.87 (s, 2H), 7.09 (s, 1H). LRMS (thermospray): m/z [MH$^+$] 331.

Example 59

1-{[4-(3,5-Dichlorophenoxy)-3-methyl-1H-pyrazol-5-yl]methyl}-1H-1,2,4-triazole

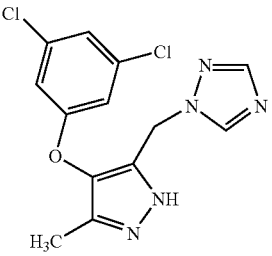

A suspension of the bromide of Preparation 8 (100 mg, 0.264 mmol), 1,2,4-triazole (92 mg, 1.32 mmol) and sodium carbonate (140 mg, 1.32 mmol) in toluene (5 ml) was heated at 100° C. for 12 hours. The suspension was cooled to room temperature and 1M aqueous sodium hydroxide solution (5 ml) was added. The mixture was extracted with ethyl acetate (3×20 ml) and the combined organic phases were dried over magnesium sulphate, filtered and concentrated under reduced pressure to leave a clear oil. The crude product was purified by flash column chromatography on silica gel eluting with dichloromethane:methanol:ammonia (95:4.5: 0.5, by volume) to provide the title compound (62 mg) as a colourless oil.

¹H-NMR (300 MHz, CDCl₃): δ=2.16 (s, 3H), 5.25 (s, 2H), 6.70 (s, 2H), 7.04 (s, 1H), 7.89 (s, 1H), 8.04 (s, 1H). LRMS (thermospray): m/z [MH⁺] 324.

Example 60

3-[(3,5-Diethyl-1H-pyrazol-4-yl)oxy]benzonitrile

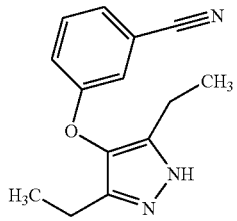

Hydrazine hydrate (153 μL, 3.14 mmol) was added to a stirred solution of the β-diketone of Preparation 9 (771 mg, 3.14 mmol) in ethanol (16 ml) and the resulting solution was heated under reflux for 12 hours. After cooling the mixture was concentrated under reduced pressure and the residue was purified by flash column chromatography on silica gel eluting with pentane:ethyl acetate (75:25, by volume) to provide the title compound (712 mg) as a yellow solid, m.p. 81–84° C.

¹H-NMR (400 MHz, CDCl₃): δ=1.15 (t, 6H), 2.47 (q, 4H), 7.11 (m, 2H), 7.24 (d, 1H), 7.35 (t, 1H). LRMS (thermospray): m/z [MH⁺] 242. Microanalysis: Found: C, 69.03; H, 6.43; N, 17.20. $C_{14}H_{15}N_3O_3 \cdot 0.13H_2O$ requires C, 69.02; H, 6.31; N, 17.25%.

Example 61

3-{[1-(2-Aminoethyl)-3,5-diethyl-1H-pyrazol-4-yl]oxy}benzonitrile

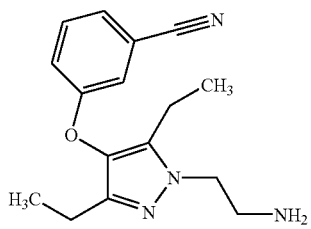

The pyrazole of Example 60 (200 mg, 0.829 mmol) and 2-chloroethylamine hydrochloride (144 mg, 1.24 mmol) were heated as a melt at 150° C. for 17 hours. After cooling the solid was dissolved in saturated aqueous sodium hydrogencarbonate (15 ml) and extracted with dichloromethane (2×10 ml). The combined organic phases were washed with 2M aqueous hydrochloric acid (20 ml) and the aqueous layer was neutralised with solid sodium carbonate and extracted with dichloromethane (3×10 ml). The combined organic phases were dried over magnesium sulphate, filtered and concentrated under reduced pressure to leave an orange gum. The crude product was purified by flash column chromatography on silica gel eluting with dichloromethane: methanol (90:10) then dichloromethane:methanol:ammonia (90:9:1, by volume) to provide the title compound (124 mg) as a pale yellow oil.

¹H-NMR (400 MHz, CDCl₃): δ=1.11 (m, 6H), 2.41 (q, 2H), 2.52 (q, 2H), 3.18 (t, 2H), 4.04 (t, 2H), 7.15 (m, 2H), 7.29 (d, 1H), 7.38 (t, 1H). LRMS (thermospray): m/z [MH⁺] 285.

Example 62

2-[4-(3-Cyanophenoxy)-3,5-diethyl-1H-pyrazol-1-yl]acetamide

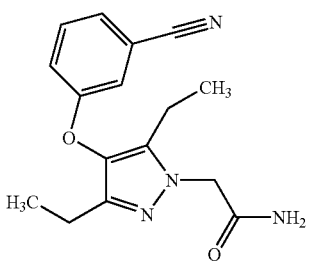

A saturated solution of ammonia in methanol (2.3 ml) was added to the ester of Example 63 (75 mg, 0.229 mmol) in a vial at room temperature then the vial was sealed and heated at 75° C. for 17 hours. After cooling to room temperature the mixture was concentrated under reduced pressure to leave a cream solid. The crude product was purified by flash column chromatography on silica gel eluting with dichloromethane then dichloromethane:methanol (99:1, by volume) to provide the title compound (49 mg) as a white solid, m.p. 159–160° C.

¹H-NMR (400 MHz, CDCl₃): δ=1.10 (t, 3H), 1.17 (t, 3H), 2.44 (q, 2H), 2.53 (q, 2H), 4.69 (s, 2H), 5.44 (br s, 1H), 6.22 (br s, 1H), 7.14 (m, 2H), 7.31 (d, 1H), 7.40 (t, 1H). LRMS (thermospray): m/z [MH⁺] 299. Microanalysis: Found: C, 64.20; H, 6.12; N, 18.79. $C_{16}H_{18}N_4O_2$ requires C, 64.41; H, 6.08; N, 18.78%.

Example 63

Ethyl [4-(3-cyanophenoxy)-3,5-diethyl-1H-pyrazol-1-yl]acetate

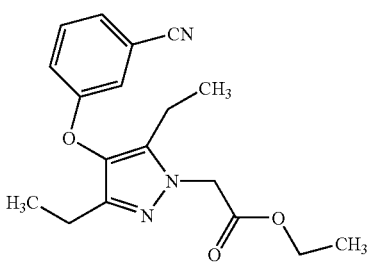

A solution of ethylhydrazinoacetate (88 mg, 0.571 mmol) in ethanol (2.0 ml) was added to a stirred solution of the β-diketone of Preparation 9 (140 mg, 0.571 mmol) and triethylamine (88 μL, 0.628 ml) in ethanol (1.0 ml) and the resulting solution was heated under reflux for 18 hours. After cooling, the mixture was concentrated under reduced pressure and the residue was partitioned between dichloromethane (20 ml) and water (10 ml). The organic layer was separated, washed with brine (10 ml), dried over magnesium sulphate, filtered and concentrated under reduced pressure. The crude product was purified by flash column chromatography on silica gel eluting with pentane:ethyl acetate (75:25, by volume) and then ethyl acetate to provide the title compound (131 mg) as a yellow oil.

$^1$H-NMR (400 MHz, CDCl$_3$): δ=1.08 (m, 6H), 1.25 (t, 3H), 2.40 (m, 4H), 4.20 (q, 2H), 4.77 (s, 2H), 7.12 (m, 2H), 7.23 (d, 1H), 7.34 (t, 1H). LRMS (thermospray): m/z [MH$^+$] 328.

Example 64

1-Allyl-4-(3,5-dichlorophenoxy)-3,5-diethyl-1H-pyrazole

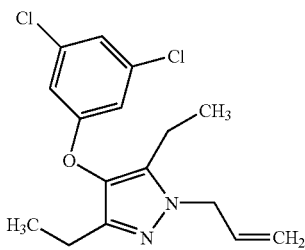

Sodium hydride (60% dispersion in oil, 770 mg, 19.2 mmol) was added to a stirred solution of allyl bromide (1.70 ml, 19.2 mmol) and the pyrazole of Example 3 (5.00 g, 17.5 mmol) in N,N-dimethylformamide (20 ml) at 0° C. under nitrogen. The reaction was warmed to room temperature and stirred for 1 hour. The reaction mixture was quenched by the addition of water (100 ml) and the aqueous phase was extracted with ether (2×50 ml). The combined organic phases were washed with water (30 ml) and brine (30 ml), dried over magnesium sulphate, filtered and concentrated under reduced pressure to leave a brown oil. The crude product was purified by flash column chromatography on silica gel eluting with pentane:ethyl acetate (80:20, by volume) to provide the title compound (5.00 g) as a yellow oil.

$^1$H-NMR (400 MHz, CDCl$_3$): δ=1.11 (m, 6H), 2.46 (m, 4H), 4.65 (d, 2H), 5.04 (d, 1H), 5.22 (d, 1H), 5.99 (m, 1H), 6.79 (s, 2H), 6.99 (s, 1H). LRMS (thermospray): m/z [MH$^+$] 325.

Example 65

N-{[4-(3,5-Dichlorophenoxy)-3-methyl-1H-pyrazol-5-yl]methyl}-N-(4-methoxybenzyl)amine

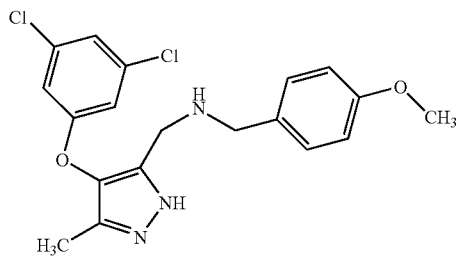

4-Methoxybenzylamine (0.104 ml, 0.800 mmol) was added in one portion to a stirred solution of the bromide of Preparation 8 (100 mg, 0.265 mmol) in isopropanol (2 ml) at room temperature. The mixture was heated at 50° C. for 1 hour, cooled to room temperature and concentrated under reduced pressure to leave a yellow oil. The oil was diluted with diethyl ether (20 ml), washed with saturated aqueous sodium hydrogen carbonate (5 ml) and water (5 ml), dried over magnesium sulphate, filtered and concentrated under reduced pressure. The crude product was purified by flash column chromatography on silica gel eluting with dichloromethane:methanol:ammonia (95:4:1, by volume) to provide the title compound (50 mg) as a colourless oil.

$^1$H-NMR (300 MHz, CDCl$_3$): δ=2.13 (s, 3H), 3.68 (s, 2H), 3.71 (s, 2H), 3.80 (s, 3H), 6.83 (m, 4H), 7.03 (s, 1H), 7.17 (m, 2H). LRMS (thermospray): m/z [MH$^+$] 392.

Examples 66 to 75

The compounds of the following tabulated Examples of the general formula:

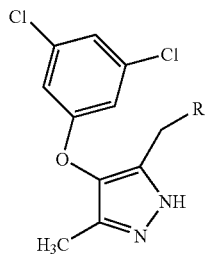

were prepared by a similar method to that of Example 65 using the appropriate amine starting material and the bromide of Preparation 8.

| Example No. | R | LRMS (thermospray) | Analytical Data |
|---|---|---|---|
| 66 | —NH—cyclopropyl | m/z [MH$^+$] 326. | $^1$H-NMR (300MHz, CDCl$_3$): δ = 0.09 (m, 2H), 0.49 (q, 2H), 0.90 (m, 1H), 2.34 (s, 3H), 2.47 (d, 2H), 3.73 (s, 2H), 6.82 (s, 2H), 7.03 (s, 1H). |
| 67 | —N(CH$_3$)$_2$ | m/z [MH$^+$] 300. | $^1$H-NMR (400MHz, CDCl$_3$): δ = 2.08 (s, 3H), 2.20 (s, 6H), 3.31 (s, 2H), 6.76 (s, 2H), 6.97 (s, 1H). |

-continued

| Example No. | R | LRMS (thermospray) | Analytical Data |
|---|---|---|---|
| 68 | ![structure] NHCH₃ | m/z [MH⁺] 286. | ¹H-NMR (400MHz, CDCl₃): δ = 2.12 (s, 3H), 2.42 (s, 3H), 3.65 (s, 2H), 6.80 (s, 2H), 7.02 (s, 1H). |
| 69 | ![structure] N-piperazinyl-CH₃ | m/z [MH⁺] 355. | ¹H-NMR (400MHz, CDCl₃): δ = 2.08 (s, 3H), 2.22 (s, 3H), 2.31 (m, 8H), 3.36 (s, 2H), 6.76 (s, 2H), 6.97 (s, 1H). |
| 70 | ![structure] piperidine-C(O)NH₂ | m/z [MH⁺] 385. | ¹H-NMR (400MHz, CDCl₃): δ = 1.50 (m, 2H), 1.60 (m, 2H), 1.90 (m, 4H), 2.41 (m, 2H), 3.25 (s, 2H), 3.75 (m, 2H), 5.52 (s, 1H), 5.80 (s, 1H), 6.67 (s, 2H), 6.86 (s, 1H). |
| 71 | ![structure] NH-CH₂CH₂-O-CH₃ | m/z [MH⁺] 330. | ¹H-NMR (400MHz, CDCl₃): δ = 2.08 (s, 3H), 2.74 (m, 2H), 3.30 (s, 3H), 3.44 (m, 2H), 3.68 (s, 2H), 6.76 (s, 2H), 6.98 (s, 1H). |
| 72 | ![structure] N-piperazinyl-C(O)CH₃ | m/z [MH⁺] 383. | ¹H-NMR (400MHz, CDCl₃): δ = 2.02 (s, 3H), 2.10 (s, 3H), 2.38 (m, 4H), 3.34 (m, 2H), 3.38 (s, 2H), 3.51 (m, 2H), 6.76 (s, 2H), 6.98 (s, 1H). |
| 73 | ![structure] NH-CH₂CH₂-NH-C(O)CH₃ | m/z [MH⁺] 357. | ¹H-NMR (400MHz, CDCl₃): δ = 1.92 (s, 3H), 2.09 (s, 3H), 2.70 (m, 2H), 3.29 (m, 2H), 3.65 (s, 2H), 6.01 (s, 1H), 6.76 (s, 2H), 6.99 (s, 1H). |
| 74 | ![structure] piperidine-NHC(O)CH₃ | m/z [MH⁺] 397. | ¹H-NMR (400MHz, CDCl₃): δ = 1.30 (m, 2H), 1.80 (m, 2H), 1.92 (s, 3H), 2.09 (m, 5H), 2.70 (m, 2H), 3.34 (s, 2H), 3.71 (m, 1H), 6.76 (s, 2H), 6.98 (s, 1H). |
| 75 | ![structure] piperidine-O-CH₃ | m/z [MH⁺] 370. | ¹H-NMR (300MHz, CDCl₃): δ = 1.60 (m, 2H), 1.80 (m, 2H), 2.13 (s, 3H), 2.20 (m, 2H), 2.71 (m, 2H), 3.22 (m, 1H), 3.33 (s, 3H), 3.39 (s, 2H), 6.81 (s, 2H), 7.03 (s, 1H). |

Example 76

3-Chloro-5-[(3,5-dimethyl-1H-pyrazol-4-yl)oxy]benzonitrile

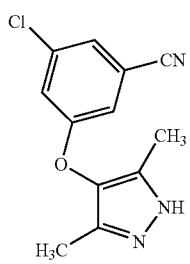

Hydrazine hydrate (1.10 ml, 21.9 mol) was added to a stirred solution of the β-diketone of Preparation 16 (5.50 g, 21.9 mmol) in glacial acetic acid (22 ml) and the resulting solution was stirred at room temperature for 14 hours. The mixture was concentrated under reduced pressure and the residue was purified by flash column chromatography on silica gel eluting with dichloromethane and then dichloromethane:ethyl acetate (85:15, by volume) to provide the title compound (4.80 g) as a yellow solid, m.p. 136–140° C.

¹H-NMR (400 MHz, CDCl₃): δ=2.09 (s, 6H), 7.02 (m, 1H), 7.10 (m, 1H), 7.25 (m, 1H). LRMS (electrospray): m/z [MH⁺] 248. Microanalysis: Found: C, 57.91; H, 4.03; N, 16.79. C₁₂H₁₀N₃OCl requires C, 58.19; H, 4.07; N, 16.97%.

Example 77

3-{[5-(Aminomethyl)-3-methyl-1H-pyrazol-4-yl]oxy}-5-chlorobenzonitrile

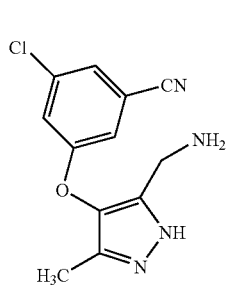

The bromide of Preparation 18 (300 mg, 0.800 mmol) was added to a saturated solution of ammonia in isopropanol (50 ml) at 0° C. The reaction was stirred for 2 hours and allowed to slowly warm to room temperature. The mixture was concentrated under reduced pressure and the resulting yellow oil was dissolved in dichloromethane (50 ml). The dichloromethane solution was washed with 1M aqueous sodium carbonate solution (20 ml), dried over magnesium sulphate, filtered and concentrated under reduced pressure to provide the title compound (220 mg) as a white foam.

$^1$H-NMR (300 MHz, CDCl$_3$): δ=2.14 (s, 3H), 3.79 (s, 2H), 7.08 (1H, s), 7.16 (1H, s), 7.31 (1H, s). LRMS (thermospray): m/z [MH$^+$] 263.

Example 78

3-Chloro-5-{[3-methyl-5-(1-piperazinylmethyl)-1H-pyrazol-4-yl]oxy}benzonitrile

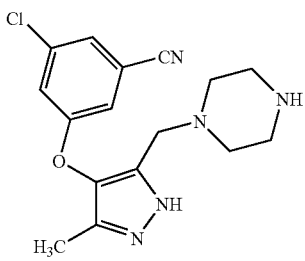

t-Butyl-1-piperazinecarboxylate (1.17 g, 6.30 mmol) was added in one portion to a stirred solution of the bromide of Preparation 18 (500 mg, 1.40 mmol) in isopropanol (20 ml) at room temperature. The mixture was heated at 60° C. for 1 hour, cooled to room temperature and concentrated under reduced pressure to leave a yellow oil. The oil was dissolved in dichloromethane (100 ml) and the resulting solution was washed with 1M aqueous sodium carbonate (20 ml) and brine (20 ml), dried over magnesium sulphate, filtered and concentrated under reduced pressure. The crude product was purified by flash column chromatography on silica gel eluting with dichloromethane:methanol:ammonia (95:4:1, by volume) to provide a yellow foam. The foam was dissolved in dichloromethane (10 ml), the resulting solution was cooled to 0° C. and trifluoroacetic acid (2 ml) was added. The reaction was allowed to warm to room temperature and stirred for 24 hours. The mixture was diluted with dichloromethane (50 ml), washed with 1M aqueous sodium carbonate (20 ml) and brine (20 ml), dried over magnesium sulphate, filtered and concentrated under reduced pressure. The crude product was purified by flash column chromatography on silica gel eluting with dichloromethane:methanol:ammonia (90:9:1, by volume) to provide the title compound (400 mg) as a white foam.

$^1$H-NMR (300 MHz, CDCl$_3$): δ=2.14 (s, 3H), 2.40 (m, 4H), 2.83 (m, 4H), 3.38 (s, 2H), 7.09 (s, 1H), 7.16 (s, 1H), 7.30 (s, 1H). LRMS (thermospray): m/z [MH$^+$] 332.

Example 79

3-Chloro-5-[(5-{[(4-cyanobenzyl)amino]methyl}-3-methyl-1H-pyrazol-4-yl)oxy]benzonitrile

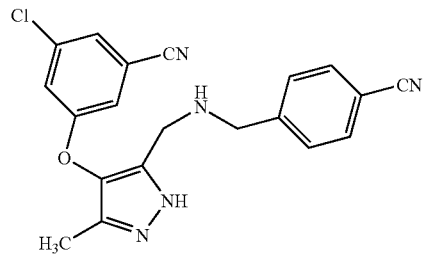

A mixture of 4-cyanobenzaldehyde (60 mg, 0.460 mmol), the amine of Example 77 (120 mg, 0.460 mmol), magnesium sulphate (500 mg) and dichloromethane (5 ml) was stirred under nitrogen at room temperature for 3 days. The mixture was concentrated under reduced pressure and the crude product was purified by flash column chromatography on silica gel eluting with methanol:ethyl acetate (5:95, by volume) to provide a foam. The foam was dissolved in methanol (5 ml), sodium borohydride (50 mg, 1.31 mmol) was added in one portion at room temperature and the reaction was stirred for 30 minutes. The mixture was concentrated under reduced pressure and the residue was dissolved in dichloromethane (20 ml). The resulting solution was washed with 1M aqueous sodium carbonate solution (10 ml) and brine (10 ml), dried over magnesium sulphate, filtered and concentrated under reduced pressure. The crude product was purified by flash column chromatography on silica gel eluting with dichloromethane:methanol:ammonia (95:4:1, by volume) to provide the title compound (35 mg) as a white foam.

$^1$H-NMR (300 MHz, CDCl$_3$): δ=2.15 (s, 3H), 3.69 (s, 2H), 3.84 (s, 2H), 7.06 (s, 1H), 7.15 (s, 1H), 7.31 (s, 1H), 7.38 (d, 2H), 7.60 (d, 2H). LRMS (thermospray): m/z [MH$^+$] 378.

Example 80

3-Chloro-5-[(3-methyl-5-{[4-(methylsulfonyl)-1-piperazinyl]methyl}-1H-pyrazol-4-yl)oxy]benzonitrile

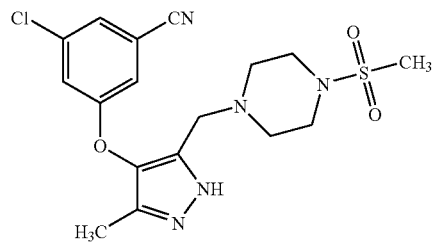

Methanesulphonyl chloride (19 μl, 0.240 mmol) was added dropwise to a stirred solution of the amine of Example 78 (80 mg, 0.240 mmol) and triethylamine (45 μL, 0.288 mmol) in dichloromethane (3 ml) at room temperature under nitrogen. The reaction was stirred for 30 minutes and then concentrated under reduced pressure to leave a yellow oil. The crude product was purified by flash column chromatography on silica gel eluting with dichloromethane and then dichloromethane:methanol:ammonia (95:4:1, by volume) to provide the title compound (65 mg) as a white foam.

¹H-NMR (400 MHz, CDCl₃): δ=2.14 (s, 3H), 2.51 (m, 4H), 2.72 (s, 3H), 3.12 (m, 4H), 3.39 (s, 2H), 7.08 (m, 1H), 7.13 (m, 1H), 7.26 (s, 1H). LRMS (thermospray): m/z [MH⁺] 410.

Example 81

3-Chloro-5-[(5-{[4-(methoxyacetyl)-1-piperazinyl]methyl}-3-methyl-1H-pyrazol-4-yl)oxy]benzonitrile

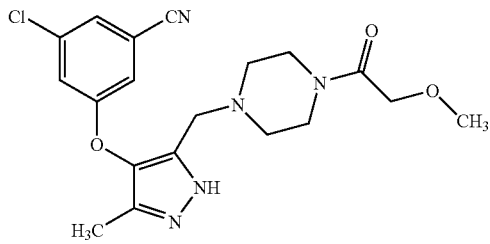

N-Benzyl-N'-cyclohexylcarbodiimide polymer bound (624 mg of 1.3 mmol/g, 0.480 mmol) was added in one portion to a stirred solution of methoxyacetic acid (37 μL, 0.480 mmol) and the amine of Example 78 (80 mg, 0.240 mmol) in dichloromethane (5 ml) at room temperature under nitrogen. The reaction was stirred for 1 hour and the polymer bound reagent was removed by filtration. The filtrate was concentrated under reduced pressure and the crude product was purified by flash column chromatography on silica gel eluting with dichloromethane:methanol:ammonia (95:4:1, by volume) to provide the title compound (45 mg) as a white foam.

¹H-NMR (400 MHz, CDCl₃): δ=2.11 (s, 3H), 2.38 (m, 4H), 3.37 (m, 7H), 3.51 (m, 2H), 4.04 (s, 2H), 7.04 (m, 1H), 7.10 (m, 1H), 7.26 (m, 1H). LRMS (thermospray): m/z [MH⁺] 404.

Example 82

Methyl 4-{[4-(3-chloro-5-cyanophenoxy)-3-methyl-1H-pyrazol-5-yl]methyl}-1-piperazinecarboxylate

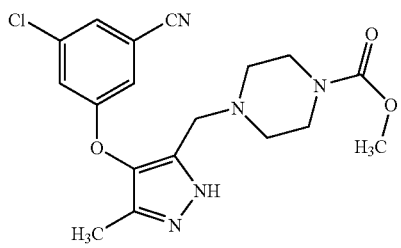

Methyl chloroformate (19 μl, 0.240 mmol) was added dropwise to a stirred solution of the amine of Example 78 (80 mg, 0.240 mmol) and triethylamine (45 μl, 0.288 mmol) in dichloromethane (5 ml) at room temperature under nitrogen. The reaction was stirred for 90 minutes and then concentrated under reduced pressure to leave a yellow oil. The crude product was purified by flash column chromatography on silica gel eluting with dichloromethane and then dichloromethane:methanol:ammonia (95:4:1, by volume) to provide the title compound (55 mg) as a white foam.

¹H-NMR (400 MHz, CDCl₃): δ=2.09 (s, 3H), 2.34 (m, 4H), 3.36 (m, 6H), 3.64 (s, 3H), 7.02 (m, 1H), 7.10 (m, 1H), 7.25 (m, 1H). LRMS (thermospray): m/z [MH⁺] 390.

Example 83

4-[({[4-(3-Chloro-5-cyanophenoxy)-3-methyl-1H-pyrazol-5-yl]methyl}amino)methyl]benzenesulfonamide

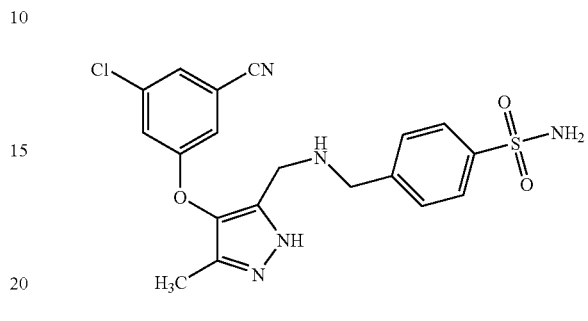

Triethylamine (125 μl, 0.860 mmol) was added in one portion to a stirred suspension of 4-aminomethylbenzenesulphonamide hydrochloride (144 mg, 0.590 mmol) and the bromide of Preparation 18 (100 mg, 0.270 mmol) in isopropanol (5 ml) at room temperature under nitrogen. The reaction was heated at 70° C. for 1 hour and then cooled to room temperature. The mixture was concentrated under reduced pressure and the crude product was purified by flash column chromatography on silica gel eluting with dichloromethane and then dichloromethane:methanol:ammonia (90:9:1, by volume) to provide a foam. The foam was further purified using a Phenomenex Luna C18 column eluting with diethylamine:methanol (0.1:99.1, by volume) to provide the title compound (8 mg) as a white foam.

¹H-NMR (400 MHz, CD₃OD): δ=2.06 (s, 3H), 3.27 (s, 2H), 3.62 (s, 2H), 3.79 (s, 2H), 7.17 (s, 1H), 7.21 (s, 1H), 7.40 (m, 3H), 7.77 (d, 2H). LRMS (thermospray): m/z [MH⁺] 432.

Example 84

4-(3,5-Dichlorophenoxy)-5-(methoxymethyl)-3-methyl-1H-pyrazole

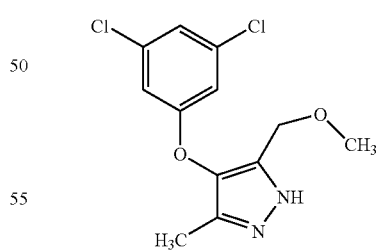

Tetrakis(triphenylphosphine)palladium (60 mg) was added in one portion to a stirred solution of the bromide of Preparation 8 (590 mg, 1.56 mmol) in methanol (20 ml) and tetrahydrofuran (20 ml) at room temperature. The mixture was heated at 80° C. under an atmosphere of carbon monoxide (690 kPa, 100 psi) for 18 hours. The reaction was cooled to room temperature and concentrated under reduced pressure to leave a brown oil. The oil was dissolved in dichloromethane (100 ml) and the resulting solution was washed with water (50 ml), dried over magnesium sulphate, filtered and evaporated under reduced pressure. The crude product was purified by flash column chromatography on silica gel eluting with ether to provide the title compound (110 mg) as a colourless oil.

$^1$H-NMR (400 MHz, CDCl$_3$): δ=2.15 (s, 3H), 3.34 (s, 3H), 4.35 (s, 2H), 6.83 (s, 2H), 7.03 (s, 1H). LRMS (thermospray): m/z [MH$^+$] 287.

Example 85

3-tert-Butyl-4-(3,5-dichlorophenoxy)-5-methyl-1H-pyrazole

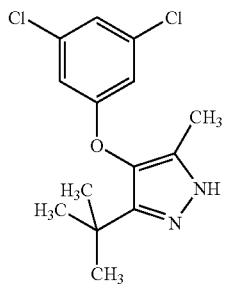

A mixture of the dione of Preparation 19 (1.00 g, 5.68 mmol), 3,5-dichlorophenol (930 mg, 5.68 mmol), cesium carbonate (1.85 g, 5.68 mmol) and acetone (20 ml) was heated at reflux for 18 hours. After cooling the solid was removed by filtration and the filtrate was concentrated under reduced pressure. The intermediate was dissolved in ethanol (20 ml), hydrazine hydrate (284 mg, 5.68 mmol) was added and the mixture was heated at 60° C. for 1 hour. After cooling the mixture was concentrated under reduced pressure and the residue was purified by flash column chromatography on silica gel eluting with ethyl acetate:pentane (25:75, by volume) to provide the title compound (200 mg) as a yellow oil.

$^1$H-NMR (400 MHz, CDCl$_3$): δ=1.30 (s, 9H), 2.06 (s, 3H), 6.81 (s, 2H), 7.02 (s, 1H). LRMS (thermospray): m/z [MH$^+$] 299.

Example 86

4-(3,5-Dichlorophenoxy)-3-ethyl-5-methyl-1H-pyrazole

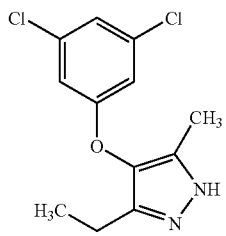

A mixture of the dione of Preparation 50 (4.50 g, 30.8 mmol), 3,5-dichlorophenol (5.00 g, 30.8 mmol), caesium carbonate (10.0 g, 30.8 mmol) and acetone (40 ml) was heated at reflux for 18 hours. After cooling the solid was removed by filtration and the filtrate was concentrated under reduced pressure. The intermediate was dissolved in ethanol (40 ml), hydrazine hydrate (1.00 ml, 30.8 mmol) was added and the mixture was heated at 60° C. for 1 hour. After cooling the mixture was concentrated under reduced pressure and the residue was purified by flash column chromatography on silica gel eluting with ethyl acetate:pentane (20:80, by volume) to provide the title compound (1.50 g) as an orange oil.

$^1$H-NMR (400 MHz, CDCl$_3$): δ=1.18 (t, 3H), 2.11 (s, 3H), 2.53 (q, 2H), 6.79 (s, 2H), 7.01 (s, 1H). LRMS (thermospray): m/z [MH$^+$] 271.

Example 87

4-Cyano-N-{[4-(3,5-dichlorophenoxy)-3-methyl-1H-pyrazol-5-yl]methyl}benzamide

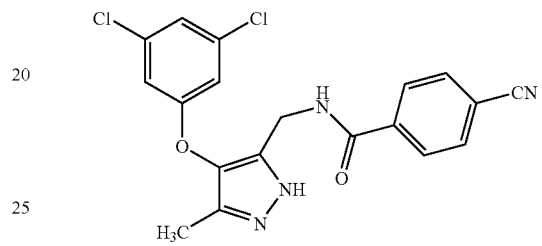

1-(3-(Dimethylamino)propyl)-3-ethylcarbodiimide (93 mg, 0.490 mmol) was added in one portion to a stirred solution of the amine of Example 109 (120 mg, 0.440 mmol) and 4-cyanobenzoic acid (71 mg, 0.490 mmol) in dichloromethane (5 ml) at room temperature under nitrogen. The reaction was stirred for 20 minutes and then washed with 1M aqueous sodium hydroxide solution (10 ml), 1M aqueous hydrochloric acid (10 ml) and water (10 ml). The organic layer was dried over magnesium sulphate, filtered and evaporated under reduced pressure to leave a yellow foam. The crude product was purified by flash column chromatography on silica gel eluting with dichloromethane:methanol:ammonia (95:4:1, by volume) to provide the title compound (110 mg) as a white foam.

$^1$H-NMR (400 MHz, CDCl$_3$): δ=2.09 (s, 3H), 4.91 (d, 2H), 6.74 (s, 2H), 6.95 (s, 1H), 6.98 (d, 1H), 7.65 (d, 2H), 7.77 (d, 2H). LRMS (thermospray): m/z [MNH$_4^+$] 418.

Example 88

3-Cyano-N-{[4-(3,5-dichlorophenoxy)-3-methyl-1H-pyrazol-5-yl]methyl}benzamide

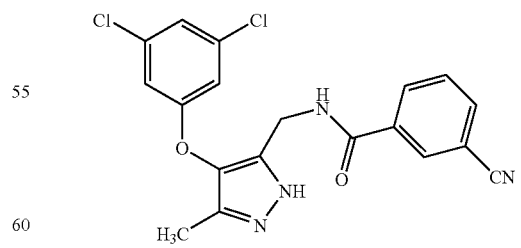

1-(3-(Dimethylamino)propyl)-3-ethylcarbodiimide (93 mg, 0.490 mmol) was added in one portion to a stirred solution of the amine of Example 109 (120 mg, 0.440 mmol) and 3-cyanobenzoic acid (71 mg, 0.490 mmol) in dichloromethane (5 ml) at room temperature under nitrogen. The reaction was stirred for 10 minutes and then washed with 1M aqueous sodium hydroxide solution (10 ml), 1M aqueous hydrochloric acid (10 ml) and brine (10 ml). The organic layer was dried over magnesium sulphate, filtered and evaporated under reduced pressure to leave a cream foam. The crude product was purified by flash column chromatography on silica gel eluting with dichloromethane:methanol:ammonia (95:4:1, by volume) to provide the title compound (100 mg) as a white foam.

$^1$H-NMR (400 MHz, CDCl$_3$): δ=2.14 (s, 3H), 4.53 (d, 2H), 6.78 (s, 2H), 6.98 (m, 2H), 7.54 (dd, 1H), 7.76 (d, 1H), 7.95 (d, 1H), 7.99 (s, 1H). LRMS (thermospray): m/z [MH$^+$] 401.

Example 89

N-{[4-(3,5-Dichlorophenoxy)-3-methyl-1H-pyrazol-5-yl]methyl}-N-(3-pyridinylmethyl)amine

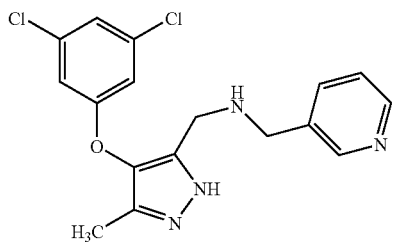

A mixture of 3-pyridinecarboxaldehyde (55 mg, 0.514 mmol), the amine of Example 109 (140 mg, 0.514 mmol), magnesium sulphate (500 mg) and dichloromethane (5 ml) was stirred under nitrogen at room temperature for 18 hours. Sodium triacetoxyborohydride (163 mg, 0.771 mmol) was added in one portion and then acetic acid (3 drops) was added. After 5 minutes the mixture was filtered. The filtrate was washed with 1M aqueous sodium carbonate solution (10 ml), water (10 ml) and brine (10 ml), dried over magnesium sulphate, filtered and concentrated under reduced pressure to leave a clear oil. The crude product was purified by flash column chromatography on silica gel eluting with dichloromethane:methanol:ammonia (95:4:1, by volume) to provide the title compound (60 mg) as a colourless oil.

$^1$H-NMR (400 MHz, CDCl$_3$): δ=2.09 (s, 3H), 3.66 (s, 2H), 3.74 (s, 2H), 6.75 (s, 2H), 6.97 (s, 1H), 7.17 (m, 1H), 7.55 (d, 1H), 8.49 (m, 2H). LRMS (electrospray): m/z [MH$^+$] 363.

Example 90

3-({5-[(4-Acetyl-1-piperazinyl)methyl]-3-methyl-1H-pyrazol-4-yl}oxy)-5-chlorobenzonitrile

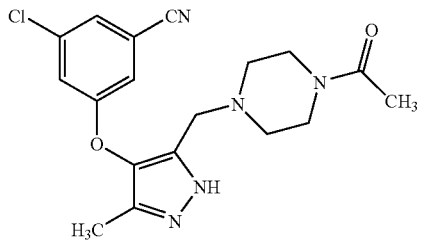

N-Acetylpiperazine (104 mg, 0.810 mmol) was added in one portion to a stirred solution of the bromide of Preparation 18 (100 mg, 0.271 mmol) in isopropanol (5 ml) at room temperature. The mixture was heated at 50° C. for 1 hour, cooled to room temperature and concentrated under reduced pressure to leave a yellow oil. The crude product was purified by flash column chromatography on silica gel eluting with dichloromethane:methanol:ammonia (95:4:1, by volume) to provide the title compound (90 mg) as a colourless oil.

$^1$H-NMR (300 MHz, CDCl$_3$): δ=2.08 (s, 3H), 2.16 (s, 3H), 2.43 (m, 4H), 3.42 (m, 4H), 3.55 (m, 2H), 7.08 (s, 1H), 7.16 (s, 1H), 7.31 (s, 1H). LRMS (thermospray): m/z [MH$^+$] 374.

Example 91

3-Chloro-5-[(5-{[(4-cyanobenzyl) (methyl)amino]methyl}-3-methyl-1H-pyrazol-4-yl)oxy]benzonitrile

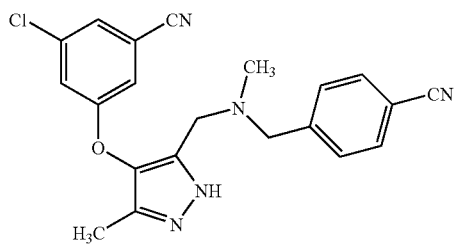

The amine of Preparation 20 (127 mg, 0.870 mmol) was added in one portion to a stirred solution of the bromide of Preparation 18 (100 mg, 0.271 mmol) in isopropanol (5 ml) at room temperature. The mixture was heated at 50° C. for 12 hours, cooled to room temperature and concentrated under reduced pressure to leave a yellow oil. The oil was dissolved in 1M hydrochloric acid and the aqueous solution was washed with ethyl acetate (10 ml). Solid sodium carbonate was added until effervescence ceased and the mixture was extracted with ethyl acetate (3×20 ml). The combined organic phases were dried over magnesium sulphate, filtered and concentrated under reduced pressure. The residue was purified by flash column chromatography on silica gel eluting with dichloromethane:methanol:ammonia (95:4:1, by volume) to provide the title compound (45 mg) as a colourless oil.

$^1$H-NMR (300 MHz, CDCl$_3$): δ=2.14 (s, 3H), 2.17 (s, 3H), 3.45 (s, 2H), 3.55 (s, 2H), 7.05 (s, 1H), 7.14 (s, 1H), 7.31 (m, 3H), 7.59 (d, 2H). LRMS (thermospray): m/z [MH$^+$] 392.

Example 92

3-Chloro-5-[(5-{[(4-cyanobenzyl)(2-hydroxyethyl)amino]methyl}-3-methyl-1H-pyrazol-4-yl)oxy]benzonitrile

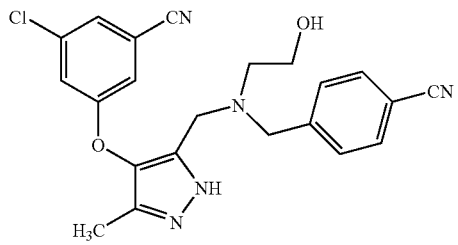

The amine of Preparation 21 (153 mg, 0.870 mmol) was added in one portion to a stirred solution of the bromide of Preparation 18 (100 mg, 0.271 mmol) in isopropanol (5 ml) at room temperature. The mixture was heated at 50° C. for 12 hours, cooled to room temperature and concentrated under reduced pressure to leave a yellow oil. The oil was dissolved in 1M aqueous sodium hydroxide solution and the resulting solution was stirred at room temperature for 1 hour. The aqueous was extracted with ethyl acetate (3×20 ml) and the combined organic phases were dried over magnesium sulphate, filtered and concentrated under reduced pressure. The residue was purified by flash column chromatography on silica gel eluting with dichloromethane:methanol:ammonia (95:4:1, by volume) to provide the title compound (20 mg) as a colourless oil.

$^1$H-NMR (300 MHz, CDCl$_3$): δ=2.14 (s, 3H), 2.71 (m, 2H), 3.50 (s, 1H), 3.58 (s, 2H), 3.67 (m, 2H), 3.72 (s, 2H), 6.99 (s, 1H), 7.09 (s, 1H), 7.31 (s, 1H), 7.41 (d, 2H), 7.58 (d, 2H). LRMS (thermospray): m/z [MH$^+$] 422.

Example 93

3-Chloro-5-({3-methyl-5-[(2-methyl-1H-imidazol-1-yl)methyl]-1H-pyrazol-4-yl}oxy)benzonitrile

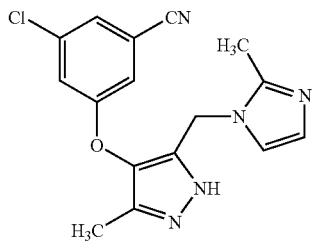

A suspension of the bromide of Preparation 18 (100 mg, 0.264 mmol), 2-methylimidazole (111 mg, 1.35 mmol) and sodium carbonate (143 mg, 1.35 mmol) in toluene (5 ml) was heated at 100° C. for 12 hours. The suspension was cooled to room temperature, 1M aqueous sodium hydroxide solution (5 ml) was added and the mixture was stirred for 1 hour. The mixture was extracted with ethyl acetate (3×20 ml) and the combined organic phases were dried over magnesium sulphate, filtered and concentrated under reduced pressure to leave a white solid. The crude product was purified by flash column chromatography on silica gel eluting with dichloromethane:methanol:ammonia (95:4.5:0.5, by volume) to provide the title compound (77 mg) as a white solid, m.p. 212–214° C.

$^1$H-NMR (300 MHz, CDCl$_3$): δ=2.14 (s, 3H), 2.33 (s, 3H), 4.92 (s, 2H), 6.76 (s, 1H), 6.79 (s, 1H), 6.86 (s, 1H), 7.27 (s, 2H). LRMS (thermospray): m/z [MH$^+$] 328.

Example 94

2-(4-(3,5-Dichlorophenoxy)-3-methyl-5-{[(3-pyridinylmethyl)amino]methyl}-1H-pyrazol-1-yl)ethanol

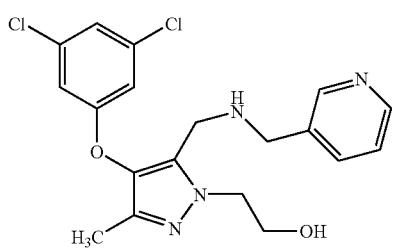

Tetrabutylammonium fluoride (0.58 ml of a 1.0M solution in tetrahydrofuran, 0.580 mmol) was added in one portion to a stirred solution of the amine of Preparation 22 (150 mg, 0.290 mmol) in dichloromethane (5 ml) at room temperature. The reaction was stirred for 12 hours and concentrated under reduced pressure to leave a colourless oil. The crude product was purified by flash column chromatography on silica gel eluting with dichloromethane:methanol:ammonia (95:4:1, by volume) to provide the title compound (100 mg) as a colourless oil.

$^1$H-NMR (400 MHz, CDCl$_3$): δ=2.07 (s, 3H), 3.65 (s, 2H), 3.76 (s, 2H), 3.96 (m, 2H), 4.24 (m, 2H), 6.76 (s, 2H), 7.02 (s, 1H), 7.26 (m, 1H), 7.59 (d, 1H), 8.50 (m, 2H). LRMS (thermospray): m/z [MH$^+$] 407.

Example 95

5-[(3-Isopropyl-5-methyl-1H-pyrazol-4-yl)oxy]isophthalonitrile

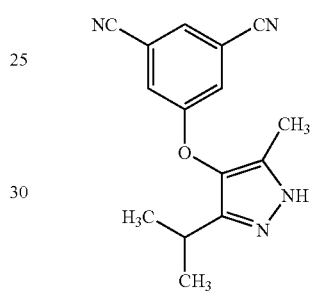

Hydrazine hydrate (110 μl, 2.24 mmol) was added to a stirred solution of the β-diketone of Preparation 24 (550 mg, 2.04 mmol) in glacial acetic acid (5 ml) and the resulting solution was stirred at room temperature for 1 hour. The mixture was concentrated under reduced pressure and the residue was purified by flash column chromatography on silica gel eluting with pentane:ethyl acetate (60:40, by volume) to provide the title compound (350 mg) as a yellow solid, m.p. 142–144° C.

$^1$H-NMR (300 MHz, CDCl$_3$): δ=1.21 (d, 6H), 2.09 (s, 3H), 2.90 (sept, 1H), 7.40 (s, 2H), 7.60 (s, 1H). LRMS (thermospray): m/z [MH$^+$] 267.

Example 96

5-{[1-(2-Hydroxyethyl)-3-isopropyl-5-methyl-1H-pyrazol-4-yl]oxy}isophthalonitrile

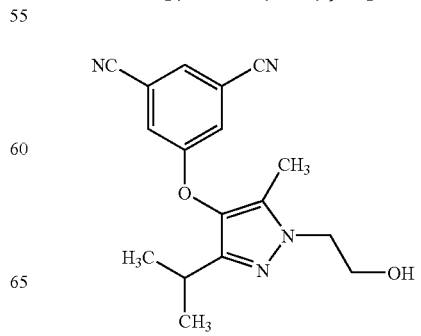

Tetrabutylammonium fluoride (0.28 ml of a 1.0M solution in tetrahydrofuran, 0.280 mmol) was added in one portion to a stirred solution of the pyrazole of Preparation 25 (60 mg, 0.140 mmol) in dichloromethane (5 ml) at room temperature. The reaction was stirred for 12 hours and concentrated under reduced pressure to leave a colourless oil. The crude product was purified by flash column chromatography on silica gel eluting with pentane:ethyl acetate (20:80, by volume) to provide the title compound (30 mg) as a white solid.

$^1$H-NMR (400 MHz, CDCl$_3$): δ=1.17 (d, 6H), 2.08 (s, 3H), 2.76 (sept, 1H), 3.52 (m, 2H), 4.10 (m, 2H), 7.40 (s, 2H), 7.59 (s, 1H). LRMS (electrospray): m/z [MH$^+$] 311. Microanalysis: Found: C, 65.44; H, 5.87; N, 17.91. C$_{17}$H$_{18}$N$_4$O$_2$ requires C, 65.79; H, 5.85; N, 18.05%.

Example 97

3-(3,5-Dichlorophenoxy)-2-ethyl-6,7-dihydropyrazolo[1,5-a]pyrazin-4(5H)-one

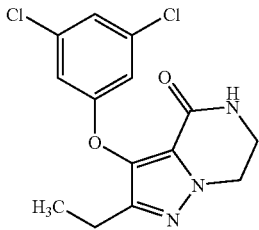

Lithium diisopropylamide (18.0 ml of a 1.5M solution in cyclohexane, 27.0 mmol) was added dropwise to a stirred solution of the pyrazole of Preparation 26 (12.3 g, 24.6 mmol) in tetrahydrofuran (120 ml) at −78° C. under nitrogen. The reaction was stirred for 14 hours, slowly warming to room temperature, and cautiously quenched with saturated aqueous ammonium chloride solution (20 ml). The mixture was concentrated under reduced pressure and the residue was dissolved in dichloromethane (200 ml). The resulting solution was washed with saturated aqueous ammonium chloride solution (100 ml), dried over magnesium sulphate, filtered and concentrated under reduced pressure to leave a white solid. The solid was triturated with a mixture of dichloromethane and pentane (100 ml and 100 ml) to give the title compound (2.63 g) as a white solid, m.p. 220–223° C.

$^1$H-NMR (400 MHz, D$_6$DMSO): δ=1.08 (t, 3H), 2.44 (q, 2H), 3.60 (m, 2H), 4.24 (t, 2H), 7.00 (s, 2H), 7.26 (s, 1H), 8.15 (s, 1H). LRMS (thermospray): m/z [MNH$_4^+$] 343. Microanalysis: Found: C, 51.52; H, 3.98; N, 12.74. C$_{14}$H$_{31}$Cl$_2$N$_3$O$_2$ requires C, 51.55; H, 4.02; N, 12.88%.

Example 98

3-(3,5-Dichlorophenoxy)-2-ethyl-4,5,6,7-tetrahydropyrazolo[1,5-a]pyrazine

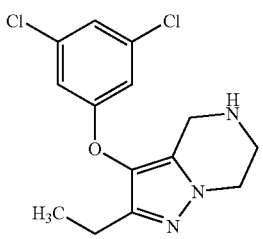

Borane (2.00 ml of a 1.0M solution in tetrahydrofuran, 2.00 mmol) was added to a stirred solution of the pyrazole of Example 97 (326 mg, 1.00 mmol) in tetrahydrofuran (10 ml) at room temperature under nitrogen. The reaction was heated under reflux for 5 hours and further borane (3.00 ml of a 1.0M solution in tetrahydrofuran, 3.00 mmol) was added. The reaction was heated under reflux for 14 hours and further borane (2.00 ml of a 1.0M solution in tetrahydrofuran, 2.00 mmol) was added. The reaction was heated under reflux for 3 hours and further borane (2.00 ml of a 1.0M solution in tetrahydrofuran, 2.00 mmol) was added. The mixture was cooled to room temperature, 2M hydrochloric acid (10 ml) was added and the mixture was heated under reflux for 1 hour. The mixture was cooled to room temperature and concentrated under reduced pressure. The residue was dissolved in dichloromethane (40 ml), washed with 1 M aqueous potassium carbonate solution (30 ml), dried over magnesium sulphate, filtered and concentrated under reduced pressure. The crude product was purified by flash column chromatography on silica gel eluting with dichloromethane:methanol (98:2, by volume), then dichloromethane:methanol (95:5, by volume) and then dichloromethane:methanol:ammonia (90:9:1, by volume) to provide the title compound (219 mg) as a white solid, m.p. 76–77° C.

$^1$H-NMR (400 MHz, CDCl$_3$): δ=1.10 (t, 3H), 2.42 (q, 2H), 3.24 (t, 2H), 3.80 (s, 2H), 4.05 (t, 2H), 6.76 (s, 2H), 6.95 (s, 1H). LRMS (thermospray): m/z [MH$^+$] 312. Microanalysis: Found: C, 53.79; H, 4.88; N, 13.14. C$_{14}$H$_{15}$Cl$_2$N$_3$O requires C, 53.86; H, 4.84; N, 13.46%.

Example 99

3-(3,5-Dichlorophenoxy)-2-ethyl-5-methyl-4,5,6,7-tetrahydropyrazolo[1,5-a]pyrazine

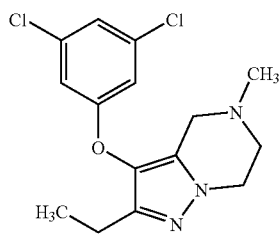

Methyl iodide (11 μl, 0.176 mmol) was added to stirred solution of potassium carbonate (24 mg, 0.176 mmol) and the amine of Example 98 (50 mg, 0.160 mmol) in N,N-dimethylformamide (2 ml) at room temperature under nitrogen. The reaction was stirred for 3 hours and then concentrated under reduced pressure. The residue was dissolved in ethyl acetate (20 ml), washed with 1M aqueous potassium carbonate solution (20 ml), dried over magnesium sulphate, filtered and concentrated under reduced pressure. The crude product was purified by flash column chromatography on silica gel eluting with dichloromethane:methanol (98:2, by volume) to provide the title compound (18 mg) as a colourless oil.

¹H-NMR (400 MHz, CDCl₃): δ=1.11 (t, 3H), 2.42 (m, 5H), 2.84 (t, 2H), 3.37 (s, 2H), 4.11 (t, 2H), 6.77 (s, 2H), 6.98 (s, 1H). LRMS (thermospray): m/z [MH⁺] 326.

Example 100

4-[(3-(3,5-Dichlorophenoxy)-2-ethyl-6,7-dihydropyrazolo[1,5-a]pyrazin-5 (4H)-yl)methyl]benzonitrile

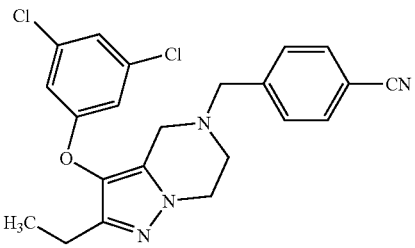

4-Cyanobenzylbromide (35 mg, 0.176 mmol) was added to a stirred solution of potassium carbonate (24 mg, 0.176 mmol) and the amine of Example 98 (50 mg, 0.160 mmol) in N,N-dimethylformamide (2 ml) at room temperature under nitrogen. The reaction was stirred for 14 hours and then concentrated under reduced pressure. The residue was dissolved in ethyl acetate (20 ml) and the resulting solution was washed with 1M aqueous potassium carbonate solution (15 ml), dried over magnesium sulphate, filtered and concentrated under reduced pressure. The crude product was purified by flash column chromatography on silica gel eluting with dichloromethane:methanol (98:2, by volume) to provide the title compound (66 mg) as a white solid, m.p. 149–150° C.

¹H-NMR (400 MHz, CDCl₃): δ=1.13 (t, 3H), 2.44 (q, 2H), 2.92 (t, 2H), 3.42 (s, 2H), 3.71 (s, 2H), 4.13 (t, 2H), 6.74 (s, 2H), 6.97 (s, 1H), 7.42 (d, 2H), 7.60 (d, 2H). LRMS (thermospray): m/z [MH⁺] 427.

Example 101

3-(3.5-Dichlorophenoxy)-2-ethyl-5-(4-methoxybenzyl)-4,5,6,7-tetrahydropyrazolo[1,5-a]pyrazine

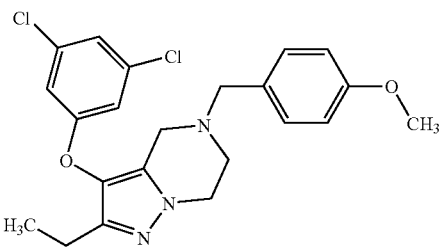

4-Methoxybenzylchloride (24 µl, 0.176 mmol) was added to a stirred solution of potassium carbonate (24 mg, 0.176 mmol) and the amine of Example 98 (50 mg, 0.160 mmol) in N,N-dimethylformamide (6 ml) at room temperature under nitrogen. The reaction was stirred for 14 hours and then potassium carbonate (12 mg, 0.088 mmol) and 4-methoxybenzylchloride (12 µl, 0.088 mmol) added. The reaction was stirred for 3 hours and then concentrated under reduced pressure. The residue was dissolved in ethyl acetate (20 ml) and the resulting solution was washed with 1M aqueous potassium carbonate solution (20 ml), dried over magnesium sulphate, filtered and concentrated under reduced pressure. The crude product was purified by flash column chromatography on silica gel eluting with dichloromethane:methanol (99:1, by volume) to provide the title compound (50 mg) as a colourless oil.

¹H-NMR (400 MHz, CDCl₃): δ=1.13 (t, 3H), 2.45 (q, 2H), 2.92 (t, 2H), 3.44 (s, 2H), 3.60 (s, 2H), 3.80 (s, 3H), 4.10 (t, 2H), 6.77 (s, 2H), 6.85 (d, 2H), 7.00 (s, 1H), 7.23 (d, 2H). LRMS (thermospray): m/z [MH⁺] 432.

Example 102

[1-(2-Aminoethyl)-4-(3,5-dichlorophenoxy)-3-ethyl-1H-pyrazol-5-yl]methanol

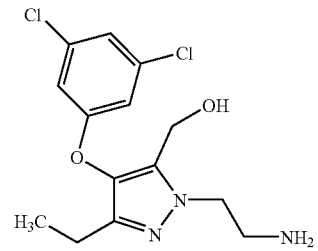

Hydrogen chloride (0.50 ml of a 4.0M solution in dioxane, 2.00 mmol) was added to a stirred solution of the pyrazole of Example 135 (86 mg, 0.200 mmol) in dioxane (0.5 ml) at room temperature under nitrogen. The reaction was stirred for 24 hours and concentrated under reduced pressure. The residue was dissolved in dichloromethane (20 ml) and the resulting solution was washed with 1M aqueous potassium carbonate solution (10 ml), dried over magnesium sulphate, filtered and concentrated under reduced pressure. The crude product was purified by flash chromatography on silica gel eluting with dichloromethane:methanol (99:1, by volume) to provide the title compound (40 mg) as a white solid, m.p. 105–107° C.

¹H-NMR (400 MHz, CDCl₃): δ=1.10 (t, 3H), 2.42 (q, 2H), 2.55 (s, 2H), 3.13 (t, 2H), 4.13 (t, 2H), 4.37 (s, 2H), 6.79 (s, 2H), 6.98 (s, 1H). LRMS (thermospray): m/z [MH⁺] 330. Microanalysis: Found: C, 50.61; H, 5.23; N, 12.31. C₁₄H₁₇Cl₂N₃O₂ requires C, 50.92; H, 5.19; N, 12.73%.

Example 103

2-[4-(3,5-Dichlorophenoxy)-5-(ethoxymethyl)-3-ethyl-1H-pyrazol-1-yl]ethylamine

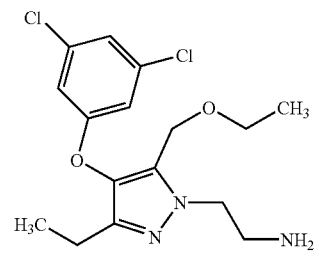

Hydrogen chloride (0.50 ml of a 4.0M solution in dioxane, 2.00 mmol) was added to a stirred solution of the pyrazole of Example 136 (60 mg, 0.130 mmol) in dioxane (0.5 ml) at room temperature under nitrogen. The reaction was stirred for 2 days and concentrated under reduced pressure. The residue was dissolved in dichloromethane (20 ml) and the resulting solution was washed with 1M aqueous potassium carbonate solution (10 ml), dried over magnesium sulphate, filtered and concentrated under reduced pressure. The crude product was purified by flash chromatography on silica gel eluting with dichloromethane:methanol:ammonia (99:9:1, by volume) to provide the title compound (32 mg) as a colourless oil.

$^1$H-NMR (400 MHz, CDCl$_3$): δ=1.10 (m, 6H), 2.42 (q, 2H), 3.15 (t, 2H), 3.40 (q, 2H), 4.11 (t, 2H), 4.29 (s, 2H), 6.79 (s, 2H), 6.98 (s, 1H). LRMS (thermospray): m/z [MH$^+$] 358.

Examples 104 to 106

The compounds of the following tabulated Examples of the general formula:

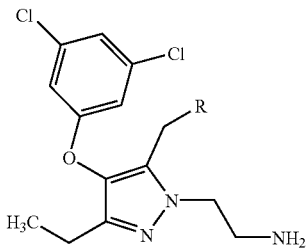

were prepared by a similar method to that of Example 103 using the appropriate starting material.

Example 107

2-[5-[(4-Acetyl-1-piperazinyl)methyl]-4-(3,5-dichlorophenoxy)-3-ethyl-1H-pyrazol-1-yl]ethylamine

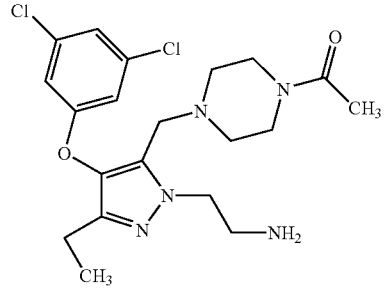

Trifluoroacetic acid (1 ml) was added to a stirred solution of the pyrazole of Example 139 (150 mg, 0.28 mmol) in dichloromethane (2 ml) at room temperature under nitrogen. The reaction was stirred for 3 hours and the mixture was concentrated under reduced pressure. The residue was dissolved in dichloromethane (20 ml) and the resulting solution was washed with 1M aqueous potassium carbonate solution (30 ml), dried over magnesium sulphate, filtered and concentrated under reduced pressure. The crude product was purified by flash chromatography on silica gel eluting with dichloromethane:methanol:ammonia (90:9:1, by volume) to provide the title compound (103 mg) as a colourless oil.

$^1$H-NMR (400 MHz, CDCl$_3$): δ=1.11 (t, 3H), 2.05 (s, 3H), 2.32 (m, 4H), 2.42 (q, 2H), 3.13 (m, 2H), 3.33 (s, 2H), 3.34 (m, 2H), 3.52 (m, 2H), 4.15 (t, 2H), 6.73 (s, 2H), 6.97 (s, 1H). LRMS (thermospray): m/z [MH$^+$] 440.

| Example No. (Starting material) | R | LRMS (thermospray) | Analytical Data |
|---|---|---|---|
| 104 (Example 140) | ![pyrazolyl] | m/z [MH$^+$] 380. | $^1$H-NMR (400MHz, CDCl$_3$): δ = 1.10 (t, 3H), 2.40 (q, 2H), 2.97 (t, 2H), 4.15 (t, 2H), 5.20 (s, 2H), 6.16 (s, 1H), 6.71 (d, 2H), 6.97 (s, 1H), 7.15 (s, 1H), 7.42 (s, 1H). Microanalysis: Found: C, 52.78; H, 5.09; N, 17.86. C$_{17}$H$_{19}$Cl$_2$N$_5$O.0.12CH$_2$Cl$_2$ requires C, 52.66; H, 4.97; N, 17.94%. |
| 105 (Example 142) | ![methoxybenzyl] | m/z [MH$^+$] 449. | $^1$H-NMR (400MHz, CDCl$_3$): CDCl$_3$): δ = 1.10 (t, 3H), 2.42 (q, 2H), 3.11 (t, 2H), 3.55 (s, 2H), 3.60 (s, 2H), 3.75 (s, 3H), 4.07 (t, 2H), 6.73 (s, 2H), 6.79 (d, 2H), 6.97 (s, 1H), 7.10 (d, 2H). Microanalysis: Found: C, 56.88; H, 5.67; N, 11.88. C$_{22}$H$_{26}$Cl$_2$N$_4$O$_2$.0.23CH$_2$Cl$_2$ requires C, 56.94; H, 5.69; N, 11.95%. |
| 106 (Example 143) | ![cyanobenzyl] | m/z [MH$^+$] 444. | $^1$H-NMR (400MHz, CDCl$_3$): δ = 1.10 (t, 3H), 2.41 (q, 2H), 3.15 (t, 2H), 3.60 (s, 2H), 3.74 (s, 2H), 4.10 (d, 2H), 6.73 (s, 2H), 6.97 (s, 1H), 7.29 (d, 2H), 7.53 (d, 2H). Microanalysis: Found: C, 57.53; H, 5.09; N, 15.05. C$_{22}$H$_{23}$Cl$_2$N$_5$O.0.22CH$_2$Cl$_2$ requires C, 57.64; H, 5.10; N, 15.12%. |

Example 108

N-[2-({[1-(2-Aminoethyl)-4-(3,5-dichlorophenoxy)-3-ethyl-1H-pyrazol-5-yl]methyl}amino)ethyl]acetamide

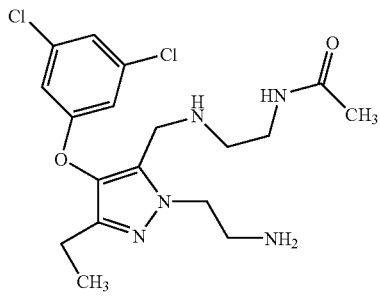

Trifluoroacetic acid (1 ml) was added to a stirred solution of the pyrazole of Example 141 (122 mg, 0.24 mmol) in dichloromethane (2 ml) at room temperature under nitrogen. The reaction was stirred for 3 hours and the mixture was concentrated under reduced pressure. The residue was dissolved in dichloromethane (50 ml) and the resulting solution was washed with 1M aqueous potassium carbonate solution (30 ml), dried over magnesium sulphate, filtered and concentrated under reduced pressure. The crude product was purified by flash chromatography on silica gel eluting with dichloromethane:methanol:ammonia (90:9:1, by volume) to provide the title compound (64 mg) as a colourless oil.

$^1$H-NMR (400 MHz, CDCl$_3$): δ=1.15 (t, 3H), 1.95 (s, 3H), 2.45 (q, 2H), 2.69 (t, 2H), 3.20 (t, 2H), 3.27 (m, 2H), 3.65 (s, 2H), 4.15 (t, 2H), 6.31 (s, 1H), 6.81 (s, 2H), 7.02 (s, 1H). LRMS (thermospray): m/z [MH$^+$] 414.

Example 109

[4-(3,5-Dichlorophenoxy)-3-methyl-1H-pyrazol-5-yl]methanamine hydrobromide

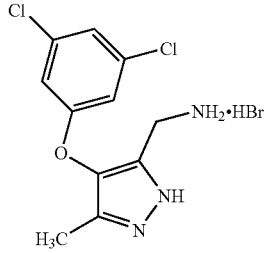

The bromide of Preparation 8 (500 mg, 1.30 mmol) was added portionwise to a saturated solution of ammonia in isopropanol (50 ml) at 0° C. The reaction was stirred for 2 hours and allowed to slowly warm to room temperature. The mixture was concentrated under reduced pressure and the resulting solid was triturated with diethyl ether to provide the title compound (340 mg) as a white solid.

$^1$H-NMR (400 MHz, CDCl$_3$): δ=2.38 (s, 3H), 4.78 (s, 2H), 6.88 (s, 2H), 7.19 (s, 1H). LRMS (thermospray): m/z [MH$^+$] 272.

Example 110

N-{[4-(3,5-Dichlorophenoxy)-3-methyl-1H-pyrazol-5-yl]methyl}-N-(4-fluorobenzyl)amine

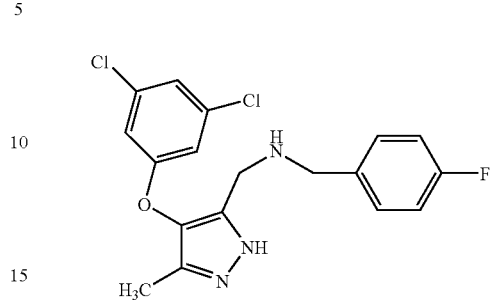

Sodium triacetoxyborohydride (36 mg, 0.160 mmol) was added in one portion to a stirred solution of the pyrazole of Example 109 (150 mg, 0.400 mmol), 4-fluorobenzaldehyde (11 mg, 0.080 mmol) and acetic acid (3 drops) in dichloromethane (15 ml) at room temperature under nitrogen. The reaction was stirred for 3 hours and then concentrated under reduced pressure. The crude product was purified by flash chromatography on silica gel eluting with dichloromethane:methanol:ammonia (90:9:1, by volume) to provide the title compound (6 mg) as a colourless oil.

$^1$H-NMR (300 MHz, CDCl$_3$): δ=2.17 (s, 3H), 3.67 (s, 2H), 3.73 (s, 2H), 6.81 (s, 2H), 6.99 (s, 2H), 7.02 (s, 1H), 7.22 (s, 2H). LRMS (electrospray): m/z [M–H$^+$] 378.

Example 111

4-[({[4-(3,5-Dichlorophenoxy)-3-methyl-1H-pyrazol-5-yl]methyl}amino)methyl]benzonitrile

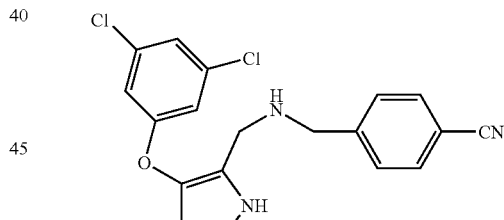

Sodium triacetoxyborohydride (216 mg, 1.09 mmol) was added in one portion to a stirred solution of the pyrazole of Example 109 (300 mg, 0.850 mmol), 4-cyanobenzaldehyde (111 mg, 0.850 mmol) and acetic acid (3 drops) in dichloromethane (25 ml) at room temperature under nitrogen. The reaction was stirred for 14 hours and then washed with 1M aqueous sodium carbonate solution (2×10 ml) and brine (10 ml), dried over magnesium sulphate, filtered and concentrated under reduced pressure. The crude product was purified by flash chromatography on silica gel eluting with dichloromethane:methanol:ammonia (95:4:1, by volume) to provide the title compound (10 mg) as a colourless oil.

$^1$H-NMR (300 MHz, CDCl$_3$): δ=2.16 (s, 3H), 3.70 (s, 2H), 3.85 (s, 2H), 6.78 (s, 2H), 7.01 (s, 2H), 7.35 (d, 2H), 7.58 (d, 2H). LRMS (electrospray): m/z [MH$^+$] 387.

Example 112

3-Chloro-5-[(1,3,5-trimethyl-1H-pyrazol-4-yl)oxy]benzonitrile

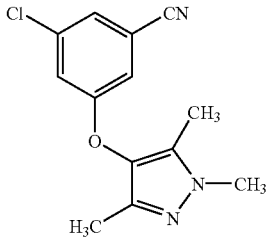

Methyl hydrazine (250 mg, 5.17 mol) was added to a stirred solution of the β-diketone of Preparation 16 (1.00 g, 3.97 mmol) in glacial acetic acid (10 ml) and the resulting solution was stirred at room temperature for 2 days. The mixture was concentrated under reduced pressure and the resulting orange oil was purified by flash column chromatography on silica gel eluting with pentane:ethyl acetate (50:50, by volume) to provide the title compound (500 mg) as a white solid, m.p. 114–116° C.

$^1$H-NMR (300 MHz, CDCl$_3$): δ=1.85 (s, 3H), 1.87 (s, 3H), 3.61 (s, 3H), 6.88 (s, 1H), 6.98 (s, 1H), 7.11 (s, 1H). LRMS (thermospray): m/z [MH$^+$] 262. Microanalysis: Found: C, 59.48; H, 4.60; N, 15.88. C$_{13}$H$_{12}$N$_3$OCl requires C, 59.66; H, 4.62; N, 16.06%.

Example 113

3-Chloro-5-[(5-{[(4-cyanobenzyl)amino]methyl-1,3-dimethyl-1H-pyrazol-4-yl)oxy]benzonitrile

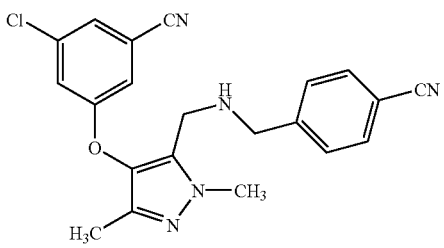

4-Cyanobenzylamine (155 mg, 1.17 mmol) was added in one portion to a stirred solution of the bromide of Example 144 (100 mg, 0.300 mmol) in isopropanol (10 ml) at room temperature. The mixture was heated at 50° C. for 1 hour, cooled to room temperature and concentrated under reduced pressure to leave a yellow oil. The crude product was purified by flash column chromatography on silica gel eluting with dichloromethane:methanol:ammonia (95:4:1, by volume) to provide the title compound (97 mg) as a colourless oil.

$^1$H-NMR (300 MHz, CDCl$_3$): δ=2.03 (s, 3H), 3.66 (s, 2H), 3.79 (s, 2H), 3.84 (s, 3H), 7.02 (s, 1H), 7.13 (s, 1H), 7.31 (s, 1H), 7.37 (d, 2H), 7.58 (d, 2H). LRMS (thermospray): m/z [MH$^+$] 392.

Example 114

3-Chloro-5-{[1-(2-hydroxyethyl)-3,5-dimethyl-1H-pyrazol-4-yl]oxy}benzonitrile

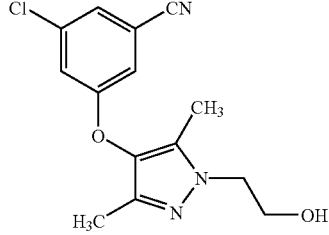

2-Hydroxyethyl hydrazine (1.80 g, 24.0 mol) was added to a stirred solution of the β-diketone of Preparation 16 (5.80 g, 23.0 mmol) in glacial acetic acid (30 ml) and the resulting solution was stirred at room temperature for 2 days. The mixture was concentrated under reduced pressure and the resulting brown oil was purified by flash column chromatography on silica gel eluting with pentane:ethyl acetate (50:50, by volume) to provide the title compound (4.80 g) as a yellow solid, m.p. 114–116° C.

$^1$H-NMR (300 MHz, CDCl$_3$): δ=2.04 (s, 3H), 2.12 (s, 3H), 3.24 (s, 1H), 4.08 (m, 4H), 7.03 (s, 1H), 7.15 (s, 1H), 7.28 (s, 1H). LRMS (thermospray): m/z [MH$^+$] 292. Microanalysis: Found: C, 57.40; H, 4.86; N, 14.14. C$_{14}$H$_{14}$N$_3$O$_2$Cl requires C, 57.69; H, 4.84; N, 14.40%.

Example 115

3-Chloro-5-{[5-{[(4-cyanobenzyl)amino]methyl}-1-(2-hydroxyethyl)-3-methyl-1H-pyrazol-4-yl]oxy}benzonitrile

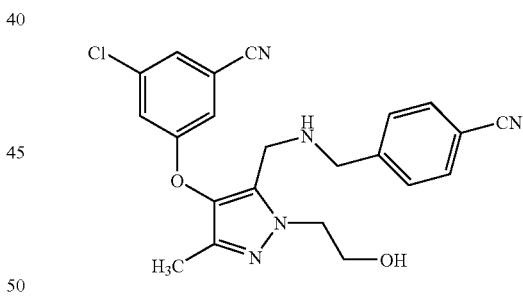

4-Cyanobenzylamine (131 mg, 0.910 mmol) was added to a stirred solution of the pyrazole of Preparation 30 (120 mg, 0.240 mmol) in N-methylpyrrolidine (10 ml) and the resulting solution was heated at 60° C. for 3 hours. The mixture was concentrated under reduced pressure and the resulting brown oil was dissolved in acetic acid (10 ml) and heated at 40° C. for 6 hours. The mixture was concentrated under reduced pressure and the crude product was purified by flash column chromatography on silica gel eluting with dichloromethane:methanol:ammonia (95:4:1, by volume) to provide the title compound (5 mg) as a white solid.

$^1$H-NMR (300 MHz, CDCl$_3$): δ=2.05 (s, 3H), 3.04 (s, 2H), 3.91 (s, 2H), 3.99 (t, 2H), 4.32 (m, 2H), 7.06 (s, 1H), 7.11 (s, 1H), 7.33 (s, 1H), 7.46 (d, 2H), 7.62 (d, 2H). LRMS (thermospray): m/z [MNa$^+$] 444.

Example 116

4-[({[4-(3-Chloro-5-cyanophenoxy)-3-methyl-1H-pyrazol-5-yl]methyl}amino)methyl]benzamide

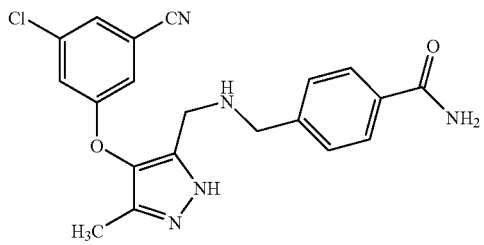

The amine of Preparation 55 (150 mg, 0.800 mmol) was added to a stirred solution of the pyrazole of Preparation 18 (100 mg, 0.270 mmol) and triethylamine (81 mg, 0.800 mmol) in isopropanol (10 ml) and N,N-dimethylformamide (5 ml) and the resulting solution was heated at 60° C. for 3 hours. The mixture was concentrated under reduced pressure and the resulting brown oil was dissolved in ethyl acetate (20 ml). The solution was washed with 1M aqueous sodium carbonate solution (2×10 ml) and brine (10 ml), dried over magnesium sulphate, filtered and concentrated under reduced pressure. The crude product was purified by flash chromatography on silica gel eluting with dichloromethane:methanol:ammonia (90:9:1, by volume) to provide the title compound (5 mg) as a colourless oil.

$^1$H-NMR (300 MHz, CDCl$_3$): δ=2.16 (s, 3H), 3.68 (s, 2H), 3.82 (s, 2H), 7.05 (s, 1H), 7.13 (s, 1H), 7.28 (s, 1H), 7.32 (d, 2H), 7.76 (d, 2H). LRMS (electrospray): m/z [MH$^+$] 396.

Examples 117 to 120

The compounds of the following tabulated Examples of the general formula:

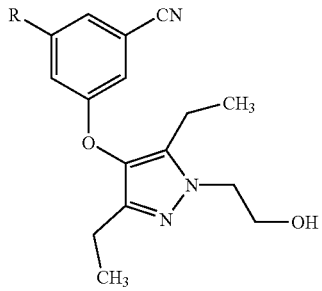

were prepared by a similar method to that of Example 114 using the appropriate diketone starting material and 2-hydroxyethylhydrazine.

| Example No. (Diketone No.) | R | LRMS | Analytical Data |
|---|---|---|---|
| 117 (Preparation 43) | F | m/z [MH$^+$] 303. (thermospray) | $^1$H-NMR(300 MHz, CDCl$_3$): δ = 1.10(m, 6H), 2.39(q, 2H), 2.49(q, 2H), 4.04(m, 4H), 6.85(dd, 1H), 6.99(s, 1H), 7.00(dd, 1H). Microanalysis: Found: C, 62.96; H, 5.94; N, 13.75. C$_{16}$H$_{18}$N$_3$O$_2$F requires C, 63.35; H, 5.98; N, 13.85%. |
| 118 (Preparation 44) | Me | m/z [MH$^+$] 300. (electrospray) | $^1$H-NMR(400 MHz, CDCl$_3$): δ = 1.09(t, 3H), 1.12(t, 3H), 2.34(s, 3H), 2.39(q, 2H), 2.50(q, 2H), 3.70(s, 1H), 4.60(m, 4H), 6.91(s, 1H), 6.97(s, 1H), 7.10(s, 1H). |
| 119 (Preparation 45) | CN | m/z [MH$^+$] 311. (electrospray) | $^1$H-NMR(400 MHz, CDCl$_3$): δ = 1.13(m, 6H), 2.40(q, 2H), 2.53(q, 2H), 3.53(m, 1H), 4.11(m, 4H), 7.40(s, 2H), 7.58(s, 1H). Microanalysis: Found: C, 65.64; H, 5.84; N, 18.05. C$_{17}$H$_{18}$N$_4$O$_2$ requires C, 65.79; H, 5.85; N, 18.05%. m.p. 120–121° C. |
| 120 (Preparation 46) | Cl | m/z [MH$^+$] 320. (thermospray) | $^1$H-NMR(400 MHz, CDCl$_3$): δ = 1.08(m, 6H), 2.39(q, 2H), 2.50(q, 2H), 4.01(m, 2H), 4.08(m, 2H), 7.03(s, 1H), 7.13(s, 1H), 7.24(s, 1H). Microanalysis: Found: C, 59.67; H, 5.71; N, 12.99. C$_{16}$H$_{18}$N$_3$O$_2$Cl requires C, 60.09; H, 5.67; N, 13.14%. |

Examples 121 to 124

The compounds of the following tabulated Examples of the general formula:

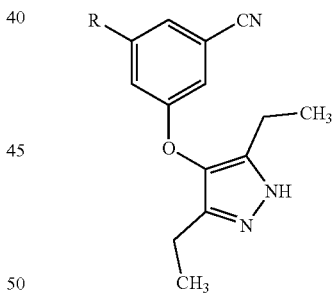

were prepared by a similar method to that of Example 76 using the appropriate diketone starting material and hydrazine.

| Example No. (Diketone No.) | R | LRMS | Analytical Data |
|---|---|---|---|
| 121 (Preparation 43) | F | m/z [MH$^+$] 260. (thermospray) | $^1$H-NMR(400 MHz, CDCl$_3$): δ = 1.18(t, 6H), 2.47(q, 4H), 6.85(dd, 1H), 6.98(s, 1H), 7.01(dd, 1H). |
| 122 (Preparation 45) | CN | m/z [MH$^+$] 267. (thermospray) | $^1$H-NMR(400 MHz, CDCl$_3$): δ = 1.20(6H, m), 2.47(q, 4H), 7.39(s, 2H), 7.59(s, |

-continued

| Example No. (Diketone No.) | R | LRMS | Analytical Data |
|---|---|---|---|
| 123 (Preparation 44) | Me | m/z [MH$^+$] 256. (electrospray) | 1H). $^1$H-NMR(400 MHz, CDCl$_3$): δ = 1.17(t, 6H), 2.34(s, 3H), 2.48(q, 4H), 6.92(s, 1H), 6.96(s, 1H), 7.10(s, 1H). |
| 124 (Preparation 46) | Cl | m/z [MH$^+$] 276. (thermospray) | $^1$H-NMR(400 MHz, CDCl$_3$): δ = 1.18(t, 6H), 2.49(q, 4H), 7.07(s, 1H), 7.13(s, 1H), 7.27(s, 1H). |

Examples 125 to 128

The compounds of the following tabulated Examples of the general formula:

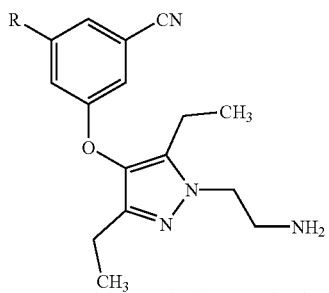

were prepared by a similar method to that of Example 13 using the appropriate pyrazole starting material and chloroethylamine hydrochloride.

| Example No. (Starting pyrazole No.) | R | LRMS | Analytical Data |
|---|---|---|---|
| 125 (Example 123) | Me | m/z [MH$^+$] 299. (electrospray) | $^1$H-NMR(400 MHz, CDCl$_3$): δ = 1.10(m, 6H), 2.34(s, 3H), 2.39(q, 2H), 2.43(q, 2H), 3.17(t, 2H), 4.04(t, 2H), 6.91(s, 1H), 6.96(s, 1H), 7.09(s, 1H). |
| 126 (Example 124) | Cl | m/z [MH$^+$] 319. (thermospray) | $^1$H-NMR(400 MHz, CDCl$_3$): δ = 1.09(m, 6H), 2.40(q, 2H), 2.51(q, 2H), 3.15(m, 2H), 4.02(m, 2H), 7.04(s, 1H), 7.12(s, 1H), 7.28(s, 1H). |
| 127 (Example 122) | CN | m/z [MH$^+$] 310. (thermospray) | $^1$H-NMR(400 MHz, CDCl$_3$): δ = 1.09(m, 6H), 2.38(q, 2H), 2.50(q, 2H), 3.15(m, 2H), 4.03(m, 2H), 7.39(s, 2H), 7.57(s, 1H). |
| 128 (Example 121) | F | m/z [MH$^+$] 303. (thermospray) | $^1$H-NMR(400 MHz, CDCl$_3$): δ = 1.06(m, 6H), 2.37(q, 2H), 2.48(q, 2H), 3.13(t, 2H), 4.03(t, 2H), 6.84(d, 1H), 6.94(s, 1H), 6.97(d, 1H). |

Examples 129 to 131

The compounds of the following tabulated Examples of the general formula:

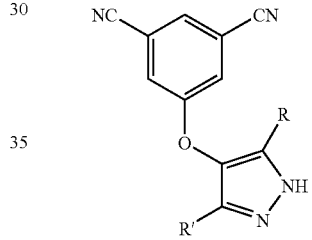

were prepared by a similar method to that of Example 76 using the appropriate diketone starting material and hydrazine.

| Example No. (Diketone No.) | R | R' | LRMS | Analytical Data |
|---|---|---|---|---|
| 129 (Preparation 52) | cycloPr | Et | m/z [MH$^+$] 279. (electrospray) | $^1$H-NMR(400 MHz, CDCl$_3$): 0.73(m, 2H), 0.81(m, 2H), 1.16(t, 3H), 1.58(m, 1H), 2.46(q, 2H), 7.42(s, 2H), 7.58(s, 1H). m.p. 136–141° C. |
| 130 (Preparation 53) | tBu | Me | m/z [MH$^+$] 281. (electrospray) | $^1$H-NMR(300 MHz, CDCl$_3$): 1.21(s, 9H), 1.94(s, 3H), 7.34(s, 2H), 7.56(s, 1H). Microanalysis: Found: C, 68.18; H, 5.74; N, 19.72. C$_{16}$H$_{16}$N$_4$O requires C, 68.55; H, 5.75; N, 19.99%. m.p. 61–63° C. |
| 131 (Preparation 54) | iPr | Et | m/z [MH$^+$] 281. (electrospray) | $^1$H-NMR(400 MHz, CDCl$_3$): 1.15(m, 9H), 2.41(q, 2H), 2.82 (m, 1H), 7.36(s, 2H), 7.58(s, 1H). m.p. 136–141° C. |

Example 132

4-(3,5-Dichlorophenoxy)-3,5-diethyl-1-(1-methyl-3-azetidinyl)-1H-pyrazole

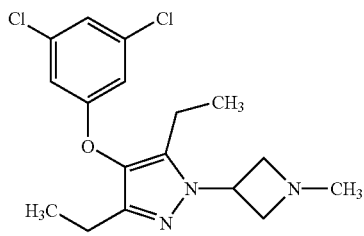

Paraformaldehyde (30 mg, 0.330 mmol) was added in one portion to a stirred solution of the pyrazole of Example 51 (120 mg, 0.330 mmol) in formic acid (2 ml) at room temperature. The mixture was heated at 100° C. for 5 hours, cooled to room temperature and concentrated under reduced pressure to leave a colourless oil. The oil was dissolved in ethyl acetate (50 ml) and the resulting solution was washed with saturated aqueous sodium hydrogencarbonate (20 ml), water (20 ml) and brine (20 ml), dried over magnesium sulphate, filtered and concentrated under reduced pressure. The crude product was purified by flash column chromatography on silica gel eluting with dichloromethane:methanol:ammonia (95:4:1, by volume) to provide the title compound (85 mg) as a colourless oil.

$^1$H-NMR (300 MHz, CDCl$_3$): δ=1.08 (t, 3H), 1.16 (t, 3H), 2.49 (m, 7H), 3.63 (m, 2H), 3.81 (m, 2H), 4.79 (m, 1H), 6.79 (s, 2H), 7.00 (s, 1H). LRMS (thermospray): m/z [MH$^+$] 354.

Examples 133–134

2-[4-(3,5-Dichlorophenoxy)-3-ethyl-1H-pyrazol-1-yl]ethylamine (Example 133) and 2-[4-(3,5-Dichlorophenoxy)-5-ethyl-1H-pyrazol-1-yl]ethylamine (Example 134)

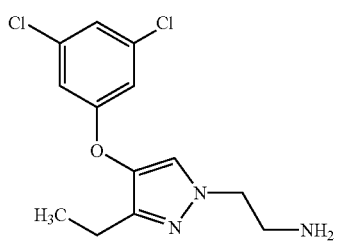
(133)

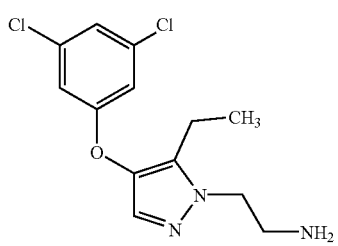
(134)

A mixture of the pyrazole (1.03 g, 4.00 mmol) of Example 42 and chloroethylamine hydrochloride (510 mg, 4.40 mmol) was stirred and heated at 150° C. for 24 hours. After cooling the mixture was partitioned between 1M aqueous potassium carbonate solution (30 ml) and dichloromethane (30 ml). The organic layer was washed with brine (30 ml), dried over magnesium sulphate, filtered and concentrated under reduced pressure. The resulting brown oil was purified by flash chromatography on silica gel eluting with dichloromethane:methanol:ammonia (93:6:1, by volume) to afford the title compounds (768 mg) in a 85:15 ratio of regioisomers as a colourless oil.

$^1$H-NMR (400 MHz, CDCl$_3$): δ=1.16 (major, t, 3H), 1.16 (minor, t, 3H), 2.48 (major, q, 2H), 2.60 (minor, q, 2H), 3.13 (major, t, 2H), 3.19 (minor, t, 2H), 4.10 (major, t, 2H), 4.10 (minor, t, 2H), 6.85 (major, s, 2H), 6.85 (minor, s, 2H), 7.02 (major, s, 1H), 7.02 (minor, s, 1H), 7.27 (major, s, 1H), 7.31 (minor, s, 1H). LRMS (thermospray): m/z [MH$^+$] 300.

Example 135 tert-Butyl 2-[4-(3,5-dichlorophenoxy)-3-ethyl-5-(hydroxymethyl)-1H-pyrazol-1-yl]ethylcarbamate

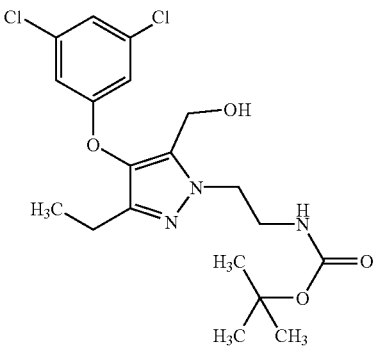

A solution of the pyrazole of Example 97 (1.96 g, 6.00 mmol) in concentrated hydrochloric acid (50 ml) was heated under reflux for 20 hours. The reaction was cooled to room temperature and concentrated under reduced pressure. The residue was dissolved in dioxane (80 ml) and water (60 ml), di-t-butyldicarbonate (1.44 g, 6.60 mmol) and sodium hydrogencarbonate (1.26 g, 15.0 mmol) were added and the reaction was stirred at room temperature for 3 days. The reaction was concentrated under reduced pressure. A solution of the residue in dichloromethane (300 ml) was washed with 2M aqueous hydrochloric acid (100 ml), dried over magnesium sulphate, filtered and concentrated under reduced pressure. A solution of the crude product in tetrahydrofuran (50 ml) was cooled to −40° C. under nitrogen and triethylamine (0.79 ml, 5.68 mmol) and isopropylchloroformate (5.68 ml of a 1.0M solution in toluene, 5.68 mmol) were added dropwise. The reaction was stirred at −40° C. for 40 minutes and then warmed to 0° C. Sodium borohydride (537 mg, 14.2 mmol) was added in one portion and then water (3 drops) was added and the reaction was stirred at 0° C. for 1 hour and at room temperature for 14 hours. The mixture was concentrated under reduced pressure and a solution of the residue in dichloromethane (100 ml) was washed with water (100 ml), dried over magnesium sulphate, filtered and concentrated under reduced pressure. The crude product was purified by flash chromatography on silica gel eluting with dichloromethane:methanol (97:3, by volume) to provide the title compound (1.37 g) as a white foam.

$^1$H-NMR (400 MHz, CDCl$_3$): δ=1.10 (t, 3H), 1.37 (s, 9H), 2.40 (q, 2H), 3.00 (s, 1H), 3.56 (m, 2H), 4.20 (t, 2H), 4.48 (d, 2H), 5.00 (m, 1H), 6.80 (s, 2H), 6.97 (s, 1H). LRMS (thermospray): m/z [MH$^+$] 430.

Example 136 tert-Butyl 2-[4-(3,5-dichlorophenoxy)-5-(ethoxymethyl)-3-ethyl-1H-pyrazol-1-yl]ethylcarbamate

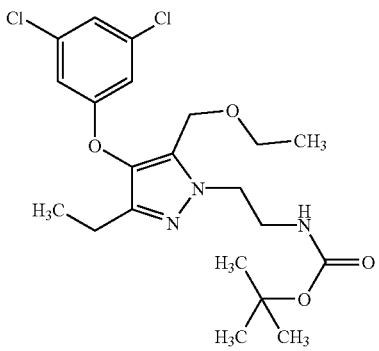

Silver(I)oxide (210 mg, 0.900 mmol) was added in one portion to a stirred solution of the alcohol of Example 135 (129 mg, 0.300 mmol) in ethyl iodide (1.75 ml) at room temperature under nitrogen. The reaction was heated at 40° C. for 1 day and then cooled to room temperature. The mixture was filtered and the residual solid was washed with dichloromethane (10 ml). The filtrate was concentrated under reduced pressure. The crude product was purified by flash chromatography on silica gel eluting with dichloromethane:methanol (99:1, by volume) to provide the title compound (60 mg) as a colourless oil.

$^1$H-NMR (400 MHz, CDCl$_3$): δ=1.15 (m, 6H), 1.44 (s, 9H), 2.45 (q, 2H), 3.45 (q, 2H), 3.58 (m, 2H), 4.18 (m, 2H), 4.29 (s, 2H), 5.26 (m, 1H), 6.92 (s, 2H), 7.00 (s, 1H). LRMS (electrospray): m/z [MNa$^+$] 480.

Example 137 tert-Butyl 2-[5-(bromomethyl)-4-(3,5-dichlorophenoxy)-3-ethyl-1H-pyrazol-1-yl]ethylcarbamate

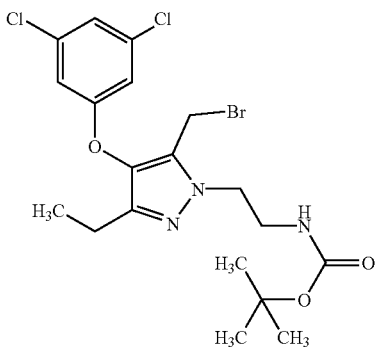

Bromine (160 1,3.12 mmol) was added dropwise to a stirred solution of triphenylphosphine (820 mg, 3.12 mmol) and imidazole (213 mg, 3.12 mmol) in dichloromethane (15 ml) at room temperature under nitrogen. A solution of the alcohol of Example 135 (1.12 g, 2.60 mmol) in dichloromethane (5 ml) was then added to the reaction. The reaction was stirred at room temperature for 2 hours, diluted with dichloromethane (50 ml), washed with brine (20 ml), dried over magnesium sulphate, filtered and concentrated under reduced pressure. The crude product was purified by flash chromatography on silica gel eluting with dichloromethane:methanol (98:2, by volume) to provide the title compound (969 mg) as a white foam.

$^1$H-NMR (400 MHz, CDCl$_3$): δ=1.10 (t, 3H), 1.40 (s, 9H), 2.40 (q, 2H), 3.60 (m, 2H), 4.18 (t, 2H), 4.27 (s, 2H), 4.95 (s, 1H), 6.82 (s, 2H), 7.00 (s, 1H). LRMS (electrospray): m/z [MH$^+$] 494. Microanalysis: Found: C, 46.22; H, 4.89; N, 8.44. C$_{19}$H$_{24}$BrCl$_2$N$_3$O$_3$ requires C, 46.27; H, 4.90; N, 8.52%.

Example 138 tert-Butyl 2-[5-(aminomethyl)-4-(3,5-dichlorophenoxy)-3-ethyl-1H-pyrazol-1-yl]ethylcarbamate

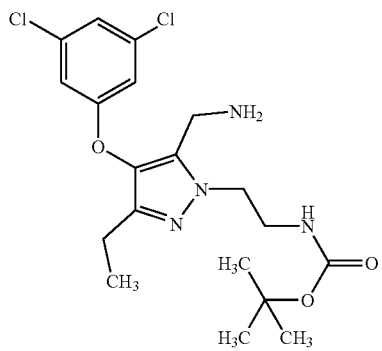

The bromide of Example 137 (444 mg, 0.900 mmol) was added to a saturated solution of ammonia in isopropanol (25 ml) and diisopropylethylamine (173μ, 1.00 mmol) at room temperature. The reaction was stirred for 5 hours and then concentrated under reduced pressure. The crude product was purified by flash chromatography on silica gel eluting with dichloromethane:methanol (95:5, by volume) to provide the title compound (359 mg) as a white solid, m.p. 112–114° C.

$^1$H-NMR (400 MHz, CDCl$_3$): δ=1.11 (t, 3H), 1.40 (s, 9H), 2.40 (q, 2H), 3.55 (m, 2H), 3.73 (s, 2H), 4.18 (t, 2H), 5.60 (s, 1H), 6.77 (s, 2H), 6.98 (s, 1H). LRMS (thermospray): m/z [MH$^+$] 429.

Example 139 tert-Butyl 2-[5-[(4-acetyl-1-piperazinyl)methyl]-4-(3,5-dichlorophenoxy)-3-ethyl-1H-pyrazol-1-yl]ethylcarbamate

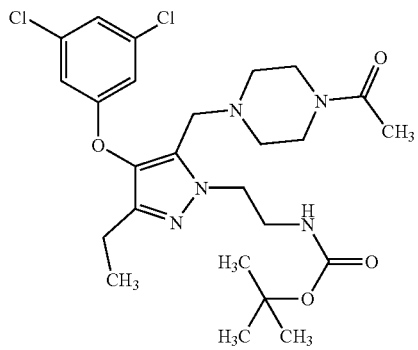

N-Acetylpiperazine (42 mg, 0.330 mmol) in N,N-dimethylformamide (1 ml) was added to a stirred solution of the bromide of Example 137 (148 mg, 0.300 mmol) and diisopropylethylamine (57 μL, 0.330 mmol) in N,N-dimethylformamide (2 ml) at room temperature. The reaction was stirred for 5 hours and the mixture was concentrated under reduced pressure. A solution of the residue in dichloromethane (30 ml) was washed with 1M aqueous potassium carbonate solution (10 ml), dried over magnesium sulphate, filtered and concentrated under reduced pressure. The crude product was purified by flash chromatography on silica gel eluting with dichloromethane:methanol (98:2, by volume) to provide the title compound (150 mg) as a colourless oil.

$^1$H-NMR (400 MHz, CDCl$_3$): δ=1.15 (t, 3H), 1.42 (s, 9H), 2.06 (s, 3H), 2.44 (m, 6H), 3.32 (s, 2H), 3.47 (m, 2H), 3.60 (m, 2H), 3.65 (m, 2H), 4.23 (m, 2H), 5.89 (s, 1H), 6.76 (s, 2H), 7.02 (s, 1H). LRMS (thermospray): m/z [MH$^+$] 540.

Example 140 tert-Butyl 2-[4-(3,5-dichlorophenoxy)-3-ethyl-5-(1H-pyrazol-1-ylmethyl)-1H-pyrazol-1-yl]ethylcarbamate

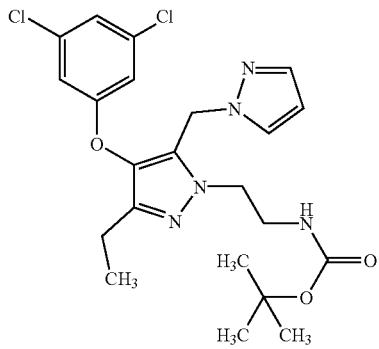

Pyrazole (23 mg, 0.330 mmol) was added in one portion to a stirred solution of the bromide of Example 137 (148 mg, 0.300 mmol) and sodium hydride (60% dispersion in oil, 13.2 mg, 0.330 mmol) in N,N-dimethylformamide (2 ml) at room temperature under nitrogen. The reaction was stirred for 5 hours, quenched with water (1.00 ml) and concentrated under reduced pressure. The residue was dissolved in dichloromethane (30 ml) and the resulting solution was washed with 1M aqueous potassium carbonate solution (10 ml), dried over magnesium sulphate, filtered and concentrated under reduced pressure. The crude product was purified by flash chromatography on silica gel eluting with dichloromethane:methanol (98:2, by volume) to provide the title compound (125 mg) as a colourless oil.

$^1$H-NMR (400 MHz, CDCl$_3$): δ=1.13 (t, 3H), 1.44 (s, 9H), 2.42 (q, 2H), 3.52 (m, 2H), 4.26 (t, 2H), 5.18 (s, 2H), 5.48 (s, 1H), 6.16 (s, 1H), 6.73 (s, 2H), 7.00 (s, 1H), 7.18 (s, 1H), 7.45 (s, 1H). LRMS (thermospray): m/z [MH$^+$] 480.

Example 141 tert-Butyl 2-[5-({[2-(acetylamino)ethyl]amino}methyl)-4-(3,5-dichlorophenoxy)-3-ethyl-1H-pyrazol-1-yl]ethylcarbamate

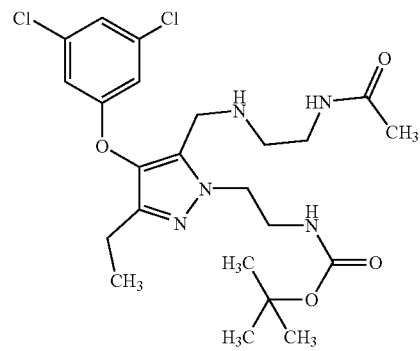

N-Acetylethylenediamine (153 mg, 1.50 mmol) in isopropanol (1 ml) was added to a stirred solution of the bromide of Example 137 (148 mg, 0.300 mmol) and diisopropylethylamine (57 μl, 0.330 mmol) in isopropanol (2 ml) at room temperature. The reaction was stirred for 5 hours and the mixture was concentrated under reduced pressure. A solution of the residue in dichloromethane (50 ml) was washed with 1M aqueous potassium carbonate solution (20 ml), dried over magnesium sulphate, filtered and concentrated under reduced pressure. The crude product was purified by flash chromatography on silica gel eluting with dichloromethane:methanol (90:10, by volume) then dichloromethane:methanol:ammonia (90:9:1, by volume) to provide the title compound (122 mg) as a colourless oil.

$^1$H-NMR (400 MHz, CDCl$_3$): δ=1.13 (t, 3H), 1.42 (s, 9H), 1.94 (d, 3H), 2.44 (q, 2H), 2.74 (m, 2H), 3.35 (m, 2H), 3.58 (m, 4H), 4.19 (m, 2H), 5.68 (s, 1H), 6.77 (s, 2H), 7.00 (s, 1H), 7.65 (s, 1H). LRMS (thermospray): m/z [MH$^+$] 514.

Example 142 tert-Butyl 2-(4-(3,5-dichlorophenoxy)-3-ethyl-5-{[(4-methoxybenzyl)amino]methyl}-1H-pyrazol-1-yl)ethylcarbamate

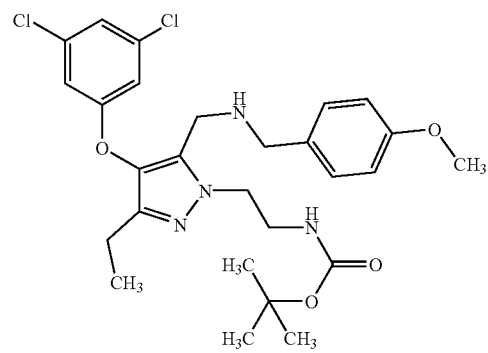

4-Methoxybenzaldehyde (46 μl, 0.380 mmol), the amine of Example 138 (172 mg, 0.400 mmol) and magnesium sulphate (200 mg) were stirred in dichloromethane (4 ml) at room temperature for 4 days. The mixture was filtered and the filtrate was concentrated under reduced pressure to leave a yellow oil. The oil was dissolved in methanol (4 ml) and sodium borohydride (18 mg, 0.480 mmol) was added with vigorous stirring. Once the addition was complete the reaction was stirred for 4 hours and then water (2 ml) was added. The mixture was concentrated under reduced pressure and the residue was dissolved in dichloromethane (50 ml). The resulting solution was washed with 1M aqueous potassium carbonate solution (20 ml), dried over magnesium sulphate, filtered and concentrated under reduced pressure. The crude product was purified by flash chromatography on silica gel eluting with dichloromethane:methanol (99:1, by volume) and then dichloromethane:methanol (95:5, by volume) to provide the title compound (142 mg) as a colourless oil.

$^1$H-NMR (400 MHz, CDCl$_3$): δ=1.10 (t, 3H), 1.40 (s, 9H), 2.42 (m, 2H), 3.55 (m, 5H), 3.66 (s, 2H), 3.77 (s, 2H), 4.15 (m, 2H), 6.11 (s, 1H), 6.74 (s, 2H), 6.80 (d, 2H), 7.00 (s, 1H), 7.11 (d, 2H). LRMS (thermospray): m/z [MH$^+$] 549.

Example 143 tert-Butyl 2-[5-{[(4-cyanobenzyl)amino]methyl}-4-(3,5-dichlorophenoxy)-3-ethyl-1H-pyrazol-1-yl]ethylcarbamate

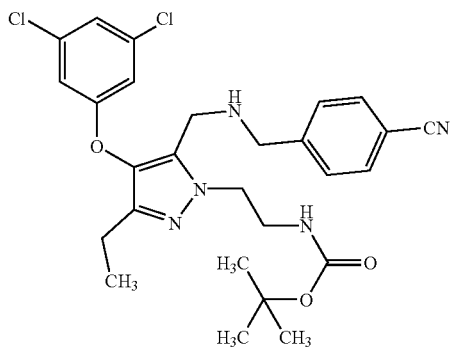

A mixture of 4-cyanobenzaldehyde (50 mg, 0.380 mmol), the amine of Example 138 (172 mg, 0.400 mmol), magnesium sulphate (200 mg) and dichloromethane (4 ml) was stirred at room temperature for 4 days. The mixture was filtered and the filtrate was concentrated under reduced pressure to leave a yellow oil. The oil was dissolved in methanol (4 ml) and sodium borohydride (18 mg, 0.480 mmol) was added with vigorous stirring. Once the addition was complete the reaction was stirred for 4 hours and then water (2 ml) was added. The mixture was concentrated under reduced pressure and the residue was dissolved in dichloromethane (50 ml). The resulting solution was washed with 1M aqueous potassium carbonate solution (20 ml), dried over magnesium sulphate, filtered and concentrated under reduced pressure. The crude product was purified by flash chromatography on silica gel eluting with dichloromethane:methanol (99:1, by volume) then dichloromethane:methanol (95:5, by volume) to provide the title compound (120 mg) as a colourless oil.

$^1$H-NMR (400 MHz, CDCl$_3$): δ=1.10 (t, 3H), 1.35 (s, 9H), 2.40 (q, 2H), 3.55 (m, 2H), 3.58 (s, 2H), 3.76 (s, 2H), 4.16 (m, 2H), 5.45 (s, 1H), 6.73 (s, 2H), 6.98 (s, 1H), 7.32 (d, 2H), 7.55 (d, 2H). LRMS (thermospray): m/z [MH$^+$] 544.

Example 144

3-{[5-(Bromomethyl)-1,3-dimethyl-1H-pyrazol-4-yl]oxy}-5-chlorobenzonitrile

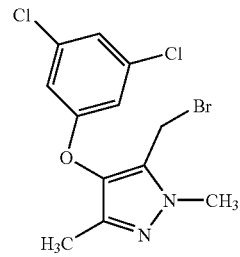

N-Bromosuccinimide (340 mg, 1.90 mmol) was added to a stirred solution of the pyrazole of Example 112 (500 mg, 1.90 mmol) in carbon tetrachloride (10 ml) and azobisisobutyronitrile (20 mg) at room temperature under nitrogen. The reaction was heated under reflux for 1 hour, cooled to room temperature and concentrated under reduced pressure. The crude product was purified by flash column chromatography on silica gel eluting with pentane:ethyl acetate (80:20, by volume) to provide the title compound (340 mg) as a white solid, m.p. 76–78° C.

$^1$H-NMR (300 MHz, CDCl$_3$): δ=2.03 (s, 3H), 3.45 (s, 3H), 4.32 (s, 2H), 7.12 (s, 1H), 7.19 (s, 1H), 7.34 (s, 1H). LRMS (thermospray): m/z [MH$^+$] 342.

Example 145

3-[(3,5-Diethyl-1-methyl-1H-pyrazol-4-yl)oxy]benzonitrile

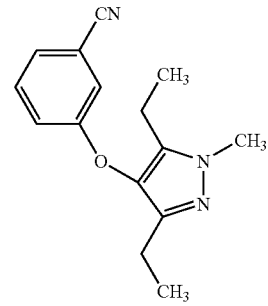

Sodium hydride (60% dispersion in oil, 22 mg, 0.53 mmol) was added to a solution of the pyrazole from Example 60 (100 mg, 0.41 mmol) and methyl iodide (34 μl, 0.53 mmol) in dimethylformamide (1.5 ml) at 0° C. under nitrogen. The reaction was allowed to warm to room temperature and was stirred for 4 hours. The reaction was quenched with water and the solvent was removed under reduced pressure. The residue was partitioned between ethyl acetate (20 ml) and water (10 ml) and the organic phase was washed with water (2×10 ml), dried over magnesium sulphate and concentrated under reduced pressure. The residual oil was purified by flash chromatography on silica gel eluting with a solvent gradient of 100% pentane changing to 100% ethyl acetate and finally ethyl acetate:methanol (10:1, by volume) to provide the title compound (65 mg) as a colourless oil.

$^1$H NMR (400 MHz, CDCl$_3$): δ=1.09 (t, 3H), 1.12 (t, 3H), 2.41 (q, 2H), 2.50 (q, 2H), 3.77 (s, 3H), 7.12–7.38 (m, 4H). LRMS (electrospray): m/z [MH$^+$] 256, [MNa$^+$] 278. Microanalysis: Found C, 70.15; H, 6.78; N, 16.42. C$_{15}$H$_{15}$N$_3$O.0.08H$_2$O requires C, 70.17; H, 6.74; N, 16.37%.

Example 146

3-{[35-Diethyl-1-(2-methoxyethyl)-1H-pyrazol-4-yl]oxy}benzonitrile

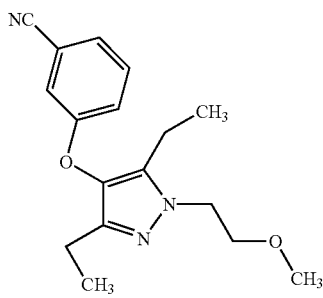

Sodium hydride (60% dispersion in oil, 22 mg, 0.54 mmol) was added to a solution of the pyrazole from Example 60 (100 mg, 0.41 mmol) and 1-bromo-2-methoxyethane (51 μl, 0.54 mmol) in dimethylformamide (1.5 ml) at 0° C. under nitrogen. The reaction was allowed to warm to room temperature and was stirred for 4 hours. The reaction was quenched with water and the solvent was removed under reduced pressure. The residue was partitioned between ethyl acetate (20 ml) and water (10 ml) and the organic phase was washed with water (2×10 ml), dried over magnesium sulphate and concentrated under reduced pressure. The residual oil was purified by flash chromatography on silica gel eluting with a solvent gradient of 100% pentane changing to 100% ethyl acetate and finally ethyl acetate:methanol (90:10, by volume) to provide the title compound (66 mg) as a colourless oil.

$^1$H NMR (400 MHz, CDCl$_3$): δ=1.09 (t, 3H), 1.12 (t, 3H), 2.42 (q, 2H), 2.54 (q, 2H), 3.34 (s, 3H), 3.75 (t, 2H), 4.16 (t, 2H), 7.11–7.38 (m, 4H). LRMS (electrospray): m/z [MH$^+$] 300, [MNa$^+$] 322. Microanalysis: Found C, 68.21; H, 7.07; N, 14.04. C$_{17}$H$_{21}$N$_3$O$_2$ requires C, 67.85; H, 7.12; N, 14.09%.

Example 147

3-({5-[2-(Benzyloxy)ethyl]-3-ethyl-1H-pyrazol-4-yl}oxy)-5-fluorobenzonitrile

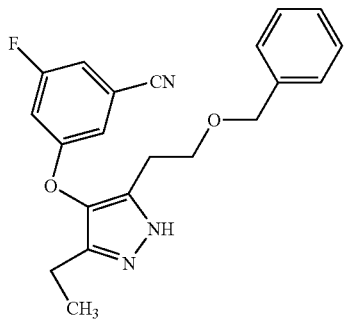

Hydrazine hydrate (390 μl, 8.00 mmol) was added to a solution of the enol from Preparation 60 (2.47 g, 6.69 mmol) in acetic acid (5 ml) under nitrogen at room temperature. After stirring for 18 hours, the mixture was concentrated under reduced pressure and purified by flash chromatography on silica gel eluting with pentane:ethyl acetate (70:30 changing to 50:50, by volume) to provide the title compound (5.8 g) as a yellow oil.

$^1$H NMR (400 MHz, CDCl$_3$): δ=1.13 (t, 3H), 2.41 (q, 2H), 2.67 (t, 2H), 3.62 (t, 2H), 4.48 (s, 2H), 6.79 (m, 1H), 6.98 (m, 2H), 7.24 (m, 5H). LRMS (electrospray): m/z [M–H$^+$] 364. Microanalysis: Found C, 66.96; H, 5.62; N, 11.25. C$_{21}$H$_{20}$N$_3$O$_2$F.0.60H$_2$O requires C, 67.04; H, 5.68; N, 11.17%.

Example 148

3-{[3-Ethyl-5-(2-hydroxyethyl)-1H-pyrazol-4-yl]oxy}-5-fluorobenzonitrile

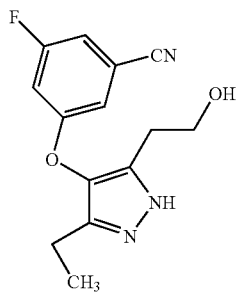

Iron(III)chloride (9.30 g, 57.5 mmol) was added to a solution of the pyrazole from Example 147 (2.10 g, 5.75 mmol) in dichloromethane (90 ml) under nitrogen at room temperature. After stirring for 20 minutes the mixture was diluted with dichloromethane (50 ml), washed with water (100 ml) then saturated aqueous sodium ethylenediaminetetraacetate solution (70 ml), dried over magnesium sulphate and concentrated under reduced pressure. The residue was purified by flash chromatography on silica gel eluting with dichloromethane:methanol (98:2 changing to 95:5, by volume) to provide the title compound (1.2 g) as a brown oil which solidified on standing.

$^1$H NMR (400 MHz, CDCl$_3$): δ=1.16 (t, 3H), 2.44 (q, 2H), 2.63 (t, 2H), 3.82 (t, 2H), 6.82 (m, 1H), 6.98 (m, 2H). LRMS (electrospray): m/z [MH$^+$] 276. Microanalysis: Found C, 60.69; H, 5.12; N, 15.08. C$_{14}$H$_{14}$N$_3$O$_2$F requires C, 61.08; H, 5.13; N, 15.26%.

Example 149

3-({5-[2-(4-Cyanophenoxy)ethyl]-3-ethyl-1H-pyrazol-4-yl}oxy)-5-fluorobenzonitrile

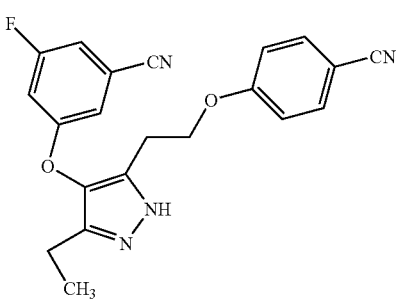

4-Hydroxy-benzonitrile (49 mg, 0.41 mmol), triphenylphosphine (106 mg, 0.41 mmol) and diethylazodicarboxylate (65 μl, 0.41 mmol) were added sequentially to a solution of the alcohol from Example 148 (74 mg, 0.27 mmol) in tetrahydrofuran (2 ml) under nitrogen at 0° C. The reaction was allowed to warm to room temperature and was stirred for 18 hours. The mixture was concentrated under reduced pressure and purified by flash chromatography on silica gel eluting with toluene:ethyl acetate (75:25, by volume) to provide the title compound (50 mg) as a yellow oil.

$^1$H NMR (400 MHz, CDCl$_3$): δ=1.18 (t, 3H), 2.49 (q, 2H), 2.98 (t, 2H), 4.21 (t, 2H), 6.82 (m, 3H), 6.99 (m, 2H), 7.56 (m, 2H). LRMS (electrospray): m/z [MH$^+$] 377.

Examples 150–152

The preparations of the following tabulated Examples of the general formula

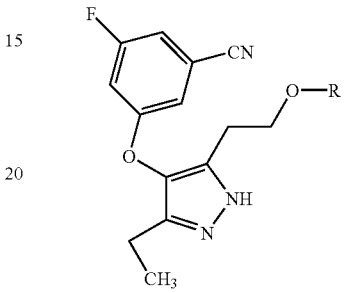

were performed by a similar method to that of Example 149 using the appropriate aryl alcohol as the starting material.

| Example No. | Starting Material Example No. | R | Analytical Data |
|---|---|---|---|
| 150[1] | 148 | 3-methylpyridin-2-yl (attached via position 3) | $^1$H NMR (400MHz, CDCl$_3$): δ = 1.18 (t, 3H), 2.42 (s, 3H), 2.52 (q, 2H), 2.99 (t, 2H), 4.18 (t, 2H), 6.83 (m, 1H), 6.99 (m, 4H), 8.04 (m, 1H). LRMS (thermospray): m/z [MH$^+$] 367. |
| 151[1] | 148 | pyridin-3-yl | $^1$H NMR (400MHz, CDCl$_3$): δ = 1.19 (t, 3H), 2.50 (q, 2H), 2.98 (t, 2H), 4.22 (t, 2H), 6.85 (m, 1H), 6.99 (m, 2H), 7.12 (m, 1H), 7.18 (m, 1H), 8.22 (m, 2H). LRMS (thermospray): m/z [MH$^+$] 353. |
| 152[1] | 148 | 2-aminopyridin-3-yl | $^1$H NMR (400MHz, CDCl$_3$): δ = 1.20 (t, 3H), 2.53 (q, 2H), 2.98 (t, 2H), 4.19 (t, 2H), 4.85 (brs, 2H), 6.58 (m, 1H), 6.83 (m, 2H), 6.99 (m, 2H), 7.63 (d, 1H). LRMS (thermospray): m/z [MH$^+$] 368. |

[1] These compounds were purified on silica gel eluting with a solvent gradient of cyclohexane:ethyl acetate (75:25 then 66:34 then 50:50, by volume) changing to ethyl acetate and finally ethyl acetate:methanol (90:10, by volume).

[1] These compounds were purified on silica gel eluting with a solvent gradient of cyclohexane:ethyl acetate (75:25 then 66:34 then 50:50, by volume) changing to ethyl acetate and finally ethyl acetate:methanol (90:10, by volume).

Example 153

5-({5-[2-(benzyloxy)ethyl]-3-ethyl-1H-pyrazol-4-yl}oxy)isophthalonitrile

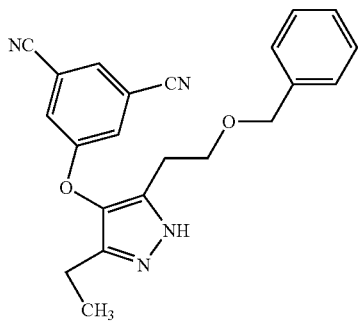

Hydrazine hydrate (177 µl, 3.66 mmol) was added to a solution of the crude enol from Preparation 61 (917 mg, 2.40 mmol) in acetic acid (10 ml) under nitrogen at room temperature. After stirring for 18 hours, the mixture was concentrated under reduced pressure and purified by flash chromatography on silica gel eluting with pentane:cyclohexane (75:25, by volume) changing to toluene:ethyl acetate (50:50, by volume) to give the product which was further purified by preparative HPLC using a Develosil combi-rp C30 50×4.6 mm 3 µm column eluting with a solvent gradient of 5:95 0.1% aqueous trifluoroacetic acid in water:acetonitrile to provide the title compound (5 mg) as a colourless oil.

$^1$H NMR (400 MHz, CDCl$_3$): δ=1.18 (t, 3H), 2.44 (q, 2H), 2.77 (t, 2H), 3.63 (t, 2H), 4.52 (s, 2H), 7.30 (m, 7H), 7.55 (s, 1H). LRMS (electrospray): m/z [MH$^+$] 231, [MNa$^+$] 253.

Example 154

5-{[3-Ethyl-5-(2-hydroxyethyl)-1H-pyrazol-4-yl]oxy}isophthalonitrile

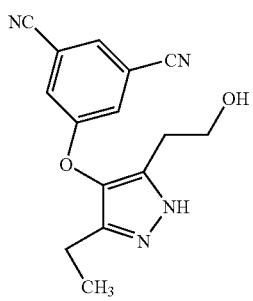

Iron(III)Chloride (217 mg, 1.30 mmol) was added to a solution of the pyrazole from Example 153 (50 mg, 0.13 mmol) in dichloromethane (5 ml) under nitrogen at room temperature. After stirring for 30 minutes the mixture was diluted with dichloromethane (20 ml), washed with water (100 ml) then saturated aqueous sodium ethylenediaminetetraacetate solution (20 ml), dried over magnesium sulphate and concentrated under reduced pressure. The residue was purified by flash chromatography on silica gel eluting with dichloromethane:methanol (98:2 changing to 95:5, by volume) to provide the title compound (20 mg) as a white solid.

$^1$H NMR (400 MHz, CDCl$_3$): δ=1.19 (t, 3H), 2.51 (q, 2H), 2.69 (t, 2H), 3.88 (t, 2H), 7.40 (s, 2H), 7.59 (s, 1H). LRMS (electrospray): m/z [MH$^+$] 283.

Example 155

3-{[5-(Aminomethyl)-1-(2-hydroxyethyl)-3-methyl-1H-pyrazol-4-yl]oxy}-5-chlorobenzonitrile

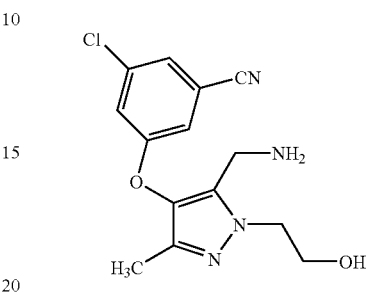

The protected alcohol from Preparation 31 (100 mg, 0.23 mmol) and tert-butyl-ammonium fluoride (360 µl of a 1M solution in tetrahydrofuran, 0.36 mmol) were stirred in dichloromethane (5 ml) at room temperature under nitrogen for 3 hours. The reaction mixture was concentrated under reduced pressure and the residue was dissolved in methanol (2 ml) and purified on a BondElut® SCX polymer supported sulphonic acid column washing with methanol (2×3 ml) to remove impurities and 2N aqueous ammonia to remove the product. This procedure was repeated twice to provide the title compound (40 mg) as a colourless oil.

$^1$H NMR (400 MHz, CD$_3$OD): δ=1.99 (s, 3H), 3.85 (t, 2H), 4.02 (s, 2H), 4.32 (t, 2H), 7.22 (s, 1H), 7.28 (s, 1H), 7.47 (s, 1H). LRMS (thermospray): m/z [MH$^+$] 309. Microanalysis: Found C, 53.32; H, 5.17; N, 16.38. C$_{14}$H$_{15}$ClN$_4$O$_2$.0.85CH$_3$OH requires C, 53.40; H, 5.55; N, 16.77%.

Example 156

5-[(1-Allyl-3-tert-butyl-5-methyl-1H-pyrazol-4-yl)oxy]isophthalonitrile

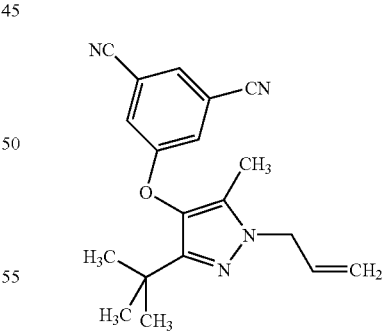

Sodium hydride (60% dispersion in oil, 120 mg, 3.15 mmol) was added to a solution of the pyrazole from Example 130 (800 mg, 2.80 mmol) and allyl bromide (345 mg, 2.80 mmol) in dimethylformamide (30 ml) at room temperature under nitrogen and the reaction was stirred for 3 hours. The reaction was diluted with ethyl acetate (50 ml), washed with water (2×50 ml) then brine (50 ml) and the organic phase was concentrated under reduced pressure. The residual oil was purified by flash chromatography on silica gel eluting with a solvent gradient of pentane changing to ethyl acetate:pentane (20:80, by volume) to provide the title compound (600 mg) as a colourless oil.

$^1$H NMR (400 MHz, CDCl$_3$): δ=1.21 (s, 9H), 1.96 (s, 3H), 4.66 (s, 2H), 5.04 (d, 1H), 5.24 (d, 1H), 5.98 (m, 1H), 7.37 (s, 2H), 7.57 (s, 1H). LRMS (thermospray): m/z [MH$^+$] 322. Microanalysis: Found C, 70.79; H, 6.29; N, 17.11. C$_{19}$H$_{20}$N$_4$O.0.05CH$_2$Cl$_2$ requires C, 70.48; H, 6.24; N, 17.26%.

Example 157

5-{[3-tert-Butyl-1-(2-hydroxyethyl)-5-methyl-1H-pyrazol-4-yl]oxy}isophthalonitrile

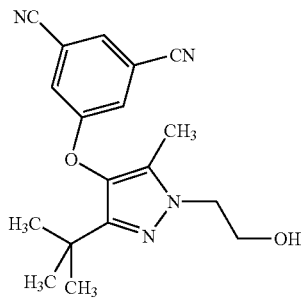

Sodium periodate (1.00 g, 4.60 mmol), osmium tetroxide (1.5% solution in tert-butanol, 190 mg, 0.02 mmol) and the pyrazole from Example 156 (600 mg, 1.86 mmol) were dissolved in acetone (9 ml) and water (3 ml) under nitrogen at room temperature, and the reaction was stirred for 5 hours. The acetone was removed under reduced pressure and the residue was extracted with ethyl acetate (30 ml). The organic phase was washed with water (2×30 ml) then brine (30 ml), dried over magnesium sulphate and concentrated under reduced pressure. The crude aldehyde was then dissolved in methanol (15 ml) and sodium borohydride (84 mg, 2.22 mmol) was added portionwise at room temperature under nitrogen. The reaction was stirred for 3 hours and the solvent was removed under reduced pressure. The residue was partitioned between ethyl acetate (10 ml) and water (10 ml) and the organic phase was washed with water (2×10 ml) then brine (10 ml), dried over magnesium sulphate and concentrated under reduced pressure. The residual oil was purified by flash chromatography on silica gel eluting with a solvent gradient of pentane changing to ethyl acetate:pentane (50:50, by volume) to provide the title compound (250 mg) as a colourless oil.

$^1$H NMR (400 MHz, CDCl$_3$): δ=1.17 (s, 9H), 1.98 (s, 3H), 3.67 (s, 1H), 4.04 (m, 4H), 7.35 (s, 2H), 7.54 (s, 1H). LRMS (thermospray): m/z [MH$^+$] 325. Microanalysis: Found C, 64.30; H, 6.10; N, 16.35. C$_{18}$H$_{20}$N$_4$O$_2$.0.20CH$_2$Cl$_2$ requires C, 64.04; H, 6.02; N, 16.41%.

Example 158

5-{[1-(2-Aminoethyl)-3-tert-butyl-5-methyl-1H-pyrazol-4-yl]oxy}isophthalonitrile

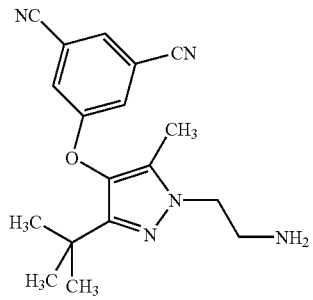

Diphenylphosphorylazide (305 mg, 1.10 mmol) was dissolved in tetrahydrofuran (5 ml) and added to a solution of the pyrazole from Example 157 (180 mg, 0.55 mmol), triphenylphosphine (291 mg, 1.10 mmol) and diethylazodicarboxylate (193 mg, 1.10 mmol) in tetrahydrofuran (20 ml) under nitrogen at room temperature. The reaction was stirred for 18 hours then triphenylphosphine (291 mg, 1.10 mmol) was added, and the reaction was stirred for a further 18 hours. Water (180 μl, 10.0 mmol) was then added and the reaction was stirred for 64 hours. The solvent was removed under reduced pressure and the residual white paste was purified by flash chromatography on silica gel eluting with dichloromethane:methanol:0.88 ammonia (95:4.5:0.5, by volume) to provide the title compound (55 mg) as a colourless oil.

$^1$H NMR (300 MHz, CDCl$_3$): δ=1.22 (s, 9H), 1.78 (s, 2H), 2.03 (s, 3H), 3.18 (t, 2H), 4.05 (m, 2H), 7.38 (s, 2H), 7.58 (s, 1H). LRMS (thermospray): m/z [MH$^+$] 324. Microanalysis: Found C, 64.46; H, 6.48; N, 20.47. C$_{18}$H$_{21}$N$_5$O.0.20CH$_2$Cl$_2$ requires C, 64.22; H, 6.34; N, 20.57%.

Example 159

3-{[3,5-Diethyl-1-(2-hydroxyethyl)-1H-pyrazol-4-yl]oxy}-5-(1H-1,2,4-triazol-1-yl)benzonitrile

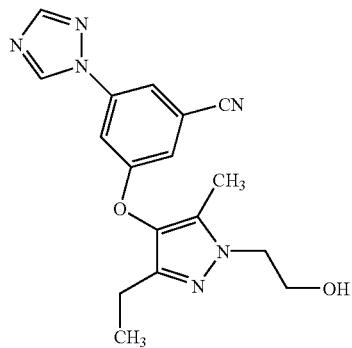

Cesium carbonate (179 mg, 0.55 mmol) was added to a solution of 1H[1,2,4]triazole (38 mg, 0.55 mmol) in dimethylsulfoxide (1 ml) under nitrogen at room temperature and the reaction was stirred for 10 minutes. The aryl fluoride from Preparation 62 (210 mg, 0.5 mmol) dissolved in dimethylsulfoxide (1 ml) was then added and the reaction was heated to 100° C. for 18 hours. After cooling to room temperature the reaction was diluted with water (15 ml) and extracted with ethyl acetate (25 ml). The organic phase was washed with brine (15 ml), dried over magnesium sulphate, concentrated under reduced pressure and the residue was purified by flash chromatography on silica gel eluting with a solvent gradient of dichloromethane:methanol (98:2 changing to 90:10, by volume) to provide the title compound (67.5 mg) as a white solid, m.p. 122–124° C.

$^1$H NMR (400 MHz, CDCl$_3$): δ=1.10 (m, 6H), 2.39 (q, 2H), 2.51 (q, 2H), 3.61 (brs, 1H), 4.04 (m, 2H), 4.07 (m, 2H), 7.10 (s, 1H), 7.52 (s, 1H), 7.60 (s, 1H), 8.07 (s, 1H), 8.54 (s, 1H). LRMS (thermospray): m/z [MH$^+$] 353. Microanalysis: Found C, 60.69; H, 5.83; N, 22.98. C$_{18}$H$_{20}$N$_6$O$_2$.0.08CH$_2$Cl$_2$ requires C, 60.46; H, 5.66; N, 23.40%.

Examples 160–162

The preparation of the following tabulated Examples of the general formula

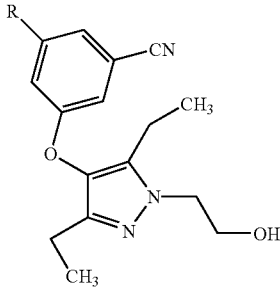

were performed by a similar method to that of Example 159 using the appropriate heterocycle as the starting material.

| Example No. (Starting Material Preparation No) | R | Analytical Data |
|---|---|---|
| 160 (62) | 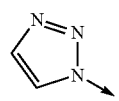 | $^1$H NMR (400MHz, CDCl$_3$): δ = 1.10 (m, 6H), 2.39 (q, 2H), 2.52 (q, 2H), 3.62 (brs, 1H), 4.02 (t, 2H), 4.08 (t, 2H), 6.44 (d, 2H), 7.14 (s, 1H), 7.16 (s, 1H), 7.25 (s, 1H), 7.49 (d, 2H). m.p. 169–170° C. LRMS (thermospray): m/z [MH$^+$] 379. Microanalysis: Found C, 65.68; H, 5.98; N, 14.31. C$_{21}$H$_{22}$N$_4$O$_3$.0.09CH$_2$Cl$_2$ requires C, 65.61; H, 5.79; N, 14.51%. |
| 161[1] (62) |  | $^1$H NMR (400MHz, CDCl$_3$): δ = 1.10 (m, 6H), 2.40 (q, 2H), 2.51 (q, 2H), 3.56 (t, 1H), 4.04 (m, 2H), 4.07 (m, 2H), 7.20 (s, 1H), 7.65 (s, 2H), 7.85 (s, 1H), 7.98 (s, 1H). LRMS (thermospray): m/z [MH$^+$] 353. HRMS: [MH$^+$] 353.1722. C$_{18}$H$_{20}$N$_6$O$_2$ requires 353.1720. |
| 162[1] (62) |  | $^1$H NMR (400MHz, CDCl$_3$): δ = 1.10 (m, 6H), 2.41 (q, 2H), 2.51 (q, 2H), 3.62 (t, 1H), 4.04 (m, 2H), 4.07 (m, 2H), 7.08 (s, 1H), 7.80 (s, 2H), 7.87 (s, 1H), 8.02 (s, 1H). LRMS (thermospray): m/z [MH$^+$] 353. HRMS: [MH$^+$] 353.1719. C$_{18}$H$_{20}$N$_6$O$_2$ requires 353.1720. |

[1]Both of these compounds were isolated from a single reaction starting from 1,2,3-triazole with Example 161 being the most polar.

Example 163

3-{[3,5-Diethyl-1-(2-hydroxyethyl)-1H-pyrazol-4-yl]oxy}-5-fluorobenzamide

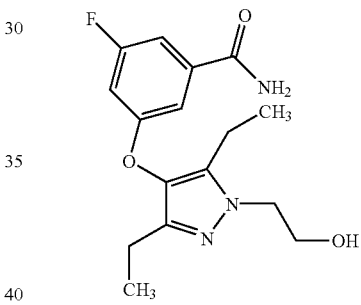

The protected alcohol from Preparation 64 (432 mg, 1.07 mmol) and p-toluene-sulphonic acid (30.3 mg, 0.11 mmol) were dissolved in methanol (4 ml) and stirred under nitrogen at room temperature for 18 hours. The solvent was removed under reduced pressure and the residue was partitioned between saturated aqueous sodium bicarbonate solution (20 ml) and dichloromethane (20 ml). The aqueous phase was extracted with dichloromethane (10 ml) and the combined organic extracts were dried over magnesium sulphate, concentrated under reduced pressure and the residue was purified by flash chromatography on silica gel eluting with a solvent gradient of dichloromethane:methanol (100:0 changing to 93:7, by volume) to provide the title compound (241 mg) as a white foam.

$^1$H NMR (400 MHz, CDCl$_3$): δ=1.10 (m, 6H), 2.39 (q, 2H), 2.49 (q, 2H), 3.68 (brs, 1H), 4.04 (m, 4H), 5.59 (brs, 1H), 5.88 (brs, 1H), 6.71 (d, 1H), 7.11 (m, 2H). LRMS (thermospray): m/z [MH$^+$] 322. Microanalysis: Found C, 57.91; H, 6.32; N, 12.56. C$_{16}$H$_{20}$FN$_3$O$_3$.0.13CH$_2$Cl$_2$.0.12H$_2$O requires C, 57.91; H, 6.18; N, 12.56%.

Examples 164–167

The preparation of the following tabulated Examples of the general formula

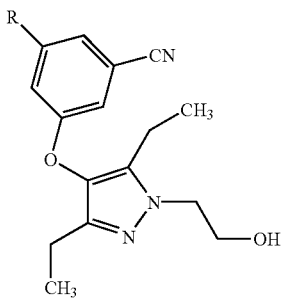

were performed by a similar method to that of Example 163 using the appropriate protected alcohol as the starting material.

| Example No. (Starting Material Preparation No.) | R | Analytical Data |
|---|---|---|
| 164[1] (65) | (pyrazol-1-yl) | $^1$H NMR (400MHz, CDCl$_3$): δ = 1.13 (m, 6H), 2.44 (q, 2H), 2.54 (q, 2H), 3.65 (brs, 1H), 4.07 (t, 2H), 4.11 (t, 2H), 6.51 (s, 1H), 7.00 (s, 1H), 7.56 (s, 1H), 7.63 (s, 1H), 7.74 (s, 1H), 7.90 (s, 1H). LRMS (electrospray): m/z [MH$^+$] 352, [MNa$^+$] 374. HRMS: [MH$^+$] Found 352.1770. C$_{19}$H$_{22}$N$_5$O$_2$ requires 352.1768. |
| 165[1] (66) | (2-oxopyridin-1-yl) | $^1$H NMR (400MHz, CDCl$_3$): δ = 1.10 (m, 6H), 2.40 (q, 2H), 2.50 (q, 2H), , 4.00 (t, 2H), 4.06 (t, 2H), 6.24 (t, 1H), 6.60 (d, 1H), 7.18 (d, 2H), 7.24 (d, 1H), 7.30 (s, 1H), 7.38 (t, 1H). LRMS (electrospray): m/z [MH$^+$] 379, [MNa$^+$] 401. HRMS: [MH$^+$] Found 379.1766. C$_{21}$H$_{23}$N$_4$O$_3$ requires 379.1765 [MNa$^+$] Found 401.1585. C$_{21}$H$_{22}$N$_4$O$_3$Na requires 401.1584. |
| 166[1] (67) | (3-oxopyridazin-2-yl) | $^1$H NMR (400MHz, CDCl$_3$): δ = 1.10 (m, 6H), 2.41 (q, 2H), 2.51 (q, 2H), 4.01 (t, 2H), 4.06 (t, 2H), 7.07 (d, 1H), 7.13 (s, 1H), 7.22 (m, 1H), 7.52 (s, 1H), 7.65 (s, 1H), 7.88 (s, 1H). LRMS (electrospray): m/z [MH$^+$] 380, [MNa$^+$] 402. HRMS: [MH$^+$] Found 380.1722. C$_{20}$H$_{22}$N$_5$O$_3$ requires 380.1717. |
| 167[2] (68) | 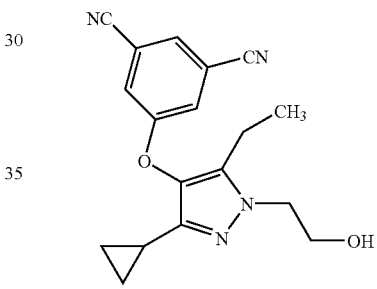 | $^1$H NMR (400MHz, CDCl$_3$): δ = 1.11 (m, 6H), 2.27 (s, 3H), 2.41 (q, 2H), 2.50 (q, 2H), 3.70 (s, 3H), 4.04 (t, 1H), 4.08 (t, 2H), 5.64 (s, 1H), 6.81 (s, 1H), 6.91 (s, 1H), 6.99 (s, 1H). LRMS (electrospray): m/z [MH$^+$] 396, [MNa$^+$] 418. HRMS: [MH$^+$] Found 396.2027. C$_{21}$H$_{26}$N$_5$O$_3$ requires 396.2030. |

[1]The eluent used for flash column chromatography purification of these compounds was dichloromethane:methanol (99:1 changing to 80:20, by volume).
[2]The eluent used for flash column chromatography purification of this compound was dichloromethane:methanol (99:1 changing to 98:2, by volume).

Example 168

5-{[3-Cyclopropyl-5-ethyl-1-(2-hydroxyethyl)-1H-pyrazol-4-yl]oxy}isophthalonitrile

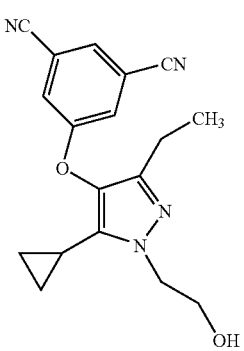

and

Example 169

5-{[5-Cyclopropyl-3-ethyl-1-(2-hydroxyethyl)-1H-pyrazol-4-yl]oxy}isophthalonitrile Potassium carbonate (91 mg, 0.66 mmol) and 2-(2-bromoethoxy)-tetrahydropyran (91 µl, 0.61 mmol) were sequentially added to a solution of the pyrazole from Example 129 (152 mg, 0.55 mmol) dissolved in dimethylformamide (4 ml) and the reaction was heated to 35° C. under nitrogen for 5 hours. Starting material still remained, so the temperature was increased to 80° C. and the reaction was stirred for a further 18 hours. The reaction was cooled to room temperature, sodium hydride (60% dispersion in oil, 24 mg, 0.60 mmol) was added and the reaction was stirred at room temperature for 1 hour. The mixture was diluted with water (50 ml) and extracted with ethyl acetate (2×50 ml). The combined organic extracts were washed with brine (30 ml), dried over magnesium sulphate, concentrated under reduced pressure and the residue was purified by flash chromatography on silica gel eluting with pentane:cyclohexane (75:25, by volume) to provide a mixture of regioisomers (239 mg). The regioisomers (239 mg, 0.55 mmol) and p-toluenesulphonic acid (10 mg, 0.05 mmol) were dissolved in methanol (5 ml) and stirred under nitrogen at room temperature for 18 hours. The solvent was removed under reduced pressure and the residue was partitioned between saturated aqueous sodium bicarbonate solution (20 ml) and dichloromethane (30 ml). The organic phase was dried over magnesium sulphate, concentrated under reduced pressure and the residual oil was purified by flash chromatography on silica gel eluting with toluene:ethyl acetate (50:50, by volume) to yield two products as colourless oils.

Least Polar Fraction (Example 168)—34 mg $^1$H NMR (400 MHz, CDCl$_3$): δ=0.76 (m, 4H), 1.05 (t, 3H), 1.45 (m, 1H), 2.48 (q, 2H), 3.39 (brs, 1H), 4.02 (m, 4H), 7.39 (s, 2H), 7.56 (s, 1H). LRMS (electrospray): m/z [M–H$^+$] 321.

Most Polar Fraction (Example 169)—9 mg $^1$H NMR (400 MHz, CDCl$_3$): δ=0.62 (m, 2H), 0.78 (m, 2H), 1.18 (t, 3H), 1.46 (m, 1H), 2.38 (q, 2H), 3.42 (brs, 1H), 4.02 (m, 2H), 4.21 (t, 2H), 7.38 (s, 2H), 7.57 (s, 1H). LRMS (electrospray): m/z [MH$^+$] 323, [MH$^-$] 321.

Example 170

5-{[5-Ethyl-1-(2-hydroxyethyl)-3-isopropyl-1H-pyrazol-4-yl]oxy}isophthalonitrile

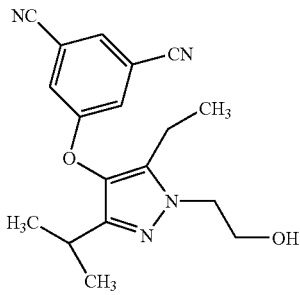

2-(2-Bromoethoxy)-tetrahydropyran (91 µl, 0.60 mmol) was added to a solution of the pyrazole from Example 131 (153 mg, 0.55 mmol) dissolved in dimethylformamide (4 ml) at room temperature under nitrogen, then sodium hydride (60% dispersion in oil, 24 mg, 0.60 mmol) was added and the reaction was stirred at room temperature for 3 hours. The mixture was diluted with water (50 ml) and extracted with ethyl acetate (2×50 ml). The combined organic extracts were washed with brine (30 ml), dried over magnesium sulphate, concentrated under reduced pressure and the residue was purified by flash chromatography on silica gel eluting with toluene:ethyl acetate (85:15, by volume) to provide the separated isomers as colourless oils (83 mg of Isomer 1, 55 mg of Isomer 2).

The least polar isomer (isomer 1) (83 mg, 0.20 mmol) and p-toluene-sulphonic acid (4 mg, 0.02 mmol) were dissolved in methanol (5 ml) and stirred under nitrogen at room temperature for 18 hours. The solvent was removed under reduced pressure and the residue was partitioned between water (30 ml) and dichloromethane (30 ml). The aqueous phase was extracted with dichloromethane (20 ml) and the combined organic extracts were dried over magnesium sulphate, concentrated under reduced pressure and the residual oil was purified by flash chromatography on silica gel eluting with toluene:ethyl acetate (66:34, by volume) to provide the title compound (39 mg) as an oil.

$^1$H NMR (400 MHz, CDCl$_3$): δ=1.05 (t, 3H), 1.14 (d, 6H), 2.44 (q, 2H), 2.68 (sept, 1H), 3.77 (brs, 1H), 4.06 (m, 4H), 7.38 (s, 2H), 7.58 (s, 1H). LRMS (electrospray): m/z [MH$^+$] 325.

Example 171

5-{[3-Ethyl-1-(2-hydroxyethyl)-5-isopropyl-1H-pyrazol-4-yl]oxy}isophthalonitrile

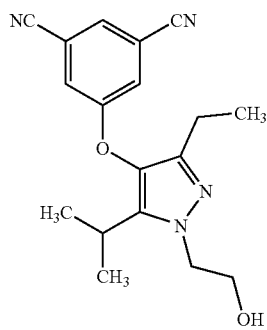

The most polar isomer (isomer 2) from Example 170 (55 mg, 0.13 mmol) and p-toluene-sulphonic acid (3 mg, 0.01 mmol) were dissolved in methanol (5 ml) and stirred under nitrogen at room temperature for 18 hours. The solvent was removed under reduced pressure and the residue was partitioned between water (30 ml) and dichloromethane (30 ml). The aqueous phase was extracted with dichloromethane (20 ml) and the combined organic extracts were dried over magnesium sulphate, concentrated under reduced pressure and the residual oil was purified by flash chromatography on silica gel eluting with toluene:ethyl acetate 66:33, by volume) to provide the title compound (39 mg) as a white solid.

$^1$H NMR (400 MHz, CDCl$_3$): δ=1.08 (t, 3H), 1.13 (d, 6H), 2.49 (q, 2H), 2.97 (sept, 1H), 3.59 (t, 1H), 4.06 (m, 4H), 7.37 (s, 2H), 7.57 (s, 1H). LRMS (electrospray): m/z [MH$^+$] 325.

Example 172

2-[4-(3,5-Dicyanophenoxy)-3,5-diethyl-1H-pyrazol-1-yl]ethyl carbamate

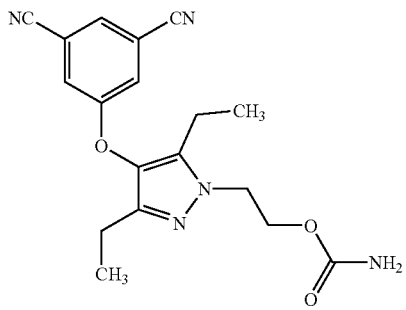

Trichloroacetyl-isocyanate (46 µl, 0.38 mmol) was added to a solution of the alcohol from Example 119 (100 mg, 0.32 mmol) dissolved in dichloromethane (3.2 ml) under nitrogen at 0° C. After stirring for 2 hours the dichloromethane was removed under reduced pressure and methanol (1.6 ml), water (1.6 ml) and potassium carbonate (134 mg, 0.96 mmol) were added and the reaction was stirred for a further 2 hours. The methanol was removed under reduced pressure and the residue was extracted with dichloromethane (3×10 ml). The combined organic extracts were dried over magnesium sulphate, concentrated under reduced pressure and the residual solid was purified by flash chromatography on silica gel eluting with dichloromethane:methanol (98:2, by volume) to provide the title compound (60 mg) as a white solid.

$^1$H NMR (400 MHz, CDCl$_3$): δ=1.10 (m, 6H), 2.39 (q, 2H), 2.48 (q, 2H), 4.26 (m, 2H), 4.44 (m, 2H), 4.62 (brs, 2H), 7.41 (s, 2H), 7.58 (s, 1H). LRMS (thermospray): m/z [MH$^+$] 354. Microanalysis: Found C, 60.00; H, 5.55; N, 19.82. C$_{18}$H$_{19}$N$_5$O$_3$.0.23EtOAc requires C, 60.30; H, 5.67; N, 18.58%.

Example 173

N-{2-[4-(3,5-Dicyanophenoxy)-3,5-diethyl-1H-pyrazol-1-yl]ethyl}sulfamide

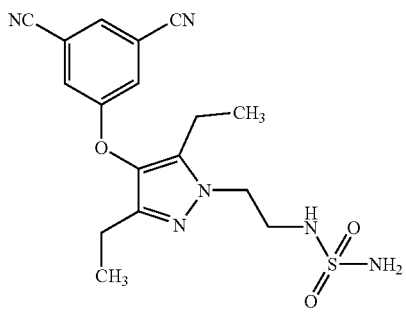

Sulfamide (31 mg, 0.32 mmol) was added to a solution of the amine from Example 127 (100 mg, 0.32 mmol) dissolved in dioxan (0.5 ml) under nitrogen at room temperature. The reaction was heated to 100° C. for 18 hours, cooled to room temperature and partitioned between ethyl acetate (15 ml) and water (15 ml). The organic phase was dried over magnesium sulphate, concentrated under reduced pressure and the residual brown oil was purified by flash chromatography on silica gel eluting with dichloromethane:methanol:0.88 ammonia (95:5:0.5, by volume) to provide the title compound (25 mg) as a white solid.

$^1$H NMR (400 MHz, CDCl$_3$): δ=1.12 (m, 6H), 2.39 (q, 2H), 2.51 (q, 2H), 3.61 (m, 2H), 4.20 (m, 2H), 4.78 (s, 2H), 5.42 (s, 1H), 7.40 (s, 2H), 7.59 (s, 1H). Microanalysis: Found C, 50.33; H, 5.07; N, 20.60. C$_{17}$H$_{20}$N$_6$O$_3$S.0.95H$_2$O requires C, 50.35; H, 5.44; N, 20.72%.

Example 174

N-{2-[4-(3,5-Dicyanophenoxy)-3,5-diethyl-1H-pyrazol-1-yl]ethyl}-2-methoxyacetamide

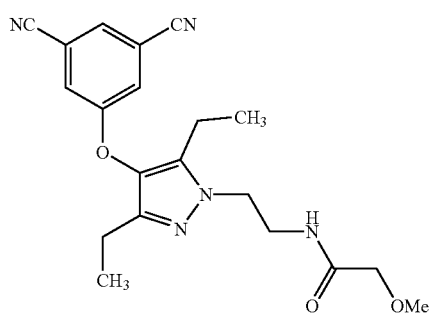

The amine from Example 127 (100 mg, 0.32 mmol), 1-(3-dimethylaminopropyl)-3-ethylcarbodiimide hydrochloride (68 mg, 0.35 mmol) and N,N-dimethylaminopyridine (43 mg, 0.35 mmol) were added to a solution of 1-methoxyacetic acid (27 µl, 0.35 mmol) dissolved in dichloromethane (10 ml) under nitrogen at room temperature. The reaction was stirred for 18 hours, concentrated under reduced pressure and the residual yellow oil was purified by flash chromatography on silica gel eluting with dichloromethane:methanol:0.88 ammonia (95:5:0.5, by volume) to provide the title compound (32 mg) as a colourless oil.

$^1$H NMR (400 MHz, CDCl$_3$): δ=1.11 (t, 3H), 1.16 (t, 3H), 2.38 (q, 2H), 2.47 (q, 2H), 3.41 (s, 3H), 3.77 (dd, 2H), 3.89 (s, 2H), 4.15 (m, 2H), 7.19 (brs, 1H), 7.40 (s, 2H), 7.59 (s, 1H). LRMS (thermospray): m/z [MH$^+$] 382. Microanalysis: Found C, 61.26; H, 6.18; N, 17.59. C$_{20}$H$_{23}$N$_5$O$_3$.0.60H$_2$O requires C, 61.24; H, 6.22; N, 17.85%.

Example 175

5-{[1-(3-Azetidinyl)-3,5-diethyl-1H-pyrazol-4-yl]oxy}isophthalonitrile

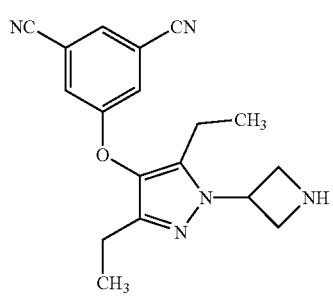

Example 176

5-{[3,5-Diethyl-1-(3-hydroxypropyl)-1H-pyrazol-4-yl]oxy}isophthalonitrile

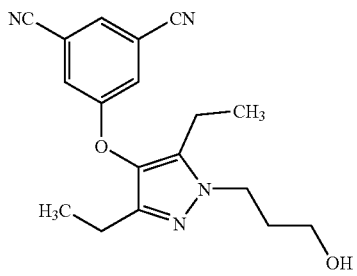

The protected alcohol from Preparation 70 (215 mg, 0.53 mmol) and p-toluene-sulphonic acid (10 mg, 0.05 mmol) were dissolved in methanol (2 ml) and stirred under nitrogen at room temperature for 18 hours. The solvent was removed under reduced pressure and the residue was partitioned between water (10 ml) and dichloromethane (10 ml). The organic phase was dried over magnesium sulphate and concentrated under reduced pressure to provide the title compound (148 mg) as a pale yellow solid, m.p. 93–95° C.

$^1$H NMR (400 MHz, CDCl$_3$): δ=1.11 (m, 6H), 2.04 (tt, 2H), 2.37 (q, 2H), 2.53 (q, 2H), 3.06 (t, 1H), 3.69 (dt, 2H), 4.18 (t, 2H), 7.38 (s, 2H), 7.58 (s, 1H). LRMS (electrospray): m/z [MH$^+$] 325, [MNa$^+$] 347. Microanalysis: Found C, 66.27; H, 6.27; N, 17.00. C$_{18}$H$_{20}$N$_4$O$_2$ requires C, 66.28; H, 6.24; N, 17.18%.

The protected amine from Preparation 69 (178 mg, 0.42 mmol) was dissolved in 4M hydrochloric acid in dioxan solution (1 ml) and dioxan (1 ml) and the reaction was stirred at room temperature for 18 hours. The solvent was removed under reduced pressure and the residue was partitioned between dichloromethane (20 ml) and saturated aqueous sodium bicarbonate solution (20 ml). The organic phase was dried over magnesium sulphate, concentrated under reduced pressure and purified by flash chromatography on silica gel eluting with a solvent gradient of dichloromethane:methanol:0.88 ammonia (100:0:0 then 98:2:0 then 95:5:0 then 95:5:0.5 then 90:10:1 then 80:20:1, by volume) to provide the title compound (33 mg) as a white solid.

$^1$H NMR (400 MHz, CDCl$_3$): δ=1.05 (t, 3H), 1.11 (t, 3H), 2.44 (m, 4H), 3.85 (m, 2H), 4.38 (m, 2H), 5.05 (m, 1H), 7.37 (s, 2H), 7.56 (s, 1H). LRMS (electrospray): m/z [MH$^+$] 322. Microanalysis: Found C, 65.87; H, 5.94; N, 20.98. C$_{18}$H$_{19}$N$_5$O.0.38H$_2$O requires C, 65.87; H, 6.07; N, 21.04%.

Example 177

5-[(3,5-Diethyl-1-methyl-1H-pyrazol-4-yl)oxy]isophthalonitrile

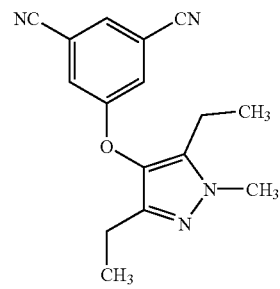

Sodium hydride (60% dispersion in oil, 33 mg, 0.82 mmol) was added to a solution of the pyrazole from Example 122 (200 mg, 0.75 mmol) in dimethylformamide (3 ml) at 0° C. under nitrogen and the reaction was stirred for 10 minutes. Methyl iodide (117 mg, 0.82 mmol) was added and the reaction was stirred at room temperature for 18 hours. The reaction was quenched with water (0.2 ml) and concentrated under reduced pressure. The residue was partitioned between dichloromethane (5 ml) and water (5 ml) and the organic phase was isolated using a 5 μM Whatman PTFE fritted cartridge, then concentrated under reduced pressure. The residue was purified by flash chromatography on silica gel eluting with a solvent gradient of ethyl acetate:pentane (20:80, by volume) changing to ethyl acetate:methanol (90:10, by volume) then dichloromethane:methanol:0.88 ammonia (90:10:1 then 80:20:1, by volume) to provide the title compound (170 mg) as a yellow solid.

$^1$H NMR (400 MHz, CDCl$_3$): δ=1.10 (m, 6H), 2.39 (q, 2H), 2.49 (q, 2H), 3.80 (s, 3H), 7.40 (s, 2H), 7.56 (s, 1H). LRMS (electrospray): m/z [MH$^+$] 281. Microanalysis: Found C, 68.41; H, 5.71; N, 19.93. C$_{16}$H$_{16}$N$_4$O requires C, 68.55; H, 5.75; N, 19.99%.

Examples 178–180

The preparation of the following tabulated Examples of the general formula

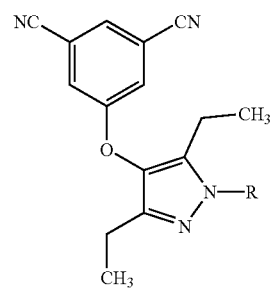

were performed by a similar method to that of Example 177 using the appropriate alkyl halide as the starting material.

| Example No. (Starting Material Example No.) | R | Analytical Data |
|---|---|---|
| 178 (122) | 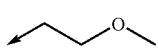 | $^1$H NMR (400MHz, CDCl$_3$): δ = 1.08 (t, 3H), 1.12 (t, 3H), 2.40 (q, 2H), 2.54 (q, 2H), 3.34 (s, 3H), 3.75 (t, 2H), 4.17 (t, 2H), 7.38 (s, 2H), 7.56 (s, 1H). LRMS (electrospray): m/z [MH$^+$] 325, [MNa$^+$] 347. Microanalysis: Found C, 65.73; H, 6.17; N, 17.08. C$_{18}$H$_{20}$N$_4$O$_3$.0.25H$_2$O requires C, 65.74; H, 6.28; N, 17.04%. |
| 179[1,2] (122) | 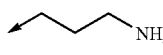 | $^1$H NMR (400MHz, CDCl$_3$): δ = 1.10 (m, 6H), 1.98 (tt, 2H), 2.38 (q, 2H), 2.51 (q, 2H), 2.76 (t, 2H), 4.09 (t, 2H), 7.38 (s, 2H), 7.57 (s, 1H). LRMS (electrospray): m/z [MH$^+$] 324. Microanalysis: Found C, 64.86; H, 6.51; N, 20.79. C$_{18}$H$_{21}$N$_5$O.0.57H$_2$O requires C, 64.79; H, 6.69; N, 20.99%. |
| 180[3] (122) | 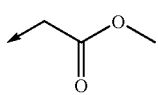 | $^1$H NMR (400MHz, CDCl$_3$): δ = 1.09 (t, 3H), 1.14 (t, 3H), 2.41 (q, 2H), 2.47 (q, 2H), 3.79 (s, 3H), 4.82 (s, 2H), 7.40 (s, 2H), 7.57 (s, 1H). LRMS (electrospray): m/z [MH$^+$] 339. Microanalysis: Found C, 63.58; H, 5.35; N, 16.35. C$_{18}$H$_{18}$N$_4$O$_3$.0.10H$_2$O requires C, 63.56; H, 5.39; N, 16.47%. |

[1]The two reagents were heated together as a melt at 160° C. for 24 hours, and the reaction was worked up by partitioning between dichloromethane and saturated sodium bicarbonate solution, extracting the organic phase with 2M aqueous hydrochloric acid and basifying the aqueous phase with sodium carbonate. After extraction with dichloromethane the organic phase was dried and concentrated to give the crude product.
[2]The eluent used for flash column chromatography purification of this compound was dichloromethane:methanol:0.88 ammonia (95:5:0.5 changing to 80:20:1, by volume).
[3]The eluent used for flash column chromatography purification of this compound was pentane:ethyl acetate (75:25 changing to 66:34 then 50:50, by volume).
[4]The hydrochloride salt of the starting alkyl halide was used.

Example 181

2-[4-(3,5-Dicyanophenoxy)-3,5-diethyl-1H-pyrazol-1-yl]acetamide

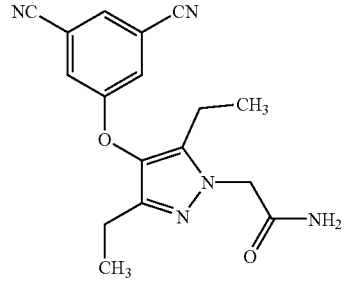

The ester from Example 180 (200 mg, 0.59 mmol) was dissolved in 2M methanolic ammonia solution (5 ml) and the reaction was stirred under nitrogen at 75° C. for 18 hours. The mixture was concentrated under reduced pressure and the residue was purified by flash chromatography on silica gel eluting with a solvent gradient of dichloromethane:methanol:0.88 ammonia (95:5:0.5, by volume) to provide the title compound (6 mg).

$^1$H NMR (400 MHz, CDCl$_3$): δ=1.10 (t, 3H), 1.15 (t, 3H), 2.44 (q, 2H), 2.54 (q, 2H), 4.69 (s, 2H), 5.55 (brs, 1H), 6.22 (brs, 1H), 7.38 (s, 2H), 7.59 (s, 1H). LRMS (electrospray): m/z [M–H$^+$] 322. Microanalysis: Found C, 68.41; H, 5.71; N, 19.93. C$_{16}$H$_{16}$N$_4$O requires C, 68.55; H, 5.75; N, 19.99%.

Example 182

5-{[3,5-Diethyl-1-(hydroxymethyl)-1H-pyrazol-4-yl]oxy}isophthalonitrile

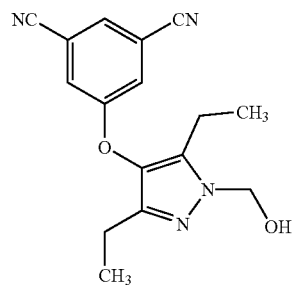

Formaldehyde (37% solution in water, 253 μl, 3.14 mmol) was added to a solution of the pyrazole from Example 122 (440 mg, 1.65 mmol) in ethanol (5 ml) and the reaction was stirred at 80° C. for 18 hours. After cooling to room temperature the solvent was removed under reduced pressure and the residual yellow solid was partitioned between ethyl acetate (15 ml) and water (10 ml) and the organic phase was removed. The aqueous phase was washed with ethyl acetate (2×15 ml) and the combined organic extracts were dried over magnesium sulphate and concentrated under reduced pressure to provide the title compound (490 mg) as a white solid.

¹H NMR (400 MHz, CDCl₃): δ=1.13 (t, 3H), 1.14 (t, 3H), 2.39 (q, 2H), 2.61 (q, 2H), 5.49 (s, 2H), 5.68 (brs, 1H), 7.40 (s, 2H), 7.56 (s, 1H). LRMS (thermospray): m/z [MH⁺] 267. Microanalysis: Found C, 64.28; H, 5.52; N, 18.47. $C_{16}H_{16}N_4O_2 \cdot 0.15H_2O$ requires C, 64.27; H, 5.49; N, 18.24%.

Example 183

3-[({[4-(3-cyano-5-fluorophenoxy)-3-methyl-1H-pyrazol-5-yl]methyl}amino)methyl]benzamide

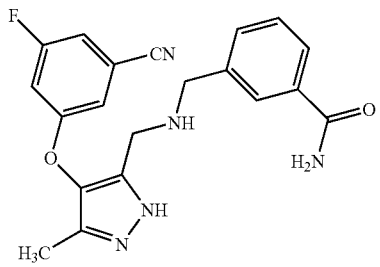

The pyrazole from Preparation 75 (320 mg, 0.91 mmol) and the amine from Preparation 80 (680 mg, 4.61 mmol) were refluxed in isopropanol (5 ml) for 1.5 hours. The solvent was removed under reduced pressure and the residue was purified by flash chromatography on silica gel eluting with dichloromethane:methanol:0.88 ammonia (95:5:0.5, by volume) to give the product which was further purified by preparative HPLC using a Develosil combi-rp C30 50×4.6 mm 3 µm column eluting with a solvent gradient of 5:95 0.1% aqueous trifluoroacetic acid in acetonitrile:acetonitrile (0–6 min 95:5 changing to 50:50; 6–7 min 50:50; 7–7.1 min 50:50 changing to 5:95; 7.1–8 min 5:95) to provide the title compound (38 mg).

¹H NMR (400 MHz, CD₃OD): δ=2.14 (s, 3H), 4.10 (s, 2H), 4.34 (s, 2H), 7.03 (m, 1H), 7.10 (s, 1H), 7.25 (m, 1H), 7.54 (t, 1H), 7.64 (d, 1H), 7.92 (d, 1H), 7.97 (s, 1H). LRMS (electrospray): m/z [MH⁺] 380. Microanalysis: Found C, 51.32; H, 3.91; N, 13.69. $C_{20}H_{18}N_5O_2F \cdot 1.00CF_3CO_2H \cdot 1.10H_2O$ requires C, 51.49; H, 4.16; N, 13.65%.

Examples 184–188

The preparation of the following tabulated Examples of the general formula

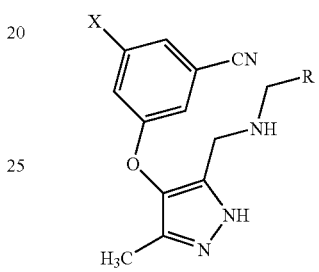

were performed by a similar method to that of Example 183 using as the starting materials the appropriate pyrazole (P) and amine (A).

| Ex. no | P prep. no. | A prep. no. | X | R | Analytical Data |
|---|---|---|---|---|---|
| 184[1] | 75 | 55 | F | 4-carbamoylphenyl | ¹H NMR (400 MHz, CDCl₃): δ = 2.09(s, 3H), 3.65(s, 2H), 3.79(s, 2H), 6.80(d, 1H), 6.93(s, 1H), 6.97(d, 1H), 7.31(d, 2H), 7.72(d, 2H). LRMS (thermospray): m/z [MH⁺] 380. |
| 185[1] | 76 | 55 | CN | 4-carbamoylphenyl | m.p. 114–116° C. ¹H NMR (400 MHz, CDCl₃): δ = 2.08(s, 3H), 3.62(s, 2H), 3.77(s, 2H), 7.34(d, 2H), 7.55(s, 1H), 7.77(d, 2H), 7.79(s, 1H). LRMS (thermospray) m/z [MH⁺] 387. |
| 186[1] | 18 | 80 | Cl | 3-carbamoylphenyl | m.p. 98–101° C. ¹H NMR (400 MHz, CDCl₃): δ = 2.04(s, 3H), 3.62(s, 2H), 3.74(s, 2H), 6.97(s, 1H), 7.07(s, 1H), 7.20(s, 1H), 7.22(d, 1H), 7.29(t, 1H), 7.62(s, 1H), 7.81(s, 1H). LRMS (thermospray): m/z [MH⁺] 396. Microanalysis: Found C, 56.98; H, 4.58; N, 17.69. $C_{20}H_{18}ClN_5O_2 \cdot 0.40CH_2Cl_2$ requires C, 57.01; H, 4.41; N, 16.29%. |

-continued

| Ex. no | P prep. no. | A prep. no. | X | R | Analytical Data |
|---|---|---|---|---|---|
| 187[1,2,3] | 77 | 55 | Me | ![structure with C(O)NH2 benzamide] | 1H NMR (400 MHz, CDCl3): δ = 2.10(s, 3H), 2.30(s, 3H), 3.65(s, 2H), 3.80(s, 2H), 6.85(s, 1H), 6.95(s, 1H), 7.10(s, 1H), 7.30(d, 2H), 7.70(d, 2H). LRMS (electrospray): m/z [MH+] 376, [M − H+] 374. Microanalysis: Found C, 65.59; H, 5.65; N, 18.19. $C_{21}H_{21}N_5O_2 \cdot 0.50H_2O$ requires C, 65.51; H, 5.77; N, 18.22%. |
| 188[4] | 78 | 55 | H | ![structure with C(O)NH2 benzamide] | 1H NMR (400 MHz, CD3OD): δ = 2.15(s, 3H), 4.10(s, 2H), 7.20(m, 2H), 7.40(m, 1H), 7.50(m, 1H), 7.55(d, 2H), 7.90(d, 2H). Microanalysis: Found C, 53.51; H, 4.13; N, 13.59. $C_{20}H_{19}N_5O_2 \cdot 1.25$ TFA requires C, 53.63; H, 4.05; N, 13.90%. |

[1] No preparative HPLC was required for purification of this compound.
[2] The eluent used for flash column chromatography purification of this compound was dichloromethane:methanol:0.88 ammonia (95:5:0.5 changing to 90:10:1, by volume).
[3] The product was triturated with dichloromethane containing a trace of methanol - a solid crystallised out which was an impurity. This was filtered off and the filtrate was concentrated under reduced pressure and the residue was purified by flash chromatography eluting with dichloromethane:methanol:0.88 ammonia (90:10:1, by volume) to give the title compound.
[4] The column used for preparative HPLC was a LUNA C18 10 μm 150 × 21.2 mm.

Example 189

5-[(3,5-Dicyclopropyl-1H-pyrazol-4-yl)oxy]isophthalonitrile

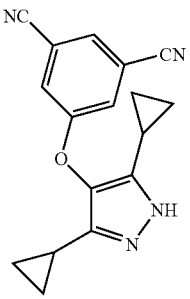

Hydrazine hydrate (133 μl, 2.75 mmol) was added to a solution of the diketone from Preparation 82 (735 mg, 2.50 mmol) in acetic acid (25 ml) under nitrogen at room temperature. After stirring for 64 hours, the mixture was concentrated under reduced pressure and the residue was partitioned between dichloromethane (25 ml) and saturated aqueous sodium bicarbonate solution (25 ml). The organic phase was dried over magnesium sulphate, concentrated under reduced pressure and the residue was purified by flash chromatography on silica gel eluting with dichloromethane:methanol (98:2 changing to 96:4, by volume) to provide the title compound (473 mg) as a white solid, m.p. 168–170° C.

1H NMR (400 MHz, CDCl3): δ=0.77 (m, 4H), 0.85 (m, 4H), 1.59 (m, 2H), 7.44 (s, 2H), 7.59 (s, 1H). LRMS (thermospray): m/z [MH+] 291. Microanalysis: Found C, 69.90; H, 4.85; N, 19.18. $C_{17}H_{14}N_4O \cdot 0.10H_2O$ requires C, 69.90; H, 4.90; N, 19.18%.

Example 190

5-{[3,5-Dicyclopropyl-1-(2-hydroxyethyl)-1H-pyrazol-4-yl]oxy}isophthalonitrile

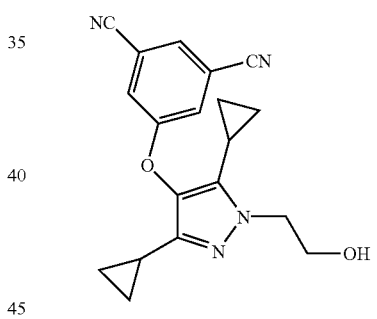

2-Hydroxyethylhydrazine (84 mg, 1.10 mmol) was added to a solution of the diketone from Preparation 82 (294 mg, 1.00 mmol) in acetic acid (10 ml) under nitrogen at room temperature. After stirring for 64 hours, the mixture was concentrated under reduced pressure and the residue was partitioned between dichloromethane (25 ml) and saturated aqueous sodium bicarbonate solution (25 ml). The organic phase was dried over magnesium sulphate, concentrated under reduced pressure and the residue was purified by flash chromatography on silica gel eluting with dichloromethane:methanol (99:1 changing to 95:5, by volume) to provide the title compound (137 mg) as a white solid, m.p. 115–117° C.

1H NMR (400 MHz, CDCl3): δ=0.67 (m, 2H), 0.80 (m, 4H), 0.85 (m, 2H), 1.52 (m, 2H), 3.39 (brs, 1H), 4.05 (m, 2H), 4.22 (t, 2H), 7.42 (s, 2H), 7.58 (s, 1H). LRMS (thermospray): m/z [MH+] 355. Microanalysis: Found C, 67.63; H, 5.55; N, 16.35. $C_{19}H_{18}N_4O_2 \cdot 0.17H_2O$ requires C, 67.63; H, 5.48; N, 16.60%.

Example 191

5-{[1-(2-Aminoethyl)-3,5-dicyclopropyl-1H-pyrazol-4-yl]oxy}isophthalonitrile

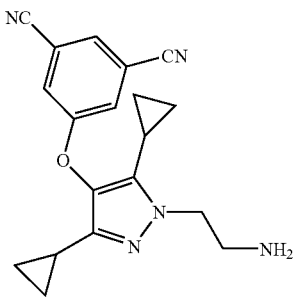

2-Chloroethylamine hydrochloride (192 mg, 1.65 mmol) and the pyrazole from Example 189 (440 mg, 1.50 mmol) were heated as a melt at 160° C. for 18 hours and the residue was partitioned between dichloromethane (25 ml) and 10% aqueous potassium carbonate solution (25 ml). The organic phase was dried over magnesium sulphate, concentrated under reduced pressure and the residue was purified by flash chromatography on silica gel eluting with dichloromethane:methanol:0.88 ammonia (95:5:0 changing to 95:5:0.5, by volume) to provide the title compound (9.2 mg) as a white solid, m.p. 175–177° C.

$^1$H NMR (400 MHz, CDCl$_3$): δ=0.70 (m, 2H), 0.79 (m, 4H), 0.88 (m, 2H), 1.57 (m, 1H), 1.66 (m, 1H), 3.46 (t, 2H), 4.41 (t, 2H), 7.62 (s, 2H), 7.58 (s, 1H).

Example 192

3-{[3-cyclopropyl-1-(2-hydroxyethyl)-5-methyl-1H-pyrazol-4-yl]oxy}-5-methylbenzonitrile

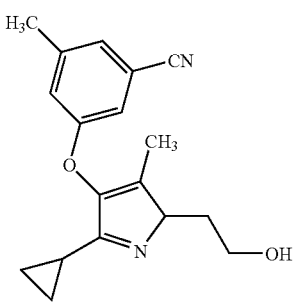

and

Example 193

3-{[5-cyclopropyl-1-(2-hydroxyethyl)-3-methyl-1H-pyrazol-4-yl]oxy}-5-methylbenzonitrile

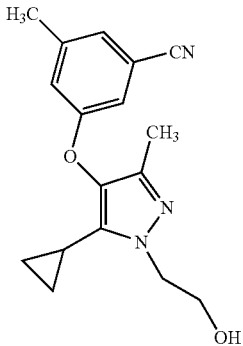

2-Hydroxy-ethyl-hydrazine (3261, 4.80 mmol) was added to a solution of the diketone from Preparation 86 (1.00 g, 4.37 mmol) in acetic acid (10 ml) under nitrogen at room temperature. After stirring for 18 hours, the mixture was concentrated under reduced pressure and the residual orange oil was purified by flash chromatography on silica gel eluting with ethyl acetate:pentane (50:50 changing to 100:0, by volume) to provide two pale yellow oils.

Least Polar Fraction (Example 192)—419 mg $^1$H NMR (400 MHz, CDCl$_3$): δ=0.69 (m, 2H), 0.82 (m, 2H), 1.54 (m, 1H), 2.00 (s, 3H), 2.35 (s, 3H), 3.46 (brs, 1H), 4.05 (t, 2H), 4.22 (t, 2H), 6.88 (s, 1H), 6.94 (s, 1H), 7.08 (s, 1H). LRMS (thermospray): m/z [MH$^+$] 298. Microanalysis: Found C, 68.29; H, 6.51; N, 13.92. C$_{17}$H$_{19}$N$_3$O$_2$ requires C, 68.67; H, 6.44; N, 14.13%.

Most Polar Fraction (Example 193)—201 mg $^1$H NMR (400 MHz, CDCl$_3$): δ=0.75 (m, 4H), 1.58 (m, 1H), 2.07 (s, 3H), 2.35 (s, 3H), 3.45 (brs, 1H), 4.00 (m, 4H), 6.92 (s, 1H), 7.00 (s, 1H), 7.10 (s, 1H). LRMS (thermospray): m/z [MH$^+$] 298. Microanalysis: Found C, 68.44; H, 6.49; N, 13.95. C$_{17}$H$_{19}$N$_3$O$_2$ requires C, 68.67; H, 6.44; N, 14.13%.

Example 194

3-[3-Cyclopropyl-1-(2-amino-ethyl)-5-methyl-1H-pyrazol-4-yloxy]-5-methyl-benzonitrile

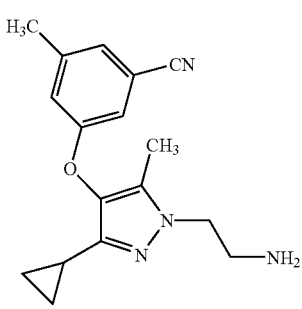

The alcohol from Example 192 (140 mg, 0.47 mmol), triphenylphosphine (309 mg, 1.18 mmol) and phthalimide (174 mg, 1.18 mmol) were dissolved in tetrahydrofuran (9 ml) at 0° C. under nitrogen and diisopropylazodicarboxylate (232 μl, 1.18 mmol) dissolved in tetrahydrofuran (2 ml) was added over 10 minutes. The reaction was allowed to warm to room temperature and was stirred for 18 hours. The solvent was removed under reduced pressure, the residue was dissolved in ethanol (11 ml) and hydrazine hydrate (114 μl, 2.35 mmol) was added. The thick white slurry was stirred for 18 h at room temperature under nitrogen, methanol (10 ml) was added and the mixture was filtered. The filtrate was concentrated under reduced pressure and the residue was dissolved in dichloromethane (20 ml). The organic phase was extracted with 2M aqueous hydrochloric acid (20 ml) and the aqueous phase was washed with dichloromethane (5×10 ml), basified with 1M aqueous sodium hydroxide and extracted with dichloromethane (50 ml). The organic phase was dried over magnesium sulphate and concentrated under reduced pressure to provide the title compound (135 mg) as a yellow oil.

$^1$H NMR (400 MHz, CDCl$_3$): δ=0.70 (m, 4H), 1.56 (m, 1H), 2.06 (s, 3H), 2.30 (s, 3H), 3.10 (t, 2H), 3.97 (t, 2H), 6.87 (s, 1H), 6.92 (s, 1H), 7.05 (s, 1H). LRMS (electrospray): m/z [MH$^+$] 297. Microanalysis: Found C, 63.81; H, 6.51; N, 17.30. C$_{17}$H$_{20}$N$_4$O.0.36CH$_2$Cl$_2$ requires C, 63.78; H, 6.39; N, 17.14%.

Example 195

3-[(3-Cyclopropyl-5-methyl-1H-pyrazol-4-yl)oxy]-5-methylbenzonitrile

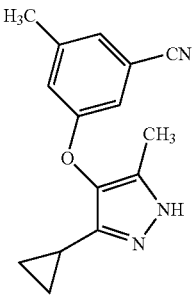

Hydrazine hydrate (31 μl, 0.64 mmol) was added to a solution of the diketone from Preparation 86 (150 mg, 0.58 mmol) in acetic acid (1.3 ml) under nitrogen at room temperature. After stirring for 24 hours, the mixture was concentrated under reduced pressure and the residue was purified by flash chromatography on silica gel eluting with pentane:ethyl acetate (60:40 changing to 40:60, by volume) to provide the title compound (140 mg).

$^1$H NMR (400 MHz, CDCl$_3$): δ=0.60 (m, 4H), 1.69 (m, 1H), 2.09 (s, 3H), 2.34 (s, 3H), 6.95 (s, 1H), 6.99 (s, 1H), 7.10 (s, 1H). LRMS (thermospray): m/z [MH$^+$] 254. Microanalysis: Found C, 68.35; H, 6.13; N, 15.10. C$_{15}$H$_{15}$N$_3$O.0.29EtOAc requires C, 68.72; H, 6.32; N, 14.88%.

Example 196

3-{[1-(3-Aminopropyl)-3,5-diethyl-1H-pyrazol-4-yl]oxy}-5-methylbenzonitrile

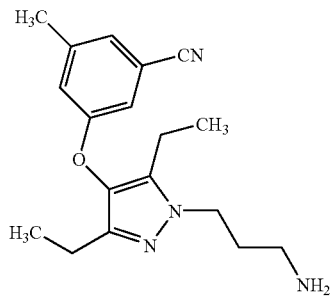

3-Chloropropylamine hydrochloride (62 mg, 0.48 mmol) and the pyrazole from Example 123 (113 mg, 0.44 mmol) were heated as a melt at 150° C. for 18 hours. After cooling the residue was purified by flash chromatography on silica gel eluting with dichloromethane:methanol:0.88 ammonia (98:2:0 changing to 95:5:0.5, by volume). An impurity remained so the oil was dissolved in acetone (3 ml) and (L)-tartaric acid (54 mg, 0.44 mmol) was added, the mixture was heated to effect dissolution and cooled. The resultant precipitate was isolated by filtration washing with acetone (10 ml) to provide the title compound (127 mg) as a white solid which was the tartrate salt.

$^1$H NMR (400 MHz, CD$_3$OD): δ=1.05 (m, 6H), 2.07 (m, 2H), 2.37 (q, 2H), 2.53 (s, 3H), 2.57 (q, 2H), 2.99 (t, 2H), 4.15 (t, 2H), 4.38 (s, 2H), 6.89 (s, 1H), 7.01 (s, 1H), 7.19 (s, 1H). LRMS (thermospray): m/z [MH$^+$] 313. Microanalysis: Found C, 56.81; H, 6.57; N, 12.06. C$_{22}$H$_{30}$N$_4$O$_7$ requires C, 57.13; H, 6.54; N, 12.11%.

Example 197

3-{[3,5-Diethyl-1-(2-hydroxyethyl)-1H-pyrazol-4-yl]oxy}-4-methoxybenzonitrile

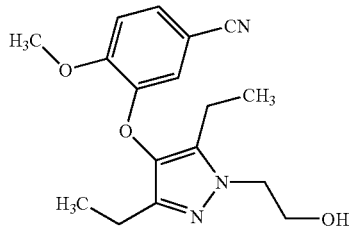

Cesium carbonate (700 mg, 2.14 mmol) was added to a stirred solution of 2-methoxy-5-cyanophenol (285 mg, 2.15 mmol) and the dione of Preparation 2 (348 mg, 2.15 mmol) in acetone (20 ml) at room temperature. The reaction was heated at 50° C. for 3 hours and then cooled to room temperature. The mixture was concentrated under reduced pressure, dissolved in dichloromethane (5 ml) and washed with water (5 ml). The organic phase was isolated using a 5 μM Whatman PTFE fritted cartridge, then concentrated under reduced pressure. The residue was dissolved in acetic acid (5.4 ml) and 2-hydroxy-ethyl-hydrazine (160 μl, 2.15 mmol) added under nitrogen at room temperature. After stirring for 18 hours, the mixture was concentrated under reduced pressure and the residual orange oil was purified by flash chromatography on silica gel eluting with a solvent gradient of ethyl acetate:pentane (25:75 changing to 50:50, by volume) to provide the title compound (182 mg).

$^1$H NMR (400 MHz, CDCl$_3$): δ=1.10 (m, 6H), 2.39 (q, 2H), 2.51 (q, 2H), 3.71 (brs, 1H), 4.00 (s, 3H), 4.08 (m, 2H), 4.09 (m, 2H), 6.89 (s, 1H), 6.99 (d, 1H), 7.32 (d, 1H). LRMS (thermospray): m/z [MH$^+$] 316. Microanalysis: Found C, 64.57; H, 6.73; N, 13.15. C$_{17}$H$_{21}$N$_3$O$_3$ requires C, 64.74; H, 6.71; N, 13.32%.

Examples 198–199

The preparation of the following tabulated Examples of the general formula

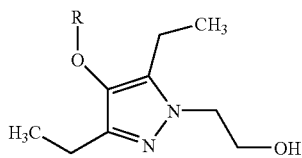

were performed by a similar method to that of Example 197 using the β-diketone of Preparation 2 and the appropriate aryl alcohol as the starting materials.

The protected alcohol from Preparation 88 (254 mg, 0.53 mmol) and p-toluene-sulphonic acid (10 mg, 0.05 mmol) were dissolved in methanol (4 ml) and stirred under nitrogen at room temperature for 18 hours. The solvent was removed under reduced pressure and the residue was partitioned between saturated aqueous sodium bicarbonate solution (20 ml) and dichloromethane (20 ml). The aqueous phase was extracted with dichloromethane (10 ml) and the combined organic extracts were dried over magnesium sulphate, concentrated under reduced pressure and purified by flash chromatography on silica gel eluting with a solvent gradient of dichloromethane:methanol (100:0 changing to 93:7, by volume) to provide the title compound (56 mg) as a white solid, m.p. 108–110° C.

$^1$H NMR (400 MHz, CDCl$_3$): δ=1.11 (m, 6H), 2.46 (q, 2H), 2.53 (q, 2H), 4.01 (t, 2H), 4.07 (t, 2H), 6.44 (s, 2H), 7.16 (s, 2H), 7.68 (s, 3H), 7.92 (s, 2H). LRMS (electrospray): m/z [MH$^+$] 393, [MNa$^+$] 415. Microanalysis: Found C, 63.62; H, 6.11; N, 21.11. C$_{21}$H$_{24}$N$_6$O$_2$·0.06CH$_2$Cl$_2$ requires C, 63.63; H, 6.12; N, 21.14%.

| Example No. | R | Analytical Data |
|---|---|---|
| 198 | 1-naphthyloxy | $^1$H NMR (400 MHz, CDCl$_3$): δ = 1.04(m, 6H), 2.42(q, 2H), 2.51 (q, 2H), 4.07(m, 2H), 4.12(m, 2H), 6.60(d, 1H), 7.25(t, 1H), 7.49(d, 1H), 7.53(m, 2H), 7.82(m, 1H), 8.41(m, 1H). LRMS (thermospray): m/z [MH$^+$] 311. |
| 199 | 2-naphthyloxy | $^1$H NMR (400 MHz, CDCl$_3$): δ = 1.19(m, 6H), 2.48(q, 2H), 2.51 (q, 2H), 4.03(m, 2H), 4.10(m, 2H), 7.06(s, 1H), 7.22(m, 1H), 7.38(t, 1H), 7.42(m, 1H), 7.69(d, 1H), 7.79(s, 1H), 7.80(s, 1H). LRMS (thermospray): m/z [MH$^+$] 311. Microanalysis: Found C, 72.16; H, 7.20; N, 8.95. C$_{19}$H$_{22}$N$_2$O$_2$·0.10EtOAc requires C, 72.45; H, 7.19; N, 8.63%. |

Example 200

2-[4-[3,5-Di(1H-pyrazol-1-yl)phenoxy]-3,5-diethyl-1H-pyrazol-1-yl]ethanol

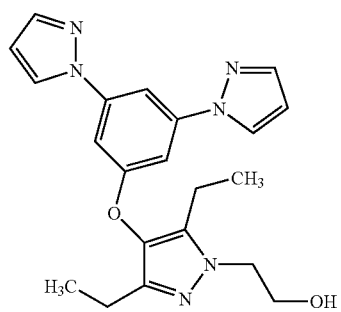

Example 201

2-{3,5-Diethyl-4-[3-fluoro-5-(1H-pyrazol-1-yl)phenoxy]-1H-pyrazol-1-yl}ethanol

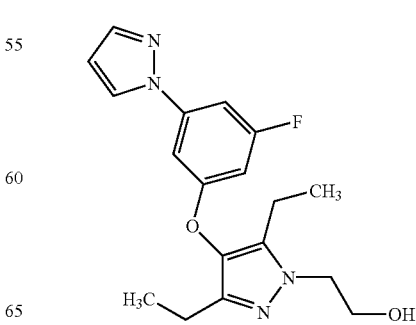

The protected alcohol from Preparation 89 (38.6 mg, 0.09 mmol) and p-toluene-sulphonic acid (3.5 mg, 0.01 mmol) were dissolved in methanol (1 ml) and stirred under nitrogen at room temperature for 18 hours. The solvent was removed under reduced pressure and the residue was partitioned between 10% aqueous potassium carbonate solution (4 ml) and dichloromethane (4 ml). The aqueous phase was extracted with dichloromethane (10 ml) and the combined organic extracts were dried over magnesium sulphate, concentrated under reduced pressure and purified by flash chromatography on silica gel eluting with a solvent gradient of dichloromethane:methanol (99:1 changing to 98:2, by volume) to provide the title compound (23 mg) as a white solid, m.p. 120–122° C.

$^1$H NMR (400 MHz, CDCl$_3$): δ=1.14 (m, 6H), 2.46 (q, 2H), 2.55 (q, 2H), 4.06 (m, 2H), 4.09 (m, 2H), 6.47 (s, 1H), 6.49 (s, 1H), 7.09 (s, 1H), 7.12 (s, 1H), 7.71 (s, 1H), 7.86 (s, 1H). LRMS (electrospray): m/z [MNa$^+$] 367. HRMS: [MH$^+$] Found 345.1717. C$_{18}$H$_{22}$FN$_4$O$_2$ requires 345.1722.

Example 202

3-{[3,5-Diethyl-1-(2-hydroxyethyl)-1H-pyrazol-4-yl]oxy}-5-methoxybenzonitrile

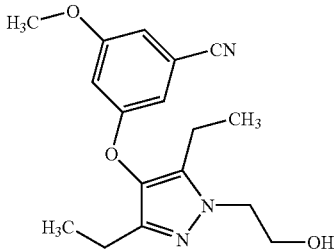

The protected alcohol from Preparation 90 (400 mg, 1.00 mmol) and p-toluene-sulphonic acid (19 mg, 0.10 mmol) were dissolved in methanol (10 ml) and stirred under nitrogen at room temperature for 18 hours. The solvent was removed under reduced pressure and the residue was partitioned between saturated aqueous sodium bicarbonate solution (20 ml) and dichloromethane (20 ml). The aqueous phase was extracted with dichloromethane (40 ml) and the combined organic extracts were dried over magnesium sulphate, concentrated under reduced pressure and purified by flash chromatography on a silica gel eluting with dichloromethane:methanol (97:3, by volume) to provide the title compound (174 mg) as an oil.

$^1$H NMR (400 MHz, CDCl$_3$): δ=1.09 (m, 6H), 2.40 (q, 2H), 2.49 (q, 2H), 3.78 (s, 3H), 4.04 (m, 2H), 4.08 (m, 2H), 6.66 (s, 1H), 6.71 (s, 1H), 6.79 (s, 1H). LRMS (electrospray): m/z [MH$^+$] 316. Microanalysis: Found C, 63.63; H, 6.76; N, 13.06. C$_{17}$H$_{21}$N$_3$O$_3$.0.08CH$_2$Cl$_2$ requires C, 63.68; H, 6.68; N, 13.04%.

Example 203

2-[4-(3,5-Difluorophenoxy)-3,5-diethyl-1H-pyrazol-1-yl]ethylamine

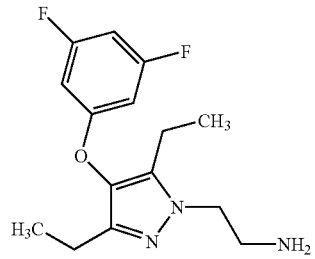

The alcohol from Example 38 (371 mg, 1.25 mmol), triphenylphosphine (984 mg, 3.75 mmol) and phthalimide (552 mg, 3.75 mmol) were dissolved in tetrahydrofuran (20 ml) at 0° C. under nitrogen and diisopropylazodicarboxylate (738 μl, 3.75 mmol) dissolved in tetrahydrofuran (2 ml) was added over 10 minutes. The reaction was allowed to warm to room temperature and was stirred for 18 hours. The solvent was removed under reduced pressure, the residue was dissolved in ethanol (25 ml) and hydrazine hydrate (303 μl, 6.25 mmol) was added. The slurry was stirred for 4 hours at 45° C. under nitrogen, concentrated under reduced pressure and the residue was dissolved in methanol. The solution was then passed through an SCX column eluting with methanol to remove impurities, then 2M methanolic ammonia solution to elute the product. The product was then purified by flash chromatography on alumina eluting with dichloromethane:methanol:0.88 ammonia (90:10:1, by volume) to provide the title compound (212 mg) as an oil.

$^1$H NMR (400 MHz, CDCl$_3$): δ=1.12 (m, 6H), 2.43 (q, 2H), 2.54 (q, 2H), 3.21 (t, 2H), 4.07 (t, 2H), 6.43 (m, 3H). Microanalysis: Found C, 59.78; H, 6.50; N, 14.35. C$_{15}$H$_{19}$F$_2$N$_3$O.0.26H$_2$O requires C, 60.05; H, 6.56; N, 14.01%.

Example 204

3-{[1-(2-Aminoethyl)-3,5-diethyl-1H-pyrazol-4-yl]oxy}-5-fluorobenzamide

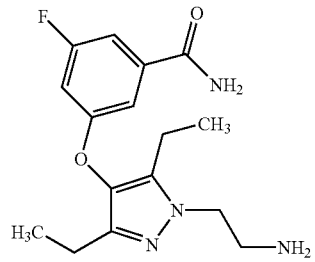

The alcohol from Example 163 (142 mg, 0.44 mmol), triphenylphosphine (346 mg, 1.32 mmol) and phthalimide (194 mg, 1.32 mmol) were dissolved in tetrahydrofuran (8 ml) at 0° C. under nitrogen and diisopropylazodicarboxylate (260 μl, 1.32 mmol) dissolved in tetrahydrofuran (1 ml) was added over 10 minutes. The reaction was allowed to warm to room temperature and was stirred for 18 hours. The solvent was removed under reduced pressure, the residue was dissolved in ethanol (9 ml) and hydrazine hydrate (107 μl, 2.2 mmol) was added. The slurry was stirred for 4 hours at 45° C. under nitrogen, concentrated under reduced pressure and the residue was dissolved in methanol. The solution was then passed through a polymer supported sulphonic acid column eluting with methanol to remove impurities, then 2M methanolic ammonia solution to elute the product. The product was then purified by flash chromatography on alumina eluting with dichloromethane:methanol:0.88 ammonia (90:10:1, by volume) to provide the title compound (60 mg) as an oil.

$^1$H NMR (400 MHz, CDCl$_3$): δ=1.11 (m, 6H), 2.43 (q, 2H), 2.53 (q, 2H), 3.17 (t, 2H), 4.05 (t, 2H), 6.01 (brs, 1H), 6.25 (brs, 1H), 6.75 (d, 1H), 7.16 (m, 2H). HRMS: [MH$^+$] Found 321.1718. C$_{16}$H$_{21}$FN$_4$O$_2$ requires 321.1722.

Example 205

3-[(3-Isopropyl-5-methyl-1H-pyrazol-4-yl)oxy]-5-methylbenzonitrile

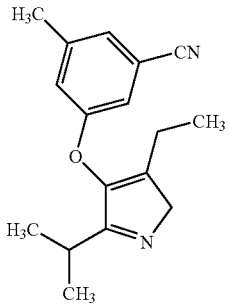

Hydrazine hydrate (100 μl, 2.10 mmol) was added to a solution of the diketone from Preparation 91 (544 mg, 2.10 mmol) in acetic acid (10 ml) under nitrogen at room temperature. After stirring for 64 hours, the mixture was concentrated under reduced pressure and the residue was purified by flash chromatography on silica gel eluting with pentane:ethyl acetate (66:34, by volume) to provide the title compound (308 mg) as a pale yellow oil.

$^1$H NMR (400 MHz, CDCl$_3$): δ=1.22 (d, 6H), 2.09 (s, 3H), 2.56 (s, 3H), 2.84 (m, 1H), 6.91 (s, 1H), 6.94 (s, 1H), 7.11 (s, 1H). LRMS (thermospray): m/z [MH$^+$] 256.

Example 206

3-{[1-(2-Aminoethyl)-3-isopropyl-5-methyl-1H-pyrazol-4-yl]oxy}-5-methylbenzonitrile

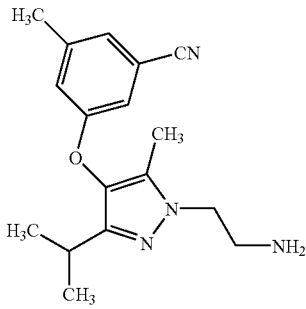

The pyrazole from Example 205 (70 mg, 0.27 mmol) and 2-chloroethylamine hydrochloride (38 mg, 0.33 mmol) were heated as a melt at 150° C. for 18 hours. The residue was cooled and purified by flash chromatography on silica gel eluting with dichloromethane:methanol:0.88 ammonia (95:5:0.5, by volume) to give the title compound (25 mg).

$^1$H NMR (400 MHz, CDCl$_3$): δ=1.18 (m, 6H), 2.06 (s, 3H), 2.35 (s, 3H), 2.79 (m, 1H), 3.19 (m, 2H), 4.04 (m, 2H), 6.89 (s, 1H), 6.97 (s, 1H), 7.12 (s, 1H). LRMS (electrospray): m/z [MH$^+$] 300.

Example 207

2-[4-(3,5-Dichlorophenoxy)-3,5-diethyl-1H-pyrazol-1-yl]-N-(2-pyridinylmethyl)acetamide

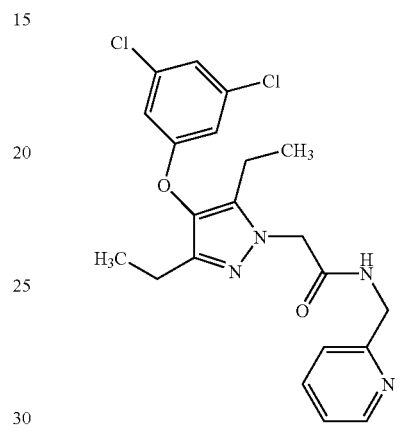

Standard solutions: The acid of Preparation 4 (800 mg, 2.33 mmol), 1H-benzotriazol-1-yl)-N,N,N',N'-tetramethyluronium hexafluorophosphate (822 mg, 3.50 mmol) and diisopropylethylamine (603 mg, 4.66 mmol) were separately dissolved in N,N-dimethylformamide (3×13 ml). 2-(Methylamino)pyridine (3 mg, 0.029 mmol) was treated with the standard solutions of the acid and coupling reagents (3×170 μl) in a 96 well plate and the mixture was shaken for 14 hours at room temperature. The solvent was removed under reduced pressure and the mixture dissolved in dimethylsulphoxide (500 μl) and purified by HPLC (Magellen C$_8$(2) 150×10 mm column; a gradient mobile phase was used, 5:95 (by volume) to 95:5 (by volume) acetonitrile:(0.1% trifluoroacetic acid in water).

Retention time: 5.69 minutes. LRMS (electrospray): m/z [MH$^+$] 434.

Example 208

[4-(3,5-Dichlorophenoxy)-3-methyl-1H-pyrazol-5-yl]acetonitrile

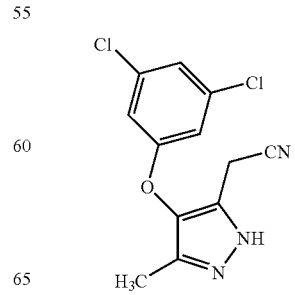

The pyrazole of Preparation 8 (1.00 g, 2.60 mmol) in tetrahydrofuran (10 ml) was added in one portion to a solution of sodium cyanide (284 mg, 5.20 mmol) in water (10 ml) at room temperature. The reaction was heated at 80° C. for 14 hours and cooled to room temperature. The solvent was removed under reduced pressure and the resulting brown solid was dissolved in dichloromethane (50 ml) and water (50 ml). The organic layer was separated, washed with water (50 ml), brine (30 ml), dried over magnesium sulphate, filtered and the solvent removed under reduced pressure to give a brown solid. The product was purified by flash chromatography on silica gel eluting with pentane:ethyl acetate (50:50, by volume) to give the title compound as a yellow solid (500 mg), m.p. 150–152° C.

$^1$H NMR (400 MHz, CDCl$_3$): δ=2.17 (s, 3H), 3.56 (s, 2H), 6.77 (s, 2H), 7.02 (s, 1H). LRMS (thermospray): m/z [MH$^+$] 282.

Example 209

1-{[4-(3,5-Dichlorophenoxy)-3-methyl-1H-pyrazol-5-yl]acetyl}piperidine

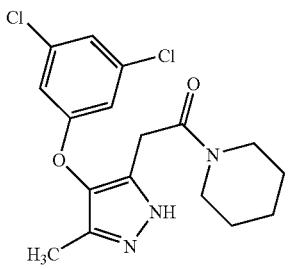

Standard solutions: The acid of Preparation 92 (680 mg, 2.16 mmol) and 1H-benzotriazol-1-yl)-N,N,N',N'-tetramethyluronium hexafluorophosphate (761 mg, 3.23 mmol) were separately dissolved in N,N-dimethylacetamide:triethylamine (96:4) (2×17 ml).

Piperidine (3 mg, 0.031 mmol) was treated with the standard solutions of the acid and coupling reagents (250 μl of each) in a 96 well plate and the mixture was shaken for 14 hours at 80° C. The solvent was removed under reduced pressure and the mixture dissolved in dimethylsulphoxide (500 μl) and purified by HPLC (Magellen C$_{18}$(2) 150×10 mm column; a gradient mobile phase was used, 5:95 (by volume) to 95:5 (by volume) acetonitrile:(0.1% trifluoroacetic acid in water).

Retention time: 4.7 minutes. LRMS (electrospray): m/z [MH$^+$] 368.

Examples 210–217

The compounds of the following tabulated Examples of the general formula:

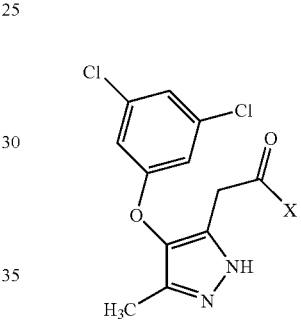

were performed by a similar method to that of Example 209 using the appropriate amine.

| Example No. | X | HPLC retention times/ min | LRMS (electrospray) m/z [MH$^+$] |
|---|---|---|---|
| 210 | ![piperidine-3-ol] | 3.9 | 384 |
| 211 | ![2,4-dichlorobenzylamine] | 5.5 | 459 |
| 212 | ![6-methylpyridin-2-ylamine] | 5.4 | 476 |

-continued

| Example No. | X | HPLC retention times/ min | LRMS (electrospray) m/z [MH+] |
|---|---|---|---|
| 213 | ◂-NH-CH2-C6H4-4-CF3 | 5.3 | 458 |
| 214 | ◂-NH-CH2-C6H4-3-Cl | 5.1 | 424 |
| 215 | ◂-NH-CH2-C6H4-2-CF3 | 5.3 | 458 |
| 216 | ◂-NH-CH2-C6H4-4-F | 4.9 | 408 |
| 217 | ◂-N(CH3)-CH2-C6H5 | 5.2 | 404 |

Example 218

3-chloro-5-[(5-{[(2-chlorobenzyl)amino]methyl}-3-methyl-1H-pyrazol-4-yl)oxy]benzonitrile

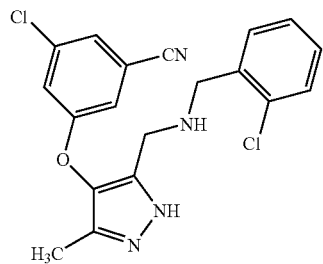

Standard solutions: The bromide of Preparation 18 (850 mg, 2.30 mmol) was dissolved in N-methylpyrolidinone (43 ml).

2-Chlorobenzylamine (19 mg, 0.13 mmol) in a 96 well plate was treated with the solution of the bromide of Preparation 18 (500 µl) and the mixture was shaken for 14 hours at 80° C. The solvent was removed under reduced pressure and the mixture dissolved in dimethylsulphoxide (500 µl) and purified by HPLC (Magellen C$_8$(2) 150×10 mm column; a gradient mobile phase was used, 5:95 (by volume) to 95:5 (by volume) acetonitrile:(0.1% trifluoroacetic acid in water).

Retention time: 5.3 minutes. LRMS (electrospray): m/z [MH+] 386.

Examples 219–249

The compounds of the following tabulated Examples of the general formula:

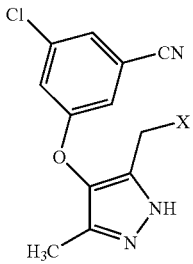

were performed by a similar method to that of Example 218 using the appropriate amine.

| Example No. | X | HPLC retention times/ min | LRMS (electrospray) m/z [MH+] |
|---|---|---|---|
| 219 | 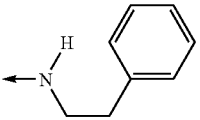 | 4.2 | 367 |
| 220 | 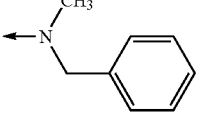 | 4.1 | 366 |
| 221 | 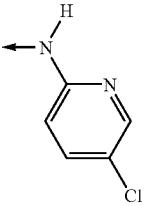 | 3.8 | 374 |
| 222 | 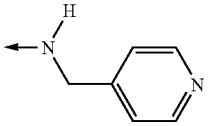 | 3.2 | 353 |
| 223 | 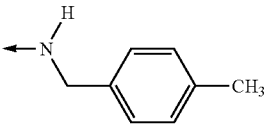 | 4.2 | 366 |
| 224 | 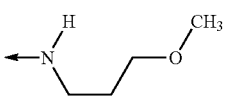 | 3.7 | 334 |
| 225 | 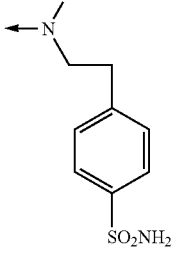 | 3.7 | 445 |
| 226 | 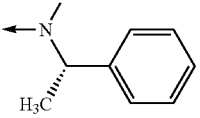 | 4.1 | 366 |
| 227 | 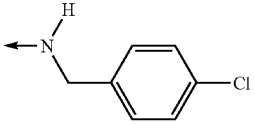 | 4.3 | 387 |

-continued

| Example No. | X | HPLC retention times/ min | LRMS (electrospray) m/z [MH+] |
|---|---|---|---|
| 228 | N(CH3)-CH2CH2-phenyl | 4.2 | 380 |
| 229 | NH-(1H-pyrazol-3-yl) | 3.6 | 328 |
| 230 | NH-CH2CH2-NH-C(O)CH3 | 3.5 | 347 |
| 231 | NH-CH2-(3-chlorophenyl) | 4.3 | 387 |
| 232 | NH-CH2-(3-fluoro-5-trifluoromethylphenyl) | 4.5 | 438 |
| 233 | NH-(6-methylpyridin-2-yl) | 3.8 | 353 |
| 234 | NH-(4-methyl-6-hydroxypyrimidin-2-yl) | 3.7 | 370 |
| 235 | NH-CH2-(4-fluorophenyl) | 4.1 | 370 |
| 236 | NH-CH(CH2OH)-phenyl (S) | 4.1 | 396 |

-continued

| Example No. | X | HPLC retention times/ min | LRMS (electrospray) m/z [MH+] |
|---|---|---|---|
| 237 | N-H-CH2-C6H5 (benzyl) | 4.1 | 352 |
| 238 | N-H-CH2-(3-methoxyphenyl) | 4.1 | 382 |
| 239 | N-H-CH2-(4-CF3-phenyl) | 4.4 | 420 |
| 240 | N-H-CH(CH(CH3)2)-CH2OH | 4.0 | 362 |
| 241 | N-H-CH2-(2-methoxyphenyl) | 4.1 | 382 |
| 242 | N-H-CH2CH2-(2-thienyl) | 4.2 | 372 |
| 243 | N-H-CH2-(3-pyridyl) | 3.2 | 353 |
| 244 | N-H-CH2-(2-CF3-phenyl) | 4.2 | 420 |
| 245 | N-H-CH2-(2,4-dichlorophenyl) | 4.4 | 421 |

| Example No. | X | HPLC retention times/ min | LRMS (electrospray) m/z [MH⁺] |
|---|---|---|---|
| 246 | ← N−CH₂−(2-pyridyl), H | 3.7 | 353 |
| 247 | ← N−CH₂−(3,4-dichlorophenyl), H | 4.4 | 421 |
| 248 | ← N−CH₂CH₂−phenyl, H | 4.1 | 382 |
| 249 | ← N−CH₂−(4-methoxyphenyl), H | 4.1 | 382 |

Example 250

3-{[3,5-Diethyl-1-(2-hydroxyethyl)-1H-pyrazol-4-yl]oxy}-5-(methylsulfanyl)benzonitrile

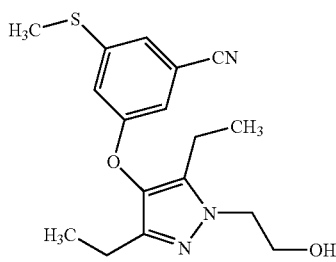

The protected alcohol from Preparation 93 (687 mg, 1.65 mmol) and p-toluene-sulphonic acid (32 mg, 0.17 mmol) were dissolved in methanol (16 ml) and stirred under nitrogen at room temperature. After 4 hours a second portion of p-toluene-sulphonic acid (32 mg, 0.17 mmol) was added. After 18 hours the solvent was removed under reduced pressure and the residue was partitioned between saturated aqueous sodium bicarbonate solution (20 ml) and dichloromethane (20 ml). The aqueous phase was extracted with dichloromethane (40 ml) and the combined organic extracts were dried over magnesium sulphate, concentrated under reduced pressure and purified by flash chromatography on silica gel eluting with dichloromethane:methanol (97:3, by volume) to provide the title compound (487 mg) as a white solid. m.p. 72° C.

$^1$H NMR (400 MHz, CDCl$_3$): δ=1.14 (m, 6H), 2.44 (q, 2H), 2.49 (s, 3H), 2.53 (q, 3H), 4.08 (m, 2H), 4.14 (m, 2H), 6.84 (s, 1H), 7.00 (s, 1H), 7.10 (s, 1H). LRMS (electrospray): m/z [MH⁺] 332. Microanalysis: Found C, 61.36; H, 6.43; N, 12.55. C$_{17}$H$_{21}$N$_3$O$_2$S requires C, 61.61; H, 6.39; N, 12.68%.

Example 251

3-{[3,5-Diethyl-1-(2-hydroxyethyl)-1H-pyrazol-4-yl]oxy}-5-(methylsulfinyl)benzonitrile

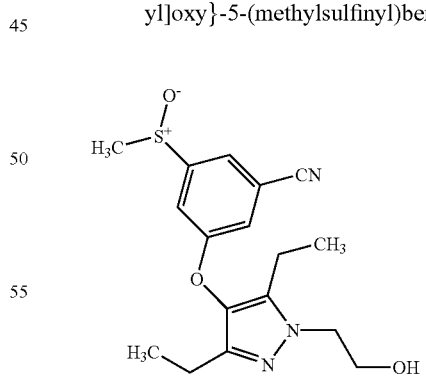

Wet alumina was prepared by adding water (1 ml) to Brockman grade I alumina (5 g). To a stirred solution of the sulphide from Example 250 (134 mg, 0.40 mmol) in dichloromethane (2 ml) was added of wet alumina (400 mg) followed by Oxone® (123 mg, 0.4 mmol) and the mixture was heated at reflux. After 1 hour a second portion of oxone (123 mg, 0.40 mmol) was added and the mixture was heated for a further 2 hours. After cooling to room temperature the reaction mixture was filtered and the resulting solids were washed with dichloromethane (20 ml). The filtrate was concentrated and was purified by flash chromatography on silica gel eluting with dichloromethane:methanol (a gradient from 99:1 to 90:10, by volume) to provide the title compound (92 mg) as an oil.

$^1$H NMR (400 MHz, CDCl$_3$): δ=1.12 (m, 6H), 2.44 (q, 2H), 2.53 (q, 2H), 2.73 (s, 3H), 4.06 (m, 2H), 4.18 (m, 2H), 7.24 (s, 1H), 7.45 (s, 1H), 7.49 (s, 1H). LRMS (electrospray): m/z [M+Na$^+$] 370.

Example 252

3-{[3,5-Diethyl-1-(2-hydroxyethyl)-1H-pyrazol-4-yl]oxy}-5-(methylsulfonyl)benzonitrile

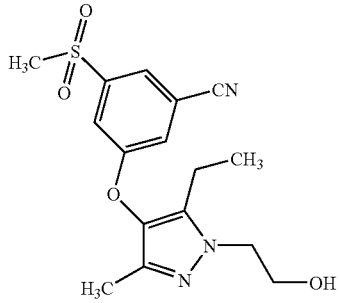

To a stirred solution of the sulphide from Example 250 (133 mg, 0.4 mmol) in dichloromethane (2 ml) at −78° C. was added a solution of meta-chloroperoxybenzoic acid (138 mg of 50% by weight mixture, 0.4 mmol) in dichloromethane (2 ml). The cooling bath was removed and the solution was stirred at room temperature for 4 hours. The mixture was quenched by addition of saturated aqueous sodium bicarbonate solution (6 ml) and extracted with dichloromethane (3×5 ml). The combined organic components were dried over magnesium sulphate and concentrated. Analysis of the $^1$H NMR (400 MHz, CDCl$_3$) suggested a mixture of the desired product and the sulphoxide from Example 251. The crude product mixture was dissolved in dichloromethane (2 ml), cooled to −78° C. and to this was added meta-chloroperoxybenzoic acid (138 mg of 50% by weight mixture, 0.4 mmol) in dichloromethane (2 ml). The cooling bath was removed and the mixture was stirred at room temperature for 1 hour. The mixture was quenched by addition of saturated aqueous sodium bicarbonate solution (6 ml) and extracted with dichloromethane (3×5 ml). The combined organic components were dried over magnesium sulphate and concentrated. The crude product mixture was purified by flash chromatography on a silica gel eluting with dichloromethane:methanol (98:2, by volume) to provide the title compound contaminated with meta-chloroperoxybenzoic acid. To a solution of this crude product in dichloromethane at −78° C. was added dimethylsulphoxide (30 μl, 0.4 mmol). The cooling bath was removed and the mixture was stirred at room temperature for 15 minutes. The mixture was quenched by addition of 10% aqueous potassium carbonate solution (10 ml) and the dichloromethane was evaporated. The remaining aqueous mixture was then extracted with diethyl ether (2×10 ml) and ethyl acetate (10 ml). The organic components were combined, dried over magnesium sulphate and concentrated to give the crude product mixture which was purified by flash chromatography on a silica gel eluting with dichloromethane:methanol (98:2, by volume) to provide the title compound (26 mg) as a white solid. m.p. 133° C.

$^1$H NMR (400 MHz, CDCl$_3$): δ=1.10 (m, 6H), 2.39 (q, 2H), 2.51 (q, 2H), 3.06 (s, 3H), 4.05 (m, 2H), 4.10 (m, 2H), 7.39 (s, 1H), 7.67 (s, 1H), 7.84 (s, 1H). LRMS (electrospray): m/z [M+Na$^+$] 385. HRMS: [MH$^+$] 364.1329. C$_{18}$H$_{20}$N$_6$O$_2$ requires 364.1326.

Example 253

3-{[3,5-Diethyl-1-(2-hydroxyethyl)-1H-pyrazol-4-yl]oxy}-5-[2-(dimethylamino)ethoxy]benzonitrile

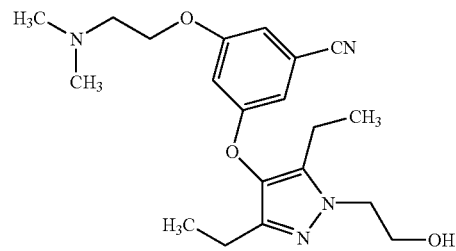

To a stirred solution of the protected alcohol from Preparation 94 (180 mg, 0.39 mmol) in methanol (4 ml) was added para-toluenesulphonic acid (89 mg, 0.47 mmol). After 18 hours at room temperature the solvent was evaporated under reduced pressure and the residue was partitioned between dichloromethane (5 ml) and 10% aqueous potassium carbonate solution (5 ml). The aqueous phase was separated and extracted with a dichloromethane (3 ml). The organic components were combined, dried over magnesium sulphate and concentrated under reduced pressure. The crude product mixture was purified by flash chromatography on silica gel eluting with dichloromethane:methanol (95:5, by volume) followed by dichloromethane:methanol:ammonia (80:20:1, by volume) to provide the title compound (63 mg) as an oil.

$^1$H NMR (400 MHz, CDCl$_3$): δ=1.13 (m, 6H), 2.43 (m, 8H), 2.52 (q, 2H), 2.85 (m, 2H), 3.81 (broad s, 1H), 4.08 (m, 6H), 6.70 (s, 1H), 6.78 (s, 1H), 6.81 (s, 1H). LRMS (APCI): m/z [MH$^+$] 373. HRMS: [MH$^+$] 373.2234. C$_{20}$H$_{29}$N$_4$O$_3$ requires 373.2234.

Examples 254–256

The compounds of the following tabulated Examples of the general formula:

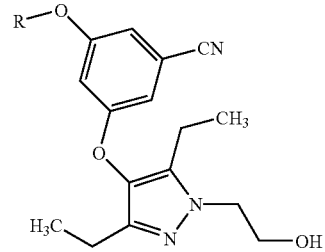

were performed by a similar method to that of Example 253 using as starting material the appropriate protected alcohol (PA) from Preparations 95–97.

| Example No. | PA prep No. | R | Analytical Data |
|---|---|---|---|
| 254 | 95 | $CH_2CH_2NHMe$ | $^1$H NMR(400 MHz, CDCl$_3$): δ = 1.13(m, 6H), 2.42(q, 2H), 2.53(q, 2H), 2.59(s, 3H), 3.12(t, 2H), 4.05(m, 2H), 4.09(m, 2H), 4.16(t, 2H), 6.75(s, 1H), 6.81(s, 1H), 6.82(s, 1H). LRMS (APCI): m/z [MH$^+$] 359 HRMS: [MH$^+$] 359.2083. $C_{19}H_{27}N_4O_3$ requires 359.2078. |
| 255 | 96 | $CH_2CONH_2$ | $^1$H NMR(400 MHz, CDCl$_3$): δ = 1.11(m, 6H), 2.41(q, 2H), 2.52(q, 2H), 4.05(t, 2H), 4.09(t, 2H), 4.46 (s, 2H), 5.74(broad s, 1H), 6.42 (broad s, 1H), 6.69(s, 1H), 6.85(s, 2H). LRMS (APCI): m/z 359 (MH$^+$) |
| 256 | 97 | $CH_2CH_2OCH_3$ | $^1$H NMR(400 MHz, CDCl$_3$): δ = 1.12(m, 6H), 2.42(q, 2H), 2.51(q, 2H), 3.44(s, 3H), 3.73(t, 2H), 4.09 (m, 6H), 6.71(s, 1H), 6.77(s, 1H), 6.83(s, 1H). LRMS (electrospray): m/z 360 (MH$^+$) HRMS: [MH$^+$] 360.1920. $C_{19}H_{26}N_3O_4$ requires 360.1918. |

Example 257

3-{[1-(2-Aminoethyl)-3,5-diethyl-1H-pyrazol-4-yl]oxy}-5-methoxybenzonitrile

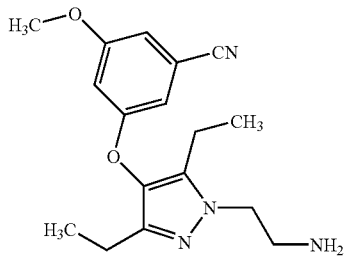

The alcohol from Example 202 (87 mg, 0.28 mmol), triphenylphosphine (220 mg, 0.84 mmol) and phthalimide (124 mg, 0.84 mmol) were dissolved in tetrahydrofuran (5 ml) at 0° C. under nitrogen and diisopropylazodicarboxylate (165 μl, 0.84 mmol) dissolved in tetrahydrofuran (1 ml) was added dropwise. The reaction was allowed to warm to room temperature and was stirred for 18 hours. The solvent was removed under reduced pressure, the residue was dissolved in ethanol (6 ml) and hydrazine hydrate (68 μl, 1.40 mmol) was added. The slurry was stirred for 48 hours at room temperature under nitrogen, concentrated under reduced pressure and the residue was dissolved in methanol. The solution was then passed through an SCX column eluting with methanol to remove impurities, then 2M ammonia in methanol solution to elute the product. The product was then purified by flash chromatography on silica gel eluting with dichloromethane:methanol (95:5) then dichloromethane:methanol:0.88 ammonia (90:10:1, by volume) to provide the title compound (67 mg) as an oil.

$^1$H NMR (400 MHz, CDCl$_3$): δ=1.13 (m, 6H), 2.19 (broad s, 2H), 2.43 (q, 2H), 2.54 (q, 2H), 3.19 (t, 2H), 3.60 (s, 3H), 4.06 (t, 2H), 6.68 (s, 1H), 6.73 (s, 1H), 6.80 (s, 1H). LRMS (electrospray): m/z 315 (MH$^+$) HRMS: [MH$^+$] 315.1819. $C_{17}H_{23}N_4O_2$ requires 315.1816.

Example 258

3-{[1-(2-Aminoethyl)-3,5-diethyl-1H-pyrazol-4-yl]oxy}-5-(1H-pyrazol-1-yl)benzonitrile

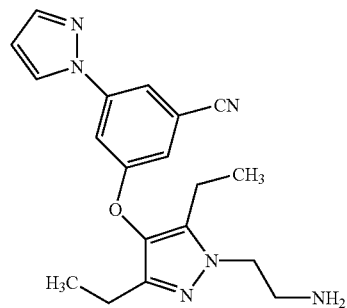

The alcohol from Example 164 (162 mg, 0.46 mmol), triphenylphosphine (362 mg, 1.38 mmol) and phthalimide (203 mg, 1.38 mmol) were dissolved in tetrahydrofuran (8 ml) at 0° C. under nitrogen and diisopropylazodicarboxylate (272 μl, 1.38 mmol) dissolved in tetrahydrofuran (1 ml) was added dropwise. The reaction was allowed to warm to room temperature and was stirred for 18 hours. The solvent was removed under reduced pressure, the residue was dissolved in ethanol (9 ml) and hydrazine hydrate (112 μl, 2.3 mmol) was added. The slurry was stirred for 48 hours at room temperature under nitrogen, concentrated under reduced pressure and the residue was dissolved in methanol. The solution was then passed through an SCX column eluting with methanol to remove impurities, then 2M ammonia in methanol solution to elute the product. The product was then purified by flash chromatography on silica gel eluting with dichloromethane:methanol (95:5) then dichloromethane:methanol:0.880 ammonia (90:10:1, by volume) to provide the title compound (62 mg) as an oil.

$^1$H NMR (400 MHz, CD$_3$OD): δ=1.15 (m, 6H), 2.46 (q, 2H), 2.63 (q, 2H), 3.13 (t, 2H), 4.13 (t, 2H), 6.54 (s, 1H), 7.17 (s, 1H), 7.69 (s, 1H), 7.72 (s, 1H), 7.82 (s, 1H), 8.32 (s, 1H). LRMS (APCI): m/z 351 (MH$^+$) HRMS: [MH$^+$] 351.1929. $C_{19}H_{22}N_4O_2$ requires 351.1928.

Example 259

3,5-Dichlorophenyl-3-methyl-5-[(3-methyl-1,2,4-oxadiazol-5-yl)methyl]-1H-pyrazol-4-yl ether

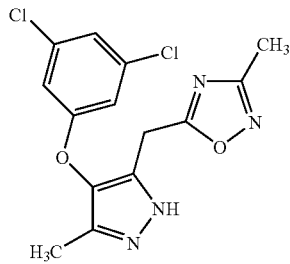

To a stirred solution of the acid (100 mg, 0.33 mmol) from Preparation 92 in dimethylformamide (2 ml) was added carbonyldiimidazole (59 mg, 0.36 mmol) in one portion. After 30 minutes at room temperature (1Z)-N'-hydroxyethanimidamide (27 mg, 0.36 mmol) was added and the reaction mixture was stirred at room temperature for 3 hours. A second portion of carbonyldiimidazole (59 mg, 0.36 mmol) was added and the mixture was heated at 100° C. for 12 hours. After cooling to room temperature water (30 ml) was added and the mixture was extracted with ethyl acetate (3×20 ml). The combined organic components were dried over magnesium sulphate and concentrated under reduced pressure to give a brown oil. The crude product mixture was purified by flash chromatography on silica gel eluting with ethyl acetate:pentane (30:70, by volume) to provide the title compound (40 mg) as a pale yellow oil.

$^1$H NMR (400 MHz, CDCl$_3$): δ=2.12 (s, 3H), 2.29 (s, 3H), 4.08 (s, 2H), 6.74 (s, 2H), 6.98 (s, 1H). LRMS (electrospray): m/z 339 (MH$^+$)

Example 260

3-Fluoro-5-{[1-(2-hydroxyethyl)-5-methyl-3-(trifluoromethyl)-1H-pyrazol-4-yl]oxy}benzonitrile

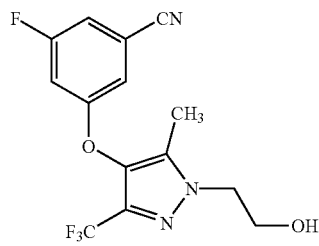

To a stirred solution of the protected alcohol (85 mg, 0.21 mmol) from Preparation 99 in methanol (0.5 ml) was added para-toluenesulphonic acid (4 mg, 0.02 mmol). After 5 hours the reaction mixture was concentrated under reduced pressure, dissolved in dichloromethane (20 ml), washed with saturated sodium bicarbonate solution (20 ml), dried over magnesium sulphate and concentrated under reduced pressure. The crude product mixture was purified by flash chromatography on silica gel eluting with pentane:ethyl acetate (60:40 followed by 40:60, by volume) to provide the title compound (54 mg) as a white solid.

$^1$H NMR (400 MHz, CDCl$_3$): δ=2.19 (s, 3H), 2.45 (t, 1H), 4.10 (m, 2H), 4.20 (m, 2H), 6.87 (d, 1H), 6.96 (s, 1H), 7.05 (d, 1H). LRMS (APCI): m/z 330 (MH$^+$) Microanalysis: Found C, 51.38; H, 3.52; N, 12.37. C$_{14}$H$_{11}$F$_4$N$_3$O$_2$ requires C, 51.07; H, 3.37; N, 12.76%.

Example 261

5-[(3,5-Diethyl-1-{2-[(2-methoxyethoxy)methoxy]ethyl}-1H-pyrazol-4-yl)oxy}isophthalonitrile

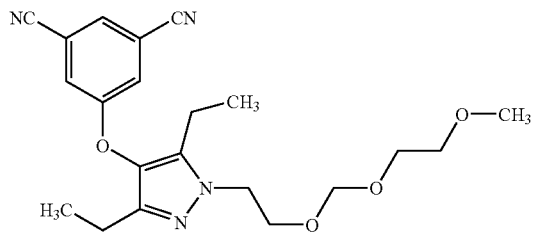

To a stirred solution of the alcohol (5.0 g, 16.11 mmol) from Example 119 in tetrahydrofuran (65 ml) at 0° C. was added 2-methoxyethoxymethylchloride (2.39 ml, 20.94 mmol) followed by sodium hydride (838 mg of a 60% by weight dispersion in oil, 20.94 mmol). After 10 minutes the reaction mixture was heated at 50° C. for 18 hours. After cooling to room temperature, the mixture was diluted with saturated aqueous ammonium chloride solution dropwise (3 ml). The mixture was concentrated under reduced pressure and the residue was partitioned between dichloromethane (250 ml) and water (200 ml). The aqueous phase was separated and extracted with dichloromethane (150 ml). The organic components were combined, dried over magnesium sulphate and concentrated under reduced pressure. The crude product mixture was purified by flash chromatography on silica gel eluting with dichloromethane, followed by dichloromethane:methanol (99:1, by volume) to provide the title compound (5.38 g) as a colourless oil.

$^1$H NMR (400 MHz, CDCl$_3$): δ=1.10 (m, 6H), 2.39 (q, 2H), 2.55 (q, 2H), 3.38 (s, 3H), 3.51 (m, 2H), 3.56 (m, 2H), 3.93 (t, 2H), 4.20 (t, 2H), 4.66 (s, 2H), 7.38 (s, 2H), 7.56 (s, 1H). LRMS (APCI): m/z 399 (MH$^+$) Microanalysis: Found C, 62.11; H, 6.67; N, 13.51. C$_{21}$H$_{26}$N$_4$O$_4$+0.43H$_2$O requires C, 62.09; H, 6.67; N, 13.79%.

Example 262

3-Cyano-5-{[3,5-diethyl-1-(2-hydroxyethyl)-1H-pyrazol-4-yl]oxy}benzamide

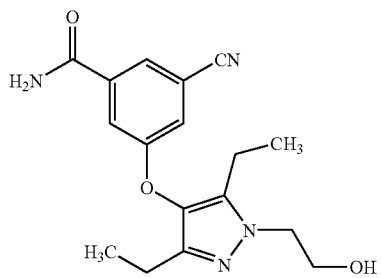

To a stirred solution of the pyrazole (60 mg) from Preparation 100 in dichloromethane (4 ml) was added aluminium trichloride (134 mg, 1 mmol). After 18 hours, ice was added, the mixture was neutralised using saturated aqueous sodium bicarbonate solution, diluted with water (30 ml) and extracted with dichloromethane (2×40 ml). The organic components were combined, dried over magnesium sulphate and concentrated under reduced pressure. The crude product mixture was purified by flash chromatography on silica gel eluting with dichloromethane:methanol (95:5, by volume) to provide the title compound (27 mg) as a colourless glass.

$^1$H NMR (400 MHz, CDCl$_3$): δ=1.10 (m, 6H), 2.40 (q, 2H), 2.52 (q, 2H), 4.07 (m, 4H), 7.25 (s, 1H), 7.60 (s, 1H), 7.65 (s, 1H). LRMS (APCI): m/z 329 (MH$^+$)

Example 263

5-{[5-Ethyl-3-(1-hydroxyethyl)-1H-pyrazol-4-yl]oxy}isophthalonitrile

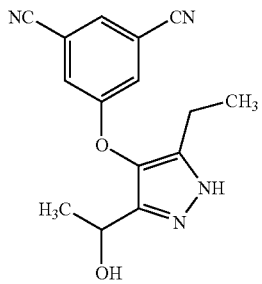

To a stirred solution of the pyrazole from Preparation 102 (219 mg, 0.57 mmol) in tetrahydrofuran (2.5 ml) was added saturated aqueous sodium carbonate solution (0.5 ml). The reaction mixture was stirred at room temperature for 4 hours and then heated at reflux for 18 hours. The reaction mixture was concentrated under reduced pressure and the residue was partitioned between dichloromethane (20 ml) and water (20 ml). The organic phase was dried over magnesium sulphate and concentrated under reduced pressure. The crude product mixture was purified by flash chromatography on silica gel eluting with dichloromethane:methanol (a gradient from 100:0 to 90:10, by volume) to provide the title compound (68 mg) as a white solid.

$^1$H NMR (400 MHz, CDCl$_3$): δ=1.21 (t, 3H), 1.51 (d, 3H), 2.54 (q, 2H), 4.89 (q, 1H), 7.25 (s, 2H), 7.43 (s, 1H). LRMS (APCI): m/z 283 (MH$^+$)

Example 264

5-{[5-Ethyl-3-(1-hydroxyethyl)-1-(2-hydroxyethyl)-1H-pyrazol-4-yl]oxy}isophthalonitrile

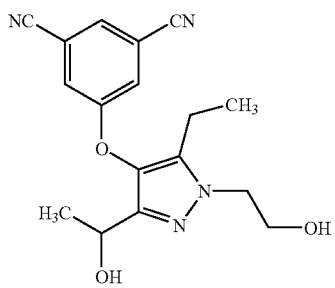

To a stirred solution of the pyrazole from Preparation 103 (80 mg, 0.19 mmol) in methanol (1 ml) was added para-toluenesulphonic acid (4 mg, 0.02 mmol). After 5 hours at room temperature the reaction mixture was concentrated under reduced pressure and the residue was partitioned between dichloromethane (20 ml) and water (20 ml). The organic component was dried over magnesium sulphate and concentrated under reduced pressure. The crude product mixture was purified by flash chromatography on silica gel eluting with dichloromethane:methanol (a gradient from 100:0 to 95:5, by volume) to provide the title compound (44 mg) white solid.

$^1$H NMR (400 MHz, CDCl$_3$): δ=1.11 (t, 3H), 1.46 (d, 3H), 2.54 (q, 2H), 4.10 (q, 2H), 4.17 (q, 2H), 4.79 (q, 1H), 7.44 (s, 2H), 7.57 (s, 1H). LRMS (APCI): m/z 327 (MH$^+$)

Example 265

3-{[3,5-Diethyl-1-(2-hydroxyethyl)-1H-pyrazol-4-yl]oxy}-5-(5-trifluoromethyl-1,2,4-oxadiazol-3-yl)benzonitrile

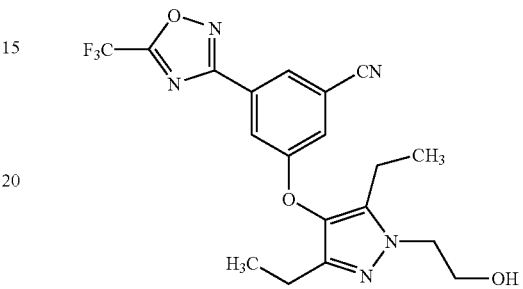

To a stirred solution of the pyrazole from Preparation 105 (235 mg, 0.46 mmol) in dichloromethane (2 ml) was added aluminium trichloride (373 mg, 2.8 mmol). The reaction mixture was stirred at room temperature for 48 hours, diluted with water (6 ml) and extracted with dichloromethane (6 ml). The organic component was concentrated under reduced pressure and purified by flash chromatography on silica gel eluting with dichloromethane:methanol (a gradient from 99:1 to 80:20, by volume) followed by dichloromethane:methanol:0.88 ammonia (80:20:1, by volume) to provide an impure sample of the title compound (44 mg) as a white solid. The product was further purified by HPLC using a Phenomenex Luna C$_{18}$ 150×21.2 mm column eluting with a solvent gradient of 5:95 0.1% aqueous trifluoroacetic acid in acetonitrile:acetonitrile (0–1 min 80:20; 1–7 min 80:20 changing to 0:100; 7–12 min 0:100; 12–12.1 min 0:100 changing to 80:20; 12.1–15 min 80:20) to provide the title compound (38 mg) as a white solid.

Retention time 5.7 minutes. LRMS (electrospray): m/z 422 (MH$^+$)

Examples 266–268

The compounds of the following tabulated Examples of the general formula:

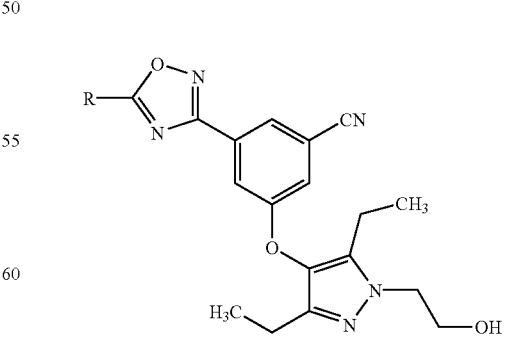

were prepared by a similar method to that of Example 265 using the appropriate protected alcohol (PA) from Preparation 106–108.

| Example No. | PA prep No. | R | Analytical Data |
|---|---|---|---|
| 266 | 106 | Me | Retention time 4.8 minutes<br>LRMS (electrospray): m/z [MH$^+$] 368 |
| 267 | 107 | Et | Retention time 5.3 minutes<br>LRMS (electrospray): m/z [MH$^+$] 382 |
| 268 | 108 | $^i$Pr | Retention time 5.7 minutes<br>LRMS (electrospray): m/z 396 (MH$^+$) |

Example 269

5-[({[4-(3-Chloro-5-cyanophenoxy)-3-methyl-1H-pyrazol-5-yl]methyl}amino)methyl]nicotinamide

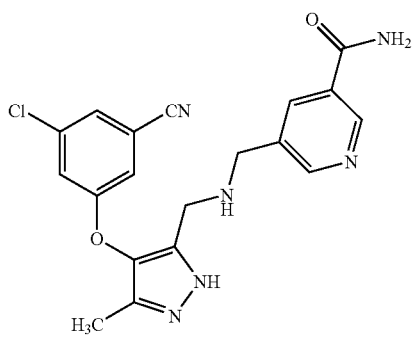

To a stirred solution of the amine from Preparation 111 (650 mg, 1.70 mmol) in iso-propyl alcohol (6 ml) was added the pyrazole from Preparation 18 (210 mg, 0.57 mmol) followed by potassium carbonate (240 mg, 1.70 mmol). The reaction mixture was heated at reflux for 1.5 hours. After cooling to room temperature the mixture was concentrated under reduced pressure and the crude product mixture was purified by flash chromatography on silica gel eluting with dichloromethane:methanol:0.88 ammonia (95:5:0.5 then 90:10:1 then 80:20:1, by volume) which gave an impure sample of the desired product. Flash chromatography was repeated eluting with dichloromethane:methanol:0.88 ammonia (100:0:0 then 95:5:0.5 then 90:10:1, by volume) to provide the title compound (10 mg) as a pale yellow solid.

$^1$H NMR (400 MHz, CD$_3$OD): δ=2.05 (s, 3H), 3.62 (s, 2H), 3.79 (s, 2H), 7.16 (m, 1H), 7.18 (m, 1H), 7.38 (s, 1H), 8.15 (s, 1H), 8.54 (s, 1H), 8.84 (s, 1H). LRMS (APCI): m/z 419 (M+Na$^+$) HRMS: [MH$^+$] 397.1173. C$_{19}$H$_{18}$N$_6$O$_2$Cl requires 397.1175.

Example 270

2-[({[4-(3-Chloro-5-cyanophenoxy)-3-methyl-1H-pyrazol-5-yl]methyl}amino)methyl]isonicotinamide

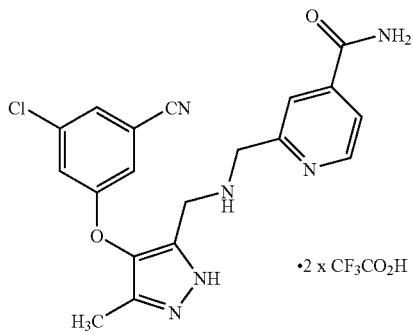

To a stirred suspension of the amine from Preparation 115 (250 mg, 1.66 mmol) and the pyrazole from Preparation 18 (155 mg, 0.42 mmol) in isopropanol (6 ml) was added tetrahydrofuran (2 ml). The mixture was heated at reflux for 2 hours after which the reaction mixture was concentrated under reduced pressure. The crude product mixture was purified by flash chromatography on silica gel eluting with dichloromethane:methanol:0.88 ammonia (85:15:1, by volume) to provide an impure sample of the title compound. The product was further purified by HPLC using a Phenomenex Luna C$_8$(II) 10 μM 150×21.2 mm column eluting with a solvent gradient of 5:95 0.1% aqueous trifluoroacetic acid in acetonitrile:acetonitrile (0–6 min 95:5 changing to 0:100; 6–10 min 0:100) to provide the title compound (65 mg) as an off-white solid.

Retention time: 3.40 minutes $^1$H NMR (400 MHz, CD$_3$OD): δ=2.14 (s, 3H), 4.21 (s, 2H), 4.50 (s, 2H), 7.19 (s, 1H), 7.27 (m, 1H), 7.43 (m, 1H), 7.48 (m, 1H), 7.78 (m, 1H), 8.68 (d, 1H) LRMS (electrospray): m/z 397 (MH$^-$) Microanalysis: Found C, 44.56; H, 3.41; N, 14.07. C$_{19}$H$_{17}$N$_6$O$_2$Cl+1.9.CF$_3$CO$_2$H requires C, 44.64; H, 3.11; N, 13.70%.

Example 271

Di(tert-butyl) 2-[4-(3,5-dicyanophenoxy)-3,5-diethyl-1H-pyrazol-1-yl]ethyl phosphate

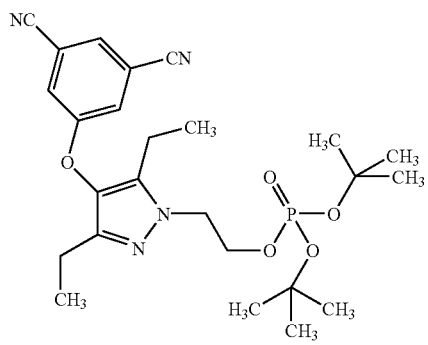

To a stirred solution of the alcohol from Example 119 (500 mg, 1.60 mmol) in dichloromethane (5 ml) was added tetrazole (226 mg, 3.20 mmol) followed by di-tert-butyl-N,N-diisopropylphosphoramidite (1.02 ml, 3.20 mmol). After stirring for 4 hours at room temperature the reaction mixture was cooled to 0° C. and meta-chloroperoxybenzoic acid (1.0 g of 50% by weight mixture, 3 mmol) was added portionwise (CARE, EXOTHERM). After 10 minutes the mixture was warmed to room temperature and was diluted with dichloromethane (50 ml). The solution was washed with saturated aqueous sodium carbonate solution (20 ml) and the aqueous component was separated and extracted with dichloromethane (20 ml). The combined organic components were washed with brine (20 ml), dried over magnesium sulphate and concentrated under reduced pressure. The crude product mixture was purified by flash chromatography on silica gel eluting with dichloromethane:methanol:0.88 ammonia (100:0:0 then 99:1:0.1 then 98:2:0.2, by volume) to provide a sample of the title compound (660 mg)

¹H NMR (400 MHz, CDCl₃): δ=1.10 (m, 6H), 1.43 (s, 18H), 2.38 (q, 2H), 2.55 (q, 2H), 4.26 (m, 4H), 7.38 (s, 2H), 7.54 (s, 1H). LRMS (electrospray): m/z 525 (MH⁺) Microanalysis: Found C, 57.77; H, 7.38; N, 10.33. C₂₅H₃₅N₄O₅P+H₂O requires C, 57.68; H, 7.16; N, 10.76%.

Example 272

2-[4-(3,5-Dicyanophenoxy)-3,5-diethyl-1H-pyrazol-1-yl]ethyl dihydrogen phosphate

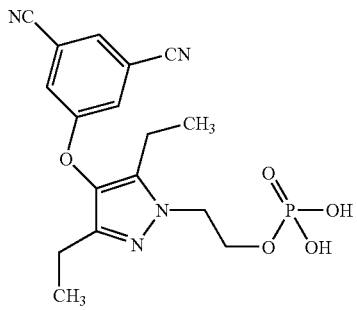

To a stirred solution of the phosphate ester from Example 271 (250 mg, 0.48 mmol) in dichloromethane (10 ml) at 0° C. was added trifluoroacetic acid (0.5 ml). The reaction mixture was allowed to warm to room temperature and after 4 hours it was concentrated under reduced pressure. The residue was purified by HPLC using a Phenomenex Luna C₈(II) 10 μM 150×21.2 mm column eluting with a solvent gradient of 5:95 0.1% aqueous trifluoroacetic acid in acetonitrile:acetonitrile (0–1.9 m in 95:5; 2–10 min 90:10 changing to 30:70; 10.0–13.8 min 30:70; 13.8–13.9 min 30:70 changing to 95:5; 13.9–15 min 95:5) to give a sample of the desired product. This sample was further purified by recrystallisation using acetonitrile/water which gave the title compound as a white solid, m.p. 198–199° C.

Retention time: 2.31 minutes. ¹H NMR (400 MHz, CD₃OD): δ=1.09 (m, 6H), 2.35 (q, 2H), 2.61 (q, 2H), 4.28 (m, 4H), 7.55 (s, 2H), 7.79 (s, 1H). LRMS (APCI): m/z 391 (MH⁺) Microanalysis: Found C, 50.99; H, 4.92; N, 14.06. C₁₇H₁₉N₄O₅P+0.5H₂O requires C, 51.13; H, 5.05; N, 14.03%.

Example 273

5-{[3,5-Diethyl-1-(2-hydroxyethyl)-1H-pyrazol-4-yl]oxy}isophthalonitrile sulfate salt

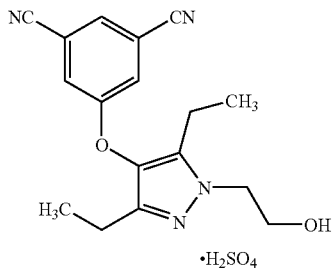

To a stirred solution of the pyrazole from Example 119 (200 mg, 0.65 mmol) in acetone (5 ml) was added sulfuric acid (0.32 ml of a 2M aqueous solution, 0.64 mmol) and the mixture was stirred at room temperature and the solvent allowed to evaporate. The residue was recrystallised (toluene/acetone) to give the title compound (160 mg) as a white powder, m.p. 105–110° C.

¹H NMR (400 MHz, CDCl₃): δ=1.22 (m, 6H), 2.70 (m, 4H), 4.12 (bs, 1H), 4.59 (m, 2H), 4.75 (bs, 1H), 7.66 (s, 1H), 7.69 (m, 1H), 7.22 (s, 1H). Microanalysis: Found C, 50.29; H, 4.90; N, 13.48. C₁₇H₁₈N₄O₂·H₂SO₄ requires C, 49.99; H, 4.93; N, 13.72%.

Example 274

5-{13,5-Diethyl-1-(2-hydroxyethyl)-1H-pyrazol-4-yl]oxy}isophthalonitrile benzenesulfonic acid salt

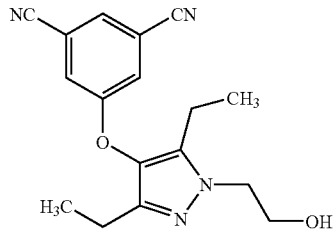

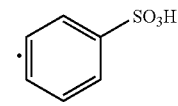

To a stirred solution of the pyrazole from Example 119 (20 g, 65 mmol) in acetone (200 ml) was added benzenesulfonic acid (10.7 g, 68 mmol) and the mixture was stirred at room temperature for 10 minutes. The reaction mixture was concentrated under reduced pressure and the residue was recrystallised twice (acetone) to give the title compound (16.2 g) as a white powder, m.p. 142–144° C.

¹H NMR (400 MHz, CDCl₃): δ=1.05–1.08 (m, 6H), 2.59 (q, 2H), 2.68 (q, 2H), 4.04 (t, 2H), 4.54 (t, 2H), 7.35–7.42 (m, 3H), 7.55 (s, 1H), 7.64 (s, 1H), 7.86 (d, 2H). Microanalysis: Found C, 58.86; H, 5.13; N, 11.88. C₂₃H₂₄N₄O₅S requires C, 58.96; H, 5.16; N, 11.96%.

Example 275

5-{[3,5-Diethyl-1-(2-hydroxyethyl)-1H-pyrazol-4-yl]oxy}isophthalonitrile tosylate salt

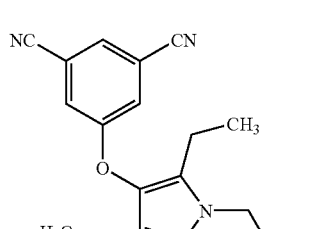

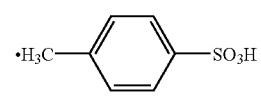

To a stirred suspension of the pyrazole from Example 119 (300 mg, 1.00 mmol) in ethanol (2 ml) was added p-toluenesulfonic acid (202 mg, 1.10 mmol) and the mixture was heated on an oil bath until the solids dissolved. The reaction mixture was cooled to room temperature and concentrated under reduced pressure. The residue was crystallised (diethyl ether), filtered and recrystallised (isopropyl alcohol) to give the title compound (200 mg) as a white solid, m.p. 120° C.

$^1$H NMR (400 MHz, DMSO-$d_6$): δ=1.00 (m, 6H), 2.24 (m, 5H), 2.49 (m, 2H), 4.00 (m, 2H), 7.11 (d, 2H), 7.45 (d, 2H), 7.73 (s, 2H), 8.09 (s, 1H). Microanalysis: Found C, 59.64; H, 5.46; N, 11.60. $C_{24}H_{26}N_4O_5S$ requires C, 59.74; H, 5.43; N, 11.61%.

Example 276

5-{[3,5-Diethyl-1-(2-hydroxyethyl)-1H-pyrazol-4-yl]oxy}isophthalonitrile mesylate salt

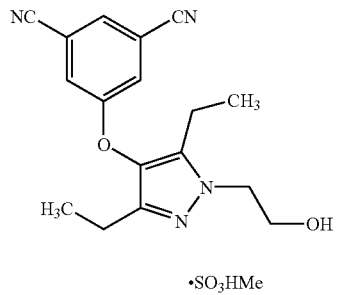

·SO$_3$HMe

To a stirred suspension of the pyrazole from Example 119 (250 mg, 0.83 mmol) in isopropyl alcohol (3 ml) was added methanesulfonic acid (52 μl, 0.91 mmol) and the mixture was heated on an oil bath until the solids dissolved. The reaction mixture was cooled to room temperature and concentrated under reduced pressure to a volume of 1 ml. A white solid precipitated out which was washed with cold isopropyl alcohol to give the title compound (239 mg) as a white solid, m.p. 144–146° C.

$^1$H NMR (400 MHz, DMSO-$d_6$): δ=1.02 (m, 6H), 2.32 (q, 2H), 2.43 (s, 3H), 2.52 (m, 2H), 3.73 (m, 2H), 4.02 (m, 2H), 7.75 (s, 2H), 8.11 (s, 1H). Microanalysis: Found C, 53.20; H, 5.52; N, 13.68. $C_{18}H_{22}N_4O_5S$ requires C, 53.19; H, 5.46; N, 13.78%.

Example 277

3-{[1-(2-Aminoethyl)-3,5-diethyl-1H-pyrazol-4-yl]oxy}-5-methylbenzonitrile bis-mesylate salt

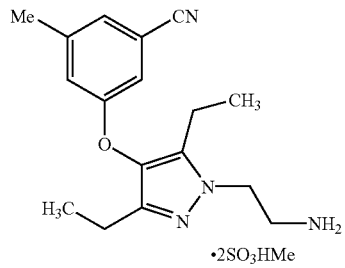

·2SO$_3$HMe

To a stirred solution of the amine from Example 125 (119 mg, 0.40 mmol) in ethanol (2 ml) was added methanesulfonic acid (1.00 ml of a 0.84M solution in ethanol, 0.84 mmol). The reaction mixture was concentrated under reduced pressure to remove some of the ethanol. A mixture of diethyl ether and acetone were added and a white solid precipitated out which was filtered and washed (diethyl ether/acetone) to give the title compound (153 mg) as a white solid, m.p. 146–148° C.

$^1$H NMR (400 MHz, CD$_3$OD): δ=1.09 (m, 6H), 2.33 (s, 3H), 2.39 (q, 2H), 2.55 (q, 2H), 2.68 (s, 6H), 3.42 (t, 2H), 4.29 (t, 2H), 6.93 (s, 1H), 7.06 (s, 1H), 7.19 (s, 1H). LRMS (thermospray): m/z [free base+H$^+$] 299 Microanalysis: Found C, 45.83; H, 6.12; N, 11.27. $C_{19}H_{30}N_4O_7S_2$·0.50H$_2$O requires C, 45.68; H, 6.25; N, 11.21%.

Example 278

3-{[1-(2-Aminoethyl)-3,5-diethyl-1H-pyrazol-4-yl]oxy}-5-methylbenzonitrile phosphate salt

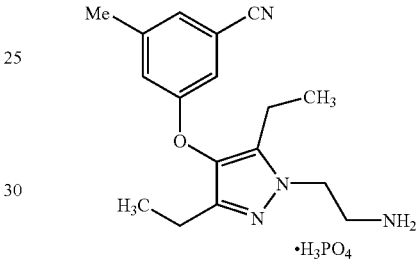

·H$_3$PO$_4$

To a stirred solution of the amine from Example 125 (251 mg, 0.84 mmol) in ethanol (5 ml) was added phosphoric acid (63 μl, 0.93 mmol). The resulting precipitate was filtered, washed (ethanol then diethyl ether) and dried to give the title compound (265 mg) as a white solid, m.p. 210–211° C.

$^1$H NMR (400 MHz, CD$_3$OD): δ=1.08 (m, 6H), 2.32 (s, 3H), 2.39 (q, 2H), 2.56 (q, 2H), 3.39 (m, 2H), 4.29 (m, 2H), 6.93 (s, 1H), 7.05 (s, 1H), 7.18 (s, 1H). LRMS (thermospray): m/z [free base+H$^+$] 299 Microanalysis: Found C, 51.26; H, 6.36; N, 14.08. $C_{17}H_{25}N_4O_5P$ requires C, 51.51; H, 6.36; N, 14.14%.

Example 279

3-{[1-(2-Aminoethyl)-3,5-diethyl-1H-pyrazol-4-yl]oxy}-5-methylbenzonitrile (L) tartrate salt

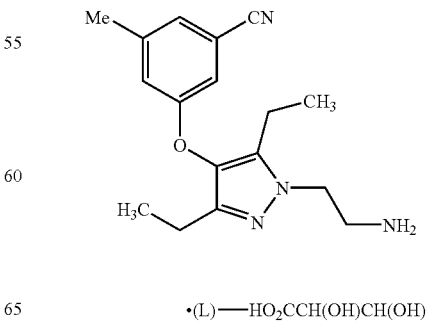

·(L)—HO$_2$CCH(OH)CH(OH)CO$_2$H

To a stirred solution of the amine from Example 125 (500 mg, 1.68 mmol) in acetone (15 ml) was added (L)-tartaric acid (252 mg, 1.68 mmol) and the mixture was heated on an oil bath until complete dissolution had occurred. The mixture was cooled to room temperature and a white precipitate formed which was filtered and washed (acetone) to give the title compound (515 mg) as a white powder, m.p. 159–161° C.

$^1$H NMR (400 MHz, CD$_3$OD): δ=1.05–1.10 (m, 6H), 2.32 (s, 3H), 2.34–2.41 (m, 2H), 2.53–2.57 (m, 2H), 3.40 (m, 2H), 4.27 (m, 2H), 4.35 (s, 2H), 6.93 (s, 1H), 7.05 (s, 1H), 7.17 (s, 1H). LRMS (electrospray): m/z [free base+H$^+$] 299 Microanalysis: Found C, 54.80; H, 6.38; N, 12.11. C$_{21}$H$_{28}$N$_4$O$_7$.0.65H$_2$O requires C, 54.81; H, 6.42; N, 12.10%.

Example 280

3-{[1-(2-Aminoethyl)-3,5-diethyl-1H-pyrazol-4-yl]oxy}-5-methylbenzonitrile succinate salt

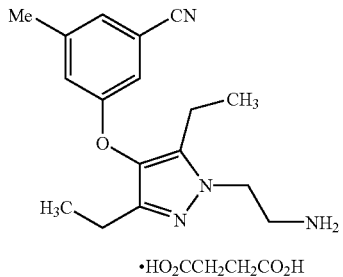

•HO$_2$CCH$_2$CH$_2$CO$_2$H

To a stirred solution of the amine from Example 125 (235 mg, 0.79 mmol) in acetone (7 ml) was added succinic acid (93 mg, 0.79 mmol). After two minutes the mixture was concentrated to ~3 ml using a stream of nitrogen gas which resulted in the formation of white crystals. The precipitate was filtered and washed (acetone) to give the title compound (172 mg) as white crystals, m.p. 155° C.

$^1$H NMR (400 MHz, CD$_3$OD): δ=1.03–1.07 (m, 6H), 2.34 (s, 3H), 2.40 (q, 2H), 2.50 (s, 4H), 2.59 (q, 2H), 3.34 (t, 2H), 4.23 (t, 2H), 6.95 (s, 1H), 7.06 (s, 1H), 7.22 (s, 1H). LRMS (electrospray): m/z [free base+H$^+$] 299 Microanalysis: Found C, 60.47; H, 6.77; N, 13.39. C$_{21}$H$_{28}$N$_4$O$_5$ requires C, 60.56; H, 6.78; N, 13.45%.

Example 281

3-{[1-(2-Aminoethyl)-3,5-diethyl-1H-Pyrazol-4-yl]oxy}-5-methylbenzonitrile (L) citrate salt

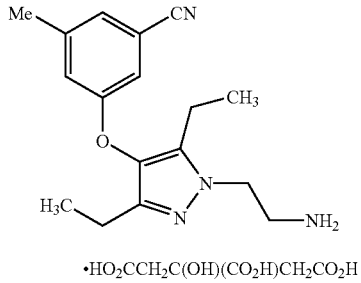

•HO$_2$CCH$_2$C(OH)(CO$_2$H)CH$_2$CO$_2$H

To a stirred solution of the amine from Example 125 (140 mg, 0.47 mmol) in acetone (3 ml) was added citric acid (90 mg, 0.47 mmol). The mixture was stirred until complete dissolution had occurred. The mixture was concentrated to ~1 ml using a stream of nitrogen gas and cooled in a freezer for 1.5 hours. A precipitate collected which was filtered to give the title compound (149 mg) as a white powder, m.p. 180–182° C.

$^1$H NMR (400 MHz, CD$_3$OD): δ=1.04–1.07 (m, 6H), 2.35 (s, 3H), 2.40 (q, 2H), 2.58 (q, 2H), 2.73 (d, 2H), 2.80 (d, 2H), 3.42 (t, 2H), 4.30 (t, 2H), 6.95 (s, 1H), 7.08 (s, 1H), 7.21 (s, 1H). LRMS (electrospray): m/z [free base+H$^+$] 299 Microanalysis: Found C, 56.19; H, 6.20; N, 11.31. C$_{23}$H$_{30}$N$_4$O$_8$ requires C, 56.32; H, 6.16; N, 11.42%.

Example 282

5-{[3,5-Diethyl-1-(2-hydroxyethyl)-1H-pyrazol-4-yl]oxy}isophthalonitrile

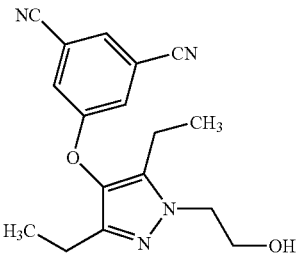

2-Hydroxyethylhydrazine (8.43 ml, 124 mmol) was added dropwise to a solution of the diketone of Preparation 45 (30.5 g, 113 mmol) in acetic acid (300 ml) at room temperature under nitrogen. The reaction was stirred at room temperature for 90 minutes and the solvent removed under reduced pressure to give an orange solid. This was combined with an orange solid from another reaction carried out in an identical manner to this. The combined crude product was purified by flash column chromatography on silica gel eluting with ethyl acetate:pentane (75:25 by volume) to provide the title compound as a white solid. Analysis of the proton nmr showed minor impurities were present so the product was purified by flash column chromatography on silica gel eluting with ethyl acetate:pentane (50:50 by volume) to provide the title compound (50 g) as a white solid, m.p. 125° C.

$^1$H-NMR (400 MHz, CDCl$_3$): δ=1.13 (6H, m), 2.40 (2H, q), 2.53 (2H, q), 3.53 (1H, m), 4.11 (4H, m), 7.40 (2H, s), 7.58 (1H, s). LRMS (electrospray): m/z [MH$^+$] 311. Microanalysis: Found: C, 65.62; H, 5.85; N, 18.04. C$_{17}$H$_{18}$N$_4$O$_2$ requires C, 65.64; H, 5.84; N, 18.05%.

Example 283

2-[4-(3,5-Dichlorophenoxy)-3-ethyl-1H-pyrazol-1-yl]ethylamine and 2-[4-(3,5-Dichlorophenoxy)-5-ethyl-1H-pyrazol-1-yl]ethylamine

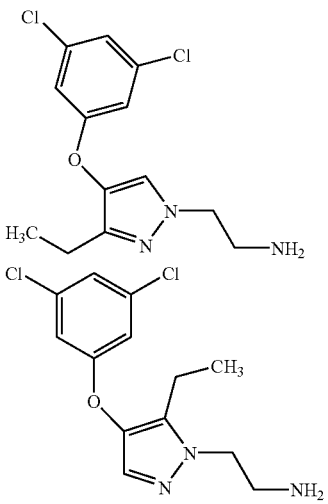

The pyrazole from Example 42 (1.03 g, 4.00 mmol) and 2-chloroethylamine hydrochloride (510 mg, 4.40 mmol) were heated as a melt at 150° C. for 24 hours. The reaction was cooled and a solution of the residue in dichloromethane (100 ml) was washed with an aqueous solution of 1M potassium carbonate (50 ml), brine (50 ml), dried over magnesium sulphate, filtered and concentrated under reduced pressure. The crude product was purified by flash chromatography on silica gel eluting with dichloromethane:methanol:ammonia (93:7:1, by volume) to afford the title compounds (768 mg) in a 85:15 ratio of regioisomers as a colourless oil.

$^1$H-NMR (400 MHz, CDCl$_3$): δ=1.16 (major, t, 3H), 1.16 (minor, t, 3H), 2.47 (major, q, 2H), 2.60 (minor, q, 2H), 3.13 (major, m, 2H), 3.13 (minor, m, 2H), 4.10 (major, m, 2H), 4.10 (minor, m, 2H), 4.24 (major, t, 2H), 4.24 (minor, t, 2H), 6.85 (major, s, 2H), 6.85 (minor, s, 2H), 7.02 (major, s, 1H), 7.02 (minor, s, 1H), 7.27 (major, s, 1H), 7.31 (minor, s, 1H). LRMS (thermospray): m/z [MH$^+$] 300.

The following Preparations describe the preparation of certain intermediates used in the preceding Examples.

Preparation 1

3-(3,5-Dichlorophenoxy)-2,4-pentanedione

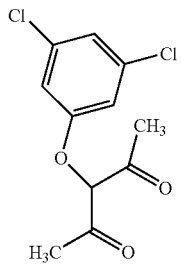

3-Chloro-2,4-pentanedione (183 μL, 1.53 mmol)) was added to a stirred suspension of 3,5-dichlorophenol (250 mg, 1.53 mmol) and potassium carbonate (233 mg, 1.69 mmol) in acetone (7.7 ml) at room temperature under nitrogen. The mixture was stirred for 30 minutes and then heated under reflux for 3½ hours. After cooling, sodium iodide (230 mg, 1.53 mmol) was added and refluxing continued for a further 3½ hours. After cooling again the mixture was diluted with water (5 ml) and concentrated under reduced pressure in a fumehood (Caution: possible residual lachrymator) to remove acetone. The resulting red aqueous solution was diluted with 2M hydrochloric acid (5 ml) and extracted with dichloromethane (3×10 ml). The combined organic layers were washed with saturated aqueous sodium sulphite solution (10 ml) and brine (10 ml), dried over magnesium sulphate, filtered and evaporated under reduced pressure to leave a red oil (344 mg). The crude product was purified by flash chromatography on silica gel eluting with pentane:ethyl acetate (20:1, by volume) to give the title compound (118 mg) as a cream solid m.p. 91–92° C.

$^1$H-NMR (400 MHz, CDCl$_3$): δ=2.04 (s, 6H), 6.84 (s, 2H), 7.06 (s, 1H), 14.38 (br.s, 1H) LRMS (thermospray): m/z [MNH$_4^+$] 278. Microanalysis: Found: C, 50.43; H, 3.84. C$_{11}$H$_{10}$Cl$_2$O$_3$ requires C, 50.60; H, 3.86%.

Preparation 2

4-Chloro-3,5-heptanedione

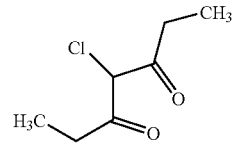

Chlorotrimethylsilane (29.7 ml, 0.234 mol) was added dropwise to a stirred pale yellow solution of tetrabutylammonium bromide (1.26 g, 3.9 mmol) in dry acetonitrile (116 ml) at room temperature under nitrogen. The resulting solution was cooled in ice and 3,5-heptanedione (10.6 ml, 78.0 mmol) and then dry dimethylsulphoxide (16.6 ml, 0.234 mol) were added dropwise over 5 minutes producing a yellow solution which was allowed to warm slowly to room temperature, with stirring, over 4 hours. The mixture was diluted with water (1 liter), stirred for 10 min and then extracted with ether (1×500 ml, 2×250 ml). The combined ether layers were dried over magnesium sulphate, filtered and concentrated under reduced pressure to leave a yellow oil. The crude product was purified by distillation under reduced pressure to afford the title compound (5.5 g) as a pale yellow oil, b.p. 102–105° C./54 mmHg containing ca. 10% 4,4-dichloro-3,5-heptanedione as estimated by microanalysis.

$^1$H-NMR (400 MHz, CDCl$_3$): δ=1.12 (t, 6H), 2.59 (q, 4H), 4.77 (s, 0.2H, diketone), 15.50 (s, 0.8H, enol). LRMS (thermospray): m/z [MNH$_4^+$] 180 for title compound and 214 for dichlorinated impurity.

Preparation 3

Ethyl 4-[4-(3,5-dichlorophenoxy)-3,5-diethyl-1H-pyrazol-1-yl]-3-oxobutanoate

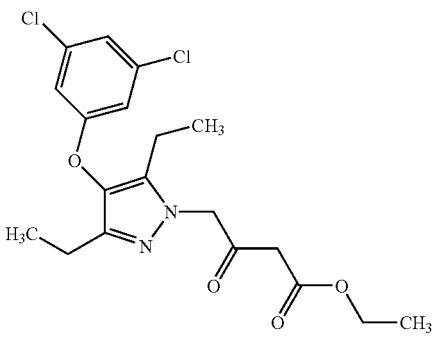

Sodium hydride (60% dispersion in oil, 250 mg, 6.17 mmol) was added to a stirred solution of 4-(3,5-dichlorophenoxy)-3,5-diethyl-1H-pyrazole (800 mg, 2.81 mmol, Example 3) in dry N,N-dimethylformamide (5 ml) at 0° C. under nitrogen. The mixture was stirred for 5 minutes during which time hydrogen was evolved and then ethyl 4-chloroacetoacetate (0.42 ml, 3.09 mmol) was added. After 30 minutes the reaction mixture was quenched by the addition of water (0.5 ml) and concentrated under reduced pressure. A solution of the residue in ethyl acetate (50 ml) was washed with saturated aqueous ammonium chloride solution (20 ml) and water (20 ml), dried over magnesium sulphate and concentrated under reduced pressure. The crude product was purified by flash chromatography on silica gel eluting with ethyl acetate:pentane (30:70, by volume) to provide the title compound (1.1 g) as a white solid, m.p. 82–84° C.

$^1$H-NMR (300 MHz, CDCl$_3$): δ=1.40 (6H, m), 1.26 (3H, t), 2.44 (4H, q), 3.47 (2H, s), 4.22 (2H, q), 4.96 (2H, s), 6.82 (2H, s), 7.02 (1H, s). LRMS (thermospray): m/z [MH$^+$] 413. Microanalysis: Found: C, 55.13; H, 5.34; N, 6.98. C$_{15}$H$_{15}$Cl$_2$N$_3$O requires C, 55.22; H, 5.37; N, 6.78%.

Preparation 4

[4-(3,5-Dichlorophenoxy)-3,5-diethyl-1H-pyrazol-1-yl]acetic acid

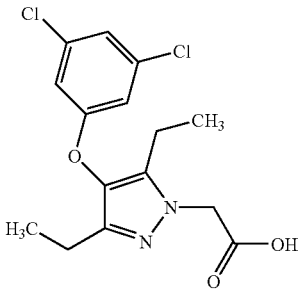

Aqueous sodium hydroxide solution (1N, 6.2 ml, 6.2 mmol) was added dropwise to a stirred solution of the ester (2 g, 5.6 mmol) of Example 9 in tetrahydrofuran (20 ml) at 0° C. After 1 hour the solvent was removed under reduced pressure and aqueous hydrochloric acid (20 ml) was added with vigorous stirring. The resulting white precipitate was collected by filtration, washed with ether (3×30 ml) and dried in a vacuum pistol at 6° C./10 mmHg to afford the title compound as a white solid (1.5 g), m.p. 157–158° C.

$^1$H-NMR (300 MHz, CDCl$_3$): δ=1.13 (6H, m), 2.52 (2H, q), 2.60 (2H, q), 5.03 (2H, s), 6.95 (2H, s), 7.14 (1H, s). LRMS (electrospray): m/z [M–H$^+$] 341.

Preparation 5

1-(3,5-Dichlorophenoxy)-2-butanone

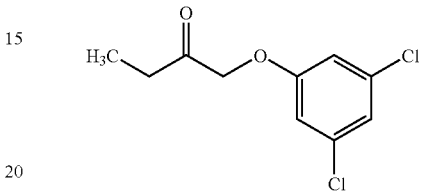

Cesium carbonate (108 g, 0.33 mol) was added in one portion to a stirred solution of 3,5-dichlorophenol (49 g, 0.30 mol) in acetone (900 ml) at room temperature under nitrogen. To this suspension a solution of 1-bromo-2-butanone (30.6 ml, 0.30 mol) in acetone (300 ml) was added dropwise and the resultant suspension was heated under reflux for 2 hours. The suspension was cooled to room temperature, water (200 ml) was added and the acetone was removed under reduced pressure. The mixture was extracted with dichloromethane (2×300 ml) and the combined organic phases were dried over magnesium sulphate, filtered and concentrated under reduced pressure to leave a clear oil. The crude product was purified by flash column chromatography on silica gel eluting with dichloromethane:cyclohexane (50:50, by volume) to provide the title compound (65 g) as a yellow oil.

$^1$H-NMR (400 MHz, CDCl$_3$): δ=1.13 (t, 3H), 2.60 (q, 2H), 4.58 (s, 2H), 6.78 (s, 2H), 7.01 (s, 1H). LRMS (thermospray): m/z [MNH$_4^+$] 250.

Preparation 6

2-(3,5-Dichlorophenoxy)-1-(dimethylamino)-1-penten-3-one

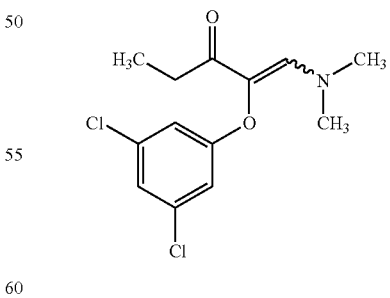

A solution of the ketone of Preparation 5 (65 g, 0.28 mol) in N,N-dimethylformamide dimethylacetal (75 ml, 0.56 mol) was heated at 100° C. using a Dean-Stark apparatus for 10 hours. The reaction was cooled and concentrated under reduced pressure to leave a brown oil. The crude product was purified by flash column chromatography on silica gel eluting with pentane:ethyl acetate (90:10, by volume) and then pentane:ethyl acetate (60:40, by volume) to provide the title compound (55 g) as a yellow oil that solidified upon standing. The resultant yellow solid was washed with pentane (100 ml) and dried to provide the title compound (28 g) as a yellow solid, m.p. 96–97° C.

$^1$H-NMR (400 MHz, CDCl$_3$): δ=0.98 (t, 3H), 2.30 (br s, 2H), 2.94 (s, 6H), 6.77 (s, 2H), 6.95 (s, 1H), 7.24 (s, 1H). LRMS (thermospray): m/z [MNH$_4^+$] 288.

Preparation 7

1-Acetyl-4-(3,5-dichlorophenoxy)-3,5-dimethyl-1H-pyrazole

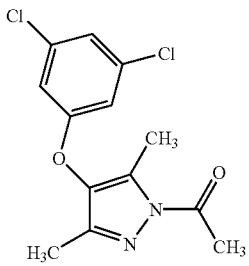

Sodium hydride (60% dispersion in oil, 684 mg, 17.1 mmol) was added to a stirred solution of acetyl chloride (1.21 ml, 17.1 mmol) and the pyrazole of Example 53 (4.00 g, 15.6 mmol) in N,N-dimethylformamide (20 ml) at 0° C. under nitrogen. The reaction was stirred at 0° C. for 1 hour and then quenched by the addition of water (100 ml). The aqueous extracted was with ether (2×50 ml). The combined organic phases were washed with water (30 ml) and brine (30 ml), dried over magnesium sulphate, filtered and concentrated under reduced pressure to leave a yellow solid. The crude product was purified by flash column chromatography on silica gel eluting with pentane:ether (90:10, by volume) to provide the title compound (3.0 g) as a white solid, m.p. <60° C.

$^1$H-NMR (300 MHz, CDCl$_3$): δ=2.11 (s, 3H), 2.43 (s, 3H), 2.70 (s, 3H), 6.78 (s, 2H), 7.03 (s, 1H). LRMS (thermospray): m/z [MH$^+$] 299.

Preparation 8

1-Acetyl-3-(bromomethyl)-4-(3,5-dichlorophenoxy)-5-methyl-1H-pyrazole

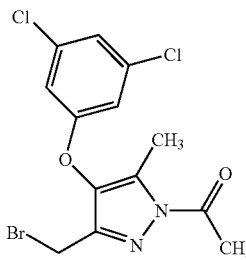

N-Bromosuccinimide (2.70 g, 15.0 mmol) was added to a stirred solution of the pyrazole of Preparation 7 (3.00 g, 10.0 mmol) in 1,1,1-trichloroethane (40 ml) at room temperature under nitrogen. The reaction was heated at 80° C. for 1 hour and then azobisisobutyronitrile (2 mg) was added and the reaction mixture was heated for a further 3 hours. The reaction was cooled to room temperature and a solid removed by filtration. The filtrate was concentrated under reduced pressure and the resulting yellow oil was dissolved in ethyl acetate (100 ml). The ethyl acetate was washed with 1M aqueous sodium carbonate solution (30 ml), water (30 ml) and brine (30 ml), dried over magnesium sulphate, filtered and concentrated under reduced pressure to leave a yellow solid. The crude product was purified by flash column chromatography on silica gel eluting with pentane:ethyl acetate (90:10, by volume) to provide a yellow solid that was washed with ice cold ether (20 ml) to provide the title compound (2.3 g) as a white solid, m.p. 111–113° C.

$^1$H-NMR (300 MHz, CDCl$_3$): δ=2.10 (s, 3H), 2.73 (s, 3H), 4.73 (s, 2H), 6.86 (s, 2H), 7.11 (s, 1H). LRMS (thermospray): m/z [MH$^+$] 379.

Preparation 9

4-(3-Cyanophenoxy)-3,5-heptanedione

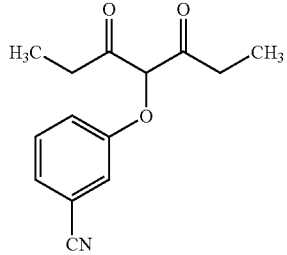

A mixture of the β-diketone of Preparation 2 (1.79 g, 11.0 mmol), 3-cyanophenol (1.31 g, 11.0 mmol), cesium carbonate (3.58 g, 11.0 mmol) and acetone (44 ml) was heated under reflux for 2 hours. After cooling, the mixture was concentrated under reduced pressure and the residue was partitioned between dichloromethane (50 ml) and water (25 ml). The organic layer was separated, washed with brine (25 ml), dried over magnesium sulphate, filtered and concentrated under reduced pressure to leave a yellow oil. The crude product was purified by flash column chromatography on silica gel eluting with ethyl acetate:pentane (10:90, by volume) to provide the title compound (1.10 g) as a yellow oil.

$^1$H-NMR (400 MHz, CDCl$_3$): δ=1.04 (t, 6H), 2.49 (q, 4H), 7.16 (m, 2H), 7.30 (d, 1H), 7.39 (t, 2H), 14.51 (s, 1H). LRMS (thermospray): m/z [MNH$_4^+$] 263.

Preparation 10 tert-Butyl 3-(hydroxymethyl)-4-morpholinecarboxylate

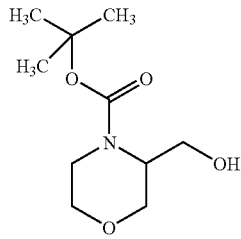

Borane (38.1 ml of a 1.0M solution in tetrahydrofuran, 38.1 mmol) was added dropwise to a stirred suspension of 3-morpholinecarboxylic acid (1.00 g, 7.63 mmol) in tetrahydrofuran (50 ml) at room temperature under nitrogen. The reaction was heated under reflux and the reaction became homogeneous and heating was continued for 12 hours. The reaction was cooled to room temperature and concentrated under reduced pressure to leave a brown oil. The residue was dissolved in 1M aqueous sodium hydroxide solution and stirred at room temperature for 5 days. After this time di-tert-butyl dicarbonate (1.66 g, 7.63 mmol) was added and the reaction was stirred for 12 hours. The reaction was diluted with ether (100 ml). The organic layer was separated, washed with brine (10 ml), dried over magnesium sulphate, filtered and concentrated under reduced pressure. The crude product was purified by flash column chromatography on silica gel eluting with pentane:ethyl acetate (50:50, by volume) and then ethyl acetate to provide the title compound (1.30 g) as a colourless oil.

$^1$H-NMR (400 MHz, CDCl$_3$): δ=1.48 (s, 9H), 2.05 (s, 1H), 3.19 (brt, 1H), 3.47 (td, 1H), 3.60 (dd, 1H), 3.87 (m, 6H). LRMS (thermospray): m/z [MH$^+$] 218.

Preparation 11 tert-Butyl 3-{[(methylsulfonyl)oxy]methyl}-4-morpholinecarboxylate

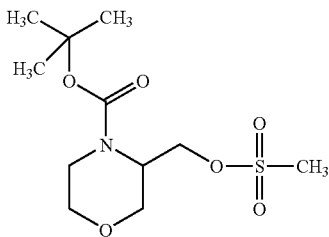

Triethylamine (1.15 ml, 8.29 mmol) was added dropwise to a stirred solution of the alcohol of Preparation 10 (1.20 g, 5.52 mmol) and methanesulfonic anhydride (1.44 g, 5.52 mmol) in dichloromethane (50 ml) at room temperature under nitrogen. The reaction was stirred for 1 hour and then poured onto water (50 ml). The organic layer was separated, dried over magnesium sulphate, filtered and concentrated under reduced pressure. The crude product was purified by flash column chromatography on silica gel eluting with pentane:ethyl acetate (50:50, by volume) to provide the title compound (1.20 g) as a colourless oil.

$^1$H-NMR (400 MHz, CDCl$_3$): δ=1.49 (s, 9H), 3.06 (s, 3H), 3.50 (td, 1H), 3.60 (dd, 1H), 3.80 (m, 4H), 4.26 (br s, 1H), 4.39 (m, 2H). LRMS (thermospray): m/z [MNH$_4^+$] 313.

Preparation 12

Methyl-2-(3,5-dichlorophenoxy)-3-oxopentanoate

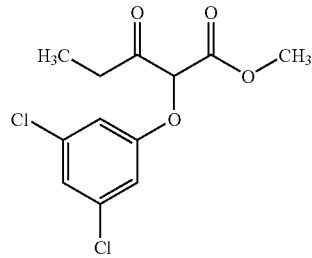

A mixture of methyl-2-chloro-3-pentanoate (25.0 g, 152 mmol), 3,5-dichlorophenol (24.6 g, 152 mmol), cesium carbonate (54.4 g, 167 mmol) and acetone (500 ml) was heated under reflux for 2 hours. After cooling the mixture was concentrated under reduced pressure and the residue was partitioned between dichloromethane (100 ml) and water (50 ml). The organic layer was separated, washed with brine (25 ml), dried over magnesium sulphate, filtered and concentrated under reduced pressure to leave an orange oil. The crude product was purified by flash column chromatography on silica gel eluting with pentane:toluene (90:10, by volume) to provide the title compound (40.0 g) as a pink oil.

$^1$H-NMR (300 MHz, CDCl$_3$): δ=1.16 (t, 3H), 2.60 (m, 2H), 3.77 (s, 3H), 5.13 (s, 1H), 6.84 (s, 2H), 7.10 (s, 1H). LRMS (thermospray): m/z [MNH$_4^+$] 308.

Preparation 13

4-(3,5-Dichlorophenoxy)-5-ethyl-2-(2-hydroxyethyl)-2,4-dihydro-3H-pyrazol-3-one

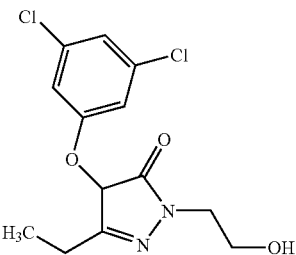

A solution of 2-hydroxyethylhydrazine (4.30 g, 56.7 mmol) in glacial acetic acid (2.0 ml) was added to a stirred solution of the ketoester of Preparation 12 (15.0 g, 51.5 mol) in glacial acetic acid (100 ml) and the resulting solution was stirred at room temperature for 48 hours. The mixture was concentrated under reduced pressure and the crude product was purified by flash column chromatography on silica gel eluting with dichloromethane:methanol (95:5, by volume) to provide the title compound (10.1 g) as a colourless oil.

$^1$H-NMR (400 MHz, CDCl$_3$): δ=1.02 (t, 3H), 2.29 (m, 2H), 3.63 (m, 2H), 3.80 (m, 2H), 6.92 (s, 2H), 7.21 (s, 1H). LRMS (thermospray): m/z [MH$^+$] 317. Microanalysis: Found: C, 48.86; H, 4.44; N, 9.01. C$_{13}$H$_{14}$N$_2$O$_3$CO$_2$ requires C, 49.23; H, 4.45; N, 8.83%.

Preparation 14

2-(2-{[tert-Butyl(dimethyl)silyl]oxy}ethyl)-4-(3,5-dichlorophenoxy)-5-ethyl-2,4-dihydro-3H-pyrazol-3-one

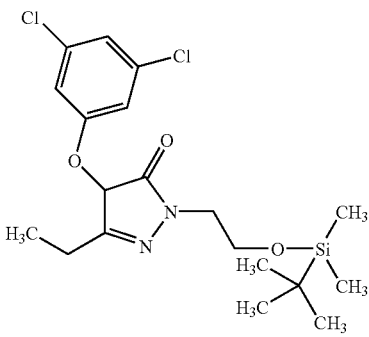

tert-Butyldimethylsilyl chloride (8.14 g, 54.0 mmol) was added in one portion to a stirred solution of the pyrazole of Preparation 13 (14.3 g, 45.0 mmol) and imidazole (3.98 g, 58.5 mmol) in N,N-dimethylformamide (90 ml) and the resulting solution was stirred at room temperature for 48 hours. The mixture was partitioned between ethyl acetate (100 ml) and water (300 ml). The organic layer was separated, dried over magnesium sulphate, filtered and concentrated under reduced pressure. The crude product was purified by flash column chromatography on silica gel eluting with dichloromethane:methanol (95:5, by volume) to provide the title compound (9.56 g) as a colourless oil.

$^1$H-NMR (400 MHz, CDCl$_3$): δ=0.15 (s, 6H), 0.94 (s, 9H), 1.16 (t, 3H), 2.45 (m, 2H), 3.94 (m, 4H), 6.85 (s, 2H), 6.97 (s, 1H). LRMS (thermospray): m/z [MH$^+$] 431. Microanalysis: Found: C, 52.87; H, 6.52; N, 6.46. C$_{19}$H$_{28}$N$_2$O$_3$Cl$_2$Si requires C, 52.90; H, 6.54; N, 6.49%.

Preparation 15

1-(2-{[tert-Butyl(dimethyl)silyl]oxy}ethyl)-4-(3,5-dichlorophenoxy-3-ethyl-1H-pyrazol-5-yl trifluoromethanesulfonate

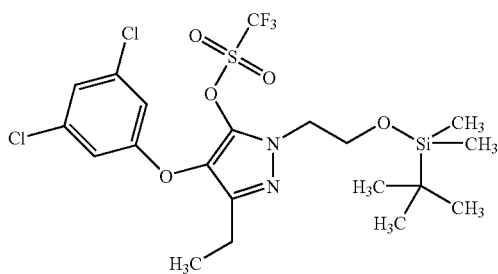

Phenyltriflamide (3.70 g, 10.5 mmol) was added in one portion to a stirred solution of the pyrazole of Preparation 14 (4.10 g, 9.50 mmol) and triethylamine (1.60 ml, 11.4 mmol) in dichloromethane (20 ml) at room temperature under nitrogen. The reaction was stirred for 2 hours and then poured onto water (50 ml). The organic layer was separated, dried over magnesium sulphate, filtered and concentrated under reduced pressure. The crude product was purified by flash column chromatography on silica gel eluting with dichloromethane to provide the title compound (5.10 g) as a purple oil.

$^1$H-NMR (300 MHz, CDCl$_3$): δ=0.01 (s, 6H), 0.86 (s, 9H), 1.17 (t, 3H), 2.45 (q, 2H), 4.01 (m, 2H), 4.14 (m, 2H), 6.84 (s, 2H), 7.08 (s, 1H). LRMS (thermospray): m/z [MH$^+$] 563.

Preparation 16

3-(1-Acetyl-2-oxopropoxy)-5-chlorobenzonitrile

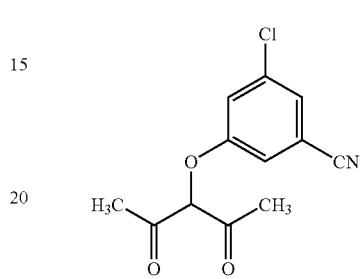

A mixture of 3-chloro-2,4-pentanedione (6.73 g, 50.0 mmol), the phenol of Preparation 36 (7.67 g, 50.0 mmol), cesium carbonate (18.0 g, 55.4 mmol) and acetone (40 ml) was heated under reflux for 2 hours. The reaction was cooled to room temperature, N,N-dimethylformamide (6 ml) and acetone (30 ml) were added and the reaction was heated at 70° C. for a further 12 hours. After cooling, the solid was removed by filtration and dissolved in 1M aqueous hydrochloric acid (150 ml). The resulting solution was extracted with dichloromethane (3×100 ml) and the combined organic phases were washed with brine (30 ml), dried over magnesium sulphate, filtered and concentrated under reduced pressure to provide the title compound (5.50 g) as a brown solid, m.p. 105–108° C.

$^1$H-NMR (300 MHz, CDCl$_3$): δ=2.04 (s, 6H), 7.13 (s, 1H), 7.19 (s, 1H), 7.35 (s, 1H), 14.40 (s, 1H).

Preparation 17

3-[(1-Acetyl-3,5-dimethyl-1H-pyrazol-4-yl)oxy]-5-chlorobenzonitrile

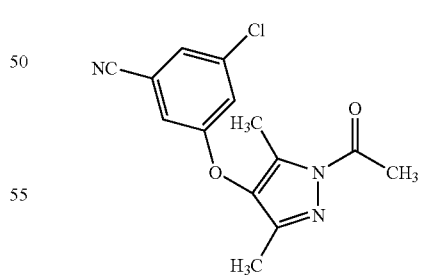

Sodium hydride (60% dispersion in oil, 840 mg, 21.0 mmol) was added to a stirred solution of acetyl chloride (1.50 ml, 21.0 mmol) and the pyrazole of Example 76 (4.80 g, 19.4 mmol) in N,N-dimethylformamide (20 ml) at 0° C. under nitrogen. The reaction was stirred at 0° C. for 15 minutes and then quenched by the addition of water (200 ml). The reaction mixture was extracted with ethyl acetate (3×120 ml). The combined organic phases were washed with water (50 ml) and brine (50 ml), dried over magnesium sulphate, filtered and concentrated under reduced pressure to leave a yellow solid. The crude product was purified by flash column chromatography on silica gel eluting with dichloromethane to provide the title compound (5.00 g) as a white solid, m.p. <60° C.

$^1$H-NMR (400 MHz, CDCl$_3$): δ=2.06 (s, 3H), 2.38 (s, 3H), 2.65 (s, 3H), 6.99 (m, 1H), 7.08 (m, 1H), 7.29 (m, 1H). LRMS (thermospray): m/z [MH$^+$] 290.

Preparation 18

3-{[1-Acetyl-3-(bromomethyl)-5-methyl-1H-pyrazol-4-yl]oxy}-5-chlorobenzonitrile

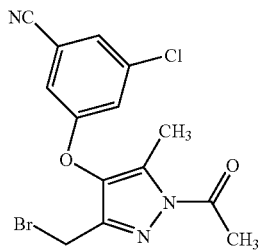

N-Bromosuccinimide (4.60 g, 25.6 mmol) was added to a stirred solution of the pyrazole of Preparation 17 (5.00 g, 17.3 mmol) in 1,1,1-trichloroethane (70 ml) and azobisisobutyronitrile (20 mg) at room temperature under nitrogen. The reaction was heated at 80° C. for 3 hours and then cooled to room temperature. A second portion of N-bromosuccinimide (2.00 g, 11.2 mmol) was added and the reaction mixture was heated at 80° C. for a further 4 hours. The reaction was cooled to room temperature and concentrated under reduced pressure and the resulting yellow oil was purified by flash column chromatography on silica gel eluting with pentane:dichloromethane (25:75, by volume) to provide the title compound (2.30 g) as a white solid, m.p. 122–123° C.

$^1$H-NMR (300 MHz, CDCl$_3$): δ=2.10 (s, 3H), 2.74 (s, 3H), 4.73 (s, 2H), 7.12 (s, 1H), 7.22 (s, 1H), 7.39 (s, 1H).

Preparation 19

3-Chloro-5,5-dimethyl-2,4-hexanedione

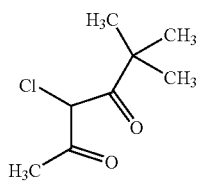

Chlorotrimethylsilane (26.8 ml, 0.21 mol) was added dropwise to a stirred pale yellow solution of tetrabutylammonium bromide (1.13 g, 3.50 mmol) in dry acetonitrile (100 ml) at room temperature under nitrogen. The resulting solution was cooled in ice and 5,5-dimethylhexane-2,4-dione (10.0 g, 70.4 mmol) and then dry dimethylsulphoxide (14.7 ml, 0.21 mol) were added dropwise over 5 minutes producing a yellow solution which was allowed to warm slowly to room temperature with stirring over 3 hours. The mixture was diluted with water (1000 ml) and stirred for 10 min and then extracted with ether (1×500 ml, 2×250 ml). The combined ether layers were dried over magnesium sulphate, filtered and concentrated under reduced pressure to leave a yellow oil. The crude product was purified by distillation under reduced pressure to provide the title compound (10.0 g) as a pale yellow oil, b.p. 220–225° C./60 mmHg.

$^1$H-NMR (400 MHz, CDCl$_3$): δ=1.25 (s, 9H), 2.39 (s, 3H), 5.10 (s, 1H). LRMS (thermospray): m/z [MNH$_4^+$] 194.

Preparation 20

4-[(Methylamino)methyl]benzonitrile

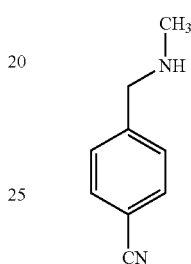

4-Cyanobenzaldehyde (12.0 g, 92.0 mmol), methylamine (69 ml of a 2.0M solution in tetrahydrofuran, 137 mmol) and magnesium sulphate (45 g) were stirred in dichloromethane (300 ml) at room temperature for 5 days. The mixture was filtered and the filtrate was concentrated under reduced pressure to leave a yellow oil. The oil was dissolved in methanol (200 ml) and sodium borohydride (4.10 g, 109 mmol) was added cautiously with vigorous stirring. Once the addition was complete the reaction was stirred for 1 hour and the mixture was concentrated under reduced pressure. The residue was dissolved in 1M aqueous sodium hydroxide solution (200 ml) and the mixture was stirred at room temperature for 1 hour. The resulting solution was extracted with dichloromethane (2×200 ml) and the combined organic phases were dried over magnesium sulphate, filtered and concentrated under reduced pressure to provide the title compound (13.4 g) as a pale yellow oil.

$^1$H-NMR (300 MHz, CDCl$_3$): δ=1.46 (s, 1H), 2.46 (s, 3H), 3.82 (s, 2H), 7.47 (d, 2H), 7.64 (d, 2H). LRMS (electrospray): m/z [MH$^+$] 147.

Preparation 21

4-{[(2-Hydroxyethyl)amino]methyl}benzonitrile

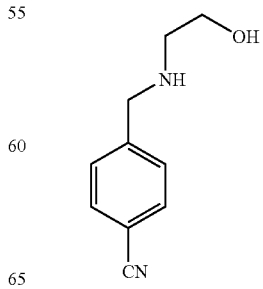

A mixture of 4-Cyanobenzaldehyde (14.1 g, 107 mmol), ethanolamine (6.56 g, 107 mmol) and toluene (100 ml) was heated under reflux for 14 hours using a Dean-Stark apparatus to remove water. The reaction was cooled to room temperature and concentrated under reduced pressure to leave a yellow oil. The oil was dissolved in dichloromethane (200 ml), cooled to 0° C. and triethylamine (16.3 ml, 117 mmol) and chlorotrimethylsilane (14.9 ml, 117 mmol) were added dropwise. A white precipitate formed and after stirring for 1 hour the mixture was filtered. The filtrate was concentrated under reduced pressure to leave an orange solid (25.0 g). The orange solid was dissolved in methanol (200 ml) and sodium borohydride (4.50 g, 122 mmol) was added cautiously with vigorous stirring. Once the addition was complete the reaction was stirred for 1 hour and the mixture was then concentrated under reduced pressure. The residue was dissolved in 1M aqueous sodium hydroxide solution (200 ml) and the mixture was stirred at room temperature for 1 hour. The resulting solution was extracted with dichloromethane (3×200 ml) and the combined organic phases were dried over magnesium sulphate, filtered and concentrated under reduced pressure. The crude product was purified by flash column chromatography on silica gel eluting with dichloromethane:methanol:ammonia (95:4:1, by volume) to provide the title compound (12.0 g) as a pale yellow oil which solidified on standing to leave a yellow solid, m.p. <60° C.

$^1$H-NMR (300 MHz, CDCl$_3$): δ=1.84 (s, 2H), 2.84 (t, 2H), 3.68 (t, 2H), 3.89 (s, 2H), 7.45 (d, 2H), 7.65 (d, 2H). LRMS (thermospray): m/z [MH$^+$] 177.

Preparation 22

N-{[1-(2-{[tert-Butyl(dimethyl)silyl]oxy}ethyl)-4-(3,5-dichlorophenoxy)-3-methyl-1H-pyrazol-5-yl]methyl}-N-(3-pyridinylmethyl)amine

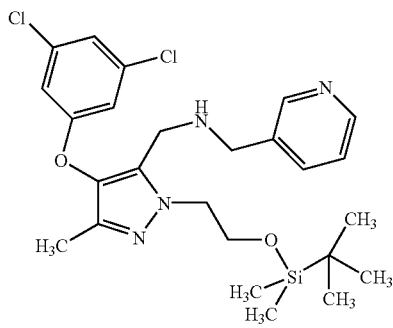

3-(Methylamino)pyridine (327 mg, 3.04 mmol) was added in one portion to a stirred solution of the bromide of Preparation 28 (300 mg, 0.610 mmol) in isopropanol (5 ml) at room temperature. The mixture was heated at 50° C. for 1 hour, cooled to room temperature and concentrated under reduced pressure to leave an orange oil. The crude product was purified by flash column chromatography on silica gel eluting with dichloromethane:methanol:ammonia (95:4:1, by volume) to provide the title compound (50 mg) as a colourless oil.

$^1$H-NMR (400 MHz, CDCl$_3$): δ=0.15 (s, 6H), 0.77 (s, 9H), 2.02 (s, 3H), 3.64 (s, 2H), 3.70 (s, 2H), 3.95 (t, 2H), 4.17 (t, 2H), 6.75 (s, 2H), 6.97 (s, 1H), 7.15 (dd, 1H), 7.53 (d, 1H), 8.47 (m, 2H). LRMS (thermospray): m/z [MH$^+$] 521.

Preparation 23

3-Chloro-5-methyl-2,4-hexanedione

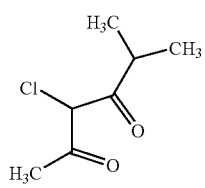

Chlorotrimethylsilane (13.4 ml, 105 mmol) was added dropwise to a stirred pale yellow solution of tetrabutylammonium iodide (566 mg, 1.53 mmol) in dry acetonitrile (100 ml) at room temperature under nitrogen. The resulting solution was cooled in ice and 5-methylhexane-2,4-dione (4.50 g, 35.1 mmol) and then dry dimethylsulphoxide (7.47 ml, 105 mmol) were added dropwise over 5 minutes producing a yellow solution which was allowed to warm slowly to room temperature with stirring over 1 hour. Tetrabutylammonium bromide (566 mg, 1.75 mmol) was then added in one portion and the reaction was stirred at room temperature for 2 hours. The mixture was diluted with water (200 ml), stirred for 10 min and then extracted with ether (3×100 ml). The combined ether layers were dried over magnesium sulphate, filtered and concentrated under reduced pressure to leave a yellow oil. The crude product was purified by flash column chromatography on silica gel eluting with pentane:ethyl acetate (98:2, by volume) to provide the title compound (2.00 g) as a colourless oil.

$^1$H-NMR (400 MHz, CDCl$_3$): δ=1.15 (d, 6H), 2.29 (s, 3H), 3.25 (sept, 1H), 15.60 (s, 1H). LRMS (thermospray): m/z [MNH$_4^+$] 180.

Preparation 24

5-(1-Acetyl-3-methyl-2-oxobutoxy)isophthalonitrile

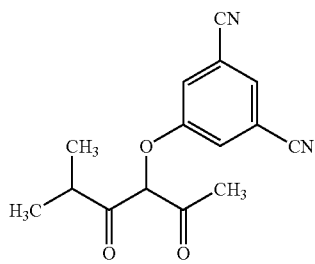

A mixture of the dione of Preparation 23 (1.12 g, 6.94 mmol), the phenol of Preparation 39 (1.00 g, 6.94 mmol), cesium carbonate (2.25 g, 6.94 mmol) and acetone (30 ml) was heated under reflux for 4 hours. The reaction was cooled to room temperature and concentrated under reduced pressure to leave a brown solid. The solid was dissolved in 1M aqueous hydrochloric acid (50 ml) and the solution was extracted with dichloromethane (3×30 ml). The combined organic phases were washed with brine (30 ml), dried over magnesium sulphate, filtered and concentrated under reduced pressure. The crude product was purified by flash column chromatography on silica gel eluting with pentane:ethyl acetate (90:10, by volume) to provide the title compound (580 mg) as a yellow solid.

$^1$H-NMR (300 MHz, CDCl$_3$): δ=1.08 (d, 6H), 2.02 (s, 3H), 2.24 (sept, 1H), 7.47 (s, 2H), 7.63 (s, 1H), 14.71 (s, 1H). LRMS (electrospray): m/z [M−H$^+$] 269.

Preparation 25

5-{[1-(2-{[tert-Butyl(dimethyl)silyl]oxy}ethyl)-3-isopropyl-5-methyl-1H-pyrazol-4-yl]oxy}isophthalonitrile

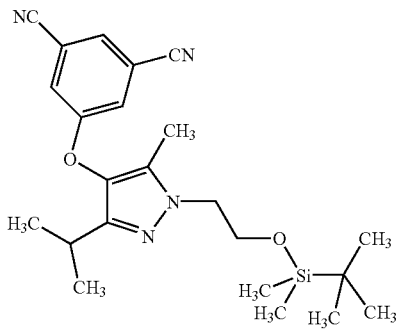

Sodium hydride (60% dispersion in oil, 45 mg, 1.12 mmol) was added to a stirred solution of 2-bromoethoxy-t-butyldimethylsilane (270 mg, 1.12 mmol) and the pyrazole of Example 95 (250 mg, 0.930 mmol) in N,N-dimethylformamide (5 ml) at 0° C. under nitrogen. The reaction was warmed to room temperature and stirred for 12 hours. The reaction mixture was quenched by the addition of water (50 ml) and the aqueous phase was extracted with ethyl acetate (3×30 ml). The combined organic phases were dried over magnesium sulphate, filtered and concentrated under reduced pressure to leave a brown oil. The crude product was purified by flash column chromatography on silica gel eluting pentane:ethyl acetate (80:20, by volume) to provide the title compound (60 mg) as a colourless oil.

$^1$H-NMR (400 MHz, CDCl$_3$): δ=0.02 (s, 6H), 0.85 (s, 9H), 1.19 (d, 6H), 2.09 (s, 3H), 2.79 (sept, 1H), 3.99 (m, 2H), 4.10 (m, 2H), 7.39 (s, 2H), 7.57 (s, 1H). LRMS (electrospray): m/z [MH$^+$] 425.

Preparation 26 di(tert-Butyl) 2-[4-(3,5-dichlorophenoxy)-3-ethyl-1H-pyrazol-1-yl]ethylimidodicarbonate and di(tert-butyl) 2-[4-(3,5-dichlorophenoxy)-5-ethyl-1H-pyrazol-1-yl]ethylimidodicarbonate

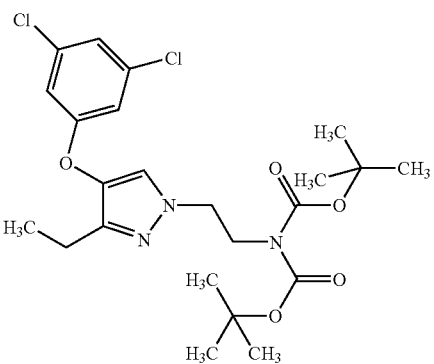

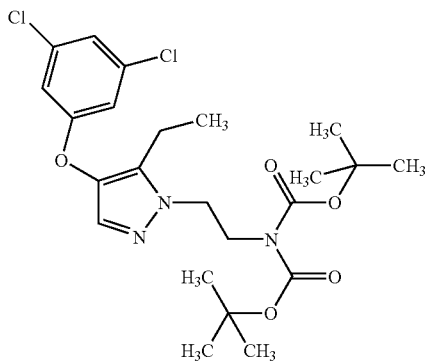

Di-t-butyldicarbonate (14.0 g, 64.2 mmol) and 4,4-dimethylaminopyridine (630 mg, 5.14 mmol) were added portionwise to a stirred solution of the amines of Example 283 (7.72 g, 25.7 mmol) in acetonitrile (128 ml) at room temperature under nitrogen. The reaction was stirred for 14 hours and concentrated under reduced pressure. A solution of the residue in dichloromethane (300 ml) was washed with water (100 ml), dried over magnesium sulphate, filtered and concentrated under reduced pressure. The crude product was purified by flash chromatography on silica gel eluting with dichloromethane:methanol (99:1, by volume) to afford the title compounds (12.3 g) in a 85:15 ratio of regioisomers as a colourless oil.

$^1$H-NMR (400 MHz, CDCl$_3$): δ=1.15 (major, t, 3H), 1.15 (minor, t, 3H), 1.52 (major, s, 18H), 1.52 (minor, s, 18H), 2.47 (major, q, 2H), 2.56 (minor, q, 2H), 4.00 (major, t, 2H), 4.00 (minor, t, 2H), 4.24 (major, t, 2H), 4.24 (minor, t, 2H), 6.85 (major, s, 2H), 6.85 (minor, s, 2H), 7.00 (major, s, 1H), 7.00 (minor, s, 1H), 7.21 (major, s, 1H), 7.25 (minor, s, 1H). LRMS (thermospray): m/z [MH$^+$] 500. Microanalysis: Found: C, 54.94; H, 6.26; N, 8.27. C$_{23}$H$_{31}$Cl$_2$N$_3$O$_5$ requires C, 55.20; H, 6.24; N, 8.40%.

Preparation 27

1-(2-{[tert-Butyl(dimethyl)silyl]oxy}ethyl)-4-(3,5-dichlorophenoxy)-3,5-dimethyl-1H-pyrazole

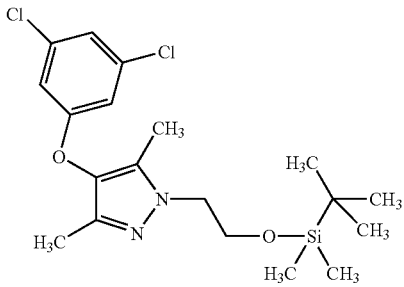

Chloro-t-butyldimethylsilane (1.93 g, 12.8 mmol) was added in one portion to a stirred solution of the pyrazole of Example 1 (3.50 g, 11.6 mmol) and imidazole (1.03 g, 15.1 mmol) in N,N-dimethylformamide (23 ml) at room temperature under nitrogen. The reaction was stirred for 2 days and water (200 ml) was added. The aqueous phase was extracted with diethyl ether (3×200 ml) and the combined organic phases were washed with water (2×50 ml) and brine (2×50 ml), dried over magnesium sulphate, filtered and concentrated under reduced pressure. The crude product was purified by flash chromatography on silica gel eluting with pentane:ethyl acetate (80:20, by volume) to provide the title compound (4.82 g) as a colourless oil.

$^1$H-NMR (400 MHz, CDCl$_3$): δ=0.09 (s, 6H), 0.78 (s, 9H), 2.01 (s, 3H), 2.05 (s, 3H), 3.88 (q, 2H), 4.02 (q, 2H), 6.76 (s, 2H), 6.88 (s, 1H). LRMS (thermospray): m/z [MH$^+$] 415.

Preparation 28

5-(Bromomethyl)-1-(2-{[tert-butyl(dimethyl)silyl]oxy}ethyl)-4-(3,5-dichlorophenoxy)-3-methyl-1H-pyrazole

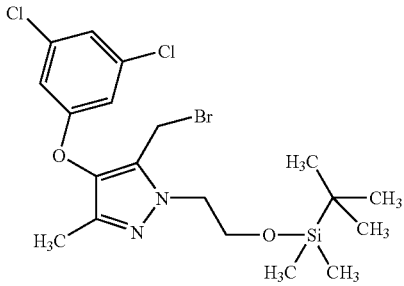

N-Bromosuccinimide (640 mg, 3.60 mmol) was added to a stirred solution of the pyrazole of Preparation 27 (1.00 g, 2.40 mmol) in carbon tetrachloride (15 ml) and azobisisobutyronitrile (20 mg) at room temperature under nitrogen. The reaction was heated under reflux for 5 hours then cooled to room temperature and filtered. The filtrate was concentrated under reduced pressure and the crude product was purified by flash column chromatography on silica gel eluting with dichloromethane:methanol:ammonia (97:2.5:0.5, by volume) to provide the title compound (300 mg) as a colourless oil.

$^1$H-NMR (300 MHz, CDCl$_3$): δ=0.04 (s, 6H), 0.82 (s, 9H), 2.02 (s, 3H), 3.96 (m, 2H), 4.22 (m, 2H), 4.41 (s, 2H), 6.81 (s, 2H), 7.01 (s, 1H). LRMS (thermospray): m/z [MH$^+$] 495.

Preparation 29

3-{[1-(2-{[tert-Butyl(dimethyl)silyl]oxy}ethyl)-3,5-dimethyl-1H-pyrazol-4-yl]oxy}-5-chlorobenzonitrile

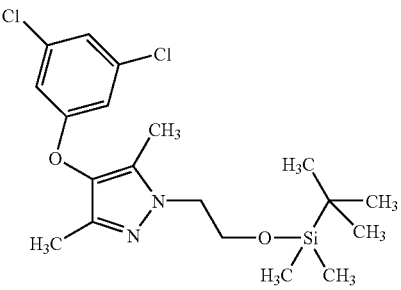

Chloro-t-butyldimethylsilane (2.78 g, 18.5 mmol) was added in one portion to a stirred solution of the pyrazole of Example 114 (4.89 g, 16.8 mmol) and imidazole (1.48 g, 21.8 mmol) in N,N-dimethylformamide (30 ml) at room temperature under nitrogen. The reaction was stirred for 3 days and water (200 ml) was added. The aqueous phase was extracted with diethyl ether (3×200 ml) and the combined organic phases were washed with water (2×50 ml) and brine (2×50 ml), dried over magnesium sulphate, filtered and concentrated under reduced pressure. The crude product was purified by flash chromatography on silica gel eluting with dichloromethane to provide the title compound (5.60 g) as a yellow oil.

$^1$H-NMR (400 MHz, CDCl$_3$): δ=−0.02 (s, 6H), 0.82 (s, 9H), 2.02 (s, 3H), 2.12 (s, 3H), 3.97 (q, 2H), 4.06 (m, 2H), 7.02 (s, 1H), 7.11 (s, 1H), 7.24 (s, 1H). LRMS (thermospray): m/z [MH$^+$] 408. Microanalysis: Found: C, 58.95; H, 6.96; N, 10.22. C$_{20}$H$_{28}$N$_3$O$_2$ClSi requires C, 59.13; H, 6.95; N, 10.35%.

Preparation 30

3-{[5-(Bromomethyl)-1-(2-{[tert-butyl(dimethyl)silyl]oxy}ethyl)-3-methyl-1H-pyrazol-4-yl]oxy}-5-chlorobenzonitrile

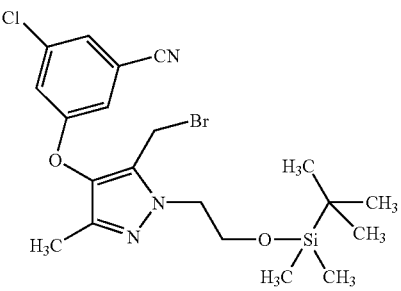

N-Bromosuccinimide (2.44 g, 13.7 mmol) was added to a stirred solution of the pyrazole of Preparation 29 (5,56 g, 13.7 mmol) in carbon tetrachloride (50 ml) and azobisisobutyronitrile (20 mg) at room temperature under nitrogen. The reaction was heated under reflux for 1 hour, cooled to room temperature and concentrated under reduced pressure. The crude product was purified by flash column chromatography on silica gel eluting with pentane:dichloromethane acetate (75:25, by volume) to provide the title compound (3.00 g) as a colourless oil.

$^1$H-NMR (300 MHz, CDCl$_3$): δ=−0.02 (s, 6H), 0.83 (s, 9H), 2.04 (s, 3H), 3.97 (q, 2H), 4.25 (m, 2H), 4.43 (s, 2H), 7.09 (s, 1H), 7.18 (s, 1H), 7.33 (s, 1H). LRMS (thermospray): m/z [MH$^+$] 486.

Preparation 31

3-{[5-(Aminomethyl)-1-(2-{[tert-butyl(dimethyl)silyl]oxy}ethyl)-3-methyl-1H-pyrazol-4-yl]oxy}-5-chlorobenzonitrile

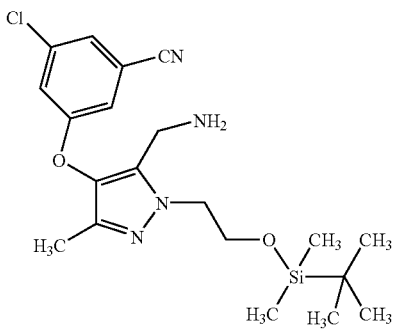

The bromide of Preparation 30 (1.58 g, 3.26 mmol) was added to a saturated solution of ammonia in isopropanol (50 ml) at 0° C. The reaction was stirred for 6 hours and allowed to slowly warm to room temperature. The mixture was concentrated under reduced pressure and the resulting yellow oil was dissolved in dichloromethane (50 ml). The solution was washed with 1M aqueous sodium carbonate solution (2×20 ml) and brine (20 ml), dried over magnesium sulphate, filtered and concentrated under reduced pressure to provide the title compound (1.00 g) as a yellow oil.

$^1$H-NMR (300 MHz, CDCl$_3$): δ=−0.23 (s, 6H), 0.62 (s, 9H), 1.22 (s, 2H), 1.82 (s, 3H), 2.56 (s, 2H), 3.78 (m, 2H), 4.02 (m, 2H), 6.85 (s, 1H), 6.96 (s, 1H), 7.06 (s, 1H). LRMS (thermospray): m/z [MH$^+$] 421.

Preparation 32

1-Bromo-3-chloro-5-methoxybenzene

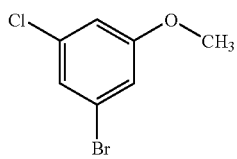

Sodium methoxide (2.20 ml of a 4.5M solution in methanol, 10.0 mmol) was added dropwise to a stirred solution of 1-fluoro-3-chloro-5-bromobenzene (1.00 g, 4.77 mmol) in methanol (28 ml) at room temperature under nitrogen. The reaction was heated under reflux for 3 days and cooled to room temperature. The mixture was concentrated under reduced pressure and the resulting yellow oil was dissolved in dichloromethane (30 ml). The resulting solution was washed with water (2×20 ml) dried over magnesium sulphate, filtered and concentrated under reduced pressure. The crude product was purified by flash column chromatography on silica gel eluting with cyclohexane to provide the title compound (302 mg) as a colourless oil.

$^1$H-NMR (400 MHz, CDCl$_3$): δ=3.77 (s, 3H), 6.82 (s, 1H), 6.94 (s, 1H), 7.09 (s, 1H). Microanalysis: Found: C, 37.94; H, 2.75. C$_7$H$_6$BrClO requires C, 37.96; H, 2.73%.

Preparation 33

3-Fluoro-5-methoxybenzonitrile

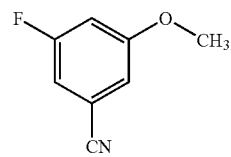

Sodium methoxide (1.50 ml of a 4.5M solution in methanol, 7.10 mmol) was added dropwise to a stirred solution of 3,5-difluorobenzonitrile (1.00 g, 7.10 mmol) in N,N-dimethylformamide (36 ml) at 0° C. under nitrogen. The reaction was allowed to warm to room temperature and stirred for 14 hours. The reaction was diluted with ether (40 ml), washed with water (3×100 ml) and brine (100 ml), dried over magnesium sulphate, filtered and concentrated under reduced pressure. The crude product was purified by flash chromatography on silica gel eluting with cyclohexane:ethyl acetate (95:5, by volume) to provide the title compound (418 mg) as a yellow oil.

$^1$H-NMR (400 MHz, CDCl$_3$): δ=3.84 (s, 3H), 6.82 (dd, 1H), 6.95 (dd, 1H), 6.96 (s, 1H). LRMS (thermospray): m/z [MNH$_4^+$] 169. Microanalysis: Found: C, 63.46; H, 3.95; N, 9.14. C$_8$H$_6$NOF requires C, 63.58; H, 4.00; N, 9.27%.

Preparation 34

3-Fluoro-5-hydroxybenzonitrile

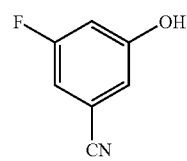

Boron trichloride (1.65 ml of a 1.0M solution in dichloromethane, 1.65 mmol) was added dropwise to a stirred solution of the nitrile of Preparation 33 (100 mg, 0.660 mmol) and tetrabutylammonium iodide (268 mg, 0.728 mmol) in dichloromethane (3 ml) at −78° C. The reaction was allowed to warm 0° C., stirred for 2 hours and then allowed to warm to room temperature and stirred for 14 hours. The reaction was cooled to 0° C., cautiously quenched with ice and then concentrated under reduced pressure. The residue was dissolved in ether (40 ml) and the resulting solution was washed with water (3×40 ml) and brine (40 ml), dried over magnesium sulphate, filtered and concentrated under reduced pressure. The crude product was purified by flash chromatography on silica gel eluting with cyclohexane:ethyl acetate (90:10, by volume) to provide the title compound (50 mg) as a white solid, m.p. 138–139° C.

$^1$H-NMR (300 MHz, CDCl$_3$): δ=5.81 (s, 1H), 6.80 (dd, 1H), 6.94 (dd, 1H), 6.95 (s, 1H). Microanalysis: Found: C, 60.99; H, 3.01; N, 10.16. C$_7$H$_4$NOF requires C, 61.32; H, 2.94; N, 10.22%.

Preparation 35

3-Chloro-5-methoxybenzonitrile

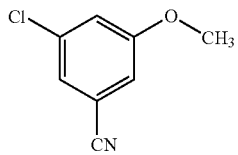

Palladiumtetrakis(triphenylphosphine) (174 mg, 0.150 mmol) was added in one portion to a stirred solution of the bromide of Preparation 32 (500 mg, 2.26 mmol) and zinc cyanide (146 mg, 1.24 mmol) in N,N-dimethylformamide (3 ml) at room temperature under nitrogen. The reaction was heated at 100° C. for 14 hours and cooled to room temperature. The mixture was concentrated under reduced pressure and the crude product was purified by flash chromatography on silica gel eluting with cyclohexane:ethyl acetate (95:5, by volume) to provide the title compound (380 mg) as a yellow oil.

$^1$H-NMR (300 MHz, CDCl$_3$): δ=3.82 (3H, s), 7.04 (s, 1H), 7.12 (s, 1H), 7.23 (s, 1H). Microanalysis: Found: C, 57.50; H, 3.63; N, 8.16. C$_8$H$_6$NOCl requires C, 57.33; H, 3.61; N, 8.36%.

Preparation 36

3-Chloro-5-hydroxybenzonitrile

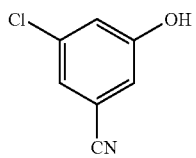

Boron trichloride (26.0 ml of a 1.0M solution in dichloromethane, 26.0 mmol) was added dropwise to a stirred solution of the nitrile of Preparation 35 (1.80 g, 10.0 mmol) and tetrabutylammonium iodide (4.36 g, 11.0 mmol) in dichloromethane (50 ml) at −78° C. The reaction was allowed to warm to room temperature and stirred for 14 hours. The reaction was cooled to 0° C., cautiously quenched with ice and diluted with dichloromethane (100 ml). The organic phase was washed with water (3×40 ml) and brine (40 ml), dried over magnesium sulphate, filtered and concentrated under reduced pressure. The crude product was purified by flash chromatography on silica gel eluting with cyclohexane:ethyl acetate (80:20, by volume) to provide the title compound (900 mg) as a white solid.

$^1$H-NMR (400 MHz, d$_6$DMSO): δ=7.12 (m, 2H), 7.38 (s, 1H), 10.65 (s, 1H). Microanalysis: Found: C, 54.76; H, 2.81; N, 8.94. C$_7$H$_4$NOCl requires C, 54.75; H, 2.63; N, 9.12%.

Preparation 37

1,3-Dibromo-5-methoxybenzene

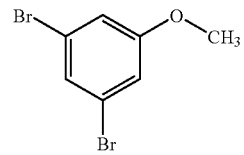

Sodium methoxide (8.80 ml of a 4.5M solution in methanol, 41.0 mmol) was added dropwise to a stirred solution of 3,5-dibromofluorobenzene (5.00 g, 19.0 mmol) in N,N-dimethylformamide (95 ml) at 0° C. under nitrogen. The reaction was allowed to warm to room temperature, stirred for 1 hour and then concentrated under reduced pressure. The residue was dissolved in ether and the resulting solution was washed with water (3×300 ml) and brine (300 ml), dried over magnesium sulphate, filtered and concentrated under reduced pressure to provide the title compound (5.13 g) as a white solid.

$^1$H-NMR (300 MHz, CDCl$_3$): δ=3.79 (S, 3H), 7.00 (s, 2H), 7.26 (s, 1H). LRMS (thermospray): m/z [MH$^+$] 266. Microanalysis: Found: C, 31.56; H, 2.29. C$_7$H$_6$OBr$_2$ requires C, 31.62; H, 2.27%.

Preparation 38

3,5-Dicyanomethoxybenzene

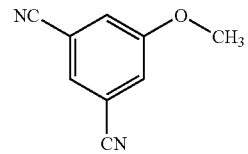

Tris(dibenzylideneacetone)dipalladium (6.53 g, 7.15 mmol) was added in one portion to a stirred solution of the bromide of Preparation 37 (38.0 g, 143 mmol) and zinc cyanide (20.0 g, 172 mmol) in N,N-dimethylformamide (300 ml) at room temperature under nitrogen. The reaction was heated at 100° C. for 14 hours and cooled to room temperature. Water (1500 ml) was added and the mixture was extracted with ethyl acetate (3×500 ml). The combined organics were filtered and the filtrate was washed with water (500 ml), dried over magnesium sulphate, filtered and concentrated under reduced pressure. The resulting solid was triturated with toluene (1000 ml) to provide the title compound (18.0 g) as a tan solid.

$^1$H-NMR (300 MHz, CDCl$_3$): δ=3.83 (3H, s), 7.31 (2H, s), 7.48 (1H, s).

Preparation 39

3,5-Dicyanohydroxybenzene

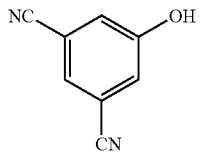

The nitrile of Preparation 38 (9.60 g, 60.7 mmol) was added portionwise to a stirred suspension of aluminium trichloride (32.4 g, 243 mmol) in dichloromethane (250 ml) at 0° C. under nitrogen. The suspension was heated to 45° C. and stirred for 6 days. The reaction was cooled to room temperature and cautiously poured onto ice (450 ml). Concentrated hydrochloric acid (450 ml) was added dropwise and the resulting suspension was stirred for 10 minutes at room temperature. The resulting solid was collected by filtration, washed with water and dried over phosphorus pentoxide to provide the title compound (7.83 g) as a tan solid containing approximately 11% starting material by $^1$H-NMR and microanalysis.

$^1$H-NMR (400 MHz, CDCl$_3$): δ=7.36 (m, 2H), 7.56 (m, 1H).

Preparation 40

3-Methoxy-5-methylphenyl trifluoromethanesulfonate

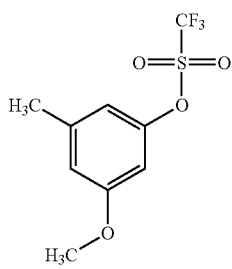

Trifluoromethanesulphonic anhydride (2.02 ml, 12.0 mmol) was added dropwise to a stirred solution of 3-methoxy-5-methylphenol (1.50 g, 10.9 mmol) in pyridine (20 ml) at −20° C. under nitrogen. The reaction was warmed to 0° C., stirred for 90 minutes and re-cooled to −20° C. More trifluoromethanesulphonic anhydride (1.01 ml, 6.00 mmol) was added dropwise. The reaction was allowed to warm to room temperature, stirred for 14 hours and cautiously poured into water (100 ml). The aqueous phase was extracted with ether (150 ml) and the organic phases were washed with water (3×75 ml), 0.2M hydrochloric acid (3×75 ml), 1.0M aqueous sodium carbonate solution (2×75 ml), water (75 ml) and brine (75 ml), dried over magnesium sulphate, filtered and concentrated under reduced pressure to provide the title compound (2.86 g) as a pale brown oil.

$^1$H-NMR (400 MHz, CDCl$_3$): δ=2.35 (s, 3H), 3.80 (s, 3H), 6.60 (s, 1H), 6.68 (s, 1H), 6.73 (s, 1H).

Preparation 41

3-Methoxy-5-methylbenzonitrile

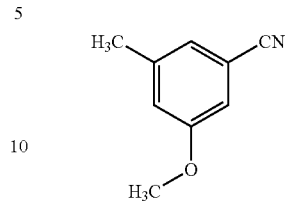

The triflate of Preparation 40 (1.94 g, 7.10 mmol), dibromobis(triphenylphosphine)nickel (369 mg, 0.490 mmol), 1,1'bis(diphenylphosphino)ferrocene (331 mg, 0.590 mmol) and potassium cyanide (1.38 g, 21.3 mmol) were added consecutively to a stirred suspension of Rieke® zinc (supplied by the Aldrich chemical company as a suspension; 5 g Zinc in 100 ml tetrahydrofuran) (74 mg, 1.14 mmol) in acetonitrile (4 ml) at room temperature. The reaction was heated to 75° C. for 8 hours and then cooled to room temperature. The mixture was partitioned between ether (200 ml) and water (150 ml) and the organic phase was separated, washed with water (2×100 ml) and brine (75 ml), dried over magnesium sulphate, filtered and concentrated under reduced pressure to give a pale brown oil. The crude product was purified by flash chromatography on silica gel eluting with pentane:ethyl acetate (85:15, by volume) to provide the title compound (815 mg) as a white solid.

$^1$H-NMR (400 MHz, CDCl$_3$): δ=2.34 (s, 3H), 3.80 (s, 3H), 6.93 (s, 1H), 6.94 (s, 1H), 7.04 (s, 1H).

Preparation 42

3-Hydroxy-5-methylbenzonitrile

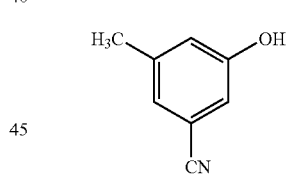

Boron trichloride (17.6 ml of a 1.0M solution in dichloromethane, 17.6 mmol) was added dropwise to a stirred solution of the nitrile of Preparation 41 (866 mg, 5.88 mmol) and tetrabutylammonium iodide (2.61 g, 7.05 mmol) in dichloromethane (50 ml) at −78° C. The reaction was allowed to warm to room temperature and stirred for 20 minutes. The reaction was cooled to 0° C., cautiously quenched with ice and diluted with dichloromethane (100 ml). The organic phase was separated, dried over magnesium sulphate, filtered and concentrated under reduced pressure. The crude product was purified by flash chromatography on silica gel eluting with pentane:ethyl acetate (50:50, by volume) to provide the title compound (677 mg) as a white solid.

$^1$H-NMR (400 MHz, CDCl$_3$): δ=2.32 (s, 3H), 5.05 (s, 1H), 6.88 (s, 1H), 6.90 (s, 1H), 7.04 (s, 1H).

Preparations 43 to 46

The compounds of the following tabulated Preparations of the general formula:

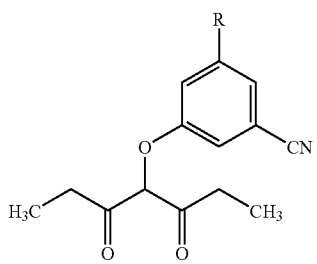

were prepared by a similar method to that of Preparation 9 using the appropriate phenol starting material and the chloride of Preparation 2.

| Preparation No. (Phenol No.) | R | LRMS | Analytical Data |
|---|---|---|---|
| 43 (Phenol Preparation 34) | F | m/z [MNH$_4^+$] 281. (thermospray) | $^1$H-NMR(300 MHz, CDCl$_3$): δ = 1.05(t, 6H), 2.27(q, 4H), 6.89(m, 1H), 7.03(s, 1H), 7.04(m, 1H). |
| 44 (Phenol Preparation 42) | Me | m/z [M − H$^+$] 258. (electrospray) | $^1$H-NMR(400 MHz, CDCl$_3$): δ = 1.09(t, 6H), 2.32(q, 4H), 2.37(s, 3H), 6.96(s, 1H), 6.97(s, 1H), 7.15(s, 1H), 14.50(s, 1H). |
| 45 (Phenol Preparation 39) | CN | m/z [M − H$^+$] 269. (electrospray) | $^1$H-NMR(300 MHz, CDCl$_3$): δ = 1.09(m, 6H), 2.30(m, 4H), 7.42(s, 2H), 7.61(s, 1H), 14.56(s, 1H). |
| 46 (Phenol Preparation 36) | Cl | m/z [MH$^+$] 280. (thermospray) | $^1$H-NMR(400 MHz, CDCl$_3$): δ = 1.08(m, 6H), 2.31(q, 4H), 7.12(s, 1H), 7.19(s, 1H), 7.31(s, 1H). |

Preparation 47

1-Cyclopropyl-1,3-pentanedione

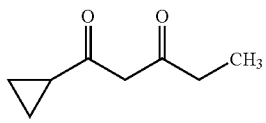

A stirred suspension of magnesium turnings (1.83 g, 75.0 mmol) in methanol (85 ml) was heated under reflux for 90 minutes. The suspension was cooled to room temperature and a solution of 3-ketopentanoic acid (17.4 g, 150.0 mmol) in methanol (15 ml) was added. The white suspension dissolved to give a pale yellow solution. The reaction was stirred at room temperature for 1 hour and then concentrated under reduced pressure to give a pale yellow solid which was dissolved in N,N-dimethylformamide (50 ml). In a separate flask carbonyldiimidazole (13.4 g, 83.0 mmol) was added portionwise to a stirred solution of cyclopropanecarboxylic acid (6.46 g, 75.0 mmol) in N,N-dimethylformamide (150 ml) at room temperature under nitrogen. The reaction was stirred for 90 minutes and then the magnesium salt previously prepared was added dropwise. The reaction was stirred for 3 days and then poured into 1.0M hydrochloric acid (150 ml). The aqueous phase was extracted with ether (3×200 ml) and the combined organic phases were dried over magnesium sulphate, filtered and concentrated under reduced pressure. The crude product was purified by flash chromatography on silica gel eluting with pentane:ethyl acetate (90:10, by volume) to provide the title compound (9.33 g) as a yellow oil.

$^1$H-NMR (400 MHz, CDCl$_3$): keto and enol forms present with enol as major component; enol signals δ=1.00 (m, 7H), 1.60 (m, 1H), 2.25 (m, 2H), 5.59 (s, 1H), 15.62 (s, 1H); keto signals δ=1.00 (m, 7H), 2.01 (m, 1H), 2.52 (m, 2H), 3.68 (s, 2H). LRMS (electrospray): m/z [M−H$^+$] 139. Microanalysis: Found: C, 68.35; H, 8.72. C$_8$H$_{12}$O$_2$ requires C, 68.55; H, 8.63%.

Preparation 48

The compound of the following tabulated Preparation of the general formula:

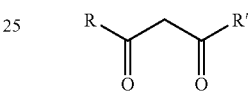

was prepared by a similar method to that of Preparation 47 using the appropriate ketoacid and carboxylic acid starting materials.

| Preparation No. | R | R' | LRMS | Analytical Data |
|---|---|---|---|---|
| 48 | iPr | Et | m/z [M − H$^+$] 141. (electrospray) | $^1$H-NMR(400 MHz, CDCl$_3$): keto and enol forms present with enol major δ = 1.12 (m, 18H, keto and enol), 2.32(m, 4H, keto and enol), 2.49 (m, 2H, keto and enol), 3.61(s, 2H, keto), 5.49(s, 1H, enol), 15.52(s, 1H, enol). Microanalysis: Found: C, 67.22; H, 9.95. C$_8$H$_{14}$O$_2$ requires C, 67.57; H, 9.92%. |

Preparations 49 to 51

The compounds of the following tabulated Preparations of the general formula:

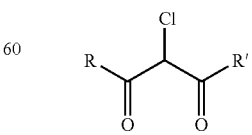

were prepared by a similar method to that of Preparation 2 using the appropriate diketone starting material.

| Preparation No. (Diketone No.) | R | R' | LRMS | Analytical Data |
|---|---|---|---|---|
| 49 (Preparation 47) | cycloPr | Et | m/z [M − H⁺] 173. (electrospray) | ¹H-NMR(400 MHz, CDCl₃): 1.10(m, 7H), 2.41 (m, 1H), 2.61(m, 2H), 15.90(s, 1H). |
| 50 (Commercially available diketone used) | Me | Et | m/z [MNH₄⁺] 166. (thermospray) | ¹H-NMR(300 MHz, CDCl₃): 1.19(m, 3H), 2.27 (s, 3H), 2.67(q, 2H), 15.40(s, 1H). |
| 51 (Preparation 48) | iPr | Et | m/z [M − H⁺] 175. (electrospray) | ¹H-NMR(400 MHz, CDCl₃): 1.18(m, 9H), 2.64 (q, 2H), 3.20(m, 1H), 15.80(s, 1H). |

Preparations 52 to 54

The compounds of the following tabulated Preparations of the general formula:

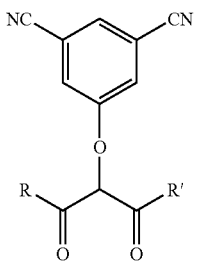

were prepared by a similar method to that of Preparation 9 using the appropriate diketone starting material and the phenol of Preparation 39.

| Preparation No. (Diketone No.) | R | R' | LRMS | Analytical Data |
|---|---|---|---|---|
| 52 (Preparation 49) | cycloPr | Et | m/z [M − H⁺] 282. (electrospray) | ¹H-NMR(400 MHz, CDCl₃): 0.93(m, 2H), 1.12(t, 3H), 1.21 (m, 2H), 1.78(m, 1H), 2.29(q, 2H), 7.49(s, 2H), 7.61 (s, 1H), 14.87(s, 1H). |
| 53 (Preparation 19) | tBu | Me | m/z [MNH₄⁺] 301. (thermospray) | ¹H-NMR(400 MHz, CDCl₃): 1.08(s, 9H), 1.84 (s, 3H), 7.30(s, 1H), 7.57(s, 2H), 15.42(s, 1H). |
| 54 (Preparation 51) | iPr | Et | m/z [M − H⁺]283. (electrospray) | ¹H-NMR(400 MHz, CDCl₃): 1.03(m, 9H), 2.23(q, 2H), 2.58 (m, 1H), 7.41(s, 2H), 7.59(s, 1H), 14.63(s, 1H). |

Preparation 55

4-(Aminomethyl)benzamide

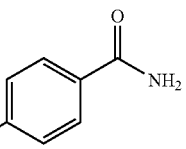

Powdered potassium hydroxide (340 mg, 6 mmol) was added in one portion to a stirred solution of 4-(aminomethyl)benzonitrile (200 mg, 1.5 mmol) in 2-methyl-2-propanol (20 ml) at reflux under nitrogen. The reaction was heated at reflux for 30 minutes and cooled to room temperature. The mixture was concentrated under reduced pressure and the crude product was purified by flash chromatography on silica gel eluting with dichloromethane:methanol:ammonia (95:5:0.5, by volume) to provide the title compound (150 mg) as a white solid.

¹H-NMR (300 MHz, CD₃OD): δ=3.85 (s, 2H), 7.43 (d, 2H), 7.82 (d, 2H). LRMS (thermospray): m/z [MH⁺] 151.

Preparation 56

3-Oxopentanoic acid

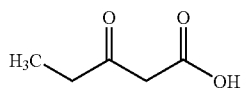

Sodium hydroxide (54 g, 1.35 mol) was added portionwise to a solution of 3-oxo-pentanoic acid methyl ester (80 g, 0.62 mol) in tetrahydrofuran (300 ml) and water (300 ml) at 0° C. The reaction was allowed to warm to room temperature and was stirred for 18 hours. The reaction mixture was washed with diethylether (500 ml) and the aqueous phase was acidified to pH 1 at 0° C. with concentrated hydrochloric acid (140 ml). The aqueous phase was extracted with dichloromethane (2×300 ml) and the combined organic extracts dried over magnesium sulphate and concentrated under reduced pressure to provide the title compound (44 g) as a white solid.

¹H NMR (400 MHz, CDCl₃): δ=1.12 (t, 3H), 2.59 (q, 2H), 3.49 (s, 2H).

Preparation 57

3-(Benzyloxy)propanoic acid

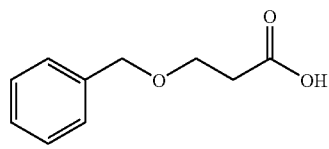

Sodium metal (249 mg, 10.8 mmol) was added to benzyl alcohol (30 g, 278 mmol) at room temperature under nitrogen and the reaction was stirred for 30 minutes. Methyl acrylate (25.9 ml, 259 mmol) was then added dropwise and the reaction was stirred at room temperature for 18 h. After quenching with saturated aqueous ammonium chloride solution (200 ml) the mixture was extracted with ethyl acetate (2×300 ml) and the combined organic extracts were washed with brine (100 ml), dried over magnesium sulphate and concentrated under reduced pressure. The residual oil was dissolved in ethanol (300 ml) and 1M aqueous sodium hydroxide solution (300 ml) was added dropwise. After 3 hours the ethanol was removed under reduced pressure and the aqueous residue was washed with dichloromethane (200 ml). The aqueous phase was then acidified with 2N aqueous hydrochloric acid (150 ml), extracted with dichloromethane (2×250 ml) and the combined organic extracts were dried over magnesium sulphate and concentrated under reduced pressure. The residual oil was dissolved in 10% aqueous potassium carbonate solution (300 ml), washed with diethylether (300 ml) and the aqueous phase was acidified to pH 1 using concentrated hydrochloric acid. The mixture was then extracted with dichloromethane (2×300 ml) and the combined organic extracts were dried over magnesium sulphate and concentrated under reduced pressure to provide the title compound (44.4 g) as a colourless oil.

$^1$H NMR (300 MHz, CDCl$_3$): δ=2.67 (t, 2H), 3.89 (t, 2H), 4.58 (s, 2H), 7.18 (m, 5H).

Preparation 58

(4Z)-1-(Benzyloxy)-5-hydroxy-4-hepten-3-one

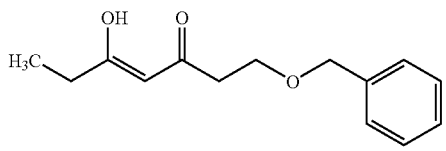

A suspension of magnesium turnings (1.74 g, 71.6 mmol) in methanol (85 ml) was heated to reflux under nitrogen for 1.5 hours, cooled to room temperature and the β-keto acid from Preparation 56 (16.6 g, 143 mmol) was added. The reaction was stirred for 1.5 hours and the solvent was removed under reduced pressure to give the magnesium salt of the acid as a white solid. Meanwhile, the acid from Preparation 57 (12.9 g, 71.6 mmol) was dissolved in dimethylformamide (150 ml) and carbonyldiimidazole (12.8 g, 78.8 mmol) was added portionwise under nitrogen at room temperature. This was stirred for 1 hour and the magnesium salt from above was added as a solution in dimethylformamide (50 ml). Evolution of gas was noted, and the reaction was allowed to stir at room temperature for 18 hours. The mixture was concentrated under reduced pressure and the residual orange oil was dissolved in dichloromethane (300 ml), washed with 0.5M aqueous hydrochloric acid (250 ml) containing methanol (10 ml) and the aqueous phase was separated and extracted with dichloromethane (2×300 ml). The combined organic extracts were washed with brine (300 ml) containing methanol (20 ml), dried over magnesium sulphate and concentrated under reduced pressure. The residual orange oil was purified by flash chromatography on silica gel eluting with cyclohexane:ethyl acetate (80:20, by volume) to provide the title compound (12.0 g) as an orange oil.

$^1$H NMR (400 MHz, CDCl$_3$): δ=1.17 (t, 3H), 2.33 (q, 2H), 2.58 (t, 2H), 3.76 (t, 2H), 4.53 (s, 2H), 5.57 (s, 1H), 7.13 (m, 5H). LRMS (electrospray): m/z [MNa$^+$] 257. Microanalysis: Found C, 71.77; H, 7.74. C$_{14}$H$_{18}$O$_3$ requires C, 71.76; H, 7.69%.

Preparation 59

(4E)-1-(Benzyloxy)-4-chloro-5-hydroxy-4-hepten-3-one

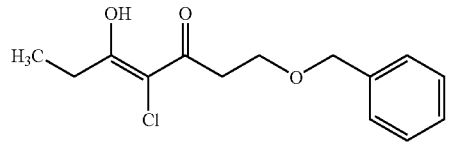

Trimethylsilyl chloride (10 ml, 51.3 mmol) was added to a solution of the enol from Preparation 58 (4.0 g, 17.1 mmol) in acetonitrile (25 ml) under nitrogen at 0° C. Dimethylsulfoxide (3.6 ml, 51.3 mmol) followed by tert-butylammonium bromide (275 mg, 0.85 mmol) were then added and the reaction was stirred at 0° C. for 2 hours. The mixture was diluted with water (100 ml), extracted with diethylether (100 ml) and the organic phase was washed with brine (50 ml), dried over magnesium sulphate and concentrated under reduced pressure. The residual pink oil was purified by flash chromatography on silica gel eluting with cyclohexane:ethyl acetate (80:20, by volume) to provide the title compound (3.76 g) as a pink oil.

$^1$H NMR (400 MHz, CDCl$_3$): δ=1.17 (t, 3H), 2.62 (q, 2H), 2.96 (t, 2H), 3.79 (t, 2H), 4.57 (s, 2H), 7.12 (m, 5H), 15.49 (s, 1H). LRMS (electrospray): m/z [MNa$^+$] 291.

Preparation 60

3-({(1E)-1-[3-(benzyloxy)propanoyl]-2-hydroxy-1-butenyl}oxy)-5-fluorobenzonitrile

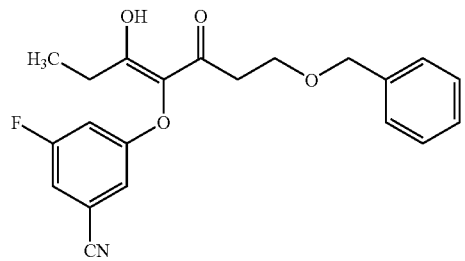

Sodium hydride (60% dispersion in oil, (1.92 g, 48.0 mmol)) was added to a stirred solution of the phenol from Preparation 34 (8.80 g, 48.0 mmol) in tetrahydrofuran (450 ml) under nitrogen at room temperature. After stirring for 1 hour, the enol from Preparation 59 (12.9 g, 48.0 mmol) was added and the reaction was stirred for 64 hours. The mixture was diluted with water (200 ml) and 2N aqueous hydrochloric acid (40 ml), extracted with ethyl acetate (2×150 ml) and the combined organic extracts were washed with brine (100 ml), dried over magnesium sulphate and concentrated under reduced pressure. The residual orange oil was purified by flash chromatography on silica gel eluting with cyclohexane:pentane (10:90, by volume) to provide the title compound (5.80 g) as an orange oil.

$^1$H NMR (400 MHz, CDCl$_3$): δ=1.08 (t, 3H), 2.31 (q, 2H), 2.59 (t, 2H), 3.75 (t, 2H), 4.45 (s, 2H), 6.92 (m, 1H), 7.02 (m, 2H), 7.29 (m, 5H), 14.50 (s, 1H). LRMS (electrospray): m/z [MNa$^+$] 392.

Preparation 61

5-({(1E)-1-[3-(Benzyloxy)propanoyl]-2-hydroxy-1-butenyl}oxy)isophthalonitrile

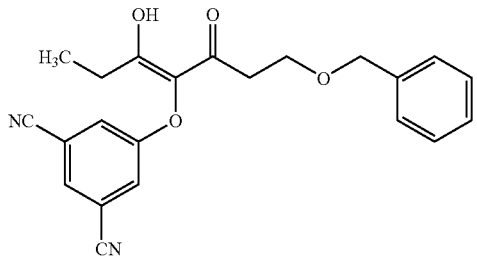

Sodium hydride (60% dispersion in oil, 412 mg, 12.3 mmol) was added to a stirred solution of the phenol from Preparation 39 (1.48 g, 10.3 mmol) in tetrahydrofuran (70 ml) under nitrogen at room temperature. After stirring for 30 minutes, the enol from Preparation 59 (2.76 g, 10.3 mmol) was added and the reaction was stirred for 18 hours. Water (100 ml) and 2N aqueous hydrochloric acid (10 ml) were cautiously added and the mixture extracted with ethyl acetate (2×150 ml). The organics were combined, washed with brine (100 ml), dried over magnesium sulphate and concentrated under reduced pressure. The residue was purified by flash column chromatography on silica gel eluting with (pentane:ethyl acetate 90:10, by volume) to provide the title compound (1.00 g) as a yellow oil. LRMS (thermospray): m/z [MH$^+$] 375.

Preparation 62

3-{[1-(2-{[tert-Butyl(dimethyl)silyl]oxy}ethyl)-3,5-diethyl-1H-pyrazol-4-yl]oxy}-5-fluorobenzonitrile

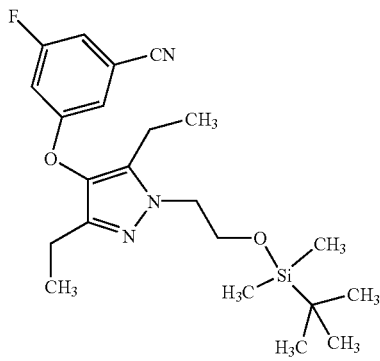

Imidazole (477 mg, 7.02 mmol) and tert-butyl-dimethylsilyl chloride (977 mg, 6.48 mmol) were sequentially added to a solution of the alcohol from Example 117 (1.65 g, 5.40 mmol) in dimethylformamide (11 ml) at room temperature under nitrogen.

The reaction was stirred for 18 hours and the mixture was diluted with water (100 ml) and extracted with diethylether (4×50 ml). The combined organic extracts were dried over magnesium sulphate, concentrated under reduced pressure and the residue was purified by flash chromatography on silica gel eluting with dichloromethane:methanol (99:1, by volume) to provide the title compound (2.12 g) as a colourless oil.

$^1$H NMR (400 MHz, CDCl$_3$): δ=0.03 (s, 6H), 0.84 (s, 9H), 1.10 (m, 6H), 2.42 (q, 2H), 2.56 (q, 2H), 4.00 (t, 2H), 4.09 (t, 2H), 6.86 (d, 1H), 6.99 (m, 2H). LRMS (thermospray): m/z [MH$^+$] 419. Microanalysis: Found C, 62.73; H, 7.83; N, 9.75. C$_{22}$H$_{32}$FN$_3$O$_2$Si.0.06CH$_2$Cl$_2$ requires C, 62.68; H, 7.66; N, 9.94%.

Preparation 63

3-({3,5-Diethyl-1-[2-(tetrahydro-2H-pyran-2-yloxy)ethyl]-1H-pyrazol-4-yl}oxy)-5-fluorobenzonitrile

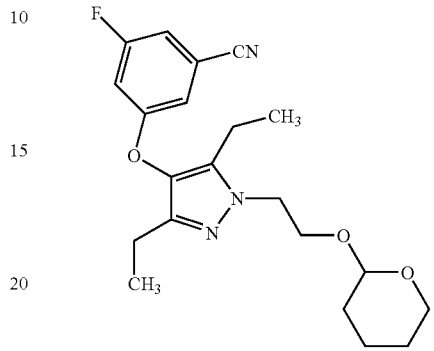

p-Toluene-sulphonic acid (32 mg, 0.17 mmol) was added to a solution of the alcohol from Example 117 (5.04 g, 16.6 mmol) and dihydropyran (7.57 ml, 83 mmol) in dichloromethane (65 ml) at room temperature under nitrogen. The reaction was stirred for 2 hours, but starting material still remained so a further aliquot of p-toluene-sulphonic acid (284 mg, 1.49 mmol) was added and the reaction was stirred for 1 hour. The mixture was diluted with diethylether (90 ml) and washed with a mixed aqueous solution (water (50 ml), brine (25 ml) and saturated aqueous sodium bicarbonate solution (25 ml)).

The aqueous phase was extracted with diethylether (2×60 ml) and the combined organic extracts were dried over magnesium sulphate, concentrated under reduced pressure and the residue was purified by flash chromatography on silica gel eluting with dichloromethane:methanol (98:2, by volume) to provide the title compound (6.31 g) as an oil.

$^1$H NMR (400 MHz, CDCl$_3$): δ=1.08 (m, 6H), 1.52 (m, 6H), 2.39 (q, 2H), 2.54 (q, 2H), 3.45 (m, 1H), 3.64 (m, 1H), 3.75 (m, 1H), 4.06 (m, 1H), 4.17 (t, 2H), 4.51 (s, 1H), 6.82 (d, 1H), 7.22 (m, 2H). LRMS (thermospray): m/z [MH$^+$] 388.

Preparation 64

3-({3,5-Diethyl-1-[2-(tetrahydro-2H-pyran-2-yloxy)ethyl]-1H-pyrazol-4-yl}oxy)-5-fluorobenzamide

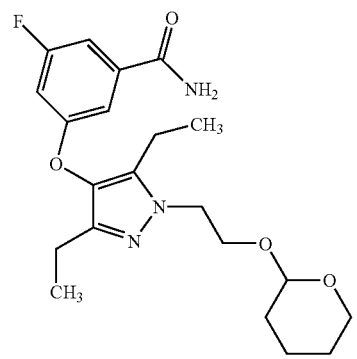

Cesium carbonate (269 mg, 0.82 mmol) was added to a solution of 3-methyl-3-pyrazolin-5-one (74 mg, 0.75 mmol) in dimethylsulfoxide (1 ml) under nitrogen at room temperature and the reaction was stirred for 15 minutes. The aryl fluoride from Preparation 63 (291 mg, 0.75 mmol) dissolved in dimethylsulfoxide (1 ml) was then added and the reaction was heated to 100° C. for 18 hours. After cooling to room temperature the reaction was diluted with water (7 ml) and extracted with diethylether (12 ml). The organic phase was washed with brine (3.5 ml), dried over magnesium sulphate, concentrated under reduced pressure and the residue was purified by flash chromatography on silica gel eluting with a solvent gradient of dichloromethane:methanol (99:1 changing to 95:5, by volume) to provide the unexpected title compound (108 mg) as an oil.

$^1$H NMR (400 MHz, CDCl$_3$): δ=1.12 (m, 6H), 1.56 (m, 6H), 2.44 (q, 2H), 2.59 (q, 2H), 3.48 (m, 1H), 3.69 (m, 1H), 3.79 (m, 1H), 4.08 (m, 1H), 4.20 (t, 2H), 4.54 (s, 1H), 6.72 (d, 1H), 7.15 (m, 2H). LRMS (thermospray): m/z [MH$^+$] 406. Microanalysis: Found C, 60.57; H, 6.97; N, 9.97. C$_{21}$H$_{28}$FN$_3$O$_4$.0.08CH$_2$Cl$_2$.0.32H$_2$O requires C, 60.57; H, 6.94; N, 10.05%.

Preparation 65

3-({3,5-Diethyl-1-[2-(tetrahydro-2H-pyran-2-yloxy) ethyl]-1H-pyrazol-4-yl}oxy)-5-(1H-pyrazol-1-yl) benzonitrile

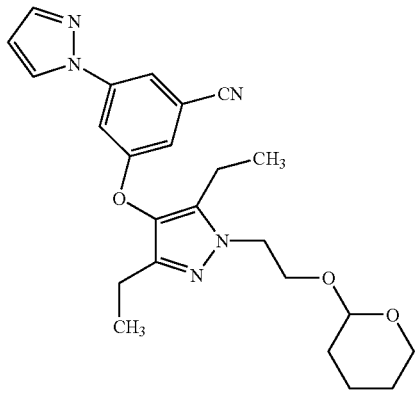

Cesium Carbonate (269 mg, 0.82 mmol) was added to a solution of pyrazole (51 mg, 0.75 mmol) in dry dimethylsulfoxide (1 ml) under nitrogen at room temperature and the reaction was stirred for 15 minutes. The aryl fluoride from Preparation 63 (291 mg, 0.75 mmol) dissolved in dry dimethylsulfoxide (1 ml) was then added and the reaction was heated to 100° C. for 18 hours. After cooling to room temperature the reaction was diluted with water (7 ml) and extracted with diethylether (10 ml). The organic phase was washed with brine (3 ml), dried over magnesium sulphate, concentrated under reduced pressure and the residue was purified by flash chromatography on silica gel eluting with a solvent gradient of dichloromethane:methanol (100:0 changing to 90:10, by volume) to provide the title compound (55 mg).

$^1$H NMR (400 MHz, CDCl$_3$): δ=1.13 (m, 6H), 1.58 (m, 6H), 2.44 (q, 2H), 2.60 (q, 2H), 3.49 (m, 1H), 3.69 (m, 1H), 3.80 (m, 1H), 4.10 (m, 1H), 4.21 (t, 2H), 4.55 (s, 1H), 6.50 (s, 1H), 6.98 (s, 1H), 7.57 (s, 1H), 7.63 (s, 1H), 7.72 (s, 1H), 7.89 (s, 1H). LRMS (thermospray): m/z [MH$^+$] 436, [MNa$^+$] 458. HRMS: [MH$^+$] Found 436.2352. C$_{24}$H$_{30}$N$_5$O$_3$ requires 436.2343 [MNa$^+$] Found 458.2168. C$_{24}$H$_{29}$N$_5$O$_3$Na requires 458.2162.

Preparations 66–68

The preparation of the following tabulated Preparations of the general formula

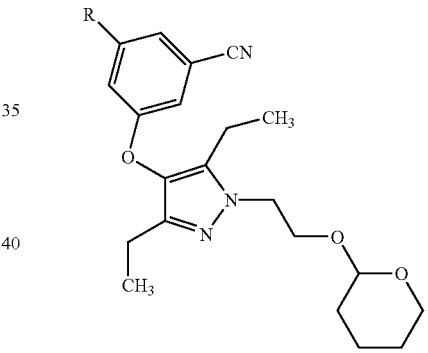

were performed by a similar method to that of Preparation 65 using the appropriate heterocycle as the starting material.

| Preparation No. (Starting material preparation no.) | R | Analytical Data |
|---|---|---|
| 66 (63) | 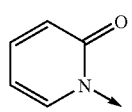 | $^1$H NMR (400 MHz, CDCl$_3$): δ = 1.13(m, 6H), 1.63(m, 6H), 2.44(q, 2H), 2.60(q, 2H), 3.46(m, 1H), 3.67(m, 1H), 3.79(m, 1H), 4.08(m, 1H), 4.20(t, 2H), 4.53(s, 1H), 6.26(t, 1H), 6.64(d, 1H), 7.17(s, 1H), 7.21(s, 1H), 7.34(s, 1H), 7.41(t, 1H). LRMS (thermospray): m/z [MH$^+$] 463, [MNa$^+$] 485. HRMS: [MH$^+$] Found 463.2353. C$_{26}$H$_{31}$N$_4$O$_4$ requires 463.2340 [MNa$^+$ Found 485.2166. C$_{26}$H$_{30}$N$_4$O$_4$Na requires 485.2159. |

-continued

| Preparation No. (Starting material preparation no.) | R | Analytical Data |
|---|---|---|
| 67 (63) | 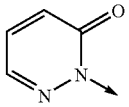 | $^1$H NMR (400 MHz, CDCl$_3$): δ = 1.10(m, 6H), 1.56(m, 6H), 2.41(q, 2H), 2.56(q, 2H), 3.44(m, 1H), 3.64(m, 1H), 3.75(m, 1H), 4.05(m, 1H), 4.17(t, 2H), 4.50(s, 1H), 7.00(d, 1H), 7.08(s, 1H), 7.20(m, 1H), 7.51(s, 1H), 7.64(s, 1H), 7.86(s, 1H). LRMS (thermospray): m/z [MH$^+$] 464, [MNa$^+$] 486. HRMS: [MH$^+$]$^{Found\ 464.2297.}$ C$_{25}$H$_{30}$N$_5$O$_4$ requires 464.2293 [MNa$^+$ Found 486.2113. C$_{25}$H$_{29}$N$_5$O$_4$Na requires 486.2112. |
| 68[1] (63) | 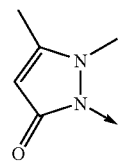 | $^1$H NMR (400 MHz, CDCl$_3$): δ = 1.08(m, 6H), 1.48(m, 6H), 2.23(s, 3H), 2.38(q, 2H), 2.53(q, 2H), 3.43(m, 1H), 3.63(m, 1H), 3.66(s, 3H), 3.73(m, 1H), 4.04(m, 1H), 4.15(t, 2H), 4.50(s, 1H), 5.59(s, 1H), 6.76(s, 1H), 6.88(s, 1H), 6.95(s, 1H). LRMS (thermospray): m/z [MH$^+$] 480, [MNa$^+$] 502. |

[1]The eluent used for flash column chromatography purification of this compound was dichloromethane:methanol (99:1 changing to 95:5, by volume).

Preparation 69 tert-Butyl 3-[4-(3,5-dicyanophenoxy)-3,5-diethyl-1H-pyrazol-1-yl]-1-azetidinecarboxylate

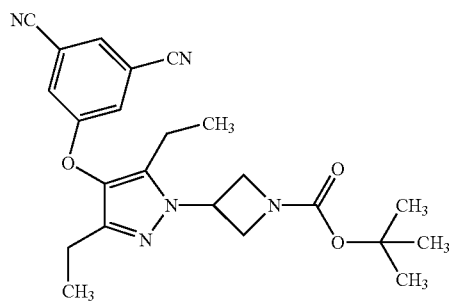

Sodium hydride (60% dispersion in oil, 33 mg, 0.82 mmol) was added to a solution of the pyrazole from Example 122 (200 mg, 0.75 mmol) in dimethylformamide (3 ml) at 0° C. under nitrogen and the reaction was stirred for 10 minutes. 3-Iodo-azetidine-1-carboxylic acid tert-butyl ester (234 mg, 0.82 mmol) was added and the reaction was stirred at room temperature for 18 hours. The reaction was quenched with water (0.2 ml) and concentrated under reduced pressure. The residue was partitioned between dichloromethane (5 ml) and water (5 ml) and the organic phase was isolated using a 5 μM Whatman PTFE fritted cartridge, then concentrated under reduced pressure. The residue was purified by flash chromatography on silica gel eluting with a solvent gradient of ethyl acetate:pentane (20:80 then 25:75 then 34:66 then 50:50 then 75:25 then 100:0, by volume) changing to ethyl acetate:methanol (10:1, by volume) then dichloromethane:methanol:0.88 ammonia (90:10:1 then 80:20:1, by volume) to provide the title compound (189 mg) as a pale yellow oil.

$^1$H NMR (400 MHz, CDCl$_3$): δ=1.03–1.17 (m, 6H), 1.49 (s, 9H), 2.39–2.52 (m, 4H), 4.32 (m, 2H), 4.50 (m, 2H), 4.94 (m, 1H), 7.38 (s, 2H), 7.56 (s, 1H). LRMS (thermospray): m/z [MH$^+$] 422, [MNa$^+$] 444. Microanalysis: Found C, 65.08; H, 6.49; N, 16.48. C$_{23}$H$_{27}$N$_5$O$_3$.0.18H$_2$O requires C, 65.04; H, 6.49; N, 16.49%.

Preparation 70

5-({3,5-Diethyl-1-[3-(tetrahydro-2H-pyran-2-yloxy)propyl]-1H-pyrazol-4-yl}oxy)isophthalonitrile

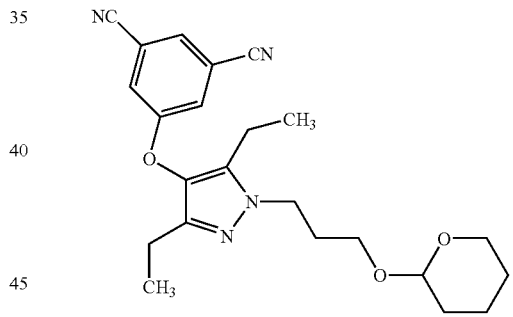

Sodium hydride (60% dispersion in oil, 33 mg, 0.82 mmol) was added to a solution of the pyrazole from Example 122 (200 mg, 0.75 mmol) in dimethylformamide (3 ml) at 0° C. under nitrogen and the reaction was stirred for 10 minutes. 2-(3-bromo-propoxy)-tetrahydro-pyran (184 mg, 0.82 mmol) was added and the reaction was stirred at room temperature for 18 hours. The reaction was quenched with water (0.2 ml) and concentrated under reduced pressure. The residue was partitioned between dichloromethane (5 ml) and water (5 ml) and the organic phase was isolated using a 5 μM Whatman PTFE fritted cartridge, then concentrated under reduced pressure. The residue was purified by flash chromatography on silica gel eluting with a solvent gradient of ethyl acetate:pentane (20:80 then 25:75 then 34:66 then 50:50 then 75:25 then 100:0, by volume) changing to ethyl acetate:methanol (10:1, by volume) then dichloromethane:methanol:0.88 ammonia (90:10:1 then 80:20:1, by volume) to provide the title compound (238 mg) as a pale yellow oil.

$^1$H NMR (400 MHz, CDCl$_3$): δ=1.09 (m, 6H), 1.47–1.63 (m, 2H), 1.66–1.88 (m, 2H), 2.15 (dd, 2H), 2.38 (q, 2H), 2.53 (q, 2H), 3.37–3.55 (m, 2H), 3.75–3.90 (m, 2H), 4.11 (m, 2H), 4.56 (m, 1H), 7.37 (s, 2H), 7.55 (s, 1H). LRMS (electro): m/z [MH$^+$] 409, [MNa$^+$] 421. Microanalysis: Found C, 66.59; H, 6.91; N, 13.40. C$_{23}$H$_{28}$N$_4$O$_3$.0.36H$_2$O requires C, 66.57; H, 6.98; N, 13.50%.

Preparation 71

3-[(1-Acetyl-3,5-dimethyl-1H-pyrazol-4-yl)oxy]-5-fluorobenzonitrile

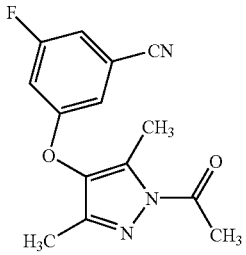

The phenol from Preparation 34 (10.0 g, 72.7 mmol), 3-chloro-2,4-pentanedione (7.10 g, 72.7 mmol) and cesium carbonate (23.6 g, 72.9 mmol) were heated to reflux in acetone (100 ml) under nitrogen for 2 hours. The reaction was cooled to room temperature, 1N aqueous hydrochloric acid (50 ml) was added slowly and the mixture was extracted with ethyl acetate (3×100 ml). The combined organic extracts dried over magnesium sulphate and concentrated under reduced pressure. The residual yellow oil was dissolved in methanol (100 ml), hydrazine (5.3 ml, 109 mmol) was added and the reaction was stirred at room temperature under nitrogen for 2 hours. The solvent was removed under reduced pressure and the residue was dissolved in dimethylformamide (50 ml) at 0° C. Acetyl chloride (5.1 ml, 72.0 mmol) was added slowly followed by sodium hydride (60% dispersion in oil, 2.8 g, 72.0 mmol) portionwise. The reaction was stirred for 15 minutes and sat. ammonium chloride solution (50 ml) was added, and the reaction was allowed to warm to room temperature. The mixture was extracted with ethyl acetate (3×100 ml) and the combined organic extracts were dried over magnesium sulphate and concentrated under reduced pressure giving an oil. After standing for 18 hours, a solid had formed within the oil which was isolated by filtration, washing with diethylether (50 ml) to provide the title compound (3.50 g) as a white solid, m.p. 109–111° C.

$^1$H NMR (400 MHz, CDCl$_3$): δ=2.06 (s, 3H), 2.37 (s, 3H), 2.65 (s, 3H), 6.81 (d, 1H), 6.91 (s, 1H), 7.04 (d, 1H). LRMS (thermospray): m/z [MH$^+$] 273. Microanalysis: Found C, 61.62; H, 4.44; N, 15.09. C$_{14}$H$_{12}$N$_3$O$_2$F requires C, 61.53; H, 4.43; N, 15.38%.

Preparations 72–74

The tabulated compounds of the general formula

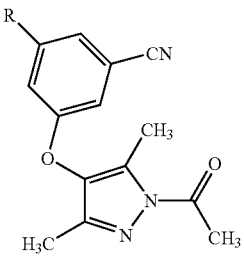

were performed by a similar method to that of Preparation 71 using the appropriate phenol as the starting material.

| Preparation no. (Starting material preparation no.) | R' | Analytical Data |
|---|---|---|
| 72 (39) | CN | m.p. 204–206° C. $^1$H NMR(400 MHz, CDCl$_3$): δ = 2.06(s, 3H), 2.38(s, 3H), 2.66(s, 3H), 7.33(s, 2H), 7.58(s, 1H). LRMS (thermospray): m/z [MH$^+$] 281. Microanalysis: Found C, 63.30; H, 4.25; N, 19.59. C$_{15}$H$_{12}$N$_4$O$_2$.0.30H$_2$O requires C, 63.06; H, 4.45; N, 19.61%. |
| 73$^1$ (42) | Me | m.p. 152–154° C. $^1$H NMR(400 MHZ, CDCl$_3$): δ = 2.05(s, 3H), 2.33(s, 3H), 2.38(s, 3H), 2.66(s, 3H), 6.88(s, 1H), 6.91(s, 1H), 7.12(s, 1H). LRMS (thermospray): m/z [MH$^+$] 270. Microanalysis: Found C, 66.67; H, 5.71; N, 15.25. C$_{15}$H$_{15}$N$_3$O$_2$ requires C, 66.9; H, 5.61; N, 15.60%. |
| 74$^2$ (Commercial) | H | m.p. 131–133° C. $^1$H NMR(400 MHz, CDCl$_3$): δ = 2.13(s, 3H), 2.40(s, 3H), 2.70(s, 3H), 7.15(m, 2H), 7.35 (m, 1H), 7.40(m, 1H). LRMS (thermospray): m/z [MH$^+$] 278. Microanalysis: Found C, 65.87; H, 5.11; N, 16.33. C$_{14}$H$_{13}$N$_3$O$_2$ requires C, 65.87; H, 5.13; N, 14.46%. |

$^1$The product was purified by flash column chromatography on silica gel eluting with ethyl acetate:pentane (10:90, by volume).
$^2$The product was purified by flash column chromatography on silica gel eluting with ethyl acetate:pentane (10:90 changing to 20:80, by volume).

Preparation 75

3-{[1-Acetyl-3-(bromomethyl)-5-methyl-1H-pyrazol-4-yl]oxy}-5-fluorobenzonitrile

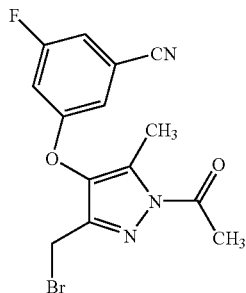

The pyrazole from Preparation 71 (1.00 g, 3.66 mmol) was dissolved in carbon tetrachloride (20 ml) and the solution was degassed by bubbling nitrogen through it for 20 minutes at room temperature. N-Bromosuccinimide (973 mg, 5.49 mmol) followed by 2,2'-azobisisobutyronitrile (30 mg) were added and the reaction was heated to 95° C. for 1 hour. The reaction was cooled to room temperature, concentrated under reduced pressure and purified by flash chromatography on silica gel eluting with pentane:ethyl acetate (80:20, by volume) to provide the title compound (1.30 g) as a pale yellow oil.

$^1$H NMR (400 MHz, CDCl$_3$): δ=2.05 (s, 3H), 2.69 (s, 3H), 4.68 (s, 2H), 6.89 (d, 1H), 6.99 (s, 1H), 7.08 (d, 1H). LRMS (thermospray): m/z [M–BrH$^+$] 272. Microanalysis: Found C, 45.08; H, 3.14; N, 11.44. C$_{14}$H$_{11}$BrN$_3$O$_2$F.1.05H$_2$O requires C, 45.31; H, 3.56; N, 11.32%.

Preparations 76–78

The preparation of the following tabulated Preparations of the general formula

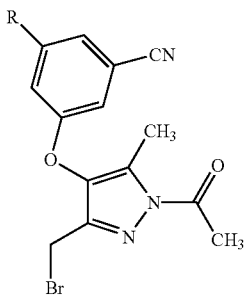

were performed by a similar method to that of Preparation 75 using the appropriate pyrazole as the starting material.

| Preparation no. (Starting material preparation no.) | R | Analytical Data |
| --- | --- | --- |
| 76 (72) | CN | m.p. 132–134° C.<br>$^1$H NMR(400 MHz, CDCl$_3$): δ = 2.06(s, 3H), 2.66(s, 3H), 4.67(s, 2H), 7.40(s, 2H), 7.63(s, 1H).<br>Microanalysis: Found C, 47.65; H, 3.03; N, 14.79. C$_{15}$H$_{11}$BrN$_4$O$_2$.0.93H$_2$O requires C, 47.92; H, 3.45; N, 14.90%. |
| 77[1,2] (73) | Me | m.p. 107–109° C.<br>$^1$H NMR(400 MHz, CDCl$_3$): δ = 2.05(s, 3H), 2.35(s, 3H), 2.70(s, 3H), 4.70(s, 2H), 6.95 (s, 1H), 6.99(s, 1H), 7.18(s, 1H).<br>Microanalysis: Found C, 50.34; H, 3.89; N, 11.58. C$_{15}$H$_{14}$BrN$_3$O$_2$.0.40H$_2$O requires C, 50.69; H, 4.20; N, 11.82%. |
| 78[1,3] (74) | H | m.p. 120–124° C.<br>$^1$H NMR(400 MHz, CDCl$_3$): δ = 2.05(s, 3H), 2.70(s, 3H), 4.75(s, 2H), 7.20(m, 2H), 7.45(m, 1H).<br>Microanalysis: Found C, 49.01; H, 3.47; N, 12.14. C$_{14}$H$_{12}$BrN$_3$O$_2$.0.50H$_2$O requires C, 49.00; H, 3.82; N, 12.24%. |

[1] A further aliquot of 2,2'-azobisisobutyronitrile (30 mg) was added to this reaction, and refluxing was continued for a further 2 hours.
[2] The product was purified by flash column chromatography on silica gel eluting with a solvent gradient of ethyl acetate:pentane (0:100 then 2:98 then 5:95 then 10:90 then 15:85 then 30:70, by volume).
[3] The product was purified by flash column chromatography on silica gel eluting with ethyl acetate:pentane (10:90 changing to 20:80, by volume).

Preparation 79

3-Cyanobenzamide

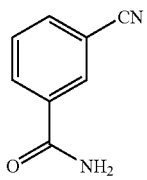

0.88 Ammonia solution (30 ml) was slowly added to a solution of 3-cyanobenzoyl chloride (10 g, 60.3 mmol) in dichloromethane (100 ml) at 0° C. under nitrogen and the reaction was stirred for 20 minutes. The mixture was filtered and the solid was washed with water (50 ml) then diethylether (50 ml), azeotroped with toluene and dried in vacuo to provide the title compound (9 g) as a white solid.

$^1$H NMR (400 MHz, CD$_3$OD): δ=7.62 (m, 1H), 7.86 (m, 1H), 8.12 (m, 1H), 8.18 (s, 1H).

Preparation 80

3-(Aminomethyl)benzamide

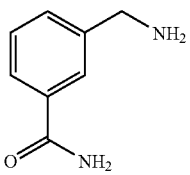

The nitrile from Preparation 79 (6.4 g, 43.8 mmol) was suspended in acetic acid (60 ml) and 10% palladium on carbon (100 mg) was added. The reaction was pressurised to 60 psi at room temperature with hydrogen, and stirred for 18 hours. Starting material remained, so a further aliquot of 10% palladium on carbon (500 mg) was added and the procedure was repeated. The reaction mixture was filtered through arbocel washing with acetic acid and the filtrate was concentrated under reduced pressure. The residue was azeotroped with toluene and purified by flash chromatography on silica gel eluting with dichloromethane:methanol:0.88 ammonia (100:0:0 changing to 90:10:1 then 85:15:1.5, by volume) to provide the title compound (5.3 g) as a colourless oil.

$^1$H NMR (400 MHz, CD$_3$OD): δ=3.83 (s, 2H), 7.39 (dd, 1H), 7.49 (d, 1H), 7.73 (d, 1H), 7.81 (s, 1H).

Preparation 81

2-Chloro-1,3-dicyclopropyl-1,3-propanedione

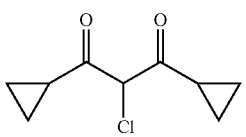

Trimethylsilyl chloride (16.6 ml, 130 mmol) was added to a solution of tert-butylammonium bromide (0.70 g, 2.17 mmol) in acetonitrile (50 ml) under nitrogen at 0° C. 1,3-Dicyclopropyl-propane-1,3-dione (ref: WO98155438) (6.62 g, 43.5 mmol) in acetonitrile (15 ml) was then added followed by dimethylsulfoxide (9.25 ml, 130 mmol) dropwise, and the reaction was allowed to warm to room temperature over 4 hours. The mixture was diluted with water (75 ml), extracted with diethylether (3×35 ml) and the combined organic extracts dried over magnesium sulphate and concentrated under reduced pressure. The residue was purified by flash chromatography on silica gel eluting with pentane:diethylether (95:5, by volume) to provide the title compound (3.76 g) as an oil, which was an 80:20 mixture of enol:keto forms.

$^1$H NMR (400 MHz, CDCl$_3$): δ=1.02 (m, 4H), 1.17 (m, 4H), 2.24 (m, 0.2H), 2.39 (m, 0.8H), 5.05 (s, 0.2H), 16.34 (s, 0.8H). Microanalysis: Found C, 57.59; H, 5.89. C$_9$H$_{11}$CO$_2$.0.02CH$_2$Cl$_2$ requires C, 57.92; H, 5.94.

Preparation 82

5-[2-Cyclopropyl-1-(cyclopropylcarbonyl)-2-oxoethoxy]isophthalonitrile

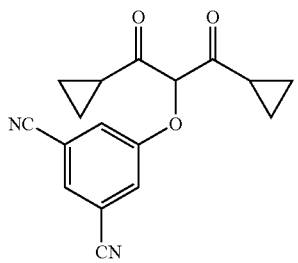

Cesium carbonate (1.97 g, 6.06 mmol) was added to a stirred solution of the phenol from Preparation 39 (0.865 g, 6.00 mmol) in acetone (24 ml) under nitrogen at reflux. After stirring for 5 minutes, the diketone from Preparation 81 (1.12 g, 6.00 mmol) in acetone (6 ml) was added and the reaction was stirred for 4 hours. After cooling the mixture was diluted with water (25 ml) and the acetone was removed under reduced pressure. The aqueous phase was acidified with 2N aqueous hydrochloric acid, extracted with dichloromethane (50 ml) and the organic phase was dried over magnesium sulphate and concentrated under reduced pressure. The residue was purified by flash chromatography on silica gel eluting with a solvent gradient of pentane:ethyl acetate (95:5 changing to 90:10 then 80:20, by volume) to provide the title compound (1.03 g) as a white solid, which existed as the enol tautomer, m.p. 135–137° C.

$^1$H NMR (400 MHz, CDCl$_3$): δ=0.93 (m, 4H), 1.19 (m, 4H), 1.74 (m, 2H), 7.53 (s, 2H), 15.25 (s, 1H). LRMS (electrospray): m/z [M–H$^+$] 293. Microanalysis: Found C, 69.18; H, 4.82; N, 9.35. C$_{17}$H$_{14}$N$_2$O$_3$ requires C, 69.38; H, 4.79; N, 9.52%.

Preparation 83

3-Oxobutanoic acid

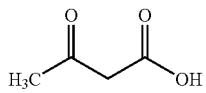

Sodium hydroxide (37.9 g, 0.947 mol) was dissolved in water (770 ml) and added to a solution of 3-oxo-butanoic acid methyl ester (100 g, 0.861 mol) at room temperature over 20 minutes. The reaction was stirred for 18 hours, quenched with ammonium sulfate (700 g) and acidified slowly with a solution of concentrated Hydrochloric acid (21.5 ml) in water (250 ml) with ice cooling. The reaction mixture was extracted with diethylether (6×200 ml) and the combined organic extracts were dried over magnesium sulphate and concentrated under reduced pressure to provide the title compound (58.2 g) as a pale yellow oil which was a mixture of keto:enol tautomers.

$^1$H NMR (400 MHz, CDCl$_3$): δ=2.00 (s, 3H-enol), 2.30 (s, 3H-keto), 3.51 (s, 2H-keto), 5.02 (s, 1H-enol).

Preparation 84

1-Cyclopropyl-1,3-butanedione

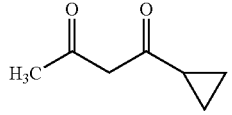

Magnesium turnings (3.04 g, 125 mmol) suspended in methanol (145 ml) were heated to reflux under nitrogen for 1 hour, cooled to room temperature and the β-keto acid from Preparation 83 (25.5 g, 250 mmol) dissolved in methanol (25 ml) was added dropwise with ice-cooling. The reaction was stirred for 1 hour at room temperature and the solvent was removed under reduced pressure to give the magnesium salt of the acid. Meanwhile, cyclopropane-carboxylic acid (9.91 ml, 125 mmol) was dissolved in dimethylformamide (200 ml) and carbonyldiimidazole (22.4 g, 138 mmol) was added portionwise under nitrogen at 0° C. This was stirred for 1.5 hour and the magnesium salt from above was added as a solution in dimethylformamide (100 ml) at 0° C. The reaction was allowed to stir at room temperature for 92 hours and the mixture was poured into 2M aqueous hydrochloric acid (85 ml) then diluted with water (170 ml). The mixture was extracted with diethylether (6×200 ml) and the combined organic extracts were washed with brine (3×200 ml), dried over magnesium sulphate and concentrated under reduced pressure. The residual orange oil was purified by flash chromatography on silica gel eluting with pentane:diethylether (100:0 changing to 90:10 then 80:20, by volume) to provide the title compound (7.39 g) as a yellow oil.

$^1$H NMR (400 MHz, CDCl$_3$): δ=0.83–0.95 (m, 2H), 1.06–1.10 (m, 2H), 1.54–1.63 (m, 1H), 2.00 (s, 3H). LRMS (electrospray): m/z [MNa$^+$] 149.

Preparation 85

2-Chloro-1-cyclopropyl-1,3-butanedione

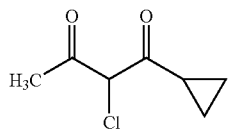

Trimethylsilyl chloride (18.9 ml, 174 mmol) was added to a solution of tert-butylammonium bromide (932 mg, 2.89 mmol) in dry acetonitrile (50 ml) under nitrogen at room temperature and the mixture was cooled to 0° C. The diketone from Preparation 84 (7.3 g, 57.9 mmol) in acetonitrile (36 ml) was then added followed by dropwise addition of dry dimethylsulfoxide (12.3 ml, 174 mmol). The reaction was stirred at 0° C. for 1.5 hours and the mixture was diluted with water (500 ml), extracted with diethylether (2×200 ml and 100 ml) and the combined organic extracts were dried over magnesium sulphate and concentrated under reduced pressure. The residual oil was purified by flash chromatography on silica gel eluting with pentane:diethylether (100:0 changing to 95:5 then 90:10, by volume) to provide the title compound (5.76 g) as a colourless oil.

$^1$H NMR (400 MHz, CDCl$_3$): δ=0.99–1.08 (m, 2H), 1.15–1.20 (m, 2H), 2.27 (s, 3H), 2.38–2.46 (m, 1H). LRMS (electrospray): m/z [M–H$^+$] 159.

Preparation 86

3-[1-(Cyclopropylcarbonyl)-2-oxopropoxy]-5-methylbenzonitrile

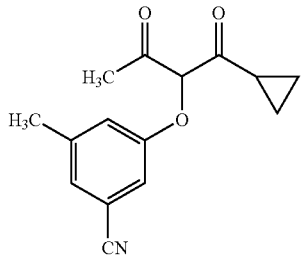

Cesium carbonate (2.45 g, 8.30 mmol) and the phenol from Preparation 42 (1 g, 7.50 mmol) were added to a stirred solution of the diketone from Preparation 85 (1.3 g, 8.30 mmol) in acetone (44 ml) under nitrogen at 60° C. and the reaction was stirred for 5 hours. After cooling the mixture was quenched with water and the acetone was removed under reduced pressure. The aqueous phase was acidified with 1N aqueous hydrochloric acid, extracted with ethyl acetate and the organic phase was dried over magnesium sulphate and concentrated under reduced pressure. The residue was purified by flash chromatography on silica gel eluting with pentane:ethyl acetate (85:15, by volume) to provide the title compound (1.03 g) as a pale red solid.

$^1$H NMR (400 MHz, CDCl$_3$): δ=0.85 (m, 2H), 1.12 (m, 2H), 1.86 (m, 1H), 1.94 (s, 3H), 2.35 (s, 3H), 6.99 (m, 2H), 7.10 (s, 1H). LRMS (electrospray) m/z [M–H$^+$] 256.

Preparation 87

4-(3,5-Difluorophenoxy)-3,5-diethyl-1-[2-(tetrahydro-2H-pyran-2-yloxy)ethyl]-1H-pyrazole

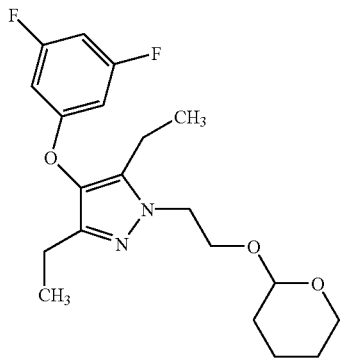

p-Toluene-sulphonic acid (360 mg, 1.89 mmol) was added to a solution of the alcohol from Example 38 (5.6 g, 18.9 mmol) and dihydropyran (8.62 ml, 94.5 mmol) in dichloromethane (75 ml) at room temperature under nitrogen. The reaction was stirred for 2 hours, diluted with diethylether (100 ml) and washed with a mixed aqueous solution (water (60 ml), brine (30 ml) and saturated aqueous sodium bicarbonate solution (30 ml)). The aqueous phase was extracted with diethylether (2×60 ml) and the combined organic extracts were dried over magnesium sulphate, concentrated under reduced pressure and the residue was purified by flash chromatography on silica gel eluting with dichloromethane:methanol (98:2, by volume) to provide the title compound (6.31 g) as an oil.

$^1$H NMR (400 MHz, CDCl$_3$): δ=1.09 (m, 6H), 1.57 (m, 6H), 2.40 (q, 2H), 2.55 (q, 2H), 3.44 (m, 1H), 3.62 (m, 1H), 3.73 (m, 1H), 4.05 (m, 1H), 4.16 (t, 2H), 4.50 (s, 1H), 6.39 (m, 3H). LRMS (thermospray): m/z [MH$^+$] 381. Microanalysis: Found C, 62.16; H, 6.92; N, 7.16. C$_{20}$H$_{26}$N$_2$O$_3$.0.09CH$_2$Cl$_2$ requires C, 62.18; H, 6.80; N, 7.22%.

Preparation 88

4-[3,5-Di(1H-pyrazol-1-yl)phenoxy]-3,5-diethyl-1-[2-(tetrahydro-2H-pyran-2-yloxy)ethyl]-1H-pyrazole

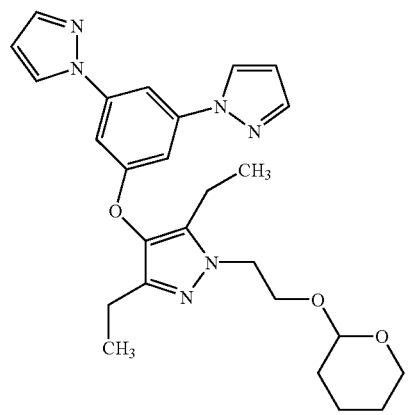

and

Preparation 89

3,5-Diethyl-4-[3-fluoro-5-(1H-pyrazol-1-yl)phenoxy]-1-[2-(tetrahydro-2H-pyran-2-yloxy)ethyl]-1H-pyrazole

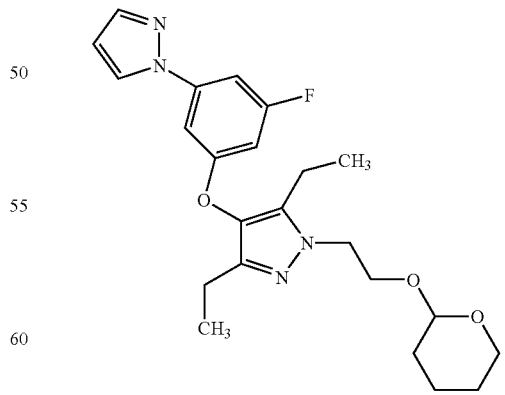

Cesium Carbonate (538 mg, 1.65 mmol) was added to a solution of pyrazole (102 mg, 1.50 mmol) in dry dimethylsulfoxide (2 ml) under nitrogen at room temperature and the reaction was stirred for 15 minutes. The aryl difluoride from Preparation 87 (570 mg, 1.50 mmol) dissolved in dry dimethylsulfoxide (2 ml) was then added and the reaction was heated to 100° C. for 18 hours. After cooling to room temperature the reaction was diluted with water (20 ml) and extracted with diethylether (2×20 ml). The organic phase was washed with brine (10 ml), dried over magnesium sulphate, concentrated under reduced pressure. Some starting material remained, so the residue was dissolved in dimethylsulfoxide (12 ml), pyrazole (510 mg, 7.50 mmol) followed by cesium carbonate (2.5 g, 7.66 mmol) were added and the reaction was heated to 100° C. for 18 hours. After cooling to room temperature the reaction was diluted with water (6 ml), extracted with diethylether (20 ml) and the organic phase was washed with brine (10 ml), dried over magnesium sulphate, concentrated under reduced pressure and the residue was purified by flash chromatography on silica gel eluting with a solvent gradient of dichloromethane:methanol (100:0 changing to 96:4, by volume). This gave two fractions, the first of which was a single product (least polar) and the other a mixture of two products. The second fraction was re-purified eluting with dichloromethane:acetonitrile (93:7 changing to 90:10, by volume) to provide the most polar product.

Least Polar Product—Preparation 88 (254 mg)
$^1$H NMR (400 MHz, CDCl$_3$): δ=1.11 (m, 6H), 1.50 (m, 6H), 2.46 (q, 2H), 2.58 (q, 2H), 3.43 (m, 1H), 3.64 (m, 1H), 3.75 (m, 1H), 4.04 (m, 1H), 4.18 (t, 2H), 4.50 (s, 1H), 6.42 (s, 2H), 7.15 (s, 2H), 7.67 (s, 3H), 7.90 (s, 2H). LRMS (electrospray): m/z [MH$^+$] 477, [MNa$^+$] 499. HRMS: [MH$^+$] Found 477.2612. C$_{26}$H$_{33}$N$_6$O$_3$ requires 477.2609.

Most Polar Product—Preparation 89 (37.7 mg)
$^1$H NMR (400 MHz, CDCl$_3$): δ=1.11 (m, 6H), 1.46 (m, 6H), 2.43 (q, 2H), 2.57 (q, 2H), 3.43 (m, 1H), 3.64 (m, 1H), 3.75 (m, 1H), 4.05 (m, 1H), 4.17 (t, 2H), 4.51 (s, 1H), 6.42 (m, 2H), 7.07 (m, 2H), 7.66 (s, 1H), 7.82 (s, 1H). LRMS (thermospray): m/z [MH$^+$] 429.

Preparation 90

3-({3,5-Diethyl-1-[2-(tetrahydro-2H-pyran-2-yloxy)ethyl]-1H-pyrazol-4-yl}oxy)-5-methoxybenzonitrile

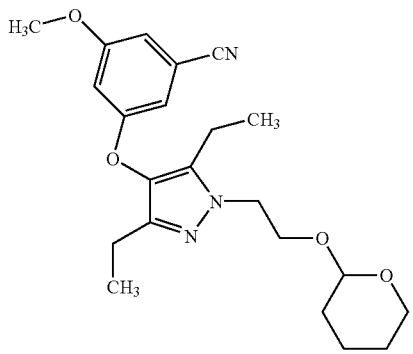

Sodium methoxide (25% w/v in methanol, 230 µl, 1.00 mmol) was added dropwise to a solution of the aryl fluoride from Preparation 63 (387 mg, 1.00 mmol) and in dimethylformamide (5 ml) at room temperature under nitrogen. The reaction was stirred for 5 hours, diluted with water (10 ml) and extracted with diethylether (50 ml). The organic phase was dried over magnesium sulphate, concentrated under reduced pressure and the residue was purified by flash chromatography on silica gel eluting with dichloromethane:methanol (97:3, by volume) to provide the title compound (400 mg) as an oil.
$^1$H NMR (400 MHz, CDCl$_3$): δ=1.09 (m, 6H), 1.49 (m, 6H), 2.41 (q, 2H), 2.55 (q, 2H), 3.46 (m, 1H), 3.66 (m, 1H), 3.77 (m+s, 4H), 4.07 (m, 1H), 4.19 (t, 2H), 4.52 (m, 1H), 6.66 (s, 1H), 6.69 (s, 1H), 6.77 (s, 1H). LRMS (thermospray): m/z [MH$^+$] 400. Microanalysis: Found C, 65.59; H, 7.32; N, 10.42. C$_{22}$H$_{29}$N$_3$O$_4$.0.04CH$_2$Cl$_2$ requires C, 65.71; H, 7.28; N, 10.43%.

Preparation 91

3-(1-Acetyl-3-methyl-2-oxobutoxy)-5-methylbenzonitrile

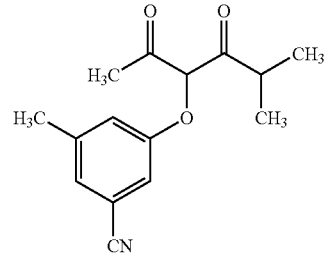

Cesium carbonate (1.50 g, 4.61 mmol) and the phenol from Preparation 42 (609 mg, 4.61 mmol) were added to a stirred solution of the diketone from Preparation 23 (750 mg, 4.61 mmol) in acetone (23 ml) under nitrogen at 50° C. and the reaction was stirred for 3 hours. After cooling the mixture was quenched with water (10 ml) and the acetone was removed under reduced pressure. The aqueous phase was extracted with dichloromethane (4×25 ml) and the combined organic extracts were dried over magnesium sulphate and concentrated under reduced pressure. The residue was purified by flash chromatography on silica gel eluting with pentane:ethyl acetate (90:10, by volume) to provide the title compound (544 mg).
$^1$H NMR (400 MHz, CDCl$_3$): δ=1.10 (m, 6H), 209 (s, 3H), 2.42 (s, 3H), 2.69 (m, 1H), 7.00 (s, 2H), 7.19 (s, 1H). LRMS (thermospray): m/z [MNH$_4^+$] 277.

Preparation 92

[4-(3,5-Dichlorophenoxy)-3-methyl-1H-pyrazol-5-yl]acetic acid

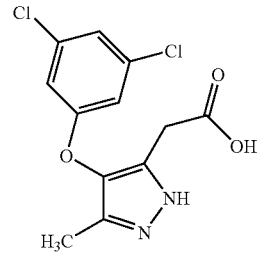

The pyrazole of Example 208 (400 mg, 1.41 mmol) was stirred at 110° C. for 14 hours in concentrated hydrochloric acid (20 ml). The mixture was cooled to room temperature and the solvent removed under reduced pressure to give a yellow solid. The solid was dissolved in dichloromethane (50 ml) and 1N aqueous hydrochloric acid (50 ml) and the organic layer was separated. The organics were washed with 1N aqueous hydrochloric acid (50 ml), dried over magnesium sulphate, filtered and the solvent removed under reduced pressure to provide the title compound (400 mg) as pale yellow solid, m.p. 156–158° C.

$^1$H NMR (400 MHz, CD$_3$OD): δ=2.02 (s, 3H), 4.89 (s, 2H), 6.82 (s, 2H), 7.02 (s, 1H). LRMS (thermospray): m/z [MH$^+$] 303. Microanalysis: Found C, 47.50; H, 3.50; N, 9.46. C$_{12}$H$_{10}$Cl$_2$N$_2$O$_3$ requires C, 47.86; H, 3.35; N, 9.30%.

Preparation 93

3-({3,5-Diethyl-1-[2-(tetrahydro-2H-pyran-2-yloxy) ethyl]-1H-pyrazol-4-yl}oxy)-5-(methylsulfanyl)benzonitrile

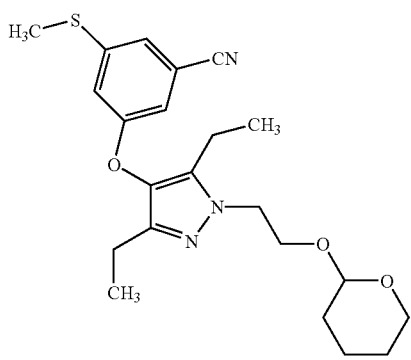

Sodium thiomethoxide (180 mg, 2 mmol) was added to a stirred solution of the aryl fluoride from Preparation 63 (774 mg, 2.00 mmol) in dimethylformamide (10 ml) at room temperature under nitrogen. The reaction mixture was stirred for 5 hours before being heated at 100° C. for 18 hours. A second portion of sodium thiomethoxide (90 mg, 1 mmol) was added and the reaction mixture was heated at 100° C. for a further 5 hours. After cooling to room temperature the mixture was diluted with water (10 ml) and extracted with diethylether (2×50 ml). The organic phase was dried over magnesium sulphate, concentrated under reduced pressure and the residue was purified by flash chromatography on silica gel eluting with dichloromethane:methanol (97:3, by volume) to provide the title compound (700 mg) as an oil.

$^1$H NMR (400 MHz, CDCl$_3$): δ=1.14 (m, 6H), 1.52 (m, 6H), 2.44 (q, 2H), 2.49 (s, 3H), 2.59 (q, 3H), 3.50 (m, 1H), 3.70 (m, 1H), 3.80 (m, 1H), 4.10 (m, 1H), 4.23 (m, 2H), 4.55 (m, 1H), 6.82 (s, 1H), 7.01 (s, 1H), 7.09 (s, 1H). LRMS (APCI+): m/z [MH$^+$] 416.

Preparation 94

3-({3,5-Diethyl-1-[2-(tetrahydro-2H-pyran-2-yloxy) ethyl]-1H-pyrazol-4-yl}oxy)-5-[2-(dimethylamino) ethoxy]benzonitrile

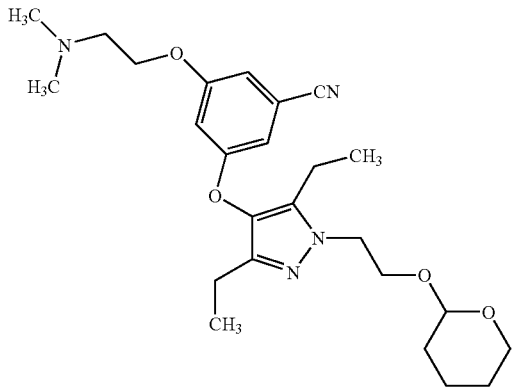

To a stirred solution of N,N-dimethylethanolamine (83 μl, 0.83 mmol) in dimethylformamide (2 ml) was added sodium hydride (36 mg of 60% by weight dispersion in oil, 0.90 mmol). After 10 minutes a solution of the aryl fluoride from Preparation 63 (291 mg, 0.75 mmol) in dimethylformamide (2 ml) was added and the reaction mixture was stirred at room temperature for 18 hours. The mixture was diluted with 10% aqueous potassium carbonate solution (12 ml) and extracted with diethyl ether (2×7 ml). The combined organic components were dried over magnesium sulphate and concentrated under reduced pressure. The crude product mixture was purified by flash chromatography on silica gel eluting with dichloromethane:methanol (a gradient from 99:1 to 90:10, by volume) to provide the title compound (180 mg) as an oil.

$^1$H NMR (400 MHz, CDCl$_3$): δ=1.09 (m, 6H), 1.50 (m, 6H), 2.39 (q, 2H), 2.47 (s, 6H), 2.55 (q, 2H), 2.87 (m, 2H), 3.47 (m, 1H), 3.67 (m, 1H), 3.78 (m, 1H), 4.05 (m, 1H), 4.17 (m, 4H), 4.52 (m, 1H), 6.70 (s, 2H), 6.79 (s, 1H). LRMS (electrospray): m/z [MH$^+$] 457. HRMS: [MH$^+$] 457.2810. C$_{25}$H$_{37}$N$_4$O$_4$ requires 457.2810.

Preparations 95–97

The preparation of the following tabulated Preparations of the general formula

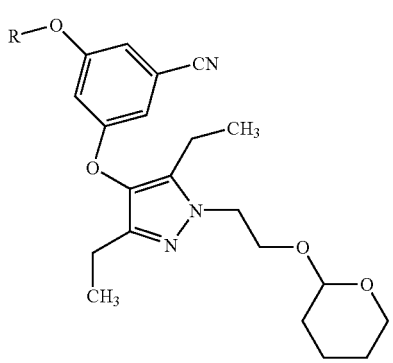

were performed by a similar method to that of Preparation 94 using the appropriate alcohol as the starting material.

| Preparation no. (Starting material preparation no) | R | Analytical Data |
|---|---|---|
| 95 (63) | $CH_2CH_2NHMe$ | $^1H$ NMR(400 MHz, $CDCl_3$): δ = 1.09(m, 6H), 1.50(m, 6H), 2.39(q, 2H), 2.54(m, 5H), 3.04(t, 2H), 3.46(m, 1H), 3.66(m, 1H), 3.78(m, 1H), 4.05(m, 1H), 4.11(t, 2H), 4.17 (t, 2H), 4.52(s, 1H), 6.70 (s, 2H), 6.81(s, 1H). LRMS (electrospray): m/z $[MH^+]$ 443 HRMS: $[MH^+]$ 443.2654. $C_{24}H_{35}N_4O_4$ requires 443.2653. |
| 96 (63) | $CH_2CONH_2$ | $^1H$ NMR(400 MHz, $CDCl_3$): δ = 1.11(m, 6H), 1.48(m, 6H), 2.43(q, 2H), 2.58(q, 2H), 3.46(m, 1H), 3.67(m, 1H), 3.80(m, 1H), 4.08 (m, 1H), 4.25(m, 2H), 4.45(s, 2H), 4.52(m, 1H), 5.54(broad s, 1H), 6.37(broad s, 1H), 6.72(s, 1H), 6.85(s, 2H). LRMS (electrospray): m/z 465 $(MH^+)$ HRMS: $[MH^+]$ 443.2282. $C_{23}H_{31}N_4O_5$ requires 443.2289. |
| 97 (63) | $CH_2CH_2OCH_3$ | $^1H$ NMR(400 MHz, $CDCl_3$): δ = 1.10(m, 6H), 1.50(m, 6H), 2.41(q, 2H), 2.55(q, 2H), 3.41(s, 3H), 3.47 (m, 1H), 3.70(m, 3H), 3.79(m, 1H), 4.06(m, 3H), 4.20(m, 2H), 4.52(s, 1H), 6.70(s, 2H), 6.79(s, 1H). LRMS (electrospray): m/z 466 $(MH^+)$ HRMS: $[MH^+]$ 443.2282. $C_{24}H_{34}N_3O_5$ requires 443.2289. |

Preparation 98

5-Methyl-1-[2-(tetrahydro-2H-pyran-2-yloxy)ethyl]-3-(trifluoromethyl)-1H-pyrazol-4-ol

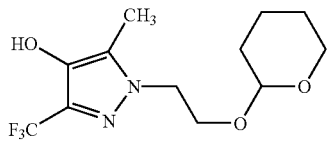

To a stirred solution of 1-(2-hydroxyethyl)-5-methyl-3-(trifluoromethyl)-1H-pyrazol-4-ol (600 mg, 2.86 mmol; Kenkyu Hokoku—Asahi Garasu Kogyo Gijutsu Shoreikai, 1988, 51, 139–49) in dichloromethane (10 ml) and ethyl acetate (4 ml) was added para-toluenesulphonic acid (27 mg, 0.14 mmol) followed by 3,4-dihydro-2H-pyran (340 µl, 3.7 mmol). The reaction mixture was stirred at room temperature for 3 hours before being concentrated under reduced pressure. The crude product mixture was purified by flash chromatography on silica gel eluting with pentane:ethyl acetate (60:40, by volume) to provide the title compound (560 mg) as white solid.

$^1H$ NMR (400 MHz, $CDCl_3$): δ=1.60 (m, 6H), 2.23 (s, 3H), 3.44 (m, 1H), 3.60 (m, 1H), 3.72 (m, 1H), 4.04 (m, 1H), 4.18 (m, 2H), 4.50 (broad s, 1H). LRMS (electrospray): m/z $[M-H^+]$ 293.

Preparation 99

3-Fluoro-5-{[5-methyl-1-[2-(tetrahydro-2H-pyran-2-yloxy)ethyl]-3-(trifluoromethyl)-1H-pyrazol-4-yl]oxy}benzonitrile

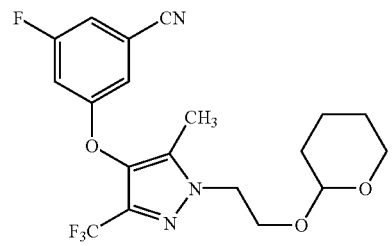

To a stirred solution of the pyrazole (214 mg, 0.73 mmol) from Preparation 98 in dimethylformamide (0.7 ml) was added 3,5-diflurobenzonitrile (304 mg, 2.2 mmol) and potassium carbonate (304 mg, 2.2 mmol). The reaction mixture was heated at 90° C. for 7 hours. After cooling to room temperature brine (20 ml) was added and the mixture was extracted with ethyl acetate (20 ml). The organic component was separated, washed with brine (20 ml), dried over magnesium sulphate and concentrated under reduced pressure. The crude product mixture was purified by flash chromatography on silica gel eluting with pentane:ethyl acetate (80:20, by volume) to provide the title compound (267 mg) as a colourless oil.

$^1H$ NMR (400 MHz, $CDCl_3$): δ=1.61 (m, 6H), 2.18 (s, 3H), 3.48 (m, 1H), 3.64 (m, 1H), 3.75 (m, 1H), 4.30 (t, 2H), 4.50 (broad s, 1H), 6.85 (d, 1H), 6.94 (s, 1H), 7.05 (d, 1H). LRMS (electrospray): m/z $[M-H^+]$ 412.

Preparation 100

3-Cyano-5-[(3,5-diethyl-1-{2-[(2-methoxyethoxy)methoxy]ethyl}-1H-pyrazol-4-yl)oxy]benzamide

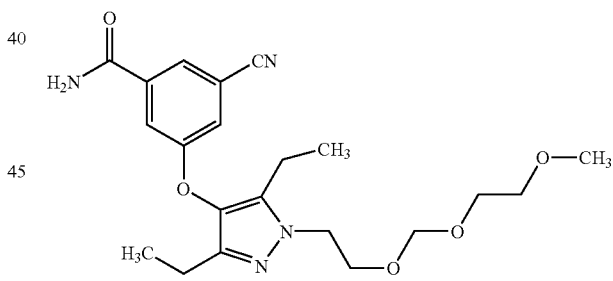

To a stirred solution of the pyrazole from Example 261 (193 mg, 0.49 mmol) in tetrahydrofuran (2 ml) was added 2M aqueous sodium hydroxide solution (8.7 µl, 0.49 mmol) and the reaction mixture was heated at 65° C. for 24 hours. After cooling to room temperature a second portion of 2M sodium hydroxide solution (8.7 µl, 0.49 mmol) was added and the mixture was heated at 65° C. for 24 hours. 6M aqueous sodium hydroxide solution (100 µl) was added and the mixture was heated at 65° C. for 24 hours. The reaction mixture was concentrated under reduced pressure, diluted with water (75 ml), neutralised to pH 7 using 2M aqueous hydrochloric acid solution and extracted with dichloromethane (2×25 ml). The combined organic components were dried over magnesium sulphate and concentrated under reduced pressure to give a crude product mixture which was purified by flash chromatography on silica gel eluting with dichloromethane:methanol (100:0, 98:2, 96.5:3.5 then 95:5, by volume) to provide the title compound (60 mg) as a colourless oil.

$^1$H NMR (400 MHz, CDCl$_3$): δ=1.10 (m, 6H), 2.40 (q, 2H), 2.55 (q, 2H), 3.36 (s, 3H), 3.50 (q, 2H), 3.59 (q, 2H), 3.94 (q, 2H), 4.20 (q, 2H), 4.64 (s, 2H), 7.30 (s, 1H), 7.59 (s, 1H), 7.70 (s, 1H).

Preparation 101

5-[(1-Acetyl-3,5-diethyl-1H-pyrazol-4-yl)oxy]isophthalonitrile

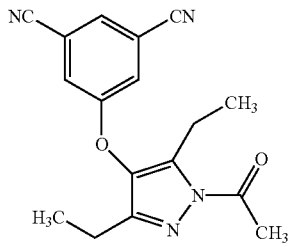

To a stirred solution of the pyrazole from Example 122 (3.0 g, 11.3 mmol) in dimethylformamide (45 ml) at 0° C. was added acetyl chloride (1.2 ml, 17.0 mmol), followed by sodium hydride portionwise (678 mg of 60% by weight dispersion in oil, 17.0 mmol). The cooling bath was removed and the reaction mixture was stirred at room temperature for 40 minutes. The reaction was quenched by addition of saturated aqueous ammonium chloride solution (4 ml) and concentrated under reduced pressure to give an orange residue. This material was partitioned between ethyl acetate (200 ml) and water (200 ml). The organic component was washed with water (100 ml), brine (75 ml) and then dried over magnesium sulphate before being concentrated under reduced pressure. The crude product mixture was purified by flash chromatography on silica gel eluting with dichloromethane:methanol (100:0, 99:1, then 98:2, by volume) to provide the title compound (2.67 g) as a white solid.

$^1$H NMR (400 MHz, CDCl$_3$): δ=1.15 (t, 3H), 1.19 (t, 3H), 2.43 (q, 2H), 2.72 (s, 3H), 3.85 (q, 2H), 7.38 (s, 2H), 7.61 (s, 1H). LRMS (electrospray): m/z 331 [M+Na$^+$].

Preparation 102

5-{[1-Acetyl-3-(1-bromoethyl)-5-ethyl-1H-pyrazol-4-yl]oxy}isophthalonitrile

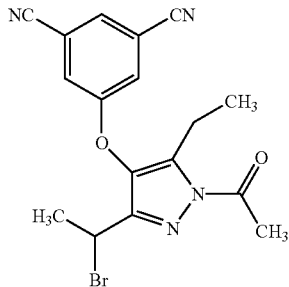

A solution of the pyrazole from Preparation 101 (881 mg, 2.86 mmol) in carbontetrachloride (12 ml) was degassed by passing a stream of nitrogen through the solution for 20 minutes. N-bromosuccinimide (763 mg, 4.28 mmol) was added followed by AIBN (30 mg) and the reaction mixture was heated at 85° C. for 4 hours. After cooling to room temperature the mixture was concentrated under reduced pressure and the residue was purified by flash chromatography on silica gel eluting with pentane:ethyl acetate (a gradient from 100:0 to 67:33, by volume) to provide the title compound (348 mg) as a colourless oil.

$^1$H NMR (400 MHz, CDCl$_3$): δ=1.10 (t, 3 h), 2.00 (d, 3H), 2.70 (s, 3H), 2.80 (m, 2H), 4.95 (q, 1H), 7.42 (s, 2H), 7.60 (s, 1H). LRMS (electrospray): m/z 283 [MH$^+$].

Preparation 103

5-({5-Ethyl-3-(1-hydroxyethyl)-1-[2-(tetrahydro-2H-pyran-2-yloxy)ethyl]-1H-pyrazol-4-yl}oxy) isophthalonitrile

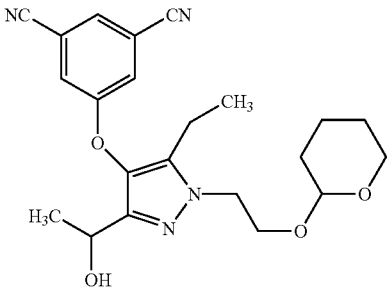

To a stirred solution of the pyrazole from Example 263 (197 mg, 0.70 mmol) in dimethylformamide (3 ml) at 0° C. was added 2-(2-bromoethoxy)tetrahydro-2H-pyran (105 μl, 0.70 mmol) followed by sodium hydride (31 mg, 0.77 mmol). After 15 minutes the cooling bath was removed and the mixture was stirred at room temperature for 60 hours. The reaction mixture was quenched by addition of saturated aqueous ammonium chloride solution (0.5 ml) and then concentrated under reduced pressure. The crude product mixture was purified by flash chromatography on silica gel eluting with dichloromethane:methanol (a gradient from 100:0 to 95:5, by volume) to provide the title compound (84 mg) as a white foam which reverts to an oil on standing.

$^1$H NMR (400 MHz, CDCl$_3$): δ=1.11 (t, 3H), 1.45 (d, 3H), 1.65 (m, 6H), 2.59 (q, 2H), 3.50 (m, 1H), 3.70 (m, 1H), 3.81 (m, 1H), 4.11 (m, 1H), 4.25 (t, 2H), 4.56 (m, 1H), 4.76 (m, 1H), 7.40 (s, 2H), 7.55 (s, 1H). LRMS (electrospray): m/z 411 [MH$^+$].

Preparation 104

3-Cyano-5-[(3,5-diethyl-1-{2-[(2-methoxyethoxy)methoxy]ethyl}-1H-pyrazol-4-yl)oxy]-N'-hydroxybenzenecarboximidamide

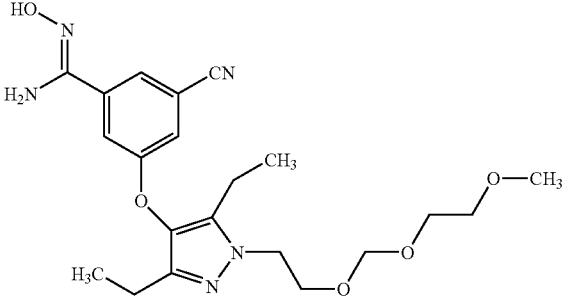

To a stirred solution of the pyrazole from Example 261 (1.5 g, 3.76 mmol) in ethanol (7.5 ml) was added a solution of sodium carbonate (200 mg, 1.88 mmol) and hydroxylamine hydrochloride (262 mg, 3.76 mmol) in water (7.5 ml). After stirring for 5 hours at room temperature the reaction mixture was concentrated under reduced pressure and the residue was partitioned between dichloromethane (50 ml) and water (40 ml). The aqueous phase was separated and extracted with dichloromethane (30 ml). The organic components were combined, dried over magnesium sulphate and concentrated under reduced pressure. The crude product mixture was purified by flash chromatography on silica gel eluting with dichloromethane:methanol (a gradient from 100:0 to 96:4, by volume) to provide the title compound (1.13 mg) as a colourless oil.

$^1$H NMR (400 MHz, CDCl$_3$): δ=1.11 (m, 6H), 2.42 (q, 2H), 2.58 (q, 2H), 3.41 (s, 3H), 3.59 (m, 4H), 3.95 (t, 2H), 4.17 (t, 2H), 4.61 (s, 2H), 4.77 (broad s, 2H), 7.38 (m, 1H), 7.49 (m, 2H). LRMS (electrospray): m/z 432 [MH$^+$]. Microanalysis: Found C, 57.50; H, 6.71; N, 16.01. C$_{21}$H$_{26}$N$_4$O$_4$+0.4H$_2$O requires C, 57.50; H, 6.85; N, 15.96%.

Preparation 105

3-[(3,5-Diethyl-1-{2-[(2-methoxyethoxy)methoxy]ethyl}-1H-pyrazol-4-yl)oxy]-5-[5-(trifluoromethyl)-1,2,4-oxadiazol-3-yl]benzonitrile

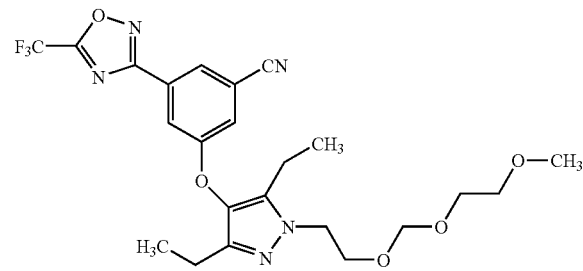

To a stirred solution of the amidoxime from Preparation 104 (300 mg, 0.70 mmol) in pyridine (3 ml) was added trifluoroacetic anhydride (118 μl, 0.83 mmol). After stirring at room temperature for 2 hours the reaction mixture was heated at 110° C. for 18 hours. After cooling to room temperature the mixture was concentrated under reduced pressure and the residue was partitioned between 2M aqueous HCl solution (6 ml) and dichloromethane (6 ml). The organic phase was separated and concentrated under reduced pressure. The residue was purified by flash chromatography on silica gel eluting with dichloromethane:methanol (a gradient from 100:0 to 90:10, by volume) to provide the title compound (259 mg) as a colourless oil.

$^1$H NMR (400 MHz, CDCl$_3$): δ=1.14 (m, 6H), 2.46 (q, 2H), 2.59 (q, 2H), 3.39 (s, 3H), 3.53 (q, 2H), 3.59 (q, 2H), 3.95 (q, 2H), 4.29 (q, 2H), 4.68 (s, 2H), 7.34 (s, 1H), 7.87 (s, 1H), 8.04 (s, 1H). LRMS (APCI): m/z 532 (MH$^+$)

Preparations 106–108

The preparation of the following tabulated Preparations of the general formula

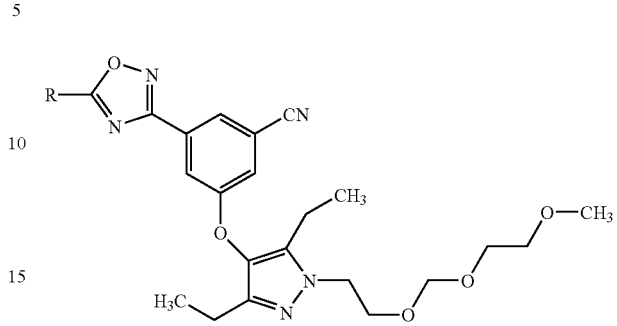

were performed by a similar method to that of Preparation 105 using the appropriate acid chloride as the acylating agent in place of trifluoroacetic anhydride.

| Preparation no. | R | Analytical Data |
| --- | --- | --- |
| 106 | Me | $^1$H NMR(400 MHz, CDCl$_3$): δ = 1.14(m, 6H), 2.46 (q, 2H), 2.59(q, 2H), 2.67(s, 3H), 3.39(s, 3H), 3.55 (q, 2H), 3.59(q, 2H), 3.95(q, 2H), 4.22(q, 2H), 4.68 (s, 2H), 7.27(s, 1H), 7.82(s, 1H), 8.00(s, 1H). LRMS (electrospray): m/z 478 [M + Na$^+$] Microanalysis: Found C, 59.91; H, 6.27; N, 15.38. C$_{23}$H$_{29}$N$_5$O$_5$ + 0.3H$_2$O requires C, 59.94; H, 6.475; N, 15.19%. |
| 107 | Et | $^1$H NMR(400 MHz, CDCl$_3$): δ = 1.14(m, 6H), 1.44(t, 3H), 2.42(q, 2H), 2.48(q, 2H), 2.98(q, 2H), 3.39(s, 3H), 3.53(q, 2H), 3.59(q, 2H), 3.95(q, 2H), 4.20(q, 2H), 4.48(s, 2H), 7.30(s, 1H), 7.84(s, 1H), 8.01(s, 1H). LRMS (electrospray): m/z 492 (M + Na$^+$) |
| 108 | $^i$Pr | $^1$H NMR(400 MHz, CDCl$_3$): δ = 1.11(m, 6H), 1.49(d, 6H), 2.44(q, 2H), 2.49(q, 2H), 3.30(sept, 1H), 3.39(s, 3H), 3.54(m, 2H), 3.59(m, 2H), 3.95(t, 2H), 4.23(t, 2H), 4.91(s, 2H), 7.22(m, 1H), 7.83(m, 1H), 8.02(m, 1H). LRMS (electrospray): m/z 506 (M + Na$^+$) Microanalysis: Found C, 61.87; H, 6.76; N, 14.62. C$_{25}$H$_{33}$N$_5$O$_5$ requires C, 62.10; H, 6.88; N, 14.48%. |

Preparation 109

Ethyl 5-{[(tert-butoxycarbonyl)amino]methyl}nicotinate

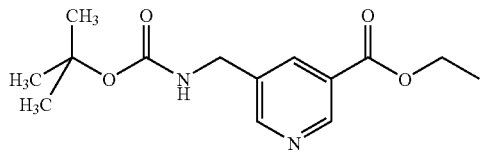

To a stirred solution of ethyl-5-cyanonicotinate (3.0 g, 17.0 mmol; Annalen Der Chemie, 1959, 621, 106–136) in ethanol (200 ml) was added concentrated hydrochloric acid (3.4 ml) followed by 5% palladium on carbon (300 mg). The reaction mixture was stirred at room temperature under an hydrogen atmosphere (50 psi) for 18 hours. The reaction mixture was filtered through Arbocel® and concentrated under reduced pressure. The crude product mixture was purified by flash chromatography on silica gel eluting with dichloromethane:methanol:0.880 ammonia (a gradient from 95:5:0.5 to 85:5:1.5, by volume) to provide the intermediate amine (2.1 g) as a yellow oily solid. This material (2.1 g, 11.7 mmol) was suspended in dichloromethane (22 ml) to which was added triethylamine (1.8 ml, 13.0 mmol) followed by di-tert-butyl dicarbonate (2.84 g, 13 mmol). After 48 hours the reaction mixture was diluted with dichloromethane (50 ml) and washed with water (50 ml). The organic component was dried over magnesium sulphate and concentrated under reduced pressure before being purified by flash chromatography on silica gel eluting with dichloromethane:methanol:0.88 ammonia (a gradient from 100:0:0 to 95:5:0.5, by volume) to provide the title compound (2.0 g) as a yellow oil $^1$H NMR (400 MHz, CDCl$_3$): δ=1.40 (m, 12H), 4.42 (m, 4H), 8.22 (s, 1H), 8.71 (s, 1H), 9.12 (s, 1H). LRMS (APCI): m/z 279 (M–H$^+$)

Preparation 110

5-{[(tert-Butoxycarbonyl)amino]methyl}nicotinic acid

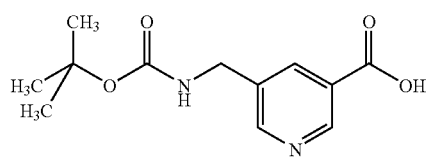

To a stirred solution of the ester from Preparation 109 (2.00 g, 7.10 mmol) in 1M aqueous sodium hydroxide solution (15 ml, 15 mmol) was added methanol (15 ml). The reaction mixture was stirred at room temperature for 18 hours, after which time the methanol was removed under reduced pressure. The aqueous solution was washed with diethyl ether (2×25 ml), cooled to 0° C. and neutralised to pH 7 by addition of 2M aqueous hydrochloric acid solution (7.5 ml). The mixture was concentrated under reduced pressure to give a yellow oil (1.5 g).

$^1$H NMR (400 MHz, (CD$_3$)$_2$SO): δ=1.37 (s, 9H), 4.16 (d, 2H), 7.51 (m, 1H), 8.07 (s, 1H), 8.50 (s, 1H), 8.88 (s, 1H). LRMS (APCI): m/z 251 (M–H$^+$)

Preparation 111

5-(Aminomethyl)nicotinamide

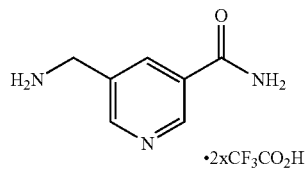

To a stirred solution of the acid from Preparation 110 (770 mg, 3.10 mmol) in dimethylformamide (15 ml) was added carbonyldiimidazole (600 mg, 3.70 mmol). After 10 minutes 0.880 ammonia (1 ml) was added. After a further 1 hour the reaction mixture was concentrated under reduced pressure and the residue was purified by flash chromatography on silica gel eluting with dichloromethane:methanol:0.88 ammonia (a gradient from 95:5:0.5 to 80:20:1, by volume) to provide the boc-protected intermediate. To a stirred solution of this material in dichloromethane (20 ml) was added trifluoroacetic acid (6 ml). After 18 hours a second portion of trifluoroacetic acid (6 ml) was added and the reaction mixture was stirred at room temperature for 24 hours. The solution was concentrated under reduced pressure to give an oily residue which was purified by flash chromatography on silica gel eluting with dichloromethane:methanol:0.88 ammonia (100:0:0 then 90:10:1 then 80:20:1, by volume) to provide the title compound (650 mg) as a yellow oil.

$^1$H NMR (400 MHz, (CD$_3$)$_2$SO): δ=4.11 (s, 2H), 7.5 (broad s), 7.59 (broad s), 8.14 (broad s), 8.31 (m, 1H), 8.72 (m, 1H), 8.90 (m, 1H). LRMS (electrospray): m/z 152 (MH$^+$) HRMS: [MH$^+$] 152.0819. C$_7$H$_{10}$N$_3$O requires 152.0818

Preparation 112

Ethyl 2-{[(tert-butoxycarbonyl)amino]methyl}isonicotinate

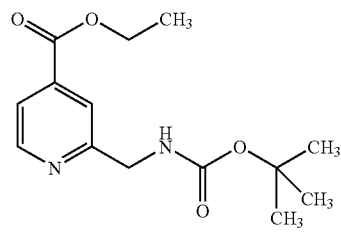

To a stirred solution of ethyl 2-cyanoisonicotinate (2.00 g, 110 mmol, J. Med. Chem., 1976,19, 483) in ethanol (20 ml) was added 2M aqueous hydrochloric acid solution (7.5 ml) followed by 5% palladium on carbon (200 mg). The reaction mixture was stirred at room temperature under a hydrogen atmosphere (60 psi) for 48 hours. The mixture was filtered through arbocel and the filtrate was concentrated under reduced pressure. The residue was dried by azeotropic distillation using toluene under reduced pressure. To a stirred solution of the residue (3.00 g) in dichloromethane (22 ml) was added triethylamine (4.6 ml, 33 mmol) followed by di-tert-butyl dicarbonate (2.62 g, 12.0 mmol). After stirring for 1 hour at room temperature the reaction mixture was diluted with dichloromethane (100 ml) and washed with water (50 ml). The organic component was washed with brine (50 ml), dried over magnesium sulphate and concentrated under reduced pressure to give a brown oily solid. The crude product mixture was purified by flash chromatography on silica gel eluting with dichloromethane:methanol:0.88 ammonia (98:2:0.2 then 97:3:0.3, by volume) to provide the title compound (2.20 g) as a yellow oil.

$^1$H NMR (400 MHz, CDCl$_3$): δ=1.38 (t, 3H), 1.45 (s, 9H), 4.38 (q, 2H), 4.50 (m, 2H), 5.50 (broad s, 1H), 7.73 (d, 1H), 7.81 (s, 1H), 8.65 (d, 1H). LRMS (electrospray): m/z 281 (MH$^+$)

Preparation 113

2-{[(tert-Butoxycarbonyl)amino]methyl}isonicotinic acid

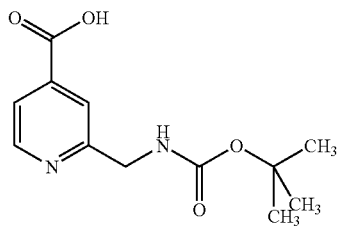

To a stirred solution of the ester from Preparation 112 (1.50 g, 5.35 mmol) in methanol (10 ml) was added 1M aqueous sodium hydroxide solution (10 ml). After 1 hour the reaction mixture was cooled to 0° C. and neutralised by addition of 2M aqueous hydrochloric acid solution (5 ml). The reaction mixture was concentrated under reduced pressure and the residue was purified by flash chromatography on silica gel eluting with dichloromethane:methanol:0.880 ammonia (80:20:1, by volume) to provide the title compound (1.30 g) as a yellow foam.

$^1$H NMR (400 MHz, (CD$_3$OD): δ=1.43 (s, 9H), 4.36, (s, 2H), 7.68 (m, 1H), 7.81 (s, 1H), 8.47 (m, 1H). LRMS (electrospray): m/z 251 (M−H$^+$) HRMS: [MH$^+$] 253.1179. C$_{12}$H$_{17}$N$_2$O$_4$ requires 253.1183

Preparation 114 tert-Butyl [4-(aminocarbonyl)-2-pyridinyl]methylcarbamate

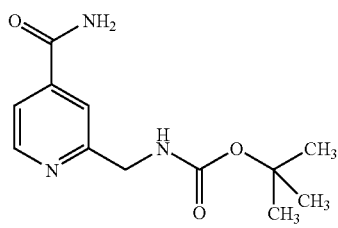

To a stirred solution of the acid from Preparation 113 (1.3 g, 5.20 mmol) in dimethylformamide (10 ml) was added 1-hydroxybenzotriazole (950 mg, 6.20 mmol) followed by 1-(3-dimethylaminopropyl)-3-ethylcarbodiimide hydrochloride salt (1.20 g, 6.20 mmol). After 1 hour 0.880 ammonia (5 ml) was added and the reaction mixture was stirred at room temperature for 1.5 hours. The mixture was concentrated under reduced pressure and dried by azeotropic distillation using toluene under reduced pressure to give a yellow semi-solid. The crude product mixture was purified by flash chromatography on silica gel eluting with dichloromethane:methanol:0.88 ammonia (95:5:0.5, by volume) to provide the title compound (1.1 g) as a clear oil which crystallised on standing. This material was further purified by triturating with diethyl ether (10 ml) which gave a sample of the desired product (1.0 g) white powder.

$^1$H NMR (400 MHz, D6-DMSO): δ=1.39 (s, 9H), 4.25 (m, 2H), 7.44 (m, 1H), 7.61 (m, 1H), 7.66 (broad s, 2H), 8.21 (broad s, 1H), 8.59 (d, 1H). LRMS (electrospray): m/z 250 (M−H$^+$) Microanalysis: Found C, 57.26; H, 6.86; N, 16.65. C$_{12}$H$_{17}$N$_3$O$_3$ requires C, 57.36; H, 6.82; N, 16.72%.

Preparation 115

2-(Aminomethyl)isonicotinamide

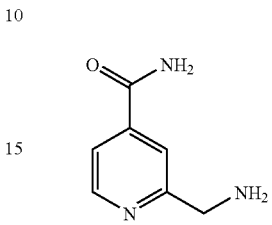

To a stirred solution of the pyridine from Preparation 114 (1.00 g, 3.98 mmol) in dichloromethane (50 ml) was added trifluoroacetic acid (15 ml). After stirring at room temperature for 18 hours the reaction mixture was concentrated under reduced pressure and purified by ion-exchange chromatography on Dowex 50-X8-200 eluting with water followed by 0.880 ammonia:methanol:water (5:5:90, by volume) to provide the title compound (265 mg) as a white solid.

$^1$H NMR (400 MHz, D6-DMSO): δ=2.1 (broad s, 1H), 3.4 (broad s, 1H), 3.85 (2H, s), 7.57 (m, 1H), 7.60 (broad s, 1H), 7.80 (m, 1H), 8.16 (broad s, 1H), 8.59 (m, 1H). LRMS (APCI): m/z 152 (MH$^+$)

What is claimed is:

1. A compound of formula (I)

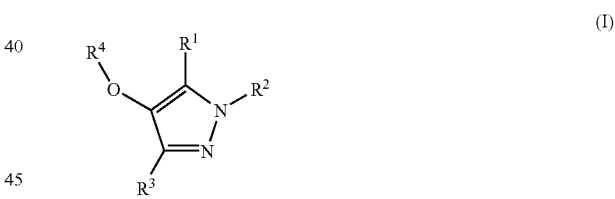

or a pharmaceutically acceptable salt, solvate or derivative thereof, wherein:

$R^1$ is H, $C_1$–$C_6$ alkyl, $C_3$–$C_7$ cycloalkyl, phenyl, benzyl, halo, —CN, —OR$^7$, —CO$_2$R$^{10}$, —CONR$^5$R$^{10}$, R$^8$ or R$^9$, said $C_1$–$C_6$ alkyl, $C_3$–$C_7$ cycloalkyl, phenyl and benzyl being optionally substituted by halo, —CN, —OR$^{10}$, S(O)$_x$R$^{10}$, —CO$_2$R$^{10}$, —CONR$^5$R$^{10}$, —OCONR$^5$R$^{10}$, —NR$^5$CO$_2$R$^{10}$, —NR$^{10}$R$^{11}$, —NR$^5$COR$^{10}$, —SO$_2$NR$^5$R$^{10}$, —NR$^5$CONR$^5$R$^{10}$, —NR$^5$SO$_2$R$^{10}$ or R$^{10}$; and $R^2$ is H, $C_1$–$C_6$ alkyl, $C_3$–$C_6$ alkenyl, $C_3$–$C_6$ alkynyl, $C_3$–$C_7$ cycloalkyl, $C_3$–$C_7$ cycloalkenyl, phenyl, benzyl, R$^8$ or R$^9$, said $C_1$–$C_6$ alkyl, $C_3$–$C_7$ cycloalkyl, phenyl and benzyl being optionally substituted by halo, —OR$^5$, —OR$^{12}$, —CN, —CO$_2$R$^7$, —OCONR$^5$R$^5$, —CONR$^5$R$^5$, —C(═NR$^5$)NR$^5$OR$^5$, —CONR$^5$NR$^5$R$^5$, —NR$^6$R$^6$, —NR$^5$R$^{12}$, —NR$^5$COR$^5$, —NR$^5$COR$^8$, —NR$^5$COR$^{12}$, —NR$^5$CO$_2$R$^5$, —NR$^5$CONR$^5$R$^5$, —SO$_2$NR$^5$R$^5$, —NR$^5$SO$_2$R$^5$, —NR$^5$SO$_2$NR$^5$R$^5$, R$^8$ or R$^9$;

R³ is H, C₁–C₆ alkyl, C₃–C₇ cycloalkyl, phenyl, benzyl, halo, —CN, —OR⁷, —CO₂R⁵, —CONR⁵R⁵, R⁸ or R⁹, said C₁–C₆ alkyl, C₃–C₇ cycloalkyl, phenyl and benzyl being optionally substituted by halo, —CN, —OR⁵, —CO₂R⁵, —CONR⁵R⁵, —OCONR⁵R⁵, —NR⁵CO₂R⁵, —NR⁶R⁶, —NR⁵COR⁵, —SO₂NR⁵R⁵, —NR⁵CONR⁵R⁵, —NR⁵SO₂R⁵, R⁸ or R⁹;

R⁴ is phenyl or naphthyl, each being optionally substituted by R⁸, halo, —CN, C₁–C₆ alkyl, C₁–C₆ haloalkyl, C₃–C₇ cycloalkyl, C₁–C₆ alkoxy, —CONR⁵R⁵, OR¹³, SOₓR⁶, O—(C₁–C₆ alkylene)—CONR⁵R⁵, O—(C₁–C₆ alkylene)—NR⁵R⁵, or O—(C₁–C₆ alkylene)—OR⁶;

each R⁵ is independently either H, C₁–C₆ alkyl or C₃–C₇ cycloalkyl or, when two R⁵ groups are attached to the same nitrogen atom, those two groups taken together with the nitrogen atom to which they are attached represent azetidinyl, pyrrolidinyl, piperidinyl, homopiperidinyl, piperazinyl, homopiperazinyl or morpholinyl, said azetidinyl, pyrrolidinyl, piperidinyl, homopiperidinyl, piperazinyl, homopiperazinyl and morpholinyl being optionally substituted by C₁–C₆ alkyl or C₃–C₇ cycloalkyl;

each R⁶ is independently either H, C₁–C₆ alkyl or C₃–C₇ cycloalkyl;

R⁷ is C₁–C₆ alkyl or C₃–C₇ cycloalkyl;

R⁸ is a five or six-membered, aromatic heterocyclic group containing (i) from 1 to 4 nitrogen heteroatom(s) or (ii) 1 or 2 nitrogen heteroatom(s) and 1 oxygen or 1 sulphur heteroatom or (iii) 1 or 2 oxygen or sulphur heteroatom(s), said heterocyclic group being optionally substituted by halo, oxo, —CN, —COR⁵, —CONR⁵R⁵, —SO₂NR⁵R⁵, —NR⁵SO₂R⁵, —OR⁵, —NR⁵R⁵, —(C₁–C₆ alkylene)—NR⁵R⁵, C₁–C₆ alkyl, fluoro(C₁–C₆)alkyl or C₃–C₇ cycloalkyl;

R⁹ is a four to seven-membered, saturated or partially unsaturated heterocyclic group containing (i) 1 or 2 nitrogen heteroatom(s) or (ii) 1 nitrogen heteroatom and 1 oxygen or 1 sulphur heteroatom or (iii) 1 oxygen or sulphur heteroatom, said heterocyclic group being optionally substituted by oxo, C₁–C₆ alkyl, C₃–C₇ cycloalkyl, —SO₂R⁵, —CONR⁵R⁵, —COOR⁵, —CO—(C₁–C₆ alkylene)—OR⁵ or —COR⁵ and optionally substituted on a carbon atom which is not adjacent to a heteroatom by halo, —OR⁵, —NR⁵R⁵, —NR⁵COR⁵, —NR⁵COOR⁵, —NR⁵CONR⁵R⁵, —NR⁵SO₂R⁵ or —CN;

R¹⁰ is H, R⁸, R⁹, R¹³, C₁–C₆ alkyl, C₃–C₇ cycloalkyl or —(C₁–C₆ alkyl)—(C₃–C₇ cycloalkyl), said C₁–C₆ alkyl and C₃–C₇ cycloalkyl being optionally substituted by —OR⁵, —OR¹³, R⁸, R⁹, R¹³ or —COR¹³;

R¹¹ is H, C₁–C₆ alkyl or C₃–C₇ cycloalkyl, said C₁–C₆ alkyl and C₃–C₇ cycloalkyl being optionally substituted by —OR⁵, —NR⁵R⁵, —NR⁵COR⁵, —CONR⁵R⁵, R⁸ or R⁹;

R¹² is C₁–C₆ alkyl substituted by R⁸, R⁹, —OR⁵, —CONR⁵R⁵, —NR⁵COR⁵ or —NR⁵R⁵;

R¹³ is phenyl optionally substituted by halo, —CN, —COR⁵, —CONR⁵R⁵, —SO₂NR⁵R⁵, —NR⁵SO₂R⁵, —OR⁵, —NR⁵R⁵, —(C₁–C₆ alkylene)—NR⁵R⁵, C₁–C₆ alkyl, halo(C₁–C₆)alkyl or C₃–C₇ cycloalkyl; and x is 0, 1 or 2;

with the proviso that:
(a) when R¹ and R³ are both phenyl, R² is not methyl; and
(b) when R¹ is ethoxy and R³ is ethoxycarbonyl, R² is not phenyl.

2. A compound of formula (I)

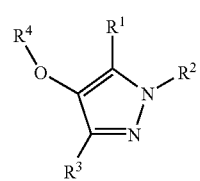

or a pharmaceutically acceptable salt thereof, wherein:

R¹ is H, C₁–C₆ alkyl, C₃–C₇ cycloalkyl, phenyl, benzyl, halo, —CN, —OR⁷, —CO₂R¹⁰, —CONR⁵R¹⁰, R⁸ or R⁹, said C₁–C₆ alkyl, C₃–C₇ cycloalkyl, phenyl and benzyl being optionally substituted by halo, —CN, —OR¹⁰, S(O)ₓR¹⁰, —CO₂R¹⁰, —CONR⁵R¹⁰, —OCONR⁵R¹⁰, —NR⁵CO₂R¹⁰, —NR¹⁰R¹¹, —NR⁵COR¹⁰, —SO₂NR⁵R¹⁰, —NR⁵CONR⁵R¹⁰, —NR⁵SO₂R¹⁰ or R¹⁰; and R² is H, C₁–C₆ alkyl, C₃–C₆ alkenyl, C₃–C₆ alkynyl, C₃–C₇ cycloalkyl, C₃–C₇ cycloalkenyl, phenyl, benzyl, R⁸ or R⁹, said C₁–C₆ alkyl, C₃–C₇ cycloalkyl, phenyl and benzyl being optionally substituted by halo, —OR⁵, —OR¹², —CN, —CO₂R⁷, —OCONR⁵R⁵, —CONR⁵R⁵, —C(=NR⁵)NR⁵OR⁵, —CONR⁵NR⁵R⁵, —NR⁶R⁶, —NR⁵R¹², —NR⁵COR⁵, —NR⁵COR⁸, —NR⁵COR¹², —NR⁵CO₂R⁵, —NR⁵CONR⁵R⁵, —SO₂NR⁵R⁵, —NR⁵SO₂R⁵, —NR⁵SO₂NR⁵R⁵, R⁸ or R⁹;

R³ is H, C₁–C₆ alkyl, C₃–C₇ cycloalkyl, phenyl, benzyl, halo, —CN, —OR⁷, —CO₂R⁵, —CONR⁵R⁵, R⁸ or R⁹, said C₁–C₆ alkyl, C₃–C₇ cycloalkyl, phenyl and benzyl being optionally substituted by halo, —CN, —OR⁵, —CO₂R⁵, —CONR⁵R⁵, —OCONR⁵R⁵, —NR⁵CO₂R⁵, —NR⁶R⁶, —NR⁵COR⁵, —SO₂NR⁵R⁵, —NR⁵CONR⁵R⁵, —NR⁵SO₂R⁵, R⁸ or R⁹;

R⁴ is phenyl or naphthyl, each being optionally substituted by R⁸, halo, —CN, C₁–C₆ alkyl, C₁–C₆ haloalkyl, C₃–C₇ cycloalkyl, C₁–C₆ alkoxy, —CONR⁵R⁵, OR¹³, SOₓR⁶, O—(C₁–C₆ alkylene)—CONR⁵R⁵, O—(C₁–C₆ alkylene)—NR⁵R⁵, or O—(C₁–C₆ alkylene)—OR⁶;

each R⁵ is independently either H, C₁–C₆ alkyl or C₃–C₇ cycloalkyl or, when two R⁵ groups are attached to the same nitrogen atom, those two groups taken together with the nitrogen atom to which they are attached represent azetidinyl, pyrrolidinyl, piperidinyl, homopiperidinyl, piperazinyl, homopiperazinyl or morpholinyl, said azetidinyl, pyrrolidinyl, piperidinyl, homopiperidinyl, piperazinyl, homopiperazinyl and morpholinyl being optionally substituted by C₁–C₆ alkyl or C₃–C₇ cycloalkyl;

each R⁶ is independently either H, C₁–C₆ alkyl or C₃–C₇ cycloalkyl;

R⁷ is C₁–C₆ alkyl or C₃–C₇ cycloalkyl;

R⁸ is a five or six-membered, aromatic heterocyclic group containing (i) from 1 to 4 nitrogen heteroatom(s) or (ii) 1 or 2 nitrogen heteroatom(s) and 1 oxygen or 1 sulphur heteroatom or (iii) 1 or 2 oxygen or sulphur heteroatom(s), said heterocyclic group being optionally substituted by halo, oxo, —CN, —COR⁵, —CONR⁵R⁵, —SO₂NR⁵R⁵, —NR⁵SO₂R⁵, —OR⁵, —NR⁵R⁵, —(C₁–C₆ alkylene)—NR⁵R⁵, C₁–C₆ alkyl, fluoro(C₁–C₆)alkyl or C₃–C₇ cycloalkyl;

R⁹ is a four to seven-membered, saturated or partially unsaturated heterocyclic group containing (i) 1 or 2 nitrogen heteroatom(s) or (ii) 1 nitrogen heteroatom and 1 oxygen or 1 sulphur heteroatom or (iii) 1 oxygen or sulphur heteroatom, said heterocyclic group being optionally substituted by oxo, $C_1$–$C_6$ alkyl, $C_3$–$C_7$ cycloalkyl, —$SO_2R^5$, —$CONR^5R^5$, —$COOR^5$, —CO—($C_1$–$C_6$ alkylene)—$OR^5$ or —$COR^5$ and optionally substituted on a carbon atom which is not adjacent to a heteroatom by halo, —$OR^5$, —$NR^5R^5$, —$NR^5COR^5$, —$NR^5COOR^5$, —$NR^5CONR^5R^5$, —$NR^5SO_2R^5$ or —CN;

$R^{10}$ is H, $R^8$, $R^9$, $R^{13}$, $C_1$–$C_6$ alkyl, $C_3$–$C_7$ cycloalkyl or —($C_1$–$C_6$ alkyl)—($C_3$–$C_7$ cycloalkyl), said $C_1$–$C_6$ alkyl and $C_3$–$C_7$ cycloalkyl being optionally substituted by —$OR^5$, —$OR^{13}$, $R^8$, $R^9$, $R^{13}$ or —$COR^{13}$;

$R^{11}$ is H, $C_1$–$C_6$ alkyl or $C_3$–$C_7$ cycloalkyl, said $C_1$–$C_6$ alkyl and $C_3$–$C_7$ cycloalkyl being optionally substituted by —$OR^5$, —$NR^5R^5$, —$NR^5COR^5$, —$CONR^5R^5$, $R^8$ or $R^9$;

$R^{12}$ is $C_1$–$C_6$ alkyl substituted by $R^8$, $R^9$, —$OR^5$, —$CONR^5R^5$, —$NR^5COR^5$ or —$NR^5R^5$;

$R^{13}$ is phenyl optionally substituted by halo, —CN, —$COR^5$, —$CONR^5R^5$, —$SO_2NR^5R^5$, —$NR^5SO_2R^5$, —$OR^5$, —$NR^5R^5$, —($C_1$–$C_6$ alkylene)—$NR^5R^5$, $C_1$–$C_6$ alkyl, halo($C_1$–$C_6$)alkyl or $C_3$–$C_7$ cycloalkyl; and x is 0, 1 or 2;

with the proviso that:
(a) when $R^1$ and $R^3$ are both phenyl, $R^2$ is not methyl; and
(b) when $R^1$ is ethoxy and $R^3$ is ethoxycarbonyl, $R^2$ is not phenyl.

3. A compound according to claim 1 wherein $R^1$, when taken separately, is H, $C_1$–$C_6$ alkyl, $C_3$–$C_7$ cycloalkyl or —$OR^7$, said $C_1$–$C_6$ alkyl and $C_3$–$C_7$ cycloalkyl being optionally substituted by halo, —CN, —$OR^{10}$, $S(O)_xR^{10}$, —$CO_2R^{10}$, —$CONR^5R^{10}$, —$OCONR^5R^{10}$, —$NR^5CO_2R^{10}$, —$NR^{10}R^{11}$, —$NR^5COR^{10}$, —$SO_2NR^5R^{10}$, —$NR^5CONR^5R^{10}$, —$NR^5SO_2R^{10}$ or $R^{10}$.

4. A compound according to claim 1 or 2, wherein $R^1$, when taken separately, is H, $C_1$–$C_6$ alkyl, $C_3$–$C_7$ cycloalkyl or —$OR^7$, said $C_1$–$C_6$ alkyl being optionally substituted by halo, —$OR^{10}$, —$NR^{10}R^{11}$, —$NR^5COR^{10}$ or $R^{10}$.

5. A compound according claim 1 or 2, wherein $R^2$, when taken separately, is H, $C_1$–$C_6$ alkyl, $C_3$–$C_6$ alkenyl or $R^9$, said $C_1$–$C_6$ alkyl being optionally substituted by halo, —$OR^5$, —$OR^{12}$, —CN, —$CO_2R^7$, —$OCONR^5R^5$, —$CONR^5R^5$, —C(=$NR^5$)$NR^5OR^5$, —$CONR^5NR^5R^5$, —$NR^6R^6$, —$NR^5R^{12}$, —$NR^5COR^5$, —$NR^5COR^8$, —$NR^5COR^{12}$, —$NR^5CO_2R^5$, —$NR^5CONR^5R^5$, —$SO_2NR^5R^5$, —$NR^5SO_2R^5$, $R^8$ or $R^9$.

6. A compound according to claim 1 or 2, wherein $R^2$, when taken separately, is H, $C_1$–$C_6$ alkyl, $C_3$–$C_6$ alkenyl or $R^9$, said $C_1$–$C_6$ alkyl being optionally substituted by —$OR^5$, —$OR^{12}$, —CN, —$CO_2R^7$, —$CONR^5R^5$, —C(=$NR^5$)$NR^5OR^5$, —$CONR^5NR^5R^5$, —$NR^6R^6$, —$NR^5R^{12}$, —$NR^5COR^8$, —$NR^5COR^{12}$, —$NR^5CO_2R^5$, $R^8$ or $R^9$.

7. A compound according to claim 1 or 2, wherein $R^3$ is H or $C_1$–$C_6$ alkyl, said $C_1$–$C_6$ alkyl being optionally substituted by halo, —CN, —$OR^5$, —$CO_2R^5$, —$CONR^5R^5$, —$OCONR^5R^5$, —$NR^5CO_2R^5$, —$NR^6R^6$, —$NR^5COR^5$, —$SO_2NR^5R^5$, —$NR^5CONR^5R^5$, —$NR^5SO_2R^5$, $R^8$ or $R^9$.

8. A compound according to claim 1 or 2, wherein $R^3$ is H or $C_1$–$C_6$ alkyl.

9. A compound according to claim 1 or 2, wherein $R^4$ is phenyl optionally substituted by $R^8$, halo, —CN, $C_1$–$C_6$ alkyl, $C_1$–$C_6$ haloalkyl, $C_3$–$C_7$ cycloalkyl, $C_1$–$C_6$ alkoxy, —$CONR^5R^5$, $OR^{13}$, $SO_xR^6$, O—($C_1$–$C_6$ alkylene)—$CONR^5R^5$, O—($C_1$–$C_6$ alkylene)—$NR^5R^5$, or O—($C_1$–$C_6$ alkylene)—$OR^6$; or naphthyl.

10. A compound according to claim 1 or 2, wherein $R^4$ is phenyl substituted by $R^8$, halo, —CN, $C_1$–$C_6$ alkyl, $C_1$–$C_6$ haloalkyl, $C_3$–$C_7$ cycloalkyl, $C_1$–$C_6$ alkoxy, —$CONR^5R^5$, $OR^{13}$, $SO_xR^6$, O—($C_1$–$C_6$ alkylene)—$CONR^5R^5$, O—($C_1$–$C_6$ alkylene)—$NR^5R^5$, or O—($C_1$–$C_6$ alkylene)—$OR^6$.

11. A compound according to claim 1 or 2, wherein $R^4$ is phenyl substituted by $R^8$, halo, —CN, $C_1$–$C_6$ alkyl, $C_1$–$C_6$ haloalkyl, $C_3$–$C_7$ cycloalkyl or $C_1$–$C_6$ alkoxy.

12. A compound according to claim 1 or 2, wherein $R^4$ is phenyl substituted by halo, —CN or $C_1$–$C_6$ alkyl.

13. A compound according to claim 1 or 2, wherein $R^8$ is pyrrolyl, imidazolyl, pyrazolyl, 1,2,3-triazolyl, 1,2,4-triazolyl, tetrazolyl, oxazolyl, isoxazolyl, thiazolyl, isothiazolyl, 1,2,4-oxadiazolyl, 1,3,4-oxadiazolyl, furanyl, thienyl, pyridinyl, pyridazinyl, pyrimidinyl or pyrazinyl, each being optionally substituted by halo, —CN, —$COR^5$, —$CONR^5R^5$, —$SO_2NR^5R^5$, —$NR^5SO_2R^5$, —$OR^5$, —$NR^5R^5$, —($C_1$–$C_6$ alkylene)—$NR^5R^5$, $C_1$–$C_6$ alkyl, fluoro($C_1$–$C_6$)alkyl or $C_3$–$C_7$ cycloalkyl.

14. A compound according to claim 1 or 2, wherein $R^8$ is imidazolyl, pyrazolyl, 1,2,4-triazolyl, 1,2,4-oxadiazolyl, 1,3,4-oxadiazolyl, pyridinyl, pyrazinyl or pyrimidinyl, each being optionally substituted by halo, —CN, —$COR^5$, —$CONR^5R^5$, —$SO_2NR^5R^5$, —$NR^5SO_2R^5$, —$OR^5$, —$NR^5R^5$, —($C_1$–$C_6$ alkylene)—$NR^5R^5$, $C_1$–$C_6$ alkyl, fluoro($C_1$–$C_6$)alkyl or $C_3$–$C_7$ cycloalkyl.

15. A compound according to claim 1 or 2, wherein $R^8$ is imidazolyl, pyrazolyl, 1,2,4-triazolyl, 1,2,4-oxadiazolyl, 1,3,4-oxadiazolyl, pyridinyl, pyrazinyl or pyrimidinyl, each being optionally substituted by —$OR^5$, —$NR^5R^5$ or $C_1$–$C_6$ alkyl.

16. A compound according to claim 1 or 2, wherein $R^9$ is azetidinyl, tetrahydropyrrolyl, piperidinyl, azepinyl, oxetanyl, tetrahydrofuranyl, tetrahydropyranyl, oxepinyl, morpholinyl, piperazinyl or diazepinyl, each being optionally substituted by oxo, $C_1$–$C_6$ alkyl, $C_3$–$C_7$ cycloalkyl, —$SO_2R^5$, —$CONR^5R^5$, —$COOR^5$, —CO—($C_1$–$C_6$ alkylene)—$OR^5$ or —$COR^5$ and optionally substituted on a carbon atom which is not adjacent to a heteroatom by halo, —$OR^5$, —$NR^5R^5$, —$NR^5COR^5$, —$NR^5COOR^5$, —$NR^5CONR^5R^5$, —$NR^5SO_2R^5$ or —CN.

17. A compound according to claim 1 or 2, wherein $R^9$ is azetidinyl, piperidinyl, tetrahydrofuranyl, piperazinyl or morpholinyl, each being optionally substituted by oxo, $C_1$–$C_6$ alkyl, $C_3$–$C_7$ cycloalkyl, —$SO_2R^5$, —$CONR^5R^5$, —$COOR^5$, —CO—($C_1$–$C_6$ alkylene)—$OR^5$ or —$COR^5$ and optionally substituted on a carbon atom which is not adjacent to a heteroatom by halo, —$OR^5$, —$NR^5R^5$, —$NR^5COR^5$, —$NR^5COOR^5$, —$NR^5CONR^5R^5$, —$NR^5SO_2R^5$ or —CN.

18. A compound according to claim 1 or 2, wherein $R^9$ is azetidinyl, piperidinyl, tetrahydrofuranyl, piperazinyl or morpholinyl, each being optionally substituted by $C_1$–$C_6$ alkyl, —$SO_2R^5$, —$CONR^5R^5$, —$COOR^5$, —CO—($C_1$–$C_6$ alkylene)—$OR^5$ or —$COR^5$ and optionally substituted on a carbon atom which is not adjacent to a heteroatom by —$OR^5$ or —$NR^5COR^5$.

19. A compound according to claim 1 or 2, wherein $R^{10}$ is H, $R^8$, $R^9$, $R^{13}$, $C_1$–$C_6$ alkyl or —($C_1$–$C_6$ alkyl)—($C_3$–$C_7$ cycloalkyl), said $C_1$–$C_6$ alkyl being optionally substituted by —$OR^5$, —$OR^{13}$, $R^8$, $R^9$, $R^{13}$ or —$COR^{13}$.

20. A compound according to claim 1 or 2, wherein $R^{10}$ is H, $R^8$, $R^9$, $R^{13}$, $C_1$–$C_6$ alkyl or —($C_1$–$C_6$ alkyl)—($C_3$–$C_7$ cycloalkyl), said $C_1$–$C_6$ alkyl being optionally substituted by —$OR^5$ or $R^{13}$.

21. A compound according to claim 1 or 2, wherein $R^{11}$ is H or $C_1$–$C_6$ alkyl, said $C_1$–$C_6$ alkyl being optionally substituted by —$OR^5$, —$NR^5R^5$, —$NR^5COR^5$, —$CONR^5R^5$, $R^8$ or $R^9$.

22. A compound according to claim 1 or 2, wherein $R^{11}$ is H or $C_1$–$C_6$ alkyl, said $C_1$–$C_6$ alkyl being optionally substituted by —$OR^5$ or —$NR^5COR^5$.

23. A compound according to claim 1 or 2, wherein $R^{12}$ is $C_1$–$C_4$ alkyl substituted by $R^8$, $R^9$, —$OR^5$, —$CONR^5R^5$, —$NR^5COR^5$ or —$NR^5R^5$.

24. A compound according to claim 1 or 2, wherein $R^{12}$ is $C_1$–$C_4$ alkyl substituted by $R^9$, —$OR^5$, —$NR^5COR^5$ or —$NR^5R^5$.

25. A compound according to claim 1 or 2, wherein $R^{13}$ is phenyl substituted by halo, —CN, —$COR^5$, —$CONR^5R^5$, —$SO_2NR^5R^5$, —$NR^5SO_2R^5$, —$OR^5$, —$NR^5R^5$, —($C_1$–$C_6$ alkylene)—$NR^5R^5$, $C_1$–$C_6$ alkyl, halo($C_1$–$C_6$)alkyl or $C_3$–$C_7$ cycloalkyl.

26. A compound according to claim 1 or 2, wherein $R^{13}$ is phenyl substituted by halo, —CN, —$CONR^5R^5$, —$SO_2NR^5R^5$ or —$OR^5$.

27. A compound selected from the group consisting of:
5-{1-(2-Hydroxyethyl)-3-isopropyl-5-methyl-1H-pyrazol-4-yl]oxy}isophthalonitrile;
3-{[3,5-diethyl-1-(2-hydroxyethyl)-1H-pyrazol-4-yl]oxy}-5-fluorobenzonitrile;
3-{[3,5-diethyl-1-(2-hydroxyethyl)-1H-pyrazol-4-yl]oxy}-5-methylbenzonitrile;
5-{[3,5-diethyl-1-(2-hydroxyethyl)-1H-pyrazol-4-yl]oxy}isophthalonitrile;
3-chloro-5-{[3,5-diethyl-1-(2-hydroxyethyl)-1H-pyrazol-4-yl]oxy}benzonitrile;
3-[(3,5-diethyl-1H-pyrazol-4-yl)oxy]-5-fluorobenzonitrile;
5-[(3,5-diethyl-1H-pyrazol-4-yl)oxy]isophthalonitrile;
3-[(3,5-diethyl-1H-pyrazol-4-yl)oxy]-5-methylbenzonitrile;
3-chloro-5-[(3,5-diethyl-1H-pyrazol-4-yl)oxy]benzonitrile;
3-{[1-(2-aminoethyl)-3,5-diethyl-1H-pyrazol-4-yl]oxy}-5-methylbenzonitrile;
3-{[1-(2-aminoethyl)-3,5-diethyl-1H-pyrazol-4-yl]oxy}-5-chlorobenzonitrile;
5-{[1-(2-aminoethyl)-3,5-diethyl-1H-pyrazol-4-yl]oxy}isophthalonitrile;
3-{[1-(2-aminoethyl)-3,5-diethyl-1H-pyrazol-4-yl]oxy}-5-fluorobenzonitrile;
5-[(3-cyclopropyl-5-ethyl-1H-pyrazol-4-yl)oxy]isophthalonitrile;
5-[(5-ethyl-3-isopropyl-1H-pyrazol-4-yl)oxy]isophthalonitrile;
5-{[3-Cyclopropyl-5-ethyl-1-(2-hydroxyethyl)-1H-pyrazol-4-yl]oxy}isophthalonitrile;
5-{[5-Ethyl-1-(2-hydroxyethyl)-3-isopropyl-1H-pyrazol-4-yl]oxy}isophthalonitrile;
5-[(3,5-Dicyclopropyl-1H-pyrazol-4-yl)oxy]isophthalonitrile;
5-{[3,5-Dicyclopropyl-1-(2-hydroxyethyl)-1H-pyrazol-4-yl]oxy}isophthalonitrile;
Di(tert-butyl) 2-[4-(3,5-dicyanophenoxy)-3,5-diethyl-1H-pyrazol-1-yl]ethyl phosphate;
2-[4-(3,5-Dicyanophenoxy)-3,5-diethyl-1H-pyrazol-1-yl] ethyl dihydrogen phosphate;
5-{[3,5-Diethyl-1-(2-hydroxyethyl)-1H-pyrazol-4-yl]oxy}isophthalonitrile sulfate salt;
5-{[3,5-Diethyl-1-(2-hydroxyethyl)-1H-pyrazol-4-yl]oxy}isophthalonitrile benzenesulfonic acid salt;
5-{[3,5-Diethyl-1-(2-hydroxyethyl)-1H-pyrazol-4-yl]oxy}isophthalonitrile tosylate salt;
5-{[3,5-Diethyl-1-(2-hydroxyethyl)-1H-pyrazol-4-yl]oxy}isophthalonitrile mesylate salt;
3-{[1-(2-Aminoethyl)-3,5-diethyl-1H-pyrazol-4-yl]oxy}-5-methylbenzonitrile bis-mesylate salt;
3-{[1-(2-Aminoethyl)-3,5-diethyl-1H-pyrazol-4-yl]oxy}-5-methylbenzonitrile phosphate salt;
3-{[1-(2-Aminoethyl)-3,5-diethyl-1H-pyrazol-4-yl]oxy}-5-methylbenzonitrile (L) tartrate salt;
3-{[1-(2-Aminoethyl)-3,5-diethyl-1H-pyrazol-4-yl]oxy}-5-methylbenzonitrile succinate salt; and
3-{[1-(2-Aminoethyl)-3,5-diethyl-1H-pyrazol-4-yl]oxy}-5-methylbenzonitrile (L) citrate salt;
or a pharmaceutically acceptable salt, solvate or derivative thereof.

28. A compound selected from the group consisting of:
3-{[3,5-diethyl-1-(2-hydroxyethyl)-1H-pyrazol-4-yl]oxy}-5-fluorobenzonitrile;
3-{[3,5-diethyl-1-(2-hydroxyethyl)-1H-pyrazol-4-yl]oxy}-5-methylbenzonitrile;
5-{[3,5-diethyl-1-(2-hydroxyethyl)-1H-pyrazol-4-yl]oxy}isophthalonitrile;
3-chloro-5-{[3,5-diethyl-1-(2-hydroxyethyl)-1H-pyrazol-4-yl]oxy}benzonitrile;
5-[(3,5-diethyl-1H-pyrazol-4-yl)oxy]isophthalonitrile;
3-[(3,5-diethyl-1H-pyrazol-4-yl)oxy]-5-methylbenzonitrile;
3-chloro-5-[(3,5-diethyl-1H-pyrazol-4-yl)oxy]benzonitrile;
3-{[1-(2-aminoethyl)-3,5-diethyl-1H-pyrazol-4-yl]oxy}-5-methylbenzonitrile;
3-{[1-(2-aminoethyl)-3,5-diethyl-1H-pyrazol-4-yl]oxy}-5-chlorobenzonitrile; and
5-{[1-(2-aminoethyl)-3,5-diethyl-1H-pyrazol-4-yl]oxy}isophthalonitrile;
or a pharmaceutically acceptable salt, solvate or derivative thereof.

29. A compound of formula (I):

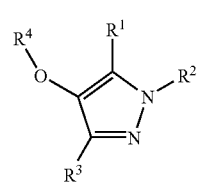

or a pharmaceutically acceptable salt or solvate thereof, wherein:

$R^1$ is H, $C_1$–$C_6$ alkyl, —$OC_1$–$C_6$ alkyl, —$OC_3$–$C_7$ cycloalkyl, said $C_1$–$C_6$ alkyl being optionally substituted by $R^{15}$;

$R^2$ is H, $C_1$–$C_3$ alkyl, propenyl or C-linked $R^{15}$, said $C_1$–$C_3$ alkyl being optionally substituted by —OH, —$OCH_3$, —$OCH_2CH_2NH_2$, —CN, —$CO_2CH_3$, —$CONH_2$, —C(=NH)$NH_2$, —$CONHNH_2$, —$NH_2$, —$NHCH_3$, —N($CH_3$)$_2$, —$NHCH_2CH_2NHCOCH_3$, —$NHCH_2CH_2OCH_3$, —$NHCH_2R^{15}$, —$NHCOR^{15}$, —$NHCOCH_2OCH_3$, or $R^{15}$ $R^{15}$ is azetidinyl, tetrahydrofuranyl, morpholinyl, piperazinyl, pyrazolyl, oxadiazolyl, pyridinyl or pyrimidinyl each being optionally substituted by —OH, —NH$_2$, oxo or $C_1$–$C_6$ alkyl or —CO($C_1$–$C_6$ alkyl);

$R^3$ is $C_1$–$C_6$ alkyl; and $R^4$ is phenyl optionally substituted by halo, —CN, $C_1$–$C_6$ alkyl, $C_1$–$C_6$ haloalkyl, $C_3$–$C_7$ cycloalkyl or $C_1$–$C_6$ alkoxy.

30. 5-{[3,5-diethyl-1-(2-hydroxyethyl)-1H-pyrazol-4-yl]oxy}isophthalonitrile;

or a pharmaceutically acceptable salt, solvate or derivative thereof.

31. 5-{[3,5-diethyl-1-(2-hydroxyethyl)-1H-pyrazol-4-yl]oxy}isophthalonitrile;

or a pharmaceutically acceptable salt thereof.

32. A pharmaceutical composition comprising a therapeutically effective amount of a compound according to claim 1 or a pharmaceutically acceptable salt, solvate or derivative thereof.

33. A pharmaceutical composition comprising a therapeutically effective amount of a compound according to claim 27 or a pharmaceutically acceptable salt, solvate or derivative thereof.

34. A pharmaceutical composition comprising a therapeutically effective amount of a compound according to claim 30 or a pharmaceutically acceptable salt, solvate or derivative thereof.

35. A method of treatment of a mammal, including a human being, with a reverse transcriptase inhibitor or modulator which method comprises treating said mammal with a therapeutically effective amount of a compound according to claim 1 or a pharmaceutically acceptable salt, solvate or derivative thereof, or with a pharmaceutical composition according to claim 32.

* * * * *